United States Patent
Chan Chun Kong et al.

(10) Patent No.: US 7,985,769 B2
(45) Date of Patent: *Jul. 26, 2011

(54) **COMPOUNDS AND METHODS FOR THE TREATMENT OR PREVENTION OF *FLAVIVIRUS* INFECTIONS**

(75) Inventors: Laval Chan Chun Kong, Kirkland (CA); Jean Bedard, Laval (CA); Sanjoy Kumar Das, Laval (CA); Nghe Nguyen Ba, LaPrairie (CA); Oswy Z. Pereira, Kirkland (CA); Thumkunta Jagadeeswar Reddy, St-Laurent (CA); Mohammad Arshad Siddiqui, Cambridge, MA (US); Wuyi Wang, Silver Spring, MD (US); Constanin Yannopoulos, Ile Perrot (CA)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 236 days.

This patent is subject to a terminal disclaimer.

(21) Appl. No.: 11/042,442

(22) Filed: Jan. 26, 2005

(65) Prior Publication Data
US 2006/0142347 A1  Jun. 29, 2006

Related U.S. Application Data

(63) Continuation of application No. 10/166,031, filed on Jun. 11, 2002, now Pat. No. 6,881,741.

(51) Int. Cl.
*A61K 31/35* (2006.01)
*C07D 333/38* (2006.01)
*C07D 333/36* (2006.01)

(52) U.S. Cl. .......... 514/445; 514/447; 514/448; 549/61; 549/68

(58) Field of Classification Search ........... 514/445, 514/447, 448; 549/61–67, 68–75
See application file for complete search history.

(56) References Cited

U.S. PATENT DOCUMENTS

| | | |
|---|---|---|
| 3,076,817 A | 2/1963 | Flesselmann et al. |
| 3,470,151 A | 9/1969 | Doyle et al. |
| 3,823,161 A | 7/1974 | Lesser |
| 3,855,243 A | 12/1974 | Ruschig et al. |
| 4,180,662 A | 12/1979 | Pfister et al. |
| 4,544,655 A | 10/1985 | Pfister et al. |
| 4,666,502 A | 5/1987 | Seckinger et al. |
| 4,710,506 A | 12/1987 | Davies |
| 4,877,793 A | 10/1989 | Davies |
| 5,276,009 A | 1/1994 | Muenster |
| 5,679,678 A | 10/1997 | Binder |
| 5,783,705 A | 7/1998 | Blok et al. |
| 5,807,854 A | 9/1998 | Bartroli |
| 5,888,941 A | 3/1999 | Bartroli |
| 5,942,387 A | 8/1999 | Hollinshead |
| 6,140,351 A | 10/2000 | Arnaiz |
| 6,187,799 B1 | 2/2001 | Wood et al. |
| 6,248,767 B1 | 6/2001 | Blok et al. |
| 6,344,476 B1 | 2/2002 | Ranges |
| 6,380,214 B1 | 4/2002 | Gant et al. |
| 6,410,586 B1 | 6/2002 | Moller |
| 6,414,013 B1 | 7/2002 | Fancelli et al. |
| 6,271,225 B1 | 8/2002 | Seio |
| 6,432,994 B1 | 8/2002 | Wu et al. |
| 6,448,290 B1 | 9/2002 | Ohuchida et al. |
| 6,458,805 B2 | 10/2002 | Blok et al. |
| 6,476,023 B1 | 11/2002 | Cirillo |
| 6,515,002 B2 | 2/2003 | Illig |
| 6,534,501 B2 | 3/2003 | Abraham |
| 6,562,840 B1 | 5/2003 | Illig |
| 6,602,874 B2 | 8/2003 | Howard |
| 6,620,767 B1 | 9/2003 | Ducray et al. |
| 6,660,728 B2 | 12/2003 | Scheunemann et al. |
| 6,660,732 B2 | 12/2003 | Betageri et al. |
| 6,683,103 B2 | 1/2004 | Wu et al. |
| 6,689,754 B1 | 2/2004 | Fan |
| 6,734,207 B2 | 5/2004 | Uckun et al. |
| 6,747,057 B2 | 6/2004 | Ruzafa et al. |
| 6,835,745 B2 * | 12/2004 | Coghlan et al. ............... 514/448 |
| 6,858,223 B2 * | 2/2005 | Hafner .......................... 424/434 |
| 6,867,217 B1 | 3/2005 | South |
| 6,881,741 B2 * | 4/2005 | Chan Chun Kong et al. .. 514/91 |
| 6,887,877 B2 | 5/2005 | Kong et al. |
| 6,892,279 B2 * | 5/2005 | Mekhiel ........................ 711/118 |

(Continued)

FOREIGN PATENT DOCUMENTS

AU  2003204708  7/2003

(Continued)

OTHER PUBLICATIONS

Gol'dfarb et al., Zhurnal Obshchei Khimii, vol. 29, 1959, pp. 3636-4.*
NIH, Flaviviridae definition, printed Mar. 12, 2009 from NIH website.*
NIH, Heptatitis C Virius deifnition, printed Mar. 12, 2009 from NIH website.*
David McKinnon et al., "The Conversions of Izothiazolium Salts into Thiophenecarboxylic Ester Derivatives", *Can. J. Chem.*, 1984, vol. 62, pp. 1580-1584.
Pilar Goya et al., Synthesis of 4-Oxo- 3,4-dihydro-1*H*-thieno [3,4-c] and thieno [3,2-c][1,2,6]thiadiazine 2,2-Dioxides, *Synthesis*, Apr. 1989, pp. 280-282.

(Continued)

*Primary Examiner* — Susannah Chung
(74) *Attorney, Agent, or Firm* — Honigman, Miller, Schwartz and Cohn; Kathryn D. Soulier; Jonathan P. O'Brien

(57) ABSTRACT

The present invention provides novel compounds represented by formula I:

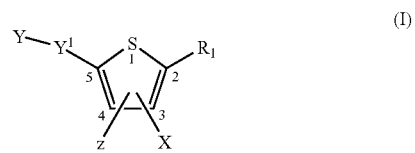

or pharmaceutically acceptable salts thereof useful for treating flaviviridae viral infection.

61 Claims, No Drawings

U.S. PATENT DOCUMENTS

| | | |
|---|---|---|
| 6,294,276 B1 | 8/2005 | Sorenson et al. |
| 6,924,276 B2 | 8/2005 | Sorenson |
| 6,960,594 B2 * | 11/2005 | Labrecque et al. ............ 514/275 |
| 6,982,279 B2 | 1/2006 | Peukert |
| 6,984,737 B2 * | 1/2006 | Hartmann et al. ............... 549/68 |
| 7,015,223 B1 | 3/2006 | South |
| 7,019,027 B2 * | 3/2006 | Linden et al. .................. 514/447 |
| 7,084,170 B2 * | 8/2006 | Grossman et al. ............ 514/445 |
| 7,084,171 B2 * | 8/2006 | Grainger et al. .............. 514/445 |
| 7,098,240 B2 * | 8/2006 | Griffiths et al. ................ 514/447 |
| 7,098,241 B2 * | 8/2006 | Grossmann et al. .......... 514/448 |
| 7,101,878 B1 | 9/2006 | Anderson |
| 7,105,565 B2 | 9/2006 | Walter |
| 7,125,896 B2 | 10/2006 | Faull |
| 7,135,550 B2 | 11/2006 | Come |
| 7,138,530 B2 * | 11/2006 | Subasinghe et al. ............ 549/65 |
| 7,166,639 B2 * | 1/2007 | Wan et al. ...................... 514/447 |
| 7,157,585 B2 | 2/2007 | Lively |
| 7,179,836 B2 * | 2/2007 | Adams et al. .................. 514/447 |
| 7,220,777 B2 | 5/2007 | Armstrong |
| 7,285,557 B2 | 10/2007 | Carpenter |
| 7,329,670 B1 | 2/2008 | Dumas |
| 7,338,978 B2 | 3/2008 | Lahm |
| 7,358,376 B2 | 4/2008 | Baxter |
| 7,402,608 B2 | 7/2008 | Kong |
| 7,470,701 B2 | 12/2008 | Jefferson |
| 7,560,564 B2 | 7/2009 | Annis |
| 7,569,600 B2 * | 8/2009 | Denis et al. .................... 514/447 |
| 2003/0004172 A1 | 1/2003 | Harter et al. |
| 2003/0194375 A1 | 10/2003 | Weaver et al. |
| 2004/0023961 A1 | 2/2004 | Dumas |
| 2004/0087577 A1 | 5/2004 | Pratt |
| 2004/0097492 A1 | 5/2004 | Pratt |
| 2004/0162285 A1 | 8/2004 | Pratt |
| 2004/0167123 A1 | 8/2004 | Pratt |
| 2005/0009804 A1 | 1/2005 | Chan Chun Kong et al. |
| 2005/0075331 A1 | 4/2005 | Pratt |
| 2005/0119332 A1 | 6/2005 | Jeppesen |
| 2005/0256121 A1 | 11/2005 | Jefferson |
| 2006/0142347 A1 | 6/2006 | Kong |
| 2006/0199844 A1 | 9/2006 | Buchstaller et al. |
| 2006/0205748 A1 | 9/2006 | Annis |
| 2007/0099929 A1 | 5/2007 | Thede |
| 2007/0123516 A1 | 5/2007 | Jung |
| 2007/0244120 A1 | 10/2007 | Dumas et al. |
| 2008/0269481 A1 | 10/2008 | Kong |

FOREIGN PATENT DOCUMENTS

| | | |
|---|---|---|
| CA | 2137976 | 6/1995 |
| CA | 2 496 680 A1 | 11/1998 |
| CA | 2 385 972 A1 | 4/2001 |
| CN | 1401732 | 3/2003 |
| DD | 146952 | 3/1981 |
| DD | 263055 | 12/1998 |
| DE | 1 055 077 | 4/1959 |
| DE | 1055007 | 4/1959 |
| DE | 1083830 | 6/1960 |
| DE | 199 03 398 A1 | 8/2000 |
| DE | 199 20 247 A1 | 11/2000 |
| EP | 0 269 295 | 6/1988 |
| EP | 603755 | 6/1994 |
| EP | 0603755 | 6/1994 |
| FR | 2689129 | 10/1993 |
| GB | 2114566 | 8/1983 |
| JP | 57116077 | 7/1982 |
| JP | 63-126884 | 5/1988 |
| JP | 63126884 | 5/1988 |
| JP | 63-141984 A | 6/1988 |
| JP | 05117263 | 5/1993 |
| JP | 06025221 | 2/1994 |
| JP | 7-48360 | 2/1995 |
| JP | 2001-010957 | 1/2001 |
| JP | 2001354658 | 12/2001 |
| JP | 2003073357 | 3/2003 |
| WO | WO 9705130 | 2/1997 |
| WO | WO 9705131 | 2/1997 |
| WO | 98/49162 A1 | 11/1998 |
| WO | WO 98/52558 | 11/1998 |
| WO | WO 98/52559 A1 | 11/1998 |
| WO | WO 9911647 | 3/1999 |
| WO | WO 99 32106 | 7/1999 |
| WO | WO 9932110 | 7/1999 |
| WO | WO 9932111 | 7/1999 |
| WO | WO 9932455 | 7/1999 |
| WO | WO 9932477 | 7/1999 |
| WO | WO 9940088 | 8/1999 |
| WO | WO 9946237 | 9/1999 |
| WO | WO 9946244 | 9/1999 |
| WO | WO 9952896 | 10/1999 |
| WO | WO 00/20358 A2 | 4/2000 |
| WO | WO 0047194 | 8/2000 |
| WO | WO 0047578 | 8/2000 |
| WO | WO 0055152 | 9/2000 |
| WO | 00/66094 | 11/2000 |
| WO | WO 0144226 | 6/2001 |
| WO | WO 0149289 | 7/2001 |
| WO | WO 0158890 | 8/2001 |
| WO | WO 0181345 | 11/2001 |
| WO | WO 02/28353 | 4/2002 |
| WO | WO 02/38542 A1 | 5/2002 |
| WO | WO 02/100851 | 12/2002 |
| WO | WO 03028731 | 4/2003 |
| WO | WO 03037886 | 5/2003 |
| WO | WO 03 093290 | 11/2003 |
| WO | WO2004041818 | 5/2004 |
| WO | WO 2004/052879 A1 | 6/2004 |
| WO | WO 2005/063734 A2 | 7/2005 |
| WO | 2006/072348 A2 | 7/2006 |
| WO | WO 2006/072347 | 7/2006 |

OTHER PUBLICATIONS

Bo Sung Kim et al., "Reactions of Thiaroylketene S,N-Acetals with 1,3-Dicarbonyl Compounds in the Presence of Mercury (II) Acetate: A General Route to 2-Acyl-and 2 Aroyl-3-(alkylamino)-5-arylthiopenes and 2-(Ethoxycarbonyl)-3-(methylamino)-5-arylthiopenes", *J. Org. Chem.*, 1998, vol. 63, pp. 6086-6087.

Bo Sung et al., "A Facile and Convenient Synthesis of 3-Alkylamino-5-arylthiopenes with a Variety of Substituents at C-2 and Studies of Reaction Mechanisms", *J. Org. Chem*, 2000, vol. 65, pp. 3690-3699.

Ya. L. Gol'dfarb et al., "Action of Alkali Metals in Liquid Ammonia on Substituted Thiophenes. Communication 9. Preparation of 5-Mercapto-4-Ketoalkanoic Acids by Reductive Cleavage of 4-Acetylamino- and 4-Nitrothiophene-2-Carboxylic Acids", *Izv. Akad. Nauk* SSSR. *Ser. Khim.*, 1984, vol. 10, pp. 2136-2139.

J. R. Desai et al.; J. Ind. Chem. Soc., vol. 74, 1997, p. 160, "Thieno[3,2-d]pyrimidines—Part-I: Preparation and Antimicrobial Activity of 3-N-Substituted-tioureido-2-methyl-6-phenylthieno[3,2-d]pyrimidin-4(3H)-ones", ISR ref. XP002220249.

E. Marchand, G. Morel, Bull. Soc. Chim. Fr. vol. 133, No. 9, 1996, p. 903-912, "Alpha-Thioxothioamides Reactions de cycloaddition [4+2] avec l'acetylenedicarboxylate de dimethyle et le propiolate de methyle", ISR ref. XP002220251.

Patent Abstract for Japanese Patent Publication No. 2001-010957, Jan. 16, 2001.

W. Kantlehner et al., J. Prakt. Chem., vol. 338, 1996, p. 403-413; "Orthoamide, IL. Umsetzungen von Orthoamid-Derivaten mit Schwefel und Selen, Synthesen von 1,3-Thiazol- und 1,3-Selenazolderivaten" ISR ref. XP002220245.

S. Vega et al., Eur. J. Med. Chem. vol. 23, No. 4, 1988, p. 329-334; "Thiophene Isosteres: Synthesis and Pharmacological Study of 3-(azol-l-yl)thieno isothiazole-1,1-dioxides" ISR ref. XP002220246.

R.A. Smith et al., Bioorg. Med. Chem. Lett. vol. 11, No. 20, 2001, p. 2775-2778; "Discovery of Heterocyclic Ureas as a New Class of Raf Kinase Inhibitors: Identification of a Second Generation Lead by a Combinatorial Chemistry Approach", ISR ref. XP001118699.

A.M. Redman et al., Bioorg. Med. Chem. Lett., vol. 11, 2001, p. 9-12; "P38 Kinase Inhibitors for the Treatment of Arthritis and Osteoporosis: Thienyl, Furyl, and Pyrrolyl Ureas", ISR ref. XP004225311.

D.J. Lee et al., Chemical Abstracts Service, Columbus, OH, U.S., "Novel Synthesis of 5,6-Dihydro-4H-thieno[3,2-b]pyrrol-5-ones via the Rhodium(II)-Mediated Wolff Rearrangement of 3-(2-Thienyl)-3-oxo-2-diazopropanoates"; Database accession No. 2002:151873, ISR ref. XP002220252.

M. Sugiyama et al., Chem. Pharm. Bull. vol. 37, No. 8, 1989, p. 2091-2102; "Condensed Thienopyrimidines. I. Synthesis and Gastric Antisecretory Activity of 2,3-Dihydro-5H-oxazolothienopyrimidin-5-one Derivatives", ISR ref. XP001118351.

J.C. Lancelot et al., J. Heterocycl. Chem. vol. 33, No. 2, 1996, p. 427-430; "A Facile Synthesis of New Beta-Lactams", ISR ref. XP002220247.

J.R. Desai et al., J. Inst. Chemists (India) vol. 67, 1995, p. 136-137, "Thieno[3,2-d]pyrimidines-Part—II: Preparation and Antimicrobial Activity of 2-methyl-3-N-Arylsulphonamido-6-Phenylthieno[3,2-d]Pyrimidin-4(3H)-ones", ISR ref. XP002220249.

International Search Report for Application No. PCT/CA02/00876 mailed Nov. 26, 2002.

Written Opinion and International Search Report for International Application No. PCT/CA2006/000786.

International Search Report for International Application No. PCT/CA2007/002064.

CA 139:365176, Roberts et al., "Preparation of Nucleoside Derivatives for Treating Hepatitis C Virus Infection.", 2003.

CA 142:253391, Hadziyannis et al., "Emerging Treatments in Chronic Hepatitis B.", 2004.

CA 129: 285628, Sostegni et al., "Sequential Versus Concomitant Administration of Ribavirin and Interferon alpha-3 in Patients whit Chronic Hepatitis C not Responding to Interferon Alone.", 1998.

CA 2007:977620, Vicari et al., "Safety, Pharmacokietics and Immune Effects in Normal Volunteers of CPG 10101(ACTILON).".

Office Action issued Mar. 29, 2006 in U.S. Appl. No. 10/730,272.

Office Action issued Aug. 24 2006 in U.S. Appl. No. 10/730,272.

Office Action issued Mar. 14, 2007 in U.S. Appl. No. 10/730,272.

Notice of Allowance issued Sep. 28, 2007 in U.S. Appl. No. 10/730,272.

Office Action issued May 2, 2008 in U.S. Appl. No. 11/433,749.

Registration forms of Compound from Maybridge plc. (31 pages), Feb. 8, 2001.

Office Action for U.S. Appl. No. 11/433,749 dated Sep. 8, 2008.

Laval Chan, et al., "Discovery of thiophene-2-carboxylic acids as potent inhibitors of HCV NS5B polymerase and HCV subgenomic RNA replication. Part 1: Sulfonamides", Bioorganic & Medicinal Chemistry Letters 14 (2004) pp. 5333-5337.

Laval Chan, et al., "Discovery of thiophene-2-carboxylic acids as potent inhibitors of HCV NS5B polymerase and HCV subgenomic RNA replication. Part 2: Tertiary amides", Bioorganic & Medicinal Chemistry Letters 14 (2004) pp. 797-800.

Constantin G. Yannopoulos, et al., "HCV NS5B polymerase-bound confirmation of a soluble inhibitor by 2D transferred NOESY", Bioorganic & Medicinal Chemistry Letters 14 (2004) pp. 5333-5337.

Laval Chan, et al., "Discovery of a novel class of HCV NS5B RNA dependent RNA polymerase inhibitors: SAR studies and activity in the replicon cell line", Poster submitted at 16th ICAR-Savannah, Apr. 2003, (14 pages).

Carl Poisson, "Discovery and Structure-Activity Relationship of Trisubstituted Thiophene Derivatives as Potent Inhibitors of Hepatitis C Virus Replication," 15th Québec-Ontario Minisymposium in Synthetic and Bioorganic Chemistry (QOMSBOC), Ottawa, ON, Nov. 5-7, 2004.

N. Nguyen-Ba et al., "Discovery and SAR Studies of a Novel Class of HCV NS5B RNA-dependent RNA Polymerase Inhibitors," The 16th International Conference on Antiviral Research (ICAR) convened on Apr. 27-May 1, 2003.

Zhurnal Organicheskoi Khimii (1970), 6(5), 1091-1100.

Ping Liu, et al., "Synthesis and mesogenic properties of a novel family of oligothiophene derivatives", Liquid Crystals, 2001, vol. 28, No. 4, pp. 581-589.

Translation of "Notice of Grounds for Rejection" for Japanese Patent Application No. 2003-503618 dated Oct. 7, 2008.

Abstract for Japanese Patent Application No. 2004-513163 published Apr. 30, 2004.

B. P. Fabrichnyi, et al., "Synthesis of Aliphatic amino acids from thiophene derivatives", Zhurnal Obshchei Khimii, vol. 6, No. 5, pp. 1091-1100 May 1970 (English Translation).

Bartroli, J. et al. "New Azole Antifungals. 2. Synthesis and Antifungal Activity of Heterocyclecarboxamide Derivatives of 3-Amino-2-aryl-1-azolyl-2-butanol" Journal of Medicinal Chemistry (1998), 41(11), 1855-1868.

Destevens, G.et al. "Heterocyclic Disulphonamides and Their Diuretic Properties"Journal of Medicinal & Pharmaceutical Chemistry (1959), 1, 565-76.

Doat, E.G. et al. "3,5-Dilithiated Tertiary Thiophene 2-Carboxamide. Regoiselective Entries into Diversely Substituted Thiophenes" Tetrahedron Letters (1985), 26(9), 1149-52.

Fabrichnyi, B.P. et al., "The Beckmann Rearrangement of Oximes of Thiophenocycloalkanones" Zhurnal Obshchei Khimii (1961), 31, 1244-53.

Fan, et al. Zhongguo Yiyao Gongye Zazhi Chinese Journal of Pharmaceuticals (2002), 33(8), 365-366.

Fan, et al. Abstract "Synthesis of lornoxicam" 2003:267476 HCAPLUS, (2002).

Fedorova, I.N., et al. "Synthesis and Antiflammatory Activity of Derivatives of 2-Aminothiophene-5-Acetic Acids" Translated from Khimiko-Farmatsevticheskii Zhurnal (1986), 20(1), 39-45.

Gol'Dfarb, Y.L. et al. "Reductive Acetylation of Nitrocarboxylic Acids of the Thiophene and Furan Series or their Esters" Translated from Khimiya Geterotsiklicheskikh Soedinenii (1983), (12), 1626-9.

Gol'Dfarb,Y.L. et al. "Synthesis of Aliphatic Amino Acids from Thiophene Derivatives. XV. Preparation of e-Aminodicarboxylic Acids" Translated from Zhurnal Organicheskoi Khimii (1975), 11(11), 2400-7.

IiNO, M. et al. "Rational Design and Evaluation of New Lead Compound Structures for Selective βARK1 Inhibitors" Journal of Medicinal Chemistry (2002), 45(11), 2150-2159.

Jones, D.H. et al. "Amidines and Guanidines Related to Congocidin . . ." Journal of the Chemical Society [Section] C: Organic (1968), (5), 550-4.

Kim, K. et al. "Thioaroylketene S,N-Acetals: Versatile Intermediates for the Synthesis of 3-Alkylamino-5-Arylthiophenes with a Variety of Functional Group at C-2" Phosphorus, Sulfur and Silicon and the Related Elements (1999), 153-154, 393-394.

Kohara, T. et al. "Synthesis of Thieno[2,3-b][1,5]benzoxazepine Derivatives" Journal of Heterocyclic Chemistry (2002), 39(1), 163-171.

Lee, D. G. et al. "Novel Synthesis of 5,6-Dihydro-4H-thieno[3,2-b]pyrrol-5-ones via the Rhodium(II)-Mediated Wolff Rearrangement of . . ."Organic Letters (2002), 4(6), 873-876.

Lee, J.S. "Reactions of thiobenzoylketene S,N-acetals with silyl enol ethers of cyclic ketones in the presence of desilylating reagents: . . ." Journal of the Chemical Society, Perkin Transactions 1 (2001), (21), 2774-2780.

Litvinov, "Hetaryladamantanes. 2. 3-(1-Adamantyl)-3-chloropropenal: its structure and synthesis of adamantyl-substituted nitrogen-containing heterocycles from it" Translated from Izvestiya Akademii Nauk SSSR, Seriya Khimicheskaya (1985), (8), 1858-63.

Migianu, E. et al. "Synthesis of new Thieno[b]azepinediones from a-Methylene Ketones" Synthesis (2002), (8), 1096-1100.

Migianu International Electronic Conferences on Synthetic Organic Chemistry, 5[th],6th, Sep. 1-30, 2001 and 2002 [and] 7th, 8th, Nov. 1-30, 2003 and 2004, 1302-1307.

Rarey, M., et al. "Similarity searching in large combinatorial chemistry spaces" Journal of Computer-Aided Molecular Design (2001), 15(6), 497-520.

Rudolph, M.J. et al. "Design and Synthesis of 4,5-Disubstituted-thiophene-2-amidines as Potent Urokinase Inhibitors" Bioorganic & Medicinal Chemistry Letters (2002), 12(3), 491-495.

Saito, K. et al. "A One-Step Synthesis of Thiophene Derivatives" Synthesis (1982), (12), 1056-9.

Schatz, J. "Product Class 10: Thiophenes, Thiophene 1,1-Dioxides, and Thiophene 1-Oxides" Science of Synthesis (2002), 9, 287-422.

Tronchet, J.M.J. et al. Helvetica Chimica Acta (1975), 58(6), 1735-8.

Tronchet, J.M.J., et al. Abstract, "C-glycosylic derivatives. XXVI New Routes to isoxazolic and thiophenic C-nucleosides" Helvetica Chimica Pharm. 1976:44578 HCAPLUS (1975).

Wu, C., et al. "Selective Alkylation/Acylation of DI- or Trianions: Expeditious Derivatization of Endothelin Antagonists" Synthetic Communications (2002), 32(10), 1615-1624.

WPI search results for U.S. Patent 6,602,874.

Fukunaga, et al., Abstract WO 2001081345, "Preparation of arylcarbonylaminopyrazolopyridine derivatives as glycogen synthase kinase 3β inhibitors" 2001:798223 HCAPLUS.

Seio, et al. Abstract WO 9911647 "Preparation of fused thiophene compounds as antipsychotics" 1999-184258 HCAPLUS.

Uehata, et al. Abstract JP 2003073357 "Preparation of amides as Rho kinase inhibitors" 2003:194556 HCAPLUS.

Liu, et al. Abstract CN 1401732 "Oligomer liquid crystal compound having thiophene skeleton and its manufacture" 2004:557354 HCAPLUS.

Gewald, et al. Abstract DD 146952 "Substituted 3-amino-4-cyano-5-phenylthiophenes" 1981:550416 HCAPLUS.

Gewald, et al. Abstract DD 263055 "Preparation of substituted 3-amino-5-phenylthiophenes" 1989:515019 HCAPLUS.

Rault, et al. Abstract FR 2689129 "Preparation of 3-mercapto-2-thiophenecarboxylic acid derivatives as intermediates for herbicides" 1995:289967 HCAPLUS.

Ishizaki, et al. Abstract JP 05117263 "Preparation of 3-amino-2-thiophenecarboxylic acid derivatives" 1993:580647 HCAPLUS.

Ishizaki, et al. Abstract JP 06025221 "Preparation of 3-amino-2-thiophenecarboxylic acids" 1994:435316 HCAPLUS.

Sato, et al. Abstract JP 2001354658 "Preparation of hydroxyformamidines and their use as 20-hydroxyeicosatetraenoic acid (20-HETE) formation inhibitors for treatment of kidney, cerebrovascular, and circulation disorders" 2001:930205 HCAPLUS.

Abstract JP 57116077 "Thieno[3,2-b]pyridinecarboxylic acid derivatives" 1982:616153 HCAPLUS.

Chan, L. et al. "Discovery of thiophene-2-carboxylic acids as potent inhibitors of HCV NS5B polymerase and HCV subgenomic RNA replication. Part 1: Sulfonamides" Bioorganic & Medicinal Chemistry Letters 14:793-796 (2004).

Chan, L. et al. "Identification of N,N-Disubstituted Phenylalanines as a Novel Class of Inhibitors of Hepatitis C NS5B Polymerase" J. Med. Chem. 46:1283-1285 (2003).

Supplementary European Search Report published Feb. 9, 2010 in Publication No. EP1879879 A4; Application No. EP2006000741500 filed May 15, 2006; Priority International Application No. PCT/CA2006/000786, International Filing Date: May 15, 2006; Publication No. WO2006/119646, Publication Date: Nov. 16, 2006.

Supplementary European Search Report published Feb. 11, 2010 in Publication No. EP 2104674 A4; Application No. EP 2007000845534 filed Nov. 15, 2007; Priority International Application No. PCT/CA2007/002064, International Filing Date: Nov. 15, 2007; Publication No. WO 2008058393, Publication Date: May 22, 2008.

Notice of Allowance issued Jun. 16, 2008 in U.S. Appl. No. 11/042,442.

Notice of Allowance issued Mar. 17, 2008 in U.S. Appl. No. 11/042,442.

Office Action issued Apr. 2, 2007 in U.S. Appl. No. 11/042,442.

Office Action issued Sep. 18, 2007 in U.S. Appl. No. 11/042,442.

Office Action issued Sep. 8, 2008 in U.S. Appl. No. 11/433,749.

Japanese Abstract of Application JP2004513163; Published Apr. 30, 2004; Application No. JP2002200541078, filed Nov. 6, 2001 obtained from www.delphion.com.

Desai, J.R., et al., "Thieno[3,2-d]pyrimidines—Part—I : Preparation and antimicrobial activity of 3-N-Substituted-thioureido-2-methyl-6-phenylthieno[3,2-d]pyrimidin-4(3H)-ones"; Journal Indian Chem. Soc., 74:160 (Feb. 1997), ISR ref. XP002220259.

International Search Report for International Application No. PCT/CA2003/01912, date mailed Jun. 4, 2004.

Iino, M., "Rational Design and Evaluation of New Lead Compound Structures for Selective βARK1 Inhibitors", J. Med. Chem., 45 (2002), pp. 2150-2159.

Jones, D.H., "Amidines and Guanidines Related to Congocidin. Part IV. Thiophen, Pyridine, and Benzene Analogues", J. Chem. Soc. (1968), pp. 550-554.

Andersen, H., "Discovery and SAR of a Novel Selctive and Orally Bioavailable Nonpeptide . . .", Journal Med. Chem., 45 (20), (2002), pp. 4443-4459.

Fedorova, I. "Synthesis and Anti inflammatory Activity of Derivatives of 2-Aminothiophene-5-acetic Acids", Khimiko-farmatsevticheskii Zhurnal, 20 (19), (1986), pp. 39-45.

Hadziyannis, S., "Emerging treatments in chronic hepatitis B", Expert Opinion Emerg. Drugs, 9 (2), (2004), pp. 207-221.

Hromatka, O., "Synthesis of amino-trifluoromethyl thiophenecarboxylic acid ethyl esters", Monatshefte für Chemie, 105 (1974), pp. 127-134.

Compound Registration Form from Maybridge plc., Registration Date Sep. 6, 2000, BCH No. BCH-18912 (1 page).

Compound Registration Forms from Maybridge plc., Registration Date Apr. 4, 2001, BCH Nos. BCH-20510, BCH-20511, BCH-20512, BCH-20513 (4 pages).

Compound Registration Forms from Maybridge plc., Registration Date Apr. 2, 2002, BCH Nos. BCH-24527, BCH-24541 (2 pages).

Sostegni, R., "Sequential Versus Concomitant Administration of Ribavirin and Interferon Alfa-n3 . . .", Hepatology, 28 (2), (1998), pp. 341-346.

Vicari, A., "Safety, pharmacokinetics and immune effects in normal volunteers of CPG 10101 . . .", Antiviral Therapy, 12 (5), (2007), pp. 741-751.

* cited by examiner

COMPOUNDS AND METHODS FOR THE TREATMENT OR PREVENTION OF FLAVIVIRUS INFECTIONS

This application is a continuation of U.S. application Ser. No. 10/166,031, filed Jun. 11, 2002 now U.S. Pat. No. 6,881,741.

FIELD OF THE INVENTION

The present invention relates to novel compounds and a method for the treatment or prevention of Flavivirus infections using novel compounds.

BACKGROUND OF THE INVENTION

Hepatitis is a disease occurring throughout the world. It is generally of viral nature, although there are other causes known. Viral hepatitis is by far the most common form of hepatitis. Nearly 750,000 Americans are affected by hepatitis each year, and out of those, more than 150,000 are infected with the hepatitis C virus ("HCV").

HCV is a positive-stranded RNA virus belonging to the Flaviviridae family and has closest relationship to the pestiviruses that include hog cholera virus and bovine viral diarrhea virus (BVDV). HCV is believed to replicate through the production of a complementary negative-strand RNA template. Due to the lack of efficient culture replication system for the virus, HCV particles were isolated from pooled human plasma and shown, by electron microscopy, to have a diameter of about 50-60 nm. The HCV genome is a single-stranded, positive-sense RNA of about 9,600 bp coding for a polyprotein of 3009-3030 amino-acids, which is cleaved co and post-translationally by cellular and two viral proteinases into mature viral proteins (core, E1, E2, p7, NS2, NS3, NS4A, NS4B, NS5A, NS5B). It is believed that the structural proteins, E1 and E2, the major glycoproteins are embedded into a viral lipid envelope and form stable heterodimers. It is also believed that the structural core protein interacts with the viral RNA genome to form the nucleocapsid. The nonstructural proteins designated NS2 to NS5 include proteins with enzymatic functions involved in virus replication and protein processing including a polymerase, protease and helicase.

The main source of contamination with HCV is blood. The magnitude of the HCV infection as a health problem is illustrated by the prevalence among high-risk groups. For example, 60% to 90% of hemophiliacs and more than 80% of intravenous drug abusers in western countries are chronically infected with HCV. For intravenous drug abusers, the prevalence varies from about 28% to 70% depending on the population studied. The proportion of new HCV infections associated with post-transfusion has been markedly reduced lately due to advances in diagnostic tools used to screen blood donors.

The only treatment currently available for HCV infection is interferon-α (IFN-α). However, according to different clinical studies, only 70% of treated patients normalize alanine aminotransferase (ALT) levels in the serum and after discontinuation of IFN, 35% to 45% of these responders relapse. In general, only 20% to 25% of patients have long-term responses to IFN. Clinical studies have shown that combination treatment with IFN and ribavirin (RIBA) results in a superior clinical response than IFN alone. Different genotypes of HCV respond differently to IFN therapy, genotype 1b is more resistant to IFN therapy than type 2 and 3.

There is therefore a great need for the development of anti-viral agents.

SUMMARY OF THE INVENTION

In one aspect, the present invention provides novel compounds represented by formula I:

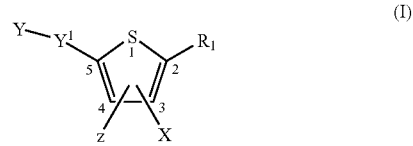

or pharmaceutically acceptable salts thereof;
wherein,
X is chosen from:

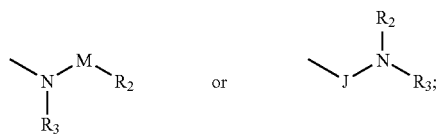

wherein,
M is chosen from:

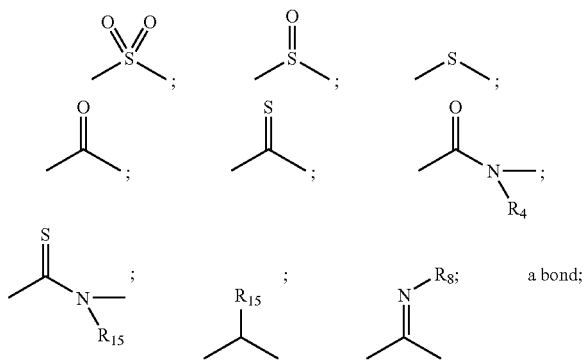

wherein,
$R_4$ is $C_{1-6}$ alkyl;
$R_8$ is chosen from H, $C_{1-12}$ alkyl, $C_{2-12}$ alkenyl, $C_{2-12}$ alkynyl, $C_{6-14}$ aryl, $C_{3-12}$ heterocycle, $C_{3-12}$ heteroaralkyl, $C_{6-16}$ aralkyl; and
$R_{15}$ is chosen from H or $C_{1-6}$ alkyl;
J is chosen from:

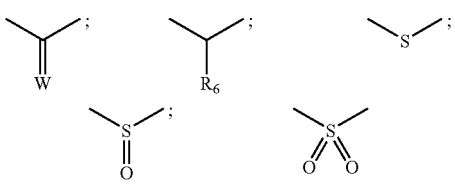

wherein W is chosen from O, S or $NR_7$,
wherein $R_7$ is chosen from H, $C_{1-12}$ alkyl, $C_{2-12}$ alkenyl, $C_{2-12}$ alkynyl, $C_{6-14}$ aryl, $C_{3-12}$ heterocycle, $C_{3-12}$ heteroaralkyl, $C_{6-16}$ aralkyl;

and $R_6$ is chosen from H. $C_{1-12}$ alkyl, $C_{6-14}$ aryl or $C_{6-16}$ aralkyl;

$Y^1$ is chosen from a bond, $C_{1-6}$ alkyl, $C_{2-6}$ alkenyl or $C_{2-6}$ alkynyl;

Y is chosen from $COOR_{16}$, $COCOOR_5$, $P(O)OR_aOR_b$, $S(O)OR_5$, $S(O)_2OR_5$, tetrazole, $CON(R_9)CH(R_5)COOR_5$, $CONR_{10}R_{11}$, $CON(R_9)$—$SO_2$—$R_5$, $CONR_9OH$ or halogen, wherein $R_9$, $R_5$, $R_{10}$ and $R_{11}$ are each independently chosen from H, $C_{1-12}$ alkyl, $C_{2-12}$ alkenyl, $C_{2-12}$ alkynyl, $C_{3-12}$ heterocycle, $C_{3-18}$ heteroaralkyl, $C_{6-18}$ aralkyl;

or $R_{10}$ and $R_{11}$ are taken together with the nitrogen to form a 3 to 10 membered heterocycle;

$R_a$ and $R_b$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl and $C_{6-18}$ aralkyl;

or $R_a$ and $R_b$ are taken together with the oxygens to form a 5 to 10 membered heterocycle;

$R_{16}$ is chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl and $C_{6-18}$ aralkyl; provided that $R_{16}$ is other than methyl or ethyl;

$R_1$ is chosen from $C_{2-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl or $C_{6-18}$ aralkyl;

$R_2$ is chosen from $C_{2-12}$ alkyl, $C_{2-12}$ alkynyl, $C_{6-14}$ aryl, $C_{3-12}$ heterocycle, $C_{3-18}$ heteroaralkyl, or $C_{6-18}$ aralkyl;

$R_3$ is chosen from H, $C_{1-12}$ alkyl, $C_{2-12}$ alkenyl, $C_{2-12}$ alkynyl, $C_{6-14}$ aryl, $C_{3-12}$-heterocycle, $C_{3-18}$ heteroaralkyl or $C_{6-18}$ aralkyl;

Z is chosen from H, halogen, $C_{1-6}$ alkyl;

with the proviso that:
i) when X is 4-Chloro-2,6-dimethyl-benzenesulfonamide and, $R_1$ is phenyl, and $R_3$ is H, and $Y^1$ is a bond, then Y is other than $CONH_2$; compound #580
ii) when X is Toluene-4-sulfonamide and $R_1$ is 4-chlorophenyl, and $R_3$ is H, and $Y^1$ is a bond, then Y is other than $CONH_2$; compound #563
iii) when X is Toluene-4-sulfonamide and $R_1$ is 4-fluorophenyl, and $R_3$ is H, and $Y^1$ is a bond, then Y is other than $CONH_2$; compound #564
iv) when X is Toluene-4-sulfonamide and $R_1$ is 4-methoxyphenyl, and $R_3$ is H, and $Y^1$ is a bond, then Y is other than $CONH_2$; compound #565
v) when X is Benzamide and $R_1$ phenyl $Y^1$ is a bond and Y is COOH then $R_3$ is other than hydrogen.

The compounds of the present invention are useful in therapy, particularly as antivirals.

In another aspect, there is provided a method of treating viral infections in a subject in need of such treatment comprising administering to the subject a therapeutically effective amount of a compound of formula (I) or composition of the invention.

In still another aspect, there is provided a method of treating viral infections in a subject in need of such treatment comprising administering to the subject a combination comprising at least one compound of formula (I) and at least one further therapeutic agent.

In another aspect, there is provided a pharmaceutical formulation comprising the compound of the invention in combination with a pharmaceutically acceptable carrier or excipient.

Another aspect of the invention is the use of a compound according to formula (I), for the manufacture of a medicament for the treatment of viral infections.

In another aspect, there is provided a method for inhibiting or reducing the activity of viral polymerase in a host comprising administering a therapeutically effective amount of a compound of formula (I).

DETAILED DESCRIPTION OF THE INVENTION

In one embodiment, compounds of the present invention comprise those wherein the following embodiments are present, either independently or in combination.

In one embodiment, the present invention provides novel compounds of formula (Ia):

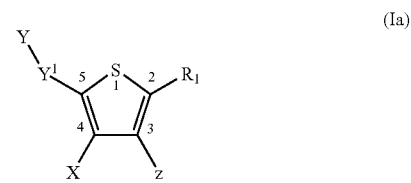

or pharmaceutically acceptable salts thereof;
wherein,
X is chosen from:

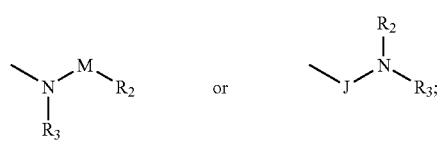

wherein,
M is chosen from:

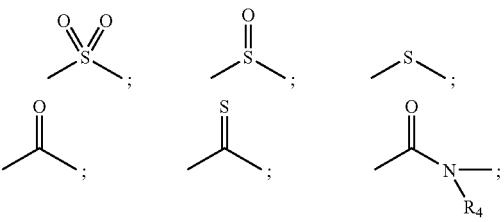

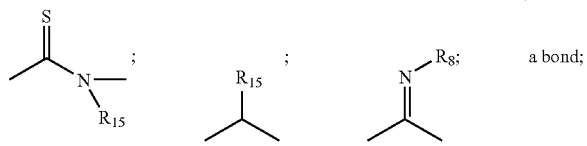

wherein,
$R_4$ is $C_{1-6}$ alkyl;
$R_8$ is chosen from H, $C_{1-12}$ alkyl, $C_{2-12}$ alkenyl, $C_{2-12}$ alkynyl, $C_{6-14}$ aryl, $C_{3-12}$ heterocycle, $C_{3-12}$ heteroaralkyl, $C_{6-16}$ aralkyl; and
$R_{15}$ is chosen from H or $C_{1-6}$ alkyl;
J is chosen from:

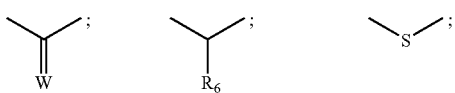

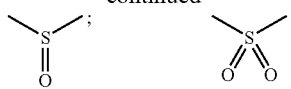

wherein W is chosen from O, S or $NR_7$, wherein $R_7$ is chosen from H, $C_{1-12}$ alkyl, $C_{2-12}$ alkenyl, $C_{2-12}$ alkynyl, $C_{6-14}$ aryl, $C_{3-12}$ heterocycle, $C_{3-12}$ heteroaralkyl, $C_{6-16}$ aralkyl;

and $R_6$ is chosen from H, $C_{1-12}$ alkyl, $C_{6-14}$ aryl or $C_{6-16}$ aralkyl;

$Y^1$ is chosen from a bond, $C_{1-6}$ alkyl, $C_{2-6}$ alkenyl or $C_{2-6}$ alkynyl;

Y is chosen from $COOR_{16}$, $COCOOR_5$, $P(O)OR_aOR_b$, $S(O)OR_5$, $S(O)_2OR_5$, tetrazole, $CON(R_9)CH(R_5)COOR_5$ $CONR_{10}R_{11}$, $CON(R_9)$—$SO_2$—$R_5$, $CONR_9OH$ or halogen, wherein $R_9$, $R_5$, $R_{10}$ and $R_{11}$ are each independently chosen from H, $C_{1-12}$ alkyl, $C_{2-12}$ alkenyl, $C_{2-12}$ alkynyl, $C_{3-12}$ heterocycle, $C_{3-18}$ heteroaralkyl, $C_{6-18}$ aralkyl;

or $R_{10}$ and $R_{11}$ are taken together with the nitrogen to form a 3 to 10 membered heterocycle;

$R_a$ and $R_b$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl and $C_{6-18}$ aralkyl;

or $R_a$ and $R_b$ are taken together with the oxygens to form a 5 to 10 membered heterocycle;

$R_{16}$ is chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl and $C_{6-18}$ aralkyl; provided that $R_{16}$ is other than methyl or ethyl;

$R_1$ is chosen from $C_{2-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl or $C_{6-18}$ aralkyl;

$R_2$ is chosen from $C_{2-12}$ alkyl, $C_{2-12}$ alkynyl, $C_{6-14}$ aryl, $C_{3-12}$ heterocycle, $C_{3-18}$ heteroaralkyl, or $C_{6-18}$ aralkyl;

$R_3$ is chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl or $C_{6-18}$ aralkyl;

Z is chosen from H, halogen, $C_{1-6}$ alkyl;

with the proviso that:

i) when X is 4-Chloro-2,6-dimethyl-benzenesulfonamide and, $R_1$ is phenyl, and $R_3$ is H, and $Y^1$ is a bond, then Y is other than $CONH_2$; compound #580 ii) when X is Toluene-4-sulfonamide and $R_1$ is 4-chlorophenyl, and $R_3$ is H, and $Y^1$ is a bond, then Y is other than $CONH_2$; compound #563 iii) when X is Toluene-4-sulfonamide and $R_1$ is 4-fluorophenyl, and $R_3$ is H, and $Y^1$ is a bond, then Y is other than $CONH_2$; compound #564.

iv) when X is Toluene-4-sulfonamide and $R_1$ is 4-methoxyphenyl, and $R_3$ is H, and $Y^1$ is a bond, then Y is other than $CONH_2$; compound #565 v) when X is Benzamide and $R_1$ is phenyl $Y^1$ is a bond and Y is COOH then $R_3$ is other than hydrogen.

In a further aspect, the present invention provides novel compounds represented by formula II:

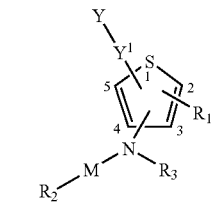

and pharmaceutically acceptable salts thereof,
wherein,
M is chosen from:

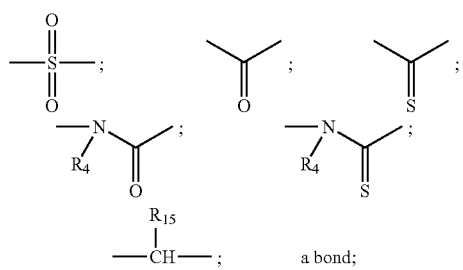

$Y^1$ is chosen from a bond, $C_{1-6}$ alkyl, $C_{2-6}$ alkenyl or C alkynyl;

Y is chosen from $COOR_{16}$, CO—$COOR_5$, $PO_3R_aR_b$, $SO_3R_5$, tetrazole, $CON(R_9)CH(R_5)$—$COOR_5$, CON $R_{10}R_{11}$ or $CONR_9OH$, wherein
each $R_5$ $R_9$, $R_{10}$, $R_{11}$, $R_{16}$ alyl $R_a$, and $R_b$ are independently chosen from H or $C_{1-6}$ alkyl;

$R_1$ is chosen from $C_{1-6}$ alkyl, $C_{2-6}$ alkenyl, $C_{2-6}$ alkynyl, $C_{6-12}$ aryl, $C_{3-10}$ heterocycle, $C_{3-10}$ heteroaralkyl, $C_{6-12}$ aralkyl, or a halogen;

$R_2$ is chosen from $C_{6-12}$ aryl, $C_{3-10}$ heterocycle, $C_{6-12}$ aralkyl or $C_{3-10}$ heteroaralkyl;

$R_3$ is chosen from H or $C_{1-6}$ alkyl; $C_{6-12}$ aralkyl or $C_{3-10}$ heteroaralkyl;

$R_4$ is chosen from H or $C_{1-6}$ alkyl;

$R_{15}$ is chosen from H or $C_{1-6}$ alkyl with the proviso that:

i) when M is

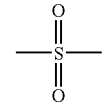

and $R_2$ is 4-chloro-2,5-dimethyl-phenyl, $R_1$ is phenyl, and $R_3$ is H, and $Y^1$ is a bond, then Y is other than $CONH_2$; compound #580 ii) when M is

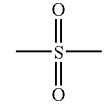

and $R_2$ is 4-methylphenyl, $R_1$ is 4-chloro-phenyl, and $R_3$ is H, and $Y^1$ is a bond, then Y is other than $CONH_2$; compound #563 iii) when M is

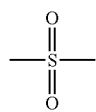

and R$_2$ is 4-methylphenyl, R$_1$ is 4-fluoro-phenyl, and R$_3$ is H, and Y$^1$ is a bond, then Y is other than CONH$_2$; compound #564 iv) when M is

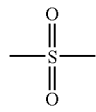

and R$_2$ is 4-methylphenyl, R$_1$ is 4-methoxy-phenyl, and R$_3$ is H, and Y$^1$ is a bond, then Y is other than CONH$_2$; compound #565

In still a further embodiment, the present invention provides novel compounds of formula (IIa):

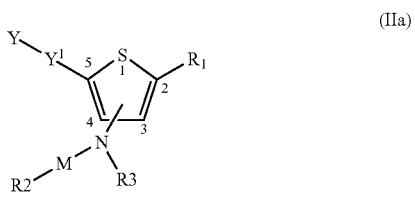

wherein,
M is chosen from:

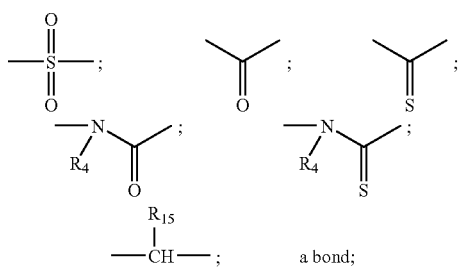

Y$^1$ is chosen from a bond, C$_{1-6}$ alkyl, C$_{2-6}$ alkenyl or C$_{2-6}$ alkynyl;
Y is chosen from COOR$_{16}$, CO—COOR$_5$, PO$_3$R$_a$R$_b$, SO$_3$R$_5$, tetrazole, CON(R$_9$)CH(R$_5$)—COOR$_5$, CON R$_{10}$R$_{11}$, or CONR$_9$OH, wherein
each R$_5$ R$_9$, R$_{10}$, R$_{11}$, R$_{16}$, R$_a$, and R$_b$ are independently chosen from H or C$_{1-6}$ alkyl;
R$_1$ is chosen from C$_{1-6}$ alkyl, C$_{2-6}$ alkenyl, C$_{2-6}$ alkynyl, C$_{6-12}$ aryl, C$_{3-10}$ heterocycle, C$_{3-10}$ heteroaralkyl, C$_{6-12}$ aralkyl, or a halogen;
R$_2$ is chosen from C$_{6-12}$ aryl, C$_{3-10}$ heterocycle, C$_{6-12}$ aralkyl or C$_{3-10}$ heteroaralkyl;
R$_3$ is chosen from H or C$_{1-6}$ alkyl; C$_{6-12}$ aralkyl or C$_{3-10}$ heteroaralkyl;
R$_4$ is chosen from H or C$_{1-6}$ alkyl;
R$_{15}$ is chosen from H or C$_{1-6}$ alkyl;

with the proviso that:
i) when M is

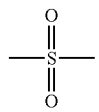

and R$_2$ is 4-chloro-2,5-dimethyl-phenyl, R$_1$ is phenyl, and R$_3$ is H, and Y$^1$ is a bond, then Y is other than CONH$_2$; compound #580 ii) when M is

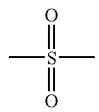

and R$_2$ is 4-methylphenyl, R$_1$ is 4-chloro-phenyl, and R$_3$ is H, and Y$^1$ is a bond, then Y is other than CONH$_2$; compound #563 iii) when M is

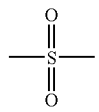

and R$_2$ is 4-methylphenyl, R$_1$ is 4-fluoro-phenyl, and R$_3$ is H, and Y$^1$ is a bond, then Y is other than CONH$_2$; compound #564 iv) when M is

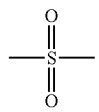

and R$_2$ is 4-methylphenyl, R$_1$ is 4-methoxy-phenyl, and R$_3$ is H, and Y$^1$ is a bond, then Y is other than CONH$_2$; compound #565.

In one embodiment, X is:

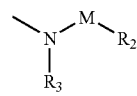

In a further embodiment, X is:

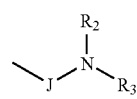

In one embodiment, Z is chosen from H, halogen, C$_{1-6}$ alkyl.

In further embodiments,

Z is H

Z is halogen

Z is fluoride

Z is $C_{1-6}$ alkyl

Z is chosen from methyl, trifluoromethyl, ethyl, propyl, isopropyl, cyclopropyl, butyl, isobutyl, cyclobutyl, pentyl, neopentyl, cyclopentyl, hexyl or cyclohexyl.

In further embodiments;

$R_1$ is chosen from $C_{2-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl or $C_{6-18}$ aralkyl.

$R_1$ is chosen from a $C_{2-12}$ alkyl, $C_{6-14}$ aryl or $C_{3-12}$ heterocycle.

$R_1$ is a $C_{2-12}$ alkyl.

$R_1$ is a $C_{6-14}$ aryl.

$R_1$ is a $C_{3-12}$ heterocycle.

$R_1$ is chosen from t-butyl, isobutyl, allyl, ethynyl, 2-phenylethenyl, isobutenyl, benzyl, phenyl, phenethyl, benzodioxolyl, thienyl, thiophenyl, pyridinyl, isoxazolyl, thiazolyl, pyrazolyl, tetrazolyl, benzofuranyl, indolyl, furanyl, or benzothiophenyl any of which can be optionally substituted by one or more substituent chosen from halogen, nitro, nitroso, $SO_2R_{12}$, $PO_3RcRd$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$-alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido;

wherein $R_{12}$, Rc, Rd, $R_{13}$ and $R_{14}$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, $C_{6-18}$ aralkyl;

or Rc and Rd are taken together with the oxygens to form a 5 to 10 membered heterocycle;

or $R_{13}$ and $R_{14}$ are taken together with the nitrogen to form a 3 to 10 membered heterocycle.

$R_1$ is chosen from thienyl, t-butyl, phenyl or pyridinyl.

$R_1$ is isoxazolyl substituted by at least one methyl.

$R_1$ is pyridinyl.

In one embodiment, $R_1$ is chosen from a $C_{1-6}$ alkyl, $C_{6-12}$ aryl or $C_{3-10}$ heterocycle.

In one embodiment, $R_1$ is chosen from t-butyl, isobutyl, allyl, ethynyl, 2-phenylethenyl, isobutenyl, benzyl, phenyl, phenethyl, benzodioxolyl, thienyl, thiophenyl, pyridinyl, isoxazolyl, thiazolyl, pyrazolyl, tetrazolyl, benzofuranyl, indolyl, furanyl, or benzothiophenyl, any of which can be substituted by at least one substituent chosen from $C_{1-6}$ alkyl, $C_{2-6}$ alkenyl, $C_{2-6}$ alkynyl, $C_{3-10}$ heterocycle, halogen, nitro, $CONR_{13}R_{14}$, $NR_{13}R_{14}$, amidino, guanido, Cyano, $SO_2$— $C_{1-6}$ alkyl, $C(O)OR_{12}$, $C_{1-6}$ alkyloxy, $C_{2-6}$ alkenyloxy, $C_{2-6}$ alkynyloxy, or $C_{6-12}$ aryloxy;

wherein $R_{12}$, $R_{13}$ and $R_{14}$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, $C_{6-18}$ aralkyl;

or $R_{13}$ and $R_{14}$ are taken together with the nitrogen to form a 3 to 10 membered heterocycle.

In one embodiment, $R_1$ is chosen from thienyl, t-butyl, phenyl, thiophenyl, pyridinyl, isoxazolyl, any of which can be substituted by at least one substituent chosen from a halogen, $C_{1-6}$ alkyl, $C_{1-6}$ alkyloxy, $C_{2-6}$ alkenyl, $C_{2-6}$ alkynyl, nitro, cyano, $SO_2$—$C_{1-6}$ alkyl, NO—$C_{1-6}$ alkyl.

In further embodiments;

$R_1$ is phenyl.

$R_1$ is phenyl substituted with fluoride.

$R_1$ is phenyl substituted with at least one fluoride $R_1$ is phenyl di-substituted with fluoride.

$R_1$ is phenyl substituted with chloride.

$R_1$ is phenyl substituted with at least one chloride $R_1$ is phenyl di-substituted with chloride.

$R_1$ is phenyl substituted with fluoride and chloride.

$R_1$ is phenyl substituted with nitro.

$R_1$ is phenyl substituted with at least one nitro.

$R_1$ is phenyl substituted with methoxy.

$R_1$ is phenyl substituted with $OCF_3$.

$R_1$ is phenyl substituted with $CF_3$.

$R_1$ is phenyl substituted with methyl.

$R_1$ is phenyl substituted with at least one methyl.

$R_1$ is phenyl-substituted with CN.

$R_1$ is phenyl substituted with $SO_2$—$CH_3$.

$R_1$ is phenyl substituted with $NH(CO)$—$CH_3$.

In further embodiments, $R_1$ is thiophenyl.

$R_1$ is thiophenyl substituted by at least one halogen.

$R_1$ is thiophenyl substituted by at least one chloride.

$R_1$ is thiophenyl substituted by at least one methyl.

$R_1$ is thiophenyl substituted by at least one methyl and one chloride.

In further embodiments, $R_1$ is thienyl.

$R_1$ is thienyl substituted by at least one halogen.

$R_1$ is thienyl substituted by at least one chloride.

$R_1$ is thienyl substituted by at least one methyl.

$R_1$ is thienyl substituted by at least one methyl and one chloride.

$R_1$ is isoxazole di-substituted with $CH_3$.

$R_1$ is pyridine.

In one embodiment, M is chosen from:

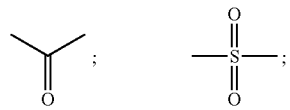

a bond

In a further embodiment, M is:

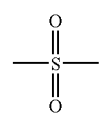

In an alternative embodiment, M is:

In one embodiment, J is chosen from:

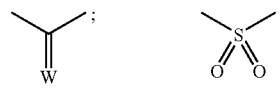

wherein, W is as defined above.

In an alternative embodiment, J is:

In a further embodiment, J is:

In one embodiment, Y is chosen from $COOR_{16}$, $COCOOR_5$, $P(O)OR_aOR_b$, $S(O)_2OR_5$, tetrazole, $CON(R_9)CH(R_5)COOR_5$, $CONR_{10}R_{11}$, $CONR_9OH$.

In a further embodiment, any of $R_5$, Ra, Rb, $R_9$, $R_{10}$, $R_{11}$ and $R_{16}$ are each independently chosen from H or $C_{1-6}$ alkyl; provided that $R_{16}$ is other than methyl or ethyl.

In one embodiment, Y is chosen from $COOR_{16}$, $CONR_{10}R_{11}$, or $CON(R_9)CH(R_5)$—$COOR_5$.

In a further embodiment, any of $R_5$, $R_9$, $R_{10}$, $R_{11}$, and $R_{16}$ are each independently chosen from H or $C_{1-6}$ alkyl; provided that $R_{16}$ is other than methyl or ethyl.

In a further embodiment, Y is chosen from $COOR_{16}$, $CONR_{10}R_{11}$ or $CON R_9CH_2COOR_5$.

In a further embodiment, Y is chosen from $COOR_5$, $CONR_5R_5$ or $CON(R_5)CH(R_5)$—$COOR_5$.

In a further embodiment, Y is COOH.

In a further embodiment, Y is $CONH_2$.

In a further embodiment, Y is $CONHCH_2COOH$.

In a further embodiment, Y is $COOCH_3$.

In a further embodiment, $Y^1$ is chosen from $CH_2$, C=CH, CH—$CH_2$ or a bond.

In further embodiments;

$R_3$ is chosen from H, $C_{1-12}$alkyl, $C_{6-18}$ aralkyl, $C_{3-12}$ heterocycle or $C_{3-18}$ heteroaralkyl.

$R_3$ is chosen from H, $C_{1-12}$ alkyl, $C_{6-18}$ aralkyl or $C_{3-12}$ heterocycle.

$R_3$ is $C_{1-12}$ alkyl.

$R_3$ is $C_{6-18}$ aralkyl.

$R_3$ is $C_{3-12}$ heterocycle.

$R_3$ is chosen from H, methyl, ethyl, i-propyl, cyclopropyl, cyclohexyl, allyl, piperidinyl, piperazinyl, pyrrolidinyl, azetidinyl, aziridinyl, pyridinyl, piperidinylmethyl, dioxanyl, dioxolanyl, azepanyl or benzyl; any of which can be optionally substituted by one or more substituent chosen from halogen, nitro, nitroso, $SO_3R_{12}$, $PO_3RcRd$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido;

wherein $R_{12}$, Rc, Rd, $R_{13}$ and $R_{14}$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, $C_{6-18}$ aralkyl;

or Rc and Rd are taken together with the oxygens to form a 5 to 10 membered heterocycle;

or $R_{13}$ and $R_{14}$ are taken together with the nitrogen to form a 3 to 10 membered heterocycle.

$R_3$ is chosen from H or Methyl, isopropyl, piperidinyl, piperidinylmethyl, dioxolanyl or cyclohexyl.

In a further embodiment, $R_3$ is H or methyl.

In a further embodiment, $R_3$ is H.

In a further embodiment, $R_3$ is methyl.

In a further embodiment, $R_3$ is benzyl; thiophenylmethyl, furanylmethyl.

In additional embodiments;

$R_2$ is $C_{2-12}$ alkyl, $C_{6-14}$ aryl or $C_{3-12}$ heterocycle;

$R_2$ is $C_{3-6}$ heterocycle.

$R_2$ is chosen from thienyl, furanyl, pyridinyl, oxazolyl, thiazolyl, pyrrolyl, benzofuranyl, indolyl, benzoxazolyl, benzothienyl, benzothiazolyl, piperazinyl, pyrrolidinyl or quinolinyl any of which can be optionally substituted by one or more substituent chosen from halogen, nitro, nitroso, $SO_3R_{12}$, $PO_3RcRd$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido;

wherein $R_{12}$, Rc, Rd, $R_{13}$ and $R_{14}$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, $C_{6-18}$ aralkyl;

or Rc and Rd are taken together with the oxygens to form a 5 to 10 membered heterocycle;

or $R_{13}$ and $R_{14}$ are taken together with the nitrogen to form a 3 to 10 membered heterocycle.

$R_2$ is a heterocycle chosen from thienyl, furanyl, pyridinyl, pyrrolyl, indolyl, piperazinyl or benzothienyl.

$R_2$ is $C_{2-12}$ alkyl.

$R_2$ is chosen from cyclopropyl, cyclobutyl, cyclopentyl, cyclopentenyl cyclohexyl, cycloheptyl, 2-(cyclopentyl)-ethyl, methyl, ethyl, vinyl, propyl, propenyl, isopropyl, butyl, butenyl isobutyl, pentyl, neopentyl or t-butyl any of which can be optionally substituted by one or more substituent chosen from halogen, nitro, nitroso, $SO_3R_{12}$, $PO_3RcRd$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-16}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, NR13R14, $C(O)OR_{12}$, cyano, azido, amidino or guanido;

wherein $R_{12}$, Rc, Rd, $R_{13}$ and $R_{14}$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, $C_{6-18}$ aralkyl;

or Rc and Rd are taken together with the oxygens to form a 5 to 10 membered heterocycle;

or $R_{13}$ and $R_{14}$ are taken together with the nitrogen to form a 3 to 10 membered heterocycle.

$R_2$ is $C_{6-12}$ aryl.

$R_2$ is an aryl chosen from indenyl, naphthyl or biphenyl.

$R_2$ is phenyl substituted by one or more substituent chosen from halogen, nitro, nitroso, $SO_3R_{12}$, $PO_3RcRd$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido;

wherein $R_{12}$, Rc, Rd, $R_{13}$ and $R_{14}$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, $C_{6-18}$ aralkyl;

or Rc and Rd are taken together with the oxygens to form a 5 to 10 membered heterocycle;

or $R_{13}$ and $R_{14}$ are taken together with the nitrogen to form a 3 to 10 membered heterocycle.

R₂ is phenyl substituted by one or two substituents chosen from halogen, nitro, nitroso, $SO_3R_{12}$, $PO_3RcRd$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido;

wherein $R_{12}$, Rc, Rd, $R_{13}$ and $R_{14}$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, $C_{6-18}$ aralkyl;

or Rc and Rd are taken together with the oxygens to form a 5 to 10 membered heterocycle;

or $R_{13}$ and $R_{14}$ are taken together with the nitrogen to form a 3 to 10 membered heterocycle.

R₂ is phenyl substituted by one or more substituent chosen from halogen, nitro, $CONR_{13}R_{14}$, $C_{1-6}$ alkyl, $C_{2-6}$ alkenyl, $C_{1-6}$ alkyloxy, $C(O)C_{1-6}$ alkyl, $C_{6-12}$ aryl, $C_{3-10}$ heterocycle, hydroxyl, $NR_{13}R_{14}$, $C(O)OR_{12}$, cyano, azido, wherein $R_{12}$, $R_{13}$ and $R_{14}$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, $C_{6-18}$ aralkyl;

or $R_{13}$ and $R_{14}$ are taken together with the nitrogen to form a 3 to 10 membered heterocycle.

R₂ is phenyl substituted by one or two substituents chosen from halogen, nitro, $CONR_{13}R_{14}$, $C_{1-6}$ alkyl, $C_{2-6}$ alkenyl, $C_{1-6}$ alkyloxy, $C(O)C_{1-6}$ alkyl, $C_{6-12}$ aryl, $C_{3-10}$ heterocycle, hydroxyl, $NR_{13}R_{14}$, $C(O)OR_{12}$, cyano, azido, wherein $R_{12}$, $R_{13}$ and $R_{14}$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, $C_{6-18}$ aralkyl;

or $R_{13}$ and $R_{14}$ are taken together with the nitrogen to form a 3 to 10 membered heterocycle.

R₂ is phenyl substituted by one or two substituents chosen from halogen, $C_{1-6}$ alkyl, $NR_{13}R_{14}$, nitro, $CONR_{13}R_{14}$, $C(O)OC_{1-6}$ alkyl, COOH or $C_{1-6}$ alkyloxy $C(O)OR_{12}$, cyano, azido, wherein $R_{12}$, $R_{13}$ and $R_{14}$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, $C_{6-18}$ aralkyl;

or $R_{13}$ and $R_{14}$ are taken together with the nitrogen to form a 3 to 10 membered heterocycle.

In one embodiment, R₂ is chosen from $C_{6-14}$ aryl, $C_{3-12}$ heterocycle, $C_{6-12}$ aralkyl or $C_{3-10}$ heteroaralkyl.

In a further embodiment, R₂ is chosen from a $C_{6-12}$ aryl or $C_{3-10}$ heterocycle.

In a further embodiment, R₂ is a $C_6$ aryl or a $C_{3-6}$ heterocycle.

In a further embodiment, R₂ is chosen from phenyl, pyridinyl, thiophenyl, benzofuran, thiazole, pyrazole, substituted with at least one substituent chosen from a halogen, $C_{1-6}$ alkyl, $C_{1-6}$ alkyloxy, $CF_3$, COOH, $COOC_{1-6}$ alkyl, cyano, $NH_2$, nitro, $NH(C_{1-6}$ alkyl), $N(C_{1-6}$ alkyl)$_2$ or a $C_{3-8}$ heterocycle.

R₂ is chosen from thienyl, furanyl, pyridyl, oxazolyl, thiazolyl, pyrrolyl, benzofuranyl, indolyl, benzoxazolyl, benzothienyl, benzothiazolyl or quinolinyl any of which can be substituted by at least one substituent chosen from $C_{1-6}$ alkyl, amino, halogen, nitro, amido, CN, $COOC_{1-6}$ alkyl, or $C_{1-6}$ alkyloxy.

R₂ is methylphenyl.

R₂ is dichlorophenyl.

In a further embodiment, R₂ is chosen from:

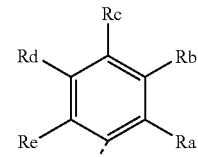 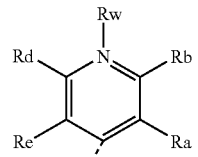

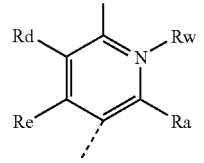 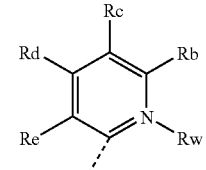

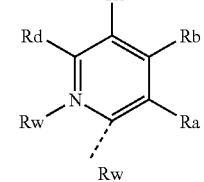 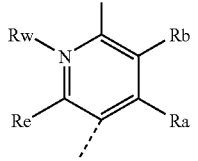

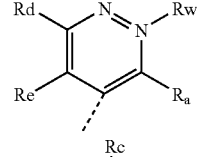 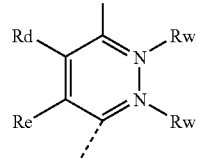

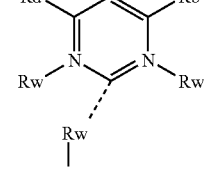 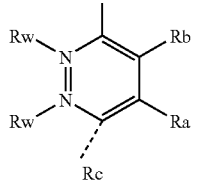

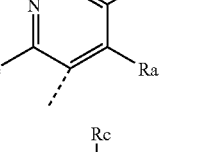 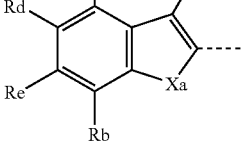

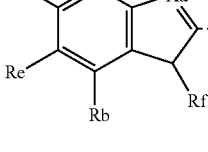 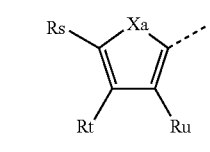

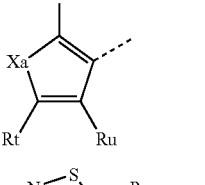 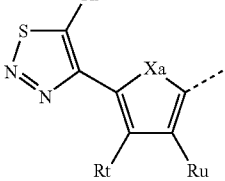

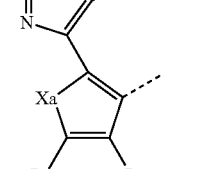 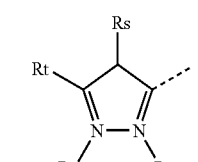

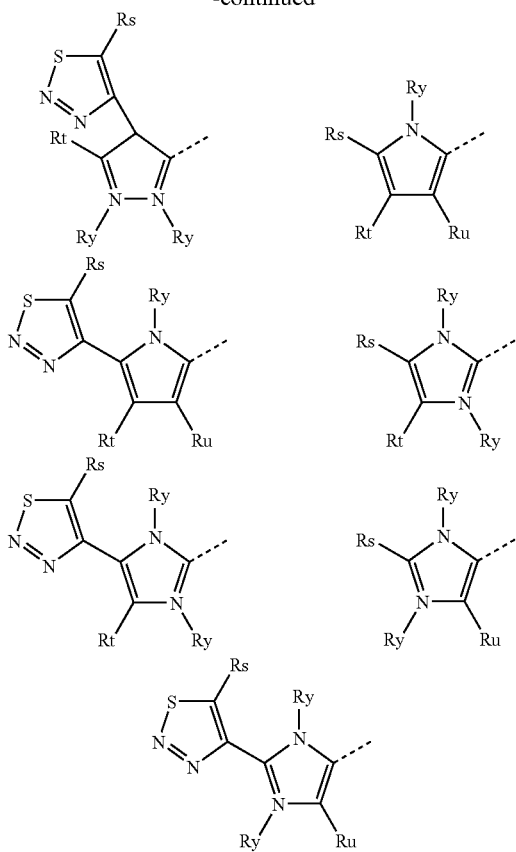

wherein:
Rw is H, O or methyl;
Ry is H or methyl;
Rw is H;
Rw is methyl;
Ry is H;
Ry is methyl;
and wherein, Xa is S, N, O or carbon.

In a further embodiment, each of Ra, Rb, Rc, Rd, Re, and Rf are independently chosen from, H, Cl, Br, I, F, $C_{1-6}$ alkyl, $OC_{1-6}$ alkyl, $CF_3$, COOH, $COOC_{1-6}$ alkyl, CN, $NH_2$, $NO_2$, $NH(C_{1-6}$ alkyl), $N(C_{1-6}$ alkyl$)_2$.

In a further embodiment, each of Ra, Rb, Rc, Rd, Re, and Rf are independently chosen from, H, Cl, Br, I, F, methyl, O-methyl, $CF_3$, COOH, $COOCH_3$', CN, $NH_2$, $NO_2$, $NH(CH_3)$ or $N(CH_3)_2$.

In a further embodiment, each of Ra, Rb, Rc, Rd, Re, and Rf are independently chosen from, H, Cl, Br, I, F, methyl, O-methyl, $CF_3$, COOH, $COOCH_3$, CN, $NH_2$, or $NO_2$.

In a further embodiment, each of Ra, Rb, Rc, Rd, Re, and Rf are independently chosen from, H, Cl, methyl, O-methyl, $CF_3$, COOH, $COOCH_3$, CN, $NH_2$, or $NO_2$.

In a further embodiment, each of Ra, Rb, Rc, Rd, Re, and Rf are independently chosen from, H, Cl, F, methyl, $CF_3$ or O-methyl.

In one embodiment, Rf is H or methyl.
In another embodiment, Rf is H.
In another embodiment, Rf is methyl.
In a further embodiment, each of Ra, Rb, Rc, Rd and Re is independently chosen from, H or Cl.
In a further embodiment, each of Ra, Rb, Rc, Rd and Re is H.

In one embodiment:
Ra is chosen from Cl, F, methyl or O-methyl;
Rb is H;
Rc is chosen from Cl, F, methyl or O-methyl;
Rd is H;
Re is chosen from Cl, F, methyl or O-methyl.

In one embodiment:
Ra is methyl;
Rb is H;
Rc is Cl;
Rd is H;
Re is methyl.

In a further embodiment, each of Rs, Rt, Ru, are independently chosen from, H, Cl, Br, I, F, $C_{1-6}$ alkyl, $OC_{1-6}$ alkyl, $CF_3$, COOH, $COOC_{1-6}$ alkyl, CN, $NH_2$, $NO_2$, $NH(C_{1-6}$ alkyl), $N(C_{1-6}$ alkyl$)_2$.

In a further embodiment, each of Rs, Rt, Ru, are independently chosen from, H, Cl, Br, I, F, methyl, O-methyl, $CF_3$, COOH, $COOCH_3$, CN, $NH_2$, $NO_2$, $NH(CH_3)$ or $N(CH_3)_2$.

In a further embodiment, each of Rs, Rt, Ru, are independently chosen from, H, Cl, Br, I, F, methyl, O-methyl, $CF_3$, COOH, $COOCH_3$, CN, $NH_2$, or $NO_2$.

In a further embodiment, each of Rs, Rt, Ru, are independently chosen from, H, Cl, Br, I, F, methyl, O-methyl, $CF_3$, COOH, $COOCH_3$, CN, $NH_2$, or $NO_2$.

In a further embodiment, each of Rs, Rt, Ru, are independently chosen from, H, Cl, methyl, O-methyl, $CF_3$, COOH, $COOCH_3$, CN, $NH_2$, or $NO_2$.

In a further embodiment, each of Rs, Rt, Ru, are independently chosen from, H, Cl, F, methyl, $CF_3$ or O-methyl.

In a further embodiment, each of Rs, Rt, Ru, are independently chosen from, H or Cl.

In a further embodiment, each of Rs, Rt, Ru, are H.

In one embodiment:
Rs and Ru are Cl and Rt is H.
Rs is Cl, Rt and Ru are H.

In one embodiment, the viral infection is chosen from Flavivirus infections.

In one embodiment, the Flavivirus infection is chosen from Hepatitis C virus (HCV), bovine viral diarrhea virus (BVDV), hog cholera virus and yellow fever virus.

In another embodiment, the Flavivirus infection is Hepatitis C viral infection.

In one embodiment, there is provided a method for treating or preventing a Flaviviridae viral infection in a host comprising administering to the host a therapeutically effective amount of at least one compound of formula (III)

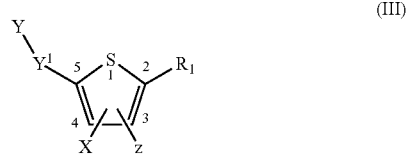

or pharmaceutically acceptable salts thereof;

wherein,
X is chosen from:

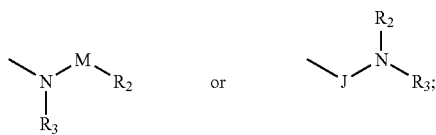

wherein,
M is chosen from:

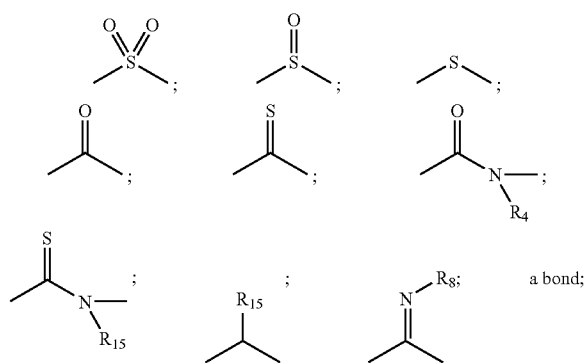

wherein,
$R_4$ is chosen from H or $C_{1-6}$ alkyl;
$R_8$ is chosen from H. $C_{1-12}$ alkyl, $C_{2-12}$ alkenyl, $C_{2-12}$ alkynyl, $C_{6-14}$ aryl, $C_{3-12}$ heterocycle, $C_{3-12}$ heteroaralkyl, $C_{6-16}$ aralkyl; and $R_{15}$ is chosen from H or $C_{1-6}$ alkyl;
J is chosen from:

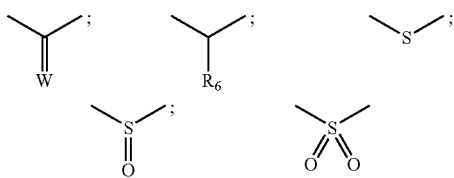

wherein
W is chosen from O, S or $NR_7$,
wherein $R_7$ is chosen from H, $C_{1-12}$ alkyl, $C_{2-12}$ alkenyl, $C_{2-12}$ alkynyl, $C_{6-12}$ aryl, $C_{3-12}$ heterocycle, $C_{3-12}$ heteroaralkyl, $C_{6-16}$ aralkyl;
and $R_6$ is chosen from H, $C_{1-12}$ alkyl, $C_{6-12}$ aryl or $C_{6-16}$ aralkyl;
$Y^1$ is chosen from a bond, $C_{1-6}$ alkyl, $C_{2-6}$ alkenyl or $C_{2-6}$ alkynyl;
Y is chosen from $COOR_{16}$, $COCOOR_5$, $P(O)OR_aOR_b$, $S(O)OR_5$, $S(O)_2OR_5$, tetrazole, $CON(R)CH(R_5)COOR_5$, $CONR_{10}R_{11}$, $CON(R_9)$—$SO_2$—$R_5$, $CONR_9OH$ or halogen, wherein $R_9$, $R_5$, $R_{10}$ and $R_{11}$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, $C_{6-18}$ aralkyl;
or $R_{10}$ and $R_{11}$ are taken together with the nitrogen to form a 3 to 10 membered heterocycle;
$R_a$ and $R_b$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl and $C_{6-18}$ aralkyl;
or $R_a$ and $R_b$ are taken together with the oxygens to form a 5 to 10 membered heterocycle;
$R_{16}$ is chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl and $C_{6-18}$ aralkyl;
$R_1$ is chosen from $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, $C_{6-18}$ aralkyl, or halogen;
$R_2$ is chosen from $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, or $C_{6-18}$ aralkyl;
$R_3$ is chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl or $C_{6-18}$ aralkyl;
Z is chosen from H, halogen, $C_{1-6}$ alkyl.

In one embodiment, there is provided a method for treating or preventing Flaviviridae viral infection in a host comprising administering to the host a therapeutically effective amount of at least one compound of formula (III), further comprising at least one antiviral agent.

In one embodiment, the antiviral agent is chosen from a viral serine protease inhibitor, viral polymerase inhibitor and viral helicase inhibitor.

In a further embodiment, the antiviral agent is chosen from interferon α and ribavirin.

In a further embodiment, said compound of formula (III) and said antiviral agent are administered sequentially.

In a further embodiment, said compound of formula (III) and said antiviral agent are administered simultaneously.

In one embodiment, there is provided a method for treating or preventing Flaviviridae viral infection in a host comprising administering to the host a therapeutically effective amount of at least one compound of formula (III) and at least one additional agent chosen from immunomudulating agent, antioxydant agent, antibacterial agent or antisense agent.

In another embodiment, the additional agent is chosen from silybum marianum, interleukine-12, amantadine, ribozyme, thymosin, N-acetyl cysteine or cyclosporin.

In further embodiments;
The compound of formula (III) and the additional agent are administered sequentially.
The compound of formula (III) and the additional agent are administered simultaneously.

In one embodiment, the present invention further provides A pharmaceutical composition comprising at least one compound having the formula III or pharmaceutically acceptable salts thereof; and at least one pharmaceutically acceptable carrier or excipient.

In a further embodiment, the pharmaceutical composition, is further comprising one or more additional agent chosen from antiviral agent, immunomudulating agent, antioxydant agent, antibacterial agent or antisense agent.

In one embodiment, the antiviral agent is chosen from a viral serine protease inhibitor, viral polymerase inhibitor and viral helicase inhibitor.

In one embodiment, the antiviral agent is chosen from interferon α and ribavirin.

In one embodiment, the additional agent is chosen from silybum marianum, interleukine-12, amantadine, ribozyme, thymosin, N-acetyl cysteine or cyclosporin.

In one embodiment, the invention further provides the use of a compound having the formula III for the manufacture of a medicament for treating or preventing a viral Flaviridea infection in a host In one embodiment, there is provided the use of a compound having the formula III or pharmaceutically acceptable salts thereof in therapy In one embodiment, the invention provides the use of a compound having the formula III for treating or preventing Flaviviridae viral infection in a host.

In one embodiment, the use of a compound having the compound of formula III for treating or preventing Flaviviridae viral infection in a host is further comprising one or more additional agent chosen from antiviral agent, immunomudulating agent, antioxydant agent, antibacterial agent or antisense agent.

In one embodiment, the antiviral agent is chosen from a viral serine protease inhibitor, viral polymerase inhibitor and viral helicase inhibitor.

In one embodiment, the antiviral agent is chosen from interferon α and ribavirin.

In one embodiment, the additional agent is chosen from silybum marianum, interleukine-12, amantadine, ribozyme, thymosin, N-acetyl cysteine or cyclosporin.

In one embodiment, the compound of formula III and the additionnal agent are administered sequentially.

In one embodiment, the compound of formula III and the additionnal agent are administered simultaneously.

In one embodiment, there is provided a method for inhibiting or reducing the activity of viral polymerase in a host comprising administering a therapeutically effective amount of a compound of formula (III).

In one embodiment, the method for inhibiting or reducing the activity of viral polymerase in a host comprising administering a therapeutically effective amount of a compound of formula (III) is further comprising one or more viral polymerase inhibitor.

In further embodiments;

The viral polymerase is a Flaviviridae viral polymerase.

The viral polymerase is a RNA-dependant RNA-polymerase.

The viral polymerase is HCV polymerase.

In one embodiment, the invention provides a method for inhibiting or reducing the activity of viral helicase in a host comprising administering a therapeutically effective amount of a compound having the formula III.

In one embodiment, the invention provides a method for inhibiting or reducing the activity of viral helicase in a host comprising administering a therapeutically effective amount of a compound chosen from:

| | |
|---|---|
| Compound #14 | 3-(4-Chloro-2,5-dimethyl-benzenesulfonylamino)-5-(4-chloro-phenyl)-thiophene-2-carboxylic acid |
| Compound #19 | 3-(4-Chloro-2,5-dimethyl-benzenesulfonylamino)-5-(4-isobutyl-phenyl)-thiophene-2-carboxylic acid |
| Compound #223 | 3-(4-Bromo-2-fluorobenzenesulfo-nylamino)-5-(4-isobutylphenyl)-thiophene-2-carboxylic acid |
| Compound #224 | 3-(4-Bromo-2-methylbenzenesulfo-nylamino)-5-(4-isobutylphenyl)-thiophene-2-carboxylic acid |
| Compound #225 | 5-(4-Isobutylphenyl 3-(3-methoxy-benzenesulfonyl-amino)-thiophene-2-carboxylic acid |
| Compound #581 | 5-(4-Isobutyl-phenyl)-3-[5-(5-trifluoromethyl-isoxazol-3-yl)-thiophene-2-sulfonylamino]-thiophene-2-carboxylic acid |
| Compound #227 | 3-[2,5-Bis-(2,2,2-trifluoroethoxy)-benzenesulfonylamino]-5-(4-isobutyl-phenyl)-thiophene-2-carboxylic acid |
| Compound #228 | 3-(2-Chloro-4-cyanobenzenesulfonylamino)-5-(4-isobutylphenyl)-thiophene-2-carboxylic acid |
| Compound #582 | 5-(4-Isobutyl-phenyl)-3-(2,3,4-trifluoro-benzenesulfonylamino)-thiophene-2-carboxylic acid | or pharmaceutically acceptable salts thereof.

In further embodiments;

The viral helicase is a flaviviridea helicase.

The viral helicase is HCV helicase.

In a further embodiment, there is provided the use of a compound having the formula III for inhibiting or reducing the activity of viral polymerase in a host.

In still a further embodiment, there is provided the use of a compound having the formula III for inhibiting or reducing the activity of viral polymerase in a host, further comprising one or more viral polymerase inhibitor.

In further embodiments;

The viral polymerase is Flaviviridae viral polymerase.

The viral polymerase is RNA-dependant RNA-polymerase.

The viral polymerase is HCV polymerase.

In one embodiment, the invention provides the use of a compound having the formula III for inhibiting or reducing the activity of viral helicase in a host.

In one embodiment, the invention provides the use of a compound chosen from:

| | |
|---|---|
| Compound #14 | 3-(4-Chloro-2,5-dimethyl-benzenesulfonylamino)-5-(4-chloro-phenyl)-thiophene-2-carboxylic acid |
| Compound #19 | 3-(4-Chloro-2,5-dimethyl-benzenesulfonylamino)-5-(4-isobutyl-phenyl)-thiophene-2-carboxylic acid isobutyl-phenyl)-thiophene-2-carboxylic acid |
| Compound #223 | 3-(4-Bromo-2-fluorobenzenesulfo-nylamino)-5-(4-isobutylphenyl)-thiophene-2-carboxylic acid |
| Compound #224 | 3-(4-Bromo-2-methylbenzenesulfo-nylamino)-5-(4-isobutylphenyl)-thiophene-2-carboxylic acid |
| Compound #225 | 5-(4-Isobutylphenyl 3-(3-methoxy-benzenesulfonyl-amino)-thiophene-2-carboxylic acid |
| Compound #581 | 5-(4-Isobutyl-phenyl)-3-[5-(5-trifluoromethyl-isoxazol-3-yl)-thiophene-2-sulfonylamino]-thiophene-2-carboxylic acid |
| Compound #227 | 3-[2,5-Bis-(2,2,2-trifluoroethoxy)-benzenesulfonylamino]-5-(4-isobutyl-phenyl)-thiophene-2-carboxylic acid |
| Compound #228 | 3-(2-Chloro-4-cyanobenzenesulfonylamino)-5-(4-isobutylphenyl)-thiophene-2-carboxylic acid |
| Compound #582 | 5-(4-Isobutyl-phenyl)-3-(2,3,4-trifluoro-benzenesulfonylamino)-thiophene-2-carboxylic acid | or pharmaceutically acceptable salts thereof for inhibiting or reducing the activity of viral helicase in a host.

In one embodiment, the invention provides the use of a compound having the formula III for inhibiting or reducing the activity of viral helicase in a host further comprising one or more viral helicase inhibitor.

In further embodiments;

The viral helicase is Flaviviridae viral helicase.

The viral helicase is HCV helicase.

In one embodiment, the present invention provides a combination comprising a compound having the formula III and one or more additionnal agent chosen from viral serine protease inhibitor, viral polymerase inhibitor and viral helicase inhibitor, immunomudulating agent, antioxydant agent, antibacterial agent or antisense agent.

In a further embodiment, the additional agent is chosen from silybum marianum, interleukine-12, amantadine, ribozyme, thymosin, N-acetyl cysteine, cyclosporin, interferon α and ribavirin.

In further embodiments;

The compound of formula (III) and the additionnal agent are administered sequentially.

The compound of formula (III) and the additionnal agent are administered simultaneously.

In still a further embodiment, the present invention provides a process for preparing a compound of formula A:

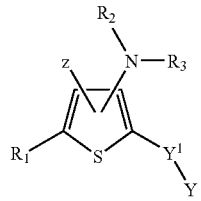

A said process comprising the steps of adding:
    an enol ether;
    an hydride donating agent; and
    an organic carboxylic acid;
to a compound of formula B:

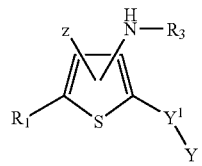

B wherein;
$Y^1$ is chosen from a bond, $C_{1-6}$ alkyl, $C_{2-6}$ alkenyl or $C_{2-6}$ alkynyl;
Y is chosen from $COOR_{16}$, $COCOOR_5$, $P(O)OR_aOR_b$, $S(O)$ $OR_5$, $S(O)_2OR_5$, tetrazole, $CON(R_9)CH(R_5)COOR_5$, $CONR_{10}R_{11}$, $CON(R_9)—SO_2—R_5$, $CONR_9OH$ or halogen, wherein $R_9$, $R_5$, $R_{10}$ and $R_{11}$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, $C_{6-18}$ aralkyl;
or $R_{10}$ and $R_{11}$ are taken together with the nitrogen to form a 3 to 10 membered heterocycle;
$R_a$ and $R_b$ are each independently chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl and $C_{6-18}$ aralkyl;
or $R_a$ and $R_b$ are taken together with the oxygens to form a 5 to 10 membered heterocycle;
$R_{16}$ is chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl and $C_{6-18}$ aralkyl;
$R_1$ is chosen from $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, $C_{6-18}$ aralkyl or halogen;
$R_2$ is chosen from $C_{1-12}$ alkyl, $C_{2-12}$ alkenyl, $C_{2-12}$ alkynyl, $C_{3-12}$ heterocycle, $C_{3-18}$ heteroaralkyl, or $C_{6-18}$ aralkyl;
$R_3$ is chosen from H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl or $C_{6-18}$ aralkyl;
Z is chosen from H, halogen, $C_{1-6}$alkyl.

It will be appreciated by those skilled in the art that the compounds of formula (I) or (Ia) can contain a chiral centre on the general formula (I). The compounds of formula (I) or (Ia) thus exist in the form of two different optical isomers (i.e. (+) or (−) enantiomers). All such enantiomers and mixtures thereof including racemic mixtures are included within the scope of the invention. The single optical isomer or enantiomer can be obtained by method well known in the art, such as chiral HPLC, enzymatic resolution and chiral auxiliary.

In accordance with the present invention, the compounds of formula (I) or (Ia) include:

| | |
|---|---|
| Compound 1 | 3-[(4-CHLORO-2,5-DIMETHYL-BENZENESULFONYL)-(3-IODO-BENZYL)-AMINO]-5-PHENYL-THIOPHENE-2-CARBOXYLIC ACID |
| Compound 2 | 3-[(3-BENZOFURAN-2-YL-BENZYL)-(4-CHLORO-2,5-DIMETHYL-BENZENESULFONYL)-AMINO]-5-PHENYL-THIOPHENE-2-CARBOXYLIC ACID |
| Compound 3 | 3-(4-CHLORO-2,5-DIMETHYL-BENZENESULFONYLAMINO)-5-PHENYL-THIOPHENE-2-CARBOXYLIC ACID |
| Compound 4 | 3-{(2,4-DICHLORO-BENZOYL)-[5-(3-TRIFLUOROMETHYL-PHENYL)-FURAN-2-YLMETHYL]-AMINO}-5-PHENYL-THIOPHENE-2-CARBOXYLIC ACID |
| Compound 5 | 3-[(4-CHLORO-2,5-DIMETHYL-BENZENESULFONYL)-METHYL-AMINO]-5-PHENYL-THIOPHENE-2-CARBOXYLIC ACID |
| Compound 6 | 5-(4-FLUORO-PHENYL)-3-(TOLUENE-4-SULFONYLAMINO)-THIOPHENE-2-CARBOXYLIC ACID |
| Compound 7 | 3-(2,4-DICHLORO-BENZENESULFONYLAMINO)-5-PHENYL-THIOPHENE-2-CARBOXYLIC ACID |
| Compound 8 | 3-(4-CHLORO-2,5-DIMETHYL-BENZENESULFONYLAMINO)-5-(4-FLUORO-PHENYL)-THIOPHENE-2-CARBOXYLIC ACID |
| Compound 9 | 3-[(2,4-DICHLORO-BENZOYL)-METHYL-AMINO]-5-PHENYL-THIOPHENE-2-CARBOXYLIC ACID |
| Compound 10 | 5-TERT-BUTYL-3-(4-CHLORO-BENZENESULFONYLAMINO)-THIOPHENE-2-CARBOXYLIC ACID |
| Compound 11 | 4-(TOLUENE-4-SULFONYLAMINO)-[2,3']BITHIOPHENYL-5-CARBOXYLIC ACID |
| Compound 12 | 3-[(5-BENZOFURAN-2-YL-THIOPHEN-2-YLMETHYL)-(2,4-DICHLORO-BENZOYL)-AMINO]-5-PHENYL-THIOPHENE-2-CARBOXYLIC ACID |
| Compound 13 | 5-PHENYL-3-(TOLUENE-4-SULFONYLAMINO)-THIOPHENE-2-CARBOXYLIC ACID |
| Compound 14 | 3-(4-CHLORO-2,5-DIMETHYL-BENZENESULFONYLAMINO)-5-(4-CHLORO-PHENYL)-THIOPHENE-2-CARBOXYLIC ACID |
| Compound 15 | 5-PHENYL-3-(TOLUENE-2-SULFONYLAMINO)-THIOPHENE-2-CARBOXYLIC ACID |
| Compound 16 | 5-PHENYL-3-(TOLUENE-3-SULFONYLAMINO)-THIOPHENE-2-CARBOXYLIC ACID |
| Compound 17 | 3-BENZENESULFONYLAMINO-5-PHENYL-THIOPHENE-2-CARBOXYLIC ACID |
| Compound 18 | 3-(4-CHLORO-BENZENESULFONYLAMINO)-5-PHENYL-THIOPHENE-2-CARBOXYLIC ACID |
| Compound 19 | 3-(4-CHLORO-2,5-DIMETHYL-BENZENESULFONYLAMINO)-5-(4-ISOBUTYL-PHENYL)-THIOPHENE-2-CARBOXYLIC ACID |
| Compound 20 | 5-TERT-BUTYL-3-(4-CHLORO-2,5-DIMETHYL-BENZENESULFONYLAMINO)-THIOPHENE-2-CARBOXYLIC ACID |

| | |
|---|---|
| Compound 21 | 3-(2,5-DIMETHYL-BENZENESULFONYLAMINO)-5-PHENYL-THIOPHENE-2-CARBOXYLIC ACID |
| Compound 22 | 3-(4-METHOXY-2,3,6-TRIMETHYL-BENZENESULFONYLAMINO)-5-PHENYL-THIOPHENE-2-CARBOXYLIC ACID |
| Compound 23 | 5-PHENYL-3-(THIOPHENE-2-SULFONYLAMINO)-THIOPHENE-2-CARBOXYLIC ACID |
| Compound 24 | 4-(4-CHLORO-2,5-DIMETHYL-BENZENESULFONYLAMINO)-[2,3']BITHIOPHENYL-5-CARBOXYLIC ACID |
| Compound 25 | 5-(3,5-BIS-TRIFLUOROMETHYL-PHENYL)-3-(4-CHLORO-2,5-DIMETHYL-BENZENESULFONYLAMINO)-THIOPHENE-2-CARBOXYLIC ACID |
| Compound 26 | 8-CHLORO-3-(4-CHLORO-2,5-DIMETHYL-BENZENESULFONYLAMINO)-4H-1,5-DITHIA-CYCLOPENTA[A]NAPHTHALENE-2-CARBOXYLIC ACID |
| Compound 27 | 3-(2,4-DIFLUORO-BENZENESULFONYLAMINO)-5-PHENYL-THIOPHENE-2-CARBOXYLIC ACID |
| Compound 28 | 3-[3-(2,6-DICHLORO-PYRIDIN-4-YL)-UREIDO]-5-PHENYL-THIOPHENE-2-CARBOXYLIC ACID |
| Compound 29 | 3-(2-CHLORO-BENZENESULFONYLAMINO)-5-PHENYL-THIOPHENE-2-CARBOXYLIC ACID |
| Compound 30 | 3-(2-FLUORO-BENZENESULFONYLAMINO)-5-PHENYL-THIOPHENE-2-CARBOXYLIC ACID |
| Compound 31 | 5-PHENYL-3-(2-TRIFLUOROMETHOXY-BENZENESULFONYLAMINO)-THIOPHENE-2-CARBOXYLIC ACID |
| Compound 32 | 3-(4-TERT-BUTYL-BENZENESULFONYLAMINO)-5-PHENYL-THIOPHENE-2-CARBOXYLIC ACID |
| Compound 33 | 3-(4-CHLORO-PHENOXYCARBONYLAMINO)-5-PHENYL-THIOPHENE-2-CARBOXYLIC ACID |
| Compound 34 | 3-(3,4-DICHLORO-BENZENESULFONYLAMINO)-5-PHENYL-THIOPHENE-2-CARBOXYLIC ACID |
| Compound 35 | 5-PHENYL-3-(2-TRIFLUOROMETHYL-BENZENESULFONYLAMINO)-THIOPHENE-2-CARBOXYLIC ACID |
| Compound 36 | 3-(5-BROMO-6-CHLORO-PYRIDINE-3-SULFONYLAMINO)-5-PHENYL-THIOPHENE-2-CARBOXYLIC ACID |
| Compound 37 | 3-(5-CHLORO-THIOPHENE-2-SULFONYLAMINO)-5-PHENYL-THIOPHENE-2-CARBOXYLIC ACID |
| Compound 38 | 3-(5-CHLORO-3-METHYL-BENZO[B]THIOPHENE-2-SULFONYLAMINO)-5-PHENYL-THIOPHENE-2-CARBOXYLIC ACID |
| Compound 39 | 3-(4-BROMO-BENZENESULFONYLAMINO)-5-PHENYL-THIOPHENE-2-CARBOXYLIC ACID |
| Compound 40 | 3-(3-CHLORO-BENZENESULFONYLAMINO)-5-PHENYL-THIOPHENE-2-CARBOXYLIC ACID |
| Compound 41 | 3-(5-CHLORO-1,3-DIMETHYL-1H-PYRAZOLE-4-SULFONYLAMINO)-5-PHENYL-THIOPHENE-2-CARBOXYLIC ACID |
| Compound 42 | 3-(3-BROMO-BENZENESULFONYLAMINO)-5-PHENYL-THIOPHENE-2-CARBOXYLIC ACID |
| Compound 43 | 3-(4-ISOPROPYL-BENZENESULFONYLAMINO)-5-PHENYL-THIOPHENE-2-CARBOXYLIC ACID |
| Compound 44 | 3-(2,6-DICHLORO-BENZENESULFONYLAMINO)-5-PHENYL-THIOPHENE-2-CARBOXYLIC ACID |
| Compound 45 | 3-(2-NITRO-BENZENESULFONYLAMINO)-5-PHENYL-THIOPHENE-2-CARBOXYLIC ACID |
| Compound 46 | 5-PHENYL-3-(5-[1,2,3]THIADIAZOL-4-YL-THIOPHENE-2-SULFONYLAMINO)-THIOPHENE-2-CARBOXYLIC ACID |
| Compound 47 | 5-PHENYL-3-(PYRIDINE-2-SULFONYLAMINO)-THIOPHENE-2-CARBOXYLIC ACID |
| Compound 48 | 3-(2,4-DICHLORO-BENZYLAMINO)-5-PHENYL-THIOPHENE-2-CARBOXYLIC ACID |
| Compound 49 | 3-(3-FLUORO-BENZENESULFONYLAMINO)-5-PHENYL-THIOPHENE-2-CARBOXYLIC ACID |
| Compound 50 | 5-PHENYL-3-(3-TRIFLUOROMETHYL-BENZENESULFONYLAMINO)-THIOPHENE-2-CARBOXYLIC ACID |
| Compound 51 | 3-(2-CARBOXY-BENZOYLAMINO)-5-PHENYL-THIOPHENE-2-CARBOXYLIC ACID METHYL ESTER |
| Compound 52 | 5-PHENYL-3-(4-TRIFLUOROMETHYL-BENZENESULFONYLAMINO)-THIOPHENE-2-CARBOXYLIC ACID |
| Compound 53 | 3-(2,5-DIFLUORO-BENZENESULFONYLAMINO)-5-PHENYL-THIOPHENE-2-CARBOXYLIC ACID |
| Compound 54 | 3-(2-CYANO-BENZENESULFONYLAMINO)-5-PHENYL-THIOPHENE-2-CARBOXYLIC ACID |
| Compound 55 | 3-(2,5-DICHLORO-THIOPHENE-3-SULFONYLAMINO)-5-PHENYL-THIOPHENE-2-CARBOXYLIC ACID |
| Compound 56 | 4-(TOLUENE-2-SULFONYLAMINO)-[2,2']BITHIOPHENYL-5-CARBOXYLIC ACID |
| Compound 57 | 5'-CHLORO-4-(TOLUENE-2-SULFONYLAMINO)-[2,2']BITHIOPHENYL-5-CARBOXYLIC ACID |
| Compound 58 | 5-(2,4-DICHLORO-PHENYL)-3-(TOLUENE-2-SULFONYLAMINO)-THIOPHENE-2-CARBOXYLIC ACID |
| Compound 59 | 5-(4-NITRO-PHENYL)-3-(TOLUENE-2-SULFONYLAMINO)-THIOPHENE-2-CARBOXYLIC ACID |
| Compound 60 | 3-(TOLUENE-2-SULFONYLAMINO)-5-(4-TRIFLUOROMETHOXY-PHENYL)-THIOPHENE-2-CARBOXYLIC ACID |
| Compound 61 | 5-QUINOLIN-8-YL-3-(TOLUENE-2-SULFONYLAMINO)-THIOPHENE-2-CARBOXYLIC ACID |

-continued

| | |
|---|---|
| Compound 62 | 5-PHENYL-3-(TOLUENE-2-SULFONYLAMINO)-THIOPHENE-2-CARBOXYLIC ACID |
| Compound 63 | 5-(3-NITRO-PHENYL)-3-(TOLUENE-2-SULFONYLAMINO)-THIOPHENE-2-CARBOXYLIC ACID |
| Compound 64 | 3-(TOLUENE-2-SULFONYLAMINO)-5-M-TOLYL-THIOPHENE-2-CARBOXYLIC ACID |
| Compound 65 | 5-(3-CHLORO-PHENYL)-3-(TOLUENE-2-SULFONYLAMINO)-THIOPHENE-2-CARBOXYLIC ACID |
| Compound 66 | 5-(4-FLUORO-PHENYL)-3-(TOLUENE-2-SULFONYLAMINO)-THIOPHENE-2-CARBOXYLIC ACID |
| Compound 67 | 5-(3-FLUORO-PHENYL)-3-(TOLUENE-2-SULFONYLAMINO)-THIOPHENE-2-CARBOXYLIC ACID |
| Compound 68 | 5-(4-CHLORO-PHENYL)-3-(TOLUENE-2-SULFONYLAMINO)-THIOPHENE-2-CARBOXYLIC ACID |
| Compound 69 | 5-(3,5-DIFLUORO-PHENYL)-3-(TOLUENE-2-SULFONYLAMINO)-THIOPHENE-2-CARBOXYLIC ACID |
| Compound 70 | 5-(3,4-DIFLUORO-PHENYL)-3-(TOLUENE-2-SULFONYLAMINO)-THIOPHENE-2-CARBOXYLIC ACID |
| Compound 71 | 3-(TOLUENE-2-SULFONYLAMINO)-5-VINYL-THIOPHENE-2-CARBOXYLIC ACID |
| Compound 72 | 3-(4-CHLORO-BENZOYLAMINO)-5-PHENYL-THIOPHENE-2-CARBOXYLIC ACID |
| Compound 73 | 3-[(4-CHLORO-BENZOYL)-METHYL-AMINO]-5-PHENYL-THIOPHENE-2-CARBOXYLIC ACID |
| Compound 74 | 5-PHENYL-3-[(THIOPHENE-2-CARBONYL)-AMINO]-THIOPHENE-2-CARBOXYLIC ACID |
| Compound 75 | 3-[METHYL-(THIOPHENE-2-CARBONYL)-AMINO]-5-PHENYL-THIOPHENE-2-CARBOXYLIC ACID |
| Compound 76 | 3-(2-BROMO-BENZENESULFONYLAMINO)-5-PHENYL-THIOPHENE-2-CARBOXYLIC ACID |
| Compound 77 | 3-(2,4-DIFLUORO-BENZOYLAMINO)-5-PHENYL-THIOPHENE-2-CARBOXYLIC ACID |
| Compound 78 | 3-[(2,4-DIFLUORO-BENZOYL)-METHYL-AMINO]-5-PHENYL-THIOPHENE-2-CARBOXYLIC ACID |
| Compound 79 | 3-(TOLUENE-2-SULFONYLAMINO)-5-TRIMETHYLSILANYLETHYNYL-THIOPHENE-2-CARBOXYLIC ACID |
| Compound 80 | 5-ETHYNYL-3-(TOLUENE-2-SULFONYLAMINO)-THIOPHENE-2-CARBOXYLIC ACID |
| Compound 81 | 3-(TOLUENE-2-SULFONYLAMINO)-5-(3-TRIFLUOROMETHOXY-PHENYL)-THIOPHENE-2-CARBOXYLIC ACID |
| Compound 82 | 5-BENZOYL-3-(TOLUENE-2-SULFONYLAMINO)-THIOPHENE-2-CARBOXYLIC ACID |
| Compound 83 | 5-(4-CYANO-PHENYL)-3-(TOLUENE-2-SULFONYLAMINO)-THIOPHENE-2-CARBOXYLIC ACID |
| Compound 84 | 5-(3-CHLORO-4-FLUORO-PHENYL)-3-(TOLUENE-2-SULFONYLAMINO)-THIOPHENE-2-CARBOXYLIC ACID |
| Compound 85 | 5-(3,4-DICHLORO-PHENYL)-3-(TOLUENE-2-SULFONYLAMINO)-THIOPHENE-2-CARBOXYLIC ACID |
| Compound 86 | 5-PYRIDIN-4-YL-3-(TOLUENE-2-SULFONYLAMINO)-THIOPHENE-2-CARBOXYLIC ACID |
| Compound 87 | 5-PYRIDIN-3-YL-3-(TOLUENE-2-SULFONYLAMINO)-THIOPHENE-2-CARBOXYLIC ACID |
| Compound 88 | 3-(TOLUENE-2-SULFONYLAMINO)-5-(4-TRIFLUOROMETHYL-PHENYL)-THIOPHENE-2-CARBOXYLIC ACID |
| Compound 89 | 5-(4-METHANESULFONYL-PHENYL)-3-(TOLUENE-2-SULFONYLAMINO)-THIOPHENE-2-CARBOXYLIC ACID |
| Compound 90 | 5-(3-ACETYLAMINO-PHENYL)-3-(TOLUENE-2-SULFONYLAMINO)-THIOPHENE-2-CARBOXYLIC ACID |
| Compound 91 | 5-(3-CHLORO-4-FLUORO-PHENYL)-3-(TOLUENE-2-SULFONYLAMINO)-THIOPHENE-2-CARBOXYLIC ACID |
| Compound 92 | 3-(4-METHYL-BENZOYLAMINO)-5-PHENYL-THIOPHENE-2-CARBOXYLIC ACID |
| Compound 93 | 3-[METHYL-(4-METHYL-BENZOYL)-AMINO]-5-PHENYL-THIOPHENE-2-CARBOXYLIC ACID |
| Compound 94 | 3-(3,5-DIMETHYL-ISOXAZOLE-4-SULFONYLAMINO)-5-PHENYL-THIOPHENE-2-CARBOXYLIC ACID |
| Compound 95 | 3-[(2-CHLORO-BENZOYL)-METHYL-AMINO]-5-PHENYL-THIOPHENE-2-CARBOXYLIC ACID |
| Compound 96 | 3-(2-METHYL-BENZOYLAMINO)-5-PHENYL-THIOPHENE-2-CARBOXYLIC ACID |
| Compound 97 | 3-[METHYL-(2-METHYL-BENZOYL)-AMINO]-5-PHENYL-THIOPHENE-2-CARBOXYLIC ACID |
| Compound 98 | 5-PHENYL-3-(5-TRIFLUOROMETHYL-PYRIDINE-2-SULFONYLAMINO)-THIOPHENE-2-CARBOXYLIC ACID |
| Compound 99 | 5-PHENYLETHYNYL-3-(TOLUENE-2-SULFONYLAMINO)-THIOPHENE-2-CARBOXYLIC ACID |
| Compound 100 | 3-(2,5-DIMETHYL-BENZENESULFONYLAMINO)-5-(4-NITRO-PHENYL)-THIOPHENE-2-CARBOXYLIC ACID |
| Compound 101 | 5-(2-FLUORO-PHENYL)-3-(TOLUENE-2-SULFONYLAMINO)-THIOPHENE-2-CARBOXYLIC ACID |
| Compound 102 | 5-(2-CYANO-PHENYL)-3-(TOLUENE-2-SULFONYLAMINO)-THIOPHENE-2-CARBOXYLIC ACID |
| Compound 103 | 5-(2-ETHOXYCARBONYL-PHENYL)-3-(TOLUENE-2-SULFONYLAMINO)-THIOPHENE-2-CARBOXYLIC ACID |
| Compound 104 | 5-(2-METHOXY-PHENYL)-3-(TOLUENE-2-SULFONYLAMINO)-THIOPHENE-2-CARBOXYLIC ACID |
| Compound 105 | 3'-METHYL-4-(TOLUENE-2-SULFONYLAMINO)-[2,2']BITHIOPHENYL-5-CARBOXYLIC ACID |

-continued

| | |
|---|---|
| Compound 106 | 3-(TOLUENE-2-SULFONYLAMINO)-5-(2-TRIFLUOROMETHYL-PHENYL)-THIOPHENE-2-CARBOXYLIC ACID |
| Compound 107 | 3-(2,5-DIMETHYL-BENZENESULFONYLAMINO)-5-(4-FLUORO-PHENYL)-THIOPHENE-2-CARBOXYLIC ACID |
| Compound 108 | 5-STYRYL-3-(TOLUENE-2-SULFONYLAMINO)-THIOPHENE-2-CARBOXYLIC ACID |
| Compound 109 | 3-(2,4-DIFLUORO-BENZENESULFONYLAMINO)-5-(4-NITRO-PHENYL)-THIOPHENE-2-CARBOXYLIC ACID |
| Compound 110 | 3-(2,4-DIFLUORO-BENZENESULFONYLAMINO)-5-(4-FLUORO-PHENYL)-THIOPHENE-2-CARBOXYLIC ACID |
| Compound 111 | 3-[[5-(3-CHLORO-4-FLUORO-PHENYL)-THIOPHEN-2-YLMETHYL]-(2,4-DICHLORO-BENZOYL)-AMINO]-5-PHENYL-THIOPHENE-2-CARBOXYLIC ACID |
| Compound 112 | 3-[(4-OXO-1-PHENYL-1,3,8-TRIAZA-SPIRO[4.5]DECANE-8-CARBONYL)-AMINO]-5-PHENYL-THIOPHENE-2-CARBOXYLIC ACID |
| Compound 113 | 3-{[4-(2-OXO-2,3-DIHYDRO-BENZOIMIDAZOL-1-YL)-PIPERIDINE-1-CARBONYL]-AMINO}-5-PHENYL-THIOPHENE-2-CARBOXYLIC ACID |
| Compound 114 | 3-{[4-(4-NITRO-PHENYL)-PIPERAZINE-1-CARBONYL]-AMINO}-5-PHENYL-THIOPHENE-2-CARBOXYLIC ACID |
| Compound 115 | 5-(2-CARBOXY-PHENYL)-3-(TOLUENE-2-SULFONYLAMINO)-THIOPHENE-2-CARBOXYLIC ACID |
| Compound 116 | 5-(4-CHLORO-PHENYL)-3-(PYRIDINE-2-SULFONYLAMINO)-THIOPHENE-2-CARBOXYLIC ACID |
| Compound 117 | 5-(3-CYANO-PHENYL)-3-(TOLUENE-2-SULFONYLAMINO)-THIOPHENE-2-CARBOXYLIC ACID |
| Compound 118 | 3-(2,5-DIMETHYL-BENZENESULFONYLAMINO)-5-P-TOLYL-THIOPHENE-2-CARBOXYLIC ACID |
| Compound 119 | 3-(2,4-DIFLUORO-BENZENESULFONYLAMINO)-5-P-TOLYL-THIOPHENE-2-CARBOXYLIC ACID |
| Compound 120 | 5-PHENETHYL-3-(TOLUENE-2-SULFONYLAMINO)-THIOPHENE-2-CARBOXYLIC ACID |
| Compound 121 | 5-(3-ETHOXYCARBONYL-PHENYL)-3-(TOLUENE-2-SULFONYLAMINO)-THIOPHENE-2-CARBOXYLIC ACID |
| Compound 122 | 5-(4-METHOXY-PHENYL)-3-(TOLUENE-2-SULFONYLAMINO)-THIOPHENE-2-CARBOXYLIC ACID |
| Compound 123 | 5-(3-METHOXY-PHENYL)-3-(TOLUENE-2-SULFONYLAMINO)-THIOPHENE-2-CARBOXYLIC ACID |
| Compound 124 | 5-(4'-BROMO-BIPHENYL-4-YL)-3-(TOLUENE-2-SULFONYLAMINO)-THIOPHENE-2-CARBOXYLIC ACID |
| Compound 125 | 5-(4-HYDROXYMETHYL-PHENYL)-3-(TOLUENE-2-SULFONYLAMINO)-THIOPHENE-2-CARBOXYLIC ACID |
| Compound 126 | 5-FURAN-3-YL-3-(TOLUENE-2-SULFONYLAMINO)-THIOPHENE-2-CARBOXYLIC ACID |
| Compound 127 | 5-BENZOFURAN-2-YL-3-(TOLUENE-2-SULFONYLAMINO)-THIOPHENE-2-CARBOXYLIC ACID |
| Compound 128 | 5-PYRIDIN-2-YL-3-(TOLUENE-2-SULFONYLAMINO)-THIOPHENE-2-CARBOXYLIC ACID |
| Compound 129 | 5-(4-NITRO-PHENYL)-3-(PYRIDINE-2-SULFONYLAMINO)-THIOPHENE-2-CARBOXYLIC ACID |
| Compound 130 | 3-[(BENZOFURAN-2-CARBONYL)-METHYL-AMINO]-5-PHENYL-THIOPHENE-2-CARBOXYLIC ACID |
| Compound 131 | 3-[(2,4-DIMETHYL-BENZOYL)-METHYL-AMINO]-5-PHENYL-THIOPHENE-2-CARBOXYLIC ACID |
| Compound 132 | 3-[[5-(2-CYANO-PHENYL)-THIOPHEN-2-YLMETHYL]-(2,4-DICHLORO-BENZOYL)-AMINO]-5-PHENYL-THIOPHENE-2-CARBOXYLIC ACID |
| Compound 133 | 5-(4-FLUORO-PHENYL)-3-(PYRIDINE-2-SULFONYLAMINO)-THIOPHENE-2-CARBOXYLIC ACID |
| Compound 134 | 5-[2-(4-CHLORO-PHENYL)-VINYL]-3-(TOLUENE-2-SULFONYLAMINO)-THIOPHENE-2-CARBOXYLIC ACID |
| Compound 135 | 3-BENZENESULFONYLAMINO-5-(4-FLUORO-PHENYL)-THIOPHENE-2-CARBOXYLIC ACID |
| Compound 136 | 3-(2,4-DIMETHYL-BENZENESULFONYLAMINO)-5-PHENYL-THIOPHENE-2-CARBOXYLIC ACID |
| Compound 137 | 5-PHENYL-3-(2-VINYL-BENZENESULFONYLAMINO)-THIOPHENE-2-CARBOXYLIC ACID |
| Compound 138 | 3-(4-BROMO-2,5-DIFLUORO-BENZENESULFONYLAMINO)-5-PHENYL-THIOPHENE-2-CARBOXYLIC ACID |
| Compound 139 | 3-(2-ACETYLAMINO-4-METHYL-THIAZOLE-5-SULFONYLAMINO)-5-PHENYL-THIOPHENE-2-CARBOXYLIC ACID |
| Compound 140 | 3-(4-ACETYL-BENZENESULFONYLAMINO)-5-PHENYL-THIOPHENE-2-CARBOXYLIC ACID |
| Compound 141 | 3-(4-FLUORO-2-TRIFLUOROMETHYL-BENZENESULFONYLAMINO)-5-PHENYL-THIOPHENE-2-CARBOXYLIC ACID |
| Compound 142 | 3-(2-METHOXY-4-METHYL-BENZENESULFONYLAMINO)-5-PHENYL-THIOPHENE-2-CARBOXYLIC ACID |
| Compound 143 | 3-(3,4-DIFLUORO-BENZENESULFONYLAMINO)-5-PHENYL-THIOPHENE-2-CARBOXYLIC ACID |
| Compound 144 | 4-(2-CARBOXY-5-PHENYL-THIOPHEN-3-YLSULFAMOYL)-5-(4-CHLORO-PHENYL)-2-METHYL-FURAN-3-CARBOXYLIC ACID ETHYL ESTER |
| Compound 145 | 3-(4-FLUORO-3-TRIFLUOROMETHYL-BENZENESULFONYLAMINO)-5-PHENYL-THIOPHENE-2-CARBOXYLIC ACID |

| | -continued |
|---|---|
| Compound 146 | 3-(2-AMINO-BENZENESULFONYLAMINO)-5-PHENYL-THIOPHENE-2-CARBOXYLIC ACID |
| Compound 147 | 3-(3-NITRO-BENZENESULFONYLAMINO)-5-PHENYL-THIOPHENE-2-CARBOXYLIC ACID |
| Compound 148 | 3-(4-NITRO-BENZENESULFONYLAMINO)-5-PHENYL-THIOPHENE-2-CARBOXYLIC ACID |
| Compound 149 | 3-[(2,4-DICHLORO-BENZOYL)-ISOPROPYL-AMINO]-5-PHENYL-THIOPHENE-2-CARBOXYLIC ACID |
| Compound 150 | 5-(3-CYANO-BENZYL)-3-(TOLUENE-2-SULFONYLAMINO)-THIOPHENE-2-CARBOXYLIC ACID |
| Compound 151 | 5-PHENYL-3-(2,4,6-TRIFLUORO-BENZENESULFONYLAMINO)-THIOPHENE-2-CARBOXYLIC ACID |
| Compound 152 | 3-(4-METHOXY-2-NITRO-BENZENESULFONYLAMINO)-5-PHENYL-THIOPHENE-2-CARBOXYLIC ACID |
| Compound 153 | 5-PHENYL-3-(2,3,4-TRICHLORO-BENZENESULFONYLAMINO)-THIOPHENE-2-CARBOXYLIC ACID |
| Compound 154 | 5-(2-CARBOXY-5-PHENYL-THIOPHEN-3-YLSULFAMOYL)-2-METHYL-FURAN-3-CARBOXYLIC ACID METHYL ESTER |
| Compound 155 | 4-(2-CARBOXY-5-PHENYL-THIOPHEN-3-YLSULFAMOYL)-2-METHYL-1,5-DIPHENYL-1H-PYRROLE-3-CARBOXYLIC ACID ETHYL ESTER |
| Compound 156 | 5-PHENYL-3-{[4-(3-TRIFLUOROMETHYL-PHENYL)-PIPERAZINE-1-CARBONYL]-AMIN}-THIOPHENE-2-CARBOXYLIC ACID |
| Compound 157 | 3-{[4-(4-FLUORO-PHENYL)-PIPERAZINE-1-CARBONYL]-AMINO}-5-PHENYL-THIOPHENE-2-CARBOXYLIC ACID |
| Compound 158 | 3-{[4-(2,6-DIMETHYL-PHENYL)-PIPERAZINE-1-CARBONYL]-AMINO}-5-PHENYL-THIOPHENE-2-CARBOXYLIC ACID |
| Compound 159 | 3-{[4-(2-CHLORO-PHENYL)-PIPERAZINE-1-CARBONYL]-AMINO}-5-PHENYL-THIOPHENE-2-CARBOXYLIC ACID |
| Compound 160 | 3-{[4-(3-CHLORO-PHENYL)-PIPERAZINE-1-CARBONYL]-AMINO}-5-PHENYL-THIOPHENE-2-CARBOXYLIC ACID |
| Compound 161 | 4,4'-BIS-(TOLUENE-2-SULFONYLAMINO)-[2,2']BITHIOPHENYL-5,5'-DICARBOXYLIC ACID |
| Compound 162 | 3-[ALLYL-(4-METHYL-BENZOYL)-AMINO]-5-PHENYL-THIOPHENE-2-CARBOXYLIC ACID |
| Compound 163 | 5-(1-DIMETHYLSULFAMOYL-1H-PYRAZOL-4-YL)-3-(TOLUENE-2-SULFONYLAMINO)-THIOPHENE-2-CARBOXYLIC ACID |
| Compound 164 | 5-(3-AMINO-PHENYL)-3-(TOLUENE-2-SULFONYLAMINO)-THIOPHENE-2-CARBOXYLIC ACID |
| Compound 165 | 5-(4-AMINO-PHENYL)-3-(TOLUENE-2-SULFONYLAMINO)-THIOPHENE-2-CARBOXYLIC ACID |
| Compound 166 | 5-(4-ACETYL-PHENYL)-3-(TOLUENE-2-SULFONYLAMINO)-THIOPHENE-2-CARBOXYLIC ACID |
| Compound 167 | 4-(2-CARBOXY-5-PHENYL-THIOPHEN-3-YLSULFAMOYL)-2,5-DIMETHYL-1H-PYRROLE-3-CARBOXYLIC ACID ETHYL ESTER |
| Compound 168 | 4-(2-CARBOXY-5-PHENYL-THIOPHEN-3-YLSULFAMOYL)-5-(4-CHLORO-PHENYL)-3-METHYL-1-PHENYL-1H-PYRROLE-2-CARBOXYLIC ACID ETHYL ESTER |
| Compound 169 | 3-(3,5-DICHLORO-4-HYDROXY-BENZENESULFONYLAMINO)-5-PHENYL-THIOPHENE-2-CARBOXYLIC ACID |
| Compound 170 | 5-(1H-PYRAZOL-4-YL)-3-(TOLUENE-2-SULFONYLAMINO)-THIOPHENE-2-CARBOXYLIC ACID |
| Compound 171 | 5-(3-HYDROXY-PHENYL)-3-(TOLUENE-2-SULFONYLAMINO)-THIOPHENE-2-CARBOXYLIC ACID |
| Compound 172 | 3-[METHYL-(3-METHYL-BUTYRYL)-AMINO]-5-PHENYL-THIOPHENE-2-CARBOXYLIC ACID |
| Compound 173 | 3-{[2-(4-FLUORO-PHENYL)-ACETYL]-METHYL-AMINO}-5-PHENYL-THIOPHENE-2-CARBOXYLIC ACID |
| Compound 174 | 3-(4-PENTYL-BENZENESULFONYLAMINO)-5-PHENYL-THIOPHENE-2-CARBOXYLIC ACID |
| Compound 175 | 3-(METHYL-PHENYLACETYL-AMINO)-5-PHENYL-THIOPHENE-2-CARBOXYLIC ACID |
| Compound 176 | 3-[2,5-BIS-(2,2,2-TRIFLUORO-ETHOXY)-BENZENESULFONYLAMINO]-5-PHENYL-THIOPHENE-2-CARBOXYLIC ACID |
| Compound 177 | 3-(4-METHYL-2-NITRO-BENZENESULFONYLAMINO)-5-PHENYL-THIOPHENE-2-CARBOXYLIC ACID |
| Compound 178 | 5-THIAZOL-2-YL-3-(TOLUENE-2-SULFONYLAMINO)-THIOPHENE-2-CARBOXYLIC ACID |
| Compound 179 | 5-PHENYL-3-[3-(3-PHENYL-PROPYL)-UREIDO]-THIOPHENE-2-CARBOXYLIC ACID |
| Compound 180 | 3-[(3,4-DIHYDRO-1H-ISOQUINOLINE-2-CARBONYL)-AMINO]-5-PHENYL-THIOPHENE-2-CARBOXYLIC ACID |
| Compound 181 | 3-{[4-(4-METHOXY-PHENYL)-PIPERAZINE-1-CARBONYL]-AMINO}-5-PHENYL-THIOPHENE-2-CARBOXYLIC ACID |
| Compound 182 | 3-{[4-(6-METHYL-PYRIDIN-2-YL)-PIPERAZINE-1-CARBONYL]-AMINO}-5-PHENYL-THIOPHENE-2-CARBOXYLIC ACID HYDROCHLORIDE |
| Compound 183 | 3-{[4-(4-CHLORO-BENZYL)-PIPERAZINE-1-CARBONYL]-AMINO}-5-PHENYL-THIOPHENE-2-CARBOXYLIC ACID HYDROCHLORIDE |
| Compound 184 | 5-(5-METHYL-PYRIDIN-2-YL)-3-(TOLUENE-2-SULFONYLAMINO)-THIOPHENE-2-CARBOXYLIC ACID |

| | |
|---|---|
| Compound 185 | 3-[ETHYL-(4-METHYL-BENZOYL)-AMINO]-5-PHENYL-THIOPHENE-2-CARBOXYLIC ACID |
| Compound 186 | 3-[(3-CHLORO-THIOPHENE-2-CARBONYL)-METHYL-AMINO]-5-PHENYL-THIOPHENE-2-CARBOXYLIC ACID |
| Compound 187 | 3-[(2-BROMO-BENZOYL)-METHYL-AMINO]-5-PHENYL-THIOPHENE-2-CARBOXYLIC ACID |
| Compound 188 | 3-[(4-BUTYL-BENZOYL)-METHYL-AMINO]-5-PHENYL-THIOPHENE-2-CARBOXYLIC ACID |
| Compound 189 | 3-(2-CHLOROMETHYL-BENZENESULFONYLAMINO)-5-PHENYL-THIOPHENE-2-CARBOXYLIC ACID |
| Compound 190 | 5-(4-HYDROXY-PHENYL)-3-(TOLUENE-2-SULFONYLAMINO)-THIOPHENE-2-CARBOXYLIC ACID |
| Compound 191 | 5-(5-CHLORO-PYRIDIN-2-YL)-3-(TOLUENE-2-SULFONYLAMINO)-THIOPHENE-2-CARBOXYLIC ACID |
| Compound 192 | 5-(4-CHLORO-PHENYL)-3-[METHYL-(4-METHYL-BENZOYL)-AMINO]-THIOPHENE-2-CARBOXYLIC ACID |
| Compound 193 | 5-(4-CYANO-PHENYL)-3-[METHYL-(4-METHYL-BENZOYL)-AMINO]-THIOPHENE-2-CARBOXYLIC ACID |
| Compound 194 | 3-[METHYL-(4-METHYL-BENZOYL)-AMINO]-5-(4-NITRO-PHENYL)-THIOPHENE-2-CARBOXYLIC ACID |
| Compound 195 | 5-(4-HYDROXYMETHYL-PHENYL)-3-[METHYL-(4-METHYL-BENZOYL)-AMINO]-THIOPHENE-2-CARBOXYLIC ACID |
| Compound 196 | 3-[METHYL-(4-METHYL-BENZOYL)-AMINO]-5-(3-NITRO-PHENYL)-THIOPHENE-2-CARBOXYLIC ACID |
| Compound 197 | 5-(4-FLUORO-PHENYL)-3-[METHYL-(4-METHYL-BENZOYL)-AMINO]-THIOPHENE-2-CARBOXYLIC ACID |
| Compound 198 | 5-(4-METHOXY-PHENYL)-3-[METHYL-(4-METHYL-BENZOYL)-AMINO]-THIOPHENE-2-CARBOXYLIC ACID |
| Compound 199 | 3-[METHYL-(4-METHYL-BENZOYL)-AMINO]-5-P-TOLYL-THIOPHENE-2-CARBOXYLIC ACID |
| Compound 200 | 5-(4-AMINO-PHENYL)-3-[METHYL-(4-METHYL-BENZOYL)-AMINO]-THIOPHENE-2-CARBOXYLIC ACID |
| Compound 201 | 3-[CYCLOPENTYL-(2,4-DICHLORO-BENZOYL)-AMINO]-5-PHENYL-THIOPHENE-2-CARBOXYLIC ACID |
| Compound 202 | 5-BENZO[1,3]DIOXOL-5-YL-3-(TOLUENE-2-SULFONYLAMINO)-THIOPHENE-2-CARBOXYLIC ACID |
| Compound 203 | 3-[(2-HYDROXY-ETHYL)-(4-METHYL-BENZOYL)-AMINO]-5-PHENYL-THIOPHENE-2-CARBOXYLIC ACID |
| Compound 204 | 3-[(2,4-DICHLORO-BENZOYL)-ISOBUTYL-AMINO]-5-PHENYL-THIOPHENE-2-CARBOXYLIC ACID |
| Compound 205 | 3-[(2-METHOXY-4-METHYL-BENZOYL)-METHYL-AMINO]-5-PHENYL-THIOPHENE-2-CARBOXYLIC ACID |
| Compound 206 | 5-(3-CYANO-PHENYL)-3-[METHYL-(4-METHYL-BENZOYL)-AMINO]-THIOPHENE-2-CARBOXYLIC ACID |
| Compound 207 | 5-(2-CHLORO-PHENYL)-3-[METHYL-(4-METHYL-BENZOYL)-AMINO]-THIOPHENE-2-CARBOXYLIC ACID |
| Compound 208 | 3-[(2,4-DICHLORO-BENZOYL)-PHENYL-AMINO]-5-PHENYL-THIOPHENE-2-CARBOXYLIC ACID |
| Compound 209 | 3-[4-(TRIFLUOROMETHYL-BENZOYL)METHYLAMINE]-5-PHENYL-THIOPHENE-2-CARBOXYLIC ACID |
| Compound 210 | 3-[(4-CHLORO-BENZOYL)-ISOPROPYL-AMINO]-5-PHENYL-THIOPHENE-2-CARBOXYLIC ACID |
| Compound 211 | 3-[ISOPROPYL-(4-METHYL-BENZOYL)-AMINO]-5-PHENYL-THIOPHENE-2-CARBOXYLIC ACID |
| Compound 212 | 5-(3,5-DIFLUORO-PHENYL)-3-[METHYL-(4-METHYL-BENZOYL)-AMINO]-THIOPHENE-2-CARBOXYLIC ACID |
| Compound 213 | 5-(3-FLUORO-PHENYL)-3-[METHYL-(4-METHYL-BENZOYL)-AMINO]-THIOPHENE-2-CARBOXYLIC ACID |
| Compound 214 | 5-(2,4-DIFLUORO-PHENYL)-3-[METHYL-(4-METHYL-BENZOYL)-AMINO]-THIOPHENE-2-CARBOXYLIC ACID |
| Compound 215 | 5-(4-HYDROXY-PHENYL)-3-[METHYL-(4-METHYL-BENZOYL)-AMINO]-THIOPHENE-2-CARBOXYLIC ACID |
| Compound 216 | 3-[METHYL-(4-METHYL-BENZOYL)-AMINO]-5-(4-TRIFLUOROMETHOXY-PHENYL)-THIOPHENE-2-CARBOXYLIC ACID |
| Compound 217 | 5-(2-HYDROXY-PHENYL)-3-(TOLUENE-2-SULFONYLAMINO)-THIOPHENE-2-CARBOXYLIC ACID |
| Compound 218 | 3-[(2-CHLORO-BENZOYL)-ISOPROPYL-AMINO]-5-PHENYL-THIOPHENE-2-CARBOXYLIC ACID |
| Compound 219 | 3-[(3,5-DICHLORO-BENZOYL)-ISOPROPYL-AMINO]-5-PHENYL-THIOPHENE-2-CARBOXYLIC ACID |
| Compound 220 | 3-(4-BROMO-2-METHYL-BENZENESULFONYLAMINO)-5-PHENYL-THIOPHENE-2-CARBOXYLIC ACID |
| Compound 221 | 3-(5-CARBOXY-4-CHLORO-2-FLUORO-BENZENESULFONYLAMINO)-5-PHENYL-THIOPHENE-2-CARBOXYLIC ACID |
| Compound 222 | 5-PHENYL-3-(2,3,4-TRIFLUORO-BENZENESULFONYLAMINO)-THIOPHENE-2-CARBOXYLIC ACID |
| Compound 223 | 3-(4-BROMO-2-FLUORO-BENZENESULFONYLAMINO)-5-(4-ISOBUTYL-PHENYL)-THIOPHENE-2-CARBOXYLIC ACID |
| Compound 224 | 3-(4-BROMO-2-METHYL-BENZENESULFONYLAMINO)-5-(4-ISOBUTYL-PHENYL)-THIOPHENE-2-CARBOXYLIC ACID |

-continued

| | |
|---|---|
| Compound 225 | 5-(4-ISOBUTYL-PHENYL)-3-(3-METHOXY-BENZENESULFONYLAMINO)-THIOPHENE-2-CARBOXYLIC ACID |
| Compound 226 | 3-[(4-FLUORO-BENZOYL)-ISOPROPYL-AMINO]-5-PHENYL-THIOPHENE-2-CARBOXYLIC ACID |
| Compound 227 | 3-[2,5-BIS-(2,2,2-TRIFLUORO-ETHOXY)-BENZENESULFONYLAMINO]-5-(4-ISOBUTYL-PHENYL)-THIOPHENE-2-CARBOXYLIC ACID |
| Compound 228 | 3-(2-CHLORO-4-CYANO-BENZENESULFONYLAMINO)-5-(4-ISOBUTYL-PHENYL)-THIOPHENE-2-CARBOXYLIC ACID |
| Compound 229 | 5'-ACETYL-4-(TOLUENE-2-SULFONYLAMINO)-[2,2']BITHIOPHENYL-5-CARBOXYLIC ACID |
| Compound 230 | 5-BENZO[B]THIOPHEN-2-YL-3-(TOLUENE-2-SULFONYLAMINO)-THIOPHENE-2-CARBOXYLIC ACID |
| Compound 231 | 5-(4-BUTYL-PHENYL)-3-(TOLUENE-2-SULFONYLAMINO)-THIOPHENE-2-CARBOXYLIC ACID |
| Compound 232 | 5-(4-ETHYL-PHENYL)-3-(TOLUENE-2-SULFONYLAMINO)-THIOPHENE-2-CARBOXYLIC ACID |
| Compound 233 | 3-[BENZYL-(2,4-DICHLORO-BENZOYL)-AMINO]-5-PHENYL-THIOPHENE-2-CARBOXYLIC ACID |
| Compound 234 | 3-[(4-CHLORO-2-METHYL-BENZOYL)-ISOPROPYL-AMINO]-5-PHENYL-THIOPHENE-2-CARBOXYLIC ACID |
| Compound 235 | 3-[(2,4-DIMETHYL-BENZENESULFONYL)-METHYL-AMINO]-5-PHENYL-THIOPHENE-2-CARBOXYLIC ACID |
| Compound 236 | 5-(4-ACETYL-PHENYL)-3-(2,4-DIMETHYL-BENZENESULFONYLAMINO)-THIOPHENE-2-CARBOXYLIC ACID |
| Compound 237 | 5-(4-ACETYL-PHENYL)-3-(TOLUENE-4-SULFONYLAMINO)-THIOPHENE-2-CARBOXYLIC ACID |
| Compound 238 | 5-(4-ACETYL-PHENYL)-3-(4-CHLORO-BENZENESULFONYLAMINO)-THIOPHENE-2-CARBOXYLIC ACID |
| Compound 239 | 5-(4-CARBOXY-PHENYL)-3-(TOLUENE-2-SULFONYLAMINO)-THIOPHENE-2-CARBOXYLIC ACID TERT-BUTYL ESTER |
| Compound 240 | 3-[(2,4-DIMETHYL-BENZENESULFONYL)-ISOPROPYL-AMINO]-5-PHENYL-THIOPHENE-2-CARBOXYLIC ACID |
| Compound 241 | 3-[ACETYL-(4-CHLORO-BENZYL)-AMINO]-5-PHENYL-THIOPHENE-2-CARBOXYLIC ACID |
| Compound 242 | 3-ETHANESULFONYLAMINO-5-PHENYL-THIOPHENE-2-CARBOXYLIC ACID |
| Compound 243 | 3-[ISOPROPYL-(4-TRIFLUOROMETHYL-BENZOYL)-AMINO]-5-PHENYL-THIOPHENE-2-CARBOXYLIC ACID |
| Compound 244 | 3-[(2,4-DICHLORO-BENZOYL)-(3-METHYL-BUT-2-ENYL)-AMINO]-5-PHENYL-THIOPHENE-2-CARBOXYLIC ACID |
| Compound 245 | 3-[(2,6-DICHLORO-PYRIDINE-3-CARBONYL)-METHYL-AMINO]-5-PHENYL-THIOPHENE-2-CARBOXYLIC ACID |
| Compound 246 | 3-[(6-CHLORO-PYRIDINE-3-CARBONYL)-ISOPROPYL-AMINO]-5-PHENYL-THIOPHENE-2-CARBOXYLIC ACID |
| Compound 247 | 3-[(4-TERT-BUTYL-BENZOYL)-METHYL-AMINO]-5-PHENYL-THIOPHENE-2-CARBOXYLIC ACID |
| Compound 248 | 5-(4-CARBOXY-PHENYL)-3-(TOLUENE-2-SULFONYLAMINO)-THIOPHENE-2-CARBOXYLIC ACID |
| Compound 249 | 5-(4-ETHOXY-PHENYL)-3-(TOLUENE-2-SULFONYLAMINO)-THIOPHENE-2-CARBOXYLIC ACID |
| Compound 250 | 3-[(2,6-DICHLORO-PYRIDINE-3-CARBONYL)-ISOPROPYL-AMINO]-5-PHENYL-THIOPHENE-2-CARBOXYLIC ACID |
| Compound 251 | 3-[(BENZO[B]THIOPHENE-2-CARBONYL)-METHYL-AMINO]-5-PHENYL-THIOPHENE-2-CARBOXYLIC ACID |
| Compound 252 | 3-[METHYL-(NAPHTHALENE-2-CARBONYL)-AMINO]-5-PHENYL-THIOPHENE-2-CARBOXYLIC ACID |
| Compound 253 | 3-[(3,4-DICHLORO-BENZOYL)-METHYL-AMINO]-5-PHENYL-THIOPHENE-2-CARBOXYLIC ACID |
| Compound 254 | 3-[(3,5-DICHLORO-BENZOYL)-METHYL-AMINO]-5-PHENYL-THIOPHENE-2-CARBOXYLIC ACID |
| Compound 255 | 3-[(4-BROMO-3-METHYL-BENZOYL)-METHYL-AMINO]-5-PHENYL-THIOPHENE-2-CARBOXYLIC ACID |
| Compound 256 | 3-[(3-CHLORO-BENZO[B]THIOPHENE-2-CARBONYL)-METHYL-AMINO]-5-PHENYL-THIOPHENE-2-CARBOXYLIC ACID |
| Compound 257 | 3-[METHYL-(4-METHYL-3-NITRO-BENZOYL)-AMINO]-5-PHENYL-THIOPHENE-2-CARBOXYLIC ACID |
| Compound 258 | 5-(4-CARBAMOYL-PHENYL)-3-(2,4-DIMETHYL-BENZENESULFONYLAMINO)-THIOPHENE-2-CARBOXYLIC ACID |
| Compound 259 | 5-(4-CARBAMOYL-PHENYL)-3-(TOLUENE-4-SULFONYLAMINO)-THIOPHENE-2-CARBOXYLIC ACID |
| Compound 260 | 5-(1H-INDOL-5-YL)-3-(TOLUENE-2-SULFONYLAMINO)-THIOPHENE-2-CARBOXYLIC ACID |
| Compound 261 | 3-[SEC-BUTYL-(2,4-DICHLORO-BENZOYL)-AMINO]-5-PHENYL-THIOPHENE-2-CARBOXYLIC ACID |
| Compound 262 | 3-[(2,4-DIMETHYL-BENZOYL)-ISOPROPYL-AMINO]-5-PHENYL-THIOPHENE-2-CARBOXYLIC ACID |
| Compound 263 | 5-(4-AZIDO-PHENYL)-3-(TOLUENE-2-SULFONYLAMINO)-THIOPHENE-2-CARBOXYLIC ACID |
| Compound 264 | 3-[(2,4-DICHLORO-BENZOYL)-(1-PHENYL-ETHYL)-AMINO]-5-PHENYL-THIOPHENE-2-CARBOXYLIC ACID |

-continued

| | |
|---|---|
| Compound 265 | 5-(4-CARBAMOYL-PHENYL)-3-(4-CHLORO-BENZENESULFONYLAMINO)-THIOPHENE-2-CARBOXYLIC ACID |
| Compound 266 | 5-(2-FLUORO-PHENYL)-3-[METHYL-(4-METHYL-BENZOYL)-AMINO]-THIOPHENE-2-CARBOXYLIC ACID |
| Compound 267 | 3-[METHYL-(4-METHYL-BENZOYL)-AMINO]-5-O-TOLYL-THIOPHENE-2-CARBOXYLIC ACID |
| Compound 268 | 3-[METHYL-(4-METHYL-BENZOYL)-AMINO]-5-M-TOLYL-THIOPHENE-2-CARBOXYLIC ACID |
| Compound 269 | 5-(3-CHLORO-PHENYL)-3-[METHYL-(4-METHYL-BENZOYL)-AMINO]-THIOPHENE-2-CARBOXYLIC ACID |
| Compound 270 | 5-(3,4-DIFLUORO-PHENYL)-3-[METHYL-(4-METHYL-BENZOYL)-AMINO]-THIOPHENE-2-CARBOXYLIC ACID |
| Compound 271 | 5-(3-AMINO-PHENYL)-3-[METHYL-(4-METHYL-BENZOYL)-AMINO]-THIOPHENE-2-CARBOXYLIC ACID |
| Compound 272 | 5-(3-ACETYL-PHENYL)-3-[METHYL-(4-METHYL-BENZOYL)-AMINO]-THIOPHENE-2-CARBOXYLIC ACID |
| Compound 273 | 5-(3-HYDROXY-PHENYL)-3-[METHYL-(4-METHYL-BENZOYL)-AMINO]-THIOPHENE-2-CARBOXYLIC ACID |
| Compound 274 | 3-[METHYL-(4-METHYL-BENZOYL)-AMINO]-5-(3-TRIFLUOROMETHYL-PHENYL)-THIOPHENE-2-CARBOXYLIC ACID |
| Compound 275 | 3-[METHYL-(4-METHYL-BENZOYL)-AMINO]-5-(4-TRIFLUOROMETHYL-PHENYL)-THIOPHENE-2-CARBOXYLIC ACID |
| Compound 276 | 3-[(3,4-DIMETHOXY-BENZOYL)-METHYL-AMINO]-5-PHENYL-THIOPHENE-2-CARBOXYLIC ACID |
| Compound 277 | 3-[METHYL-(2,4,6-TRIFLUORO-BENZOYL)-AMINO]-5-PHENYL-THIOPHENE-2-CARBOXYLIC ACID |
| Compound 278 | 3-[(2,3-DIFLUORO-4-TRIFLUOROMETHYL-BENZOYL)-METHYL-AMINO]-5-PHENYL-THIOPHENE-2-CARBOXYLIC ACID |
| Compound 279 | 3-[(3-FLUORO-4-TRIFLUOROMETHYL-BENZOYL)-METHYL-AMINO]-5-PHENYL-THIOPHENE-2-CARBOXYLIC ACID |
| Compound 280 | 3-[(2,3-DIFLUORO-4-METHYL-BENZOYL)-METHYL-AMINO]-5-PHENYL-THIOPHENE-2-CARBOXYLIC ACID |
| Compound 281 | 3-[(2-FLUORO-4-TRIFLUOROMETHYL-BENZOYL)-METHYL-AMINO]-5-PHENYL-THIOPHENE-2-CARBOXYLIC ACID |
| Compound 282 | 5-(4-CARBAMOYL-PHENYL)-3-(TOLUENE-2-SULFONYLAMINO)-THIOPHENE-2-CARBOXYLIC ACID |
| Compound 283 | 5-(4-FLUORO-PHENYL)-3-[ISOPROPYL-(4-METHYL-BENZOYL)-AMINO]-THIOPHENE-2-CARBOXYLIC ACID |
| Compound 284 | 3-[(2-BROMO-4-CHLORO-BENZOYL)-METHYL-AMINO]-5-PHENYL-THIOPHENE-2-CARBOXYLIC ACID |
| Compound 285 | 3-(2,6-DIMETHYL-BENZENESULFONYLAMINO)-5-PHENYL-THIOPHENE-2-CARBOXYLIC ACID |
| Compound 286 | 3-[METHYL-(4-METHYL-CYCLOHEXANECARBONYL)-AMINO]-5-PHENYL-THIOPHENE-2-CARBOXYLIC ACID |
| Compound 287 | 3-[(2,4-DICHLORO-BENZOYL)-ISOPROPYL-AMINO]-5-PHENYL-THIOPHENE-2-CARBOXYLIC ACID METHYL ESTER |
| Compound 288 | 5-(4-CYANO-PHENYL)-3-(2,4-DIMETHYL-BENZENESULFONYLAMINO)-THIOPHENE-2-CARBOXYLIC ACID |
| Compound 289 | 3-(4-CHLORO-BENZENESULFONYLAMINO)-5-(4-CYANO-PHENYL)-THIOPHENE-2-CARBOXYLIC ACID |
| Compound 290 | 5-(4-CYANO-PHENYL)-3-(TOLUENE-4-SULFONYLAMINO)-THIOPHENE-2-CARBOXYLIC ACID |
| Compound 291 | 5'-ACETYL-4-(2,4-DIMETHYL-BENZENESULFONYLAMINO)-[2,2']BITHIOPHENYL-5-CARBOXYLIC ACID |
| Compound 292 | 5'-ACETYL-4-(2,6-DIMETHYL-BENZENESULFONYLAMINO)-[2,2']BITHIOPHENYL-5-CARBOXYLIC ACID |
| Compound 293 | 3-[METHYL-(4-METHYL-THIOPHENE-2-CARBONYL)-AMINO]-5-PHENYL-THIOPHENE-2-CARBOXYLIC ACID |
| Compound 294 | 5-(3-CHLORO-PHENYL)-3-[(2,4-DICHLORO-BENZOYL)-ISOPROPYL-AMINO]-THIOPHENE-2-CARBOXYLIC ACID |
| Compound 295 | 5'-CYANO-4-(TOLUENE-2-SULFONYLAMINO)-[2,2']BITHIOPHENYL-5-CARBOXYLIC ACID |
| Compound 296 | 3-[METHYL-(4-METHYL-BENZOYL)-AMINO]-5-PYRIDIN-2-YL-THIOPHENE-2-CARBOXYLIC ACID |
| Compound 297 | 3-[(2,4-DICHLORO-THIOBENZOYL)-ISOPROPYL-AMINO]-5-PHENYL-THIOPHENE-2-CARBOXYLIC ACID |
| Compound 298 | 5-PHENYL-3-(2,4,6-TRIMETHYL-BENZENESULFONYLAMINO)-THIOPHENE-2-CARBOXYLIC ACID |
| Compound 299 | 3-[(1-CARBOXY-ETHYL)-(2,4-DICHLORO-BENZOYL)-AMINO]-5-PHENYL-THIOPHENE-2-CARBOXYLIC ACID |
| Compound 300 | 3-[(4-METHYL-BENZOYL)-(3-METHYL-BUT-2-ENYL)-AMINO]-5-PHENYL-THIOPHENE-2-CARBOXYLIC ACID |
| Compound 301 | 3-[(2-HYDROXY-4-METHYL-BENZOYL)-ISOPROPYL-AMINO]-5-PHENYL-THIOPHENE-2-CARBOXYLIC ACID |
| Compound 302 | 3-[METHYL-(4-METHYL-BENZOYL)-AMINO]-5-PYRIDIN-3-YL-THIOPHENE-2-CARBOXYLIC ACID |
| Compound 303 | 5'-ACETYL-4-[METHYL-(4-METHYL-BENZOYL)-AMINO]-[2,2']BITHIOPHENYL-5-CARBOXYLIC ACID |
| Compound 304 | 3-[ISOPROPYL-(4-METHYL-BENZOYL)-AMINO]-5-(3-TRIFLUOROMETHYL-PHENYL)-THIOPHENE-2-CARBOXYLIC ACID |

-continued

| | |
|---|---|
| Compound 305 | 3-[ISOPROPYL-(4-METHYL-BENZOYL)-AMINO]-5-M-TOLYL-THIOPHENE-2-CARBOXYLIC ACID |
| Compound 306 | 3-[(2-BROMO-4-CHLORO-BENZOYL)-ISOPROPYL-AMINO]-5-PHENYL-THIOPHENE-2-CARBOXYLIC ACID |
| Compound 307 | 3-[(4-CHLORO-2-FLUORO-BENZOYL)-ISOPROPYL-AMINO]-5-PHENYL-THIOPHENE-2-CARBOXYLIC ACID |
| Compound 308 | 3-(2,4-DIMETHYL-BENZENESULFONYLAMINO)-4-METHYL-5-PHENYL-THIOPHENE-2-CARBOXYLIC ACID |
| Compound 309 | 3-[(2-BROMO-4-METHYL-BENZOYL)-ISOPROPYL-AMINO]-5-PHENYL-THIOPHENE-2-CARBOXYLIC ACID |
| Compound 310 | 3-[(4-CHLORO-2-IODO-BENZOYL)-ISOPROPYL-AMINO]-5-PHENYL-THIOPHENE-2-CARBOXYLIC ACID |
| Compound 311 | 3-[(4-CYANO-BENZOYL)-ISOPROPYL-AMINO]-5-PHENYL-THIOPHENE-2-CARBOXYLIC ACID |
| Compound 312 | 3-[ALLYL-(4-METHYL-BENZOYL)-AMINO]-5-[4-(2-CARBOXY-VINYL)-PHENYL]-THIOPHENE-2-CARBOXYLIC ACID |
| Compound 313 | 3-[(4-CHLORO-2-HYDROXY-BENZOYL)-ISOPROPYL-AMINO]-5-PHENYL-THIOPHENE-2-CARBOXYLIC ACID |
| Compound 314 | 3-[(2,4-DICHLORO-BENZOYL)-ISOPROPYL-AMINO]-4-METHYL-5-PHENYL-THIOPHENE-2-CARBOXYLIC ACID |
| Compound 315 | 5-TERT-BUTYL-3-(2,4-DIMETHYL-BENZENESULFONYLAMINO)-THIOPHENE-2-CARBOXYLIC ACID |
| Compound 316 | 3-[ISOPROPYL-(4-METHYL-CYCLOHEXANECARBONYL)-AMINO]-5-PHENYL-THIOPHENE-2-CARBOXYLIC ACID |
| Compound 317 | 3-[ISOPROPYL-(4-METHYL-CYCLOHEXANECARBONYL)-AMINO]-5-PHENYL-THIOPHENE-2-CARBOXYLIC ACID |
| Compound 318 | 5-[4-(2-CARBOXY-ETHYL)-PHENYL]-3-[(4-METHYL-BENZOYL)-PROPYL-AMINO]-THIOPHENE-2-CARBOXYLIC ACID |
| Compound 319 | 5-BENZOFURAN-2-YL-3-(2,4-DIMETHYL-BENZENESULFONYLAMINO)-THIOPHENE-2-CARBOXYLIC ACID |
| Compound 320 | 3-(2,4-DIMETHYL-BENZENESULFONYLAMINO)-5-(4-HYDROXYMETHYL-PHENYL)-THIOPHENE-2-CARBOXYLIC ACID |
| Compound 321 | 3-(2,4-DIMETHYL-BENZENESULFONYLAMINO)-5-(4-METHANESULFONYL-PHENYL)-THIOPHENE-2-CARBOXYLIC ACID |
| Compound 322 | 5-[4-(2-CARBOXY-VINYL)-PHENYL]-3-(2,4-DIMETHYL-BENZENESULFONYLAMINO)-THIOPHENE-2-CARBOXYLIC ACID |
| Compound 323 | 3-[ALLYL-(4-METHYL-BENZOYL)-AMINO]-5-[3-(2-CARBOXY-VINYL)-PHENYL]-THIOPHENE-2-CARBOXYLIC ACID |
| Compound 324 | 3-[ISOPROPYL-(2,4,6-TRIMETHYL-BENZOYL)-AMINO]-5-PHENYL-THIOPHENE-2-CARBOXYLIC ACID |
| Compound 325 | 5-[3-(2-CARBOXY-ETHYL)-PHENYL]-3-[(4-METHYL-BENZOYL)-PROPYL-AMINO]-THIOPHENE-2-CARBOXYLIC ACID |
| Compound 326 | 3-[(2-FLUORO-4-TRIFLUOROMETHYL-BENZOYL)-ISOPROPYL-AMINO]-5-PHENYL-THIOPHENE-2-CARBOXYLIC ACID |
| Compound 327 | 3-[TERT-BUTYL-(2,4-DICHLORO-BENZOYL)-AMINO]-5-PHENYL-THIOPHENE-2-CARBOXYLIC ACID |
| Compound 328 | 3-[(2-AMINO-4-CHLORO-BENZOYL)-ISOPROPYL-AMINO]-5-PHENYL-THIOPHENE-2-CARBOXYLIC ACID |
| Compound 329 | 3-[(4-CHLORO-2-NITRO-BENZOYL)-ISOPROPYL-AMINO]-5-PHENYL-THIOPHENE-2-CARBOXYLIC ACID |
| Compound 330 | 3-[(4-METHYL-BENZOYL)-(3-TRIFLUOROMETHYL-BENZYL)-AMINO]-5-PHENYL-THIOPHENE-2-CARBOXYLIC ACID |
| Compound 331 | 3-[(3-FLUORO-4-METHYL-BENZOYL)-ISOPROPYL-AMINO]-5-PHENYL-THIOPHENE-2-CARBOXYLIC ACID |
| Compound 332 | 5-(4-CARBOXY-PHENYL)-3-(2,4-DIMETHYL-BENZENESULFONYLAMINO)-THIOPHENE-2-CARBOXYLIC ACID |
| Compound 333 | 3-[CYCLOPROPYL-(2,4-DICHLORO-BENZOYL)-AMINO]-5-PHENYL-THIOPHENE-2-CARBOXYLIC ACID |
| Compound 334 | 3-[(3-TERT-BUTYL-BENZYL)-(4-METHYL-BENZOYL)-AMINO]-5-PHENYL-THIOPHENE-2-CARBOXYLIC ACID |
| Compound 335 | 3-[(3-CHLORO-BENZYL)-(4-METHYL-BENZOYL)-AMINO]-5-PHENYL-THIOPHENE-2-CARBOXYLIC ACID |
| Compound 336 | 3-[(2,4-DIFLUORO-BENZYL)-(4-METHYL-BENZOYL)-AMINO]-5-PHENYL-THIOPHENE-2-CARBOXYLIC ACID |
| Compound 337 | 3-[(4-CHLORO-2,5-DIFLUORO-BENZOYL)-ISOPROPYL-AMINO]-5-PHENYL-THIOPHENE-2-CARBOXYLIC ACID |
| Compound 338 | 3-[(2,4-DICHLORO-BENZOYL)-ISOPROPYL-AMINO]-5-(2-METHYL-ALLYL)-THIOPHENE-2-CARBOXYLIC ACID |
| Compound 339 | 3-{ALLYL-[2-(4-CHLORO-PHENYL)-ACETYL]-AMINO}-5-PHENYL-THIOPHENE-2-CARBOXYLIC ACID |
| Compound 340 | 3-[BENZYL-(4-METHYL-BENZOYL)-AMINO]-5-PHENYL-THIOPHENE-2-CARBOXYLIC ACID |
| Compound 341 | 3-[(4-CHLORO-BENZYL)-(4-METHYL-BENZOYL)-AMINO]-5-PHENYL-THIOPHENE-2-CARBOXYLIC ACID |
| Compound 342 | 3-[(4-METHYL-BENZOYL)-(4-NITRO-BENZYL)-AMINO]-5-PHENYL-THIOPHENE-2-CARBOXYLIC ACID |
| Compound 343 | 3-[(4-METHYL-BENZOYL)-(2-METHYL-BENZYL)-AMINO]-5-PHENYL-THIOPHENE-2-CARBOXYLIC ACID |
| Compound 344 | 3-[(3-METHOXY-BENZYL)-(4-METHYL-BENZOYL)-AMINO]-5-PHENYL-THIOPHENE-2-CARBOXYLIC ACID |

| | -continued |
|---|---|
| Compound 345 | 3-[(2-CHLORO-BENZYL)-(4-METHYL-BENZOYL)-AMINO]-5-PHENYL-THIOPHENE-2-CARBOXYLIC ACID |
| Compound 346 | 3-[(2,4-DICHLORO-BENZOYL)-ISOPROPYL-AMINO]-5-ISOBUTYL-THIOPHENE-2-CARBOXYLIC ACID |
| Compound 347 | 3-[ALLYL-(2-NAPHTHALEN-2-YL-ACETYL)-AMINO]-5-PHENYL-THIOPHENE-2-CARBOXYLIC ACID |
| Compound 348 | 3-{ALLYL-[2-(2,4-DICHLORO-PHENYL)-ACETYL]-AMINO}-5-PHENYL-THIOPHENE-2-CARBOXYLIC ACID |
| Compound 349 | 3-{ALLYL-[2-(2-CHLORO-4-FLUORO-PHENYL)-ACETYL]-AMINO}-5-PHENYL-THIOPHENE-2-CARBOXYLIC ACID |
| Compound 350 | 3-{ALLYL-[2-(3,4-DICHLORO-PHENYL)-ACETYL]-AMINO}-5-PHENYL-THIOPHENE-2-CARBOXYLIC ACID |
| Compound 351 | 3-{ALLYL-[2-(2,4-DIFLUORO-PHENYL)-ACETYL]-AMINO}-5-PHENYL-THIOPHENE-2-CARBOXYLIC ACID |
| Compound 352 | 3-{ALLYL-[2-(4-TRIFLUOROMETHYL-PHENYL)-ACETYL]-AMINO}-5-PHENYL-THIOPHENE-2-CARBOXYLIC ACID |
| Compound 353 | 3-{ALLYL-[2-(2,6-DICHLORO-PHENYL)-ACETYL]-AMINO}-5-PHENYL-THIOPHENE-2-CARBOXYLIC ACID |
| Compound 354 | 3-[ALLYL-(2-M-TOLYL-ACETYL)-AMINO]-5-PHENYL-THIOPHENE-2-CARBOXYLIC ACID |
| Compound 355 | 5-(4-ACETYL-PHENYL)-3-[(2,4-DICHLORO-BENZOYL)-ISOPROPYL-AMINO]-THIOPHENE-2-CARBOXYLIC ACID |
| Compound 356 | 3-[(2,4-DICHLORO-BENZOYL)-ISOPROPYL-AMINO]-5-(4-FLUORO-PHENYL)-THIOPHENE-2-CARBOXYLIC ACID |
| Compound 357 | 3-[(2,4-DICHLORO-BENZOYL)-ISOPROPYL-AMINO]-5-M-TOLYL-THIOPHENE-2-CARBOXYLIC ACID |
| Compound 358 | 5'-ACETYL-4-[(2,4-DICHLORO-BENZOYL)-ISOPROPYL-AMINO]-[2,2']BITHIOPHENYL-5-CARBOXYLIC ACID |
| Compound 359 | 3-[(2,4-DICHLORO-BENZOYL)-ISOPROPYL-AMINO]-5-(3-TRIFLUOROMETHYL-PHENYL)-THIOPHENE-2-CARBOXYLIC ACID |
| Compound 360 | 4-[(2,4-DICHLORO-BENZOYL)-ISOPROPYL-AMINO]-5'-METHYL-[2,2']BITHIOPHENYL-5-CARBOXYLIC ACID |
| Compound 361 | 3-(2,4-DIMETHYL-BENZENESULFONYLAMINO)-5-(4-METHOXY-PHENYL)-THIOPHENE-2-CARBOXYLIC ACID |
| Compound 362 | 3-(CYCLOHEXANECARBONYL-ISOPROPYL-AMINO)-5-PHENYL-THIOPHENE-2-CARBOXYLIC ACID |
| Compound 363 | 3-{(2,4-DICHLORO-BENZOYL)-[1-(2,4-DICHLORO-BENZOYL)-PIPERIDIN-4-YL]-AMINO}-5-PHENYL-THIOPHENE-2-CARBOXYLIC ACID |
| Compound 364 | 4-[(2-CARBOXY-5-PHENYL-THIOPHEN-3-YL)-(4-METHYL-BENZOYL)-AMINO]-PIPERIDINE-1-CARBOXYLIC ACID TERT-BUTYL ESTER |
| Compound 365 | 4-[(2-CARBOXY-5-PHENYL-THIOPHEN-3-YL)-(2,4-DICHLORO-BENZOYL)-AMINO]-PIPERIDINE-1-CARBOXYLIC ACID TERT-BUTYL ESTER |
| Compound 366 | 3-[(4-METHYL-BENZOYL)-PIPERIDIN-4-YL-AMINO]-5-PHENYL-THIOPHENE-2-CARBOXYLIC ACID |
| Compound 367 | 5'-ACETYL-4-(2,4-DIMETHYL-BENZENESULFONYLAMINO)-[2,3'] BITHIOPHENYL-5-CARBOXYLIC ACID |
| Compound 368 | 3-[(2,4-DICHLORO-BENZOYL)-PIPERIDIN-4-YL-AMINO]-5-PHENYL-THIOPHENE-2-CARBOXYLIC ACID |
| Compound 369 | 5-(4-METHANESULFONYLAMINO-PHENYL)-3-(TOLUENE-2-SULFONYLAMINO)-THIOPHENE-2-CARBOXYLIC ACID |
| Compound 370 | 3-(4-FLUORO-2-METHYL-BENZENESULFONYLAMINO)-5-PHENYL-THIOPHENE-2-CARBOXYLIC ACID |
| Compound 371 | 3-[(3-METHYL-CYCLOHEXANECARBONYL)-ISOPROPYL-AMINO]-5-PHENYL-THIOPHENE-2-CARBOXYLIC ACID |
| Compound 372 | 3-(4-CHLORO-2-METHYL-BENZENESULFONYLAMINO)-5-PHENYL-THIOPHENE-2-CARBOXYLIC ACID |
| Compound 373 | 3-[(2,4-DICHLORO-BENZOYL)-ISOPROPYL-AMINO]-5-(4-METHANESULFONYL-PHENYL)-THIOPHENE-2-CARBOXYLIC ACID |
| Compound 374 | 3-[(2,4-DICHLORO-BENZOYL)-ISOPROPYL-AMINO]-5-(4-METHANESULFINYL-PHENYL)-THIOPHENE-2-CARBOXYLIC ACID |
| Compound 375 | 5-(4-CARBOXY-PHENYL)-3-[(2,4-DICHLORO-BENZOYL)-ISOPROPYL-AMINO]-THIOPHENE-2-CARBOXYLIC ACID |
| Compound 376 | 5-BENZOFURAN-2-YL-3-[(2,4-DICHLORO-BENZOYL)-ISOPROPYL-AMINO]-THIOPHENE-2-CARBOXYLIC ACID |
| Compound 377 | 3-[(2-ACETOXY-4-METHYL-BENZOYL)-ISOPROPYL-AMINO]-5-PHENYL-THIOPHENE-2-CARBOXYLIC ACID |
| Compound 378 | 3-[ISOPROPYL-(2-METHYL-CYCLOHEXANECARBONYL)-AMINO]-5-PHENYL-THIOPHENE-2-CARBOXYLIC ACID |
| Compound 379 | 3-[ISOPROPYL-(2-METHYL-CYCLOHEXANECARBONYL)-AMINO]-5-PHENYL-THIOPHENE-2-CARBOXYLIC ACID |
| Compound 380 | 3-(CYCLOHEPTANECARBONYL-ISOPROPYL-AMINO)-5-PHENYL-THIOPHENE-2-CARBOXYLIC ACID |
| Compound 381 | 3-[ISOPROPYL-(4-METHYL-CYCLOHEXANECARBONYL)-AMINO]-5-(3-TRIFLUOROMETHYL-PHENYL)-THIOPHENE-2-CARBOXYLIC ACID |
| Compound 382 | 3-[(2,4-DICHLORO-BENZOYL)-ISOPROPYL-AMINO]-5-METHYL-THIOPHENE-2-CARBOXYLIC ACID |
| Compound 383 | 3-[ISOPROPYL-(4-METHYL-CYCLOHEXANECARBONYL)-AMINO]-5-(3-NITRO-PHENYL)-THIOPHENE-2-CARBOXYLIC ACID |
| Compound 384 | 3-[(3-CYCLOPENTYL-PROPIONYL)-METHYL-AMINO]-5-PHENYL-THIOPHENE-2-CARBOXYLIC ACID |

| | -continued |
|---|---|
| Compound 385 | 3-(BUTYRYL-METHYL-AMINO)-5-PHENYL-THIOPHENE-2-CARBOXYLIC ACID |
| Compound 386 | 3-(METHYL-PENT-4-ENOYL-AMINO)-5-PHENYL-THIOPHENE-2-CARBOXYLIC ACID |
| Compound 387 | 3-[ISOPROPYL-(5-METHYL-3-OXO-3H-ISOINDOL-1-YL)-AMINO]-5-PHENYL-THIOPHENE-2-CARBOXYLIC ACID |
| Compound 388 | 3-[METHYL-(3-METHYL-BUTYRYL)-AMINO]-5-PHENYL-THIOPHENE-2-CARBOXYLIC ACID |
| Compound 389 | 3-(METHYL-PENTANOYL-AMINO)-5-PHENYL-THIOPHENE-2-CARBOXYLIC ACID |
| Compound 390 | 3-[METHYL-(4-METHYL-PENTANOYL)-AMINO]-5-PHENYL-THIOPHENE-2-CARBOXYLIC ACID |
| Compound 391 | 3-(CYCLOPENTANECARBONYL-ETHYL-AMINO)-5-PHENYL-THIOPHENE-2-CARBOXYLIC ACID |
| Compound 392 | 3-[(3-CYCLOPENTYL-PROPIONYL)-ETHYL-AMINO]-5-PHENYL-THIOPHENE-2-CARBOXYLIC ACID |
| Compound 393 | 3-(CYCLOBUTANECARBONYL-ETHYL-AMINO)-5-PHENYL-THIOPHENE-2-CARBOXYLIC ACID |
| Compound 394 | 3-(BUT-2-ENOYL-ETHYL-AMINO)-5-PHENYL-THIOPHENE-2-CARBOXYLIC ACID |
| Compound 395 | 3-[ISOPROPYL-(4-METHYL-2-VINYL-BENZOYL)-AMINO]-5-PHENYL-THIOPHENE-2-CARBOXYLIC ACID |
| Compound 396 | 3-[ISOPROPYL-(4-METHYL-CYCLOHEX-1-ENECARBONYL)-AMINO]-5-PHENYL-THIOPHENE-2-CARBOXYLIC ACID |
| Compound 397 | 3-(ALLYL-HEXANOYL-AMINO)-5-PHENYL-THIOPHENE-2-CARBOXYLIC ACID |
| Compound 398 | 3-(ALLYL-CYCLOBUTANECARBONYL-AMINO)-5-PHENYL-THIOPHENE-2-CARBOXYLIC ACID |
| Compound 399 | 3-(ALLYL-PENTANOYL-AMINO)-5-PHENYL-THIOPHENE-2-CARBOXYLIC ACID |
| Compound 400 | 3-[ALLYL-(4-METHYL-PENTANOYL)-AMINO]-5-PHENYL-THIOPHENE-2-CARBOXYLIC ACID |
| Compound 401 | 3-[ALLYL-(2-CYCLOPENTYL-ACETYL)-AMINO]-5-PHENYL-THIOPHENE-2-CARBOXYLIC ACID |
| Compound 402 | 3-[(2-HYDROXY-4-METHYL-CYCLOHEXANECARBONYL)-ISOPROPYL-AMINO]-5-PHENYL-THIOPHENE-2-CARBOXYLIC ACID |
| Compound 403 | 3-[(2,4-DICHLORO-BENZOYL)-(1-PHENYL-ETHYL)-AMINO]-5-PHENYL-THIOPHENE-2-CARBOXYLIC ACID |
| Compound 404 | 3-[(2,4-DICHLORO-BENZOYL)-(1-PHENYL-ETHYL)-AMINO]-5-PHENYL-THIOPHENE-2-CARBOXYLIC ACID |
| Compound 405 | 3-[ISOPROPYL-(3-METHYL-CYCLOPENT-3-ENECARBONYL)-AMINO]-5-PHENYL-THIOPHENE-2-CARBOXYLIC ACID |
| Compound 406 | 3-[(2-BENZYLOXY-4-METHYL-BENZOYL)-ISOPROPYL-AMINO]-5-(3-TRIFLUOROMETHYL-PHENYL)-THIOPHENE-2-CARBOXYLIC ACID |
| Compound 407 | 3-[(2,4-DIMETHYL-CYCLOHEXANECARBONYL)-ISOPROPYL-AMINO]-5-PHENYL-THIOPHENE-2-CARBOXYLIC ACID |
| Compound 408 | 3-[ISOPROPYL-(3-METHYL-CYCLOPENTANECARBONYL)-AMINO]-5-PHENYL-THIOPHENE-2-CARBOXYLIC ACID |
| Compound 409 | 3-[(2-HYDROXY-4-METHYL-CYCLOHEXANECARBONYL)-ISOPROPYL-AMINO]-5-PHENYL-THIOPHENE-2-CARBOXYLIC ACID |
| Compound 410 | 5-PHENYL-3-[PROPIONYL-(4-TRIFLUOROMETHYL-BENZYL)-AMINO]-THIOPHENE-2-CARBOXYLIC ACID |
| Compound 411 | 3-[ISOBUTYRYL-(4-TRIFLUOROMETHYL-BENZYL)-AMINO]-5-PHENYL-THIOPHENE-2-CARBOXYLIC ACID |
| Compound 412 | 3-[(3-METHYL-BUTYRYL)-(4-TRIFLUOROMETHYL-BENZYL)-AMINO]-5-PHENYL-THIOPHENE-2-CARBOXYLIC ACID |
| Compound 413 | 3-[CYCLOPROPANECARBONYL-(4-TRIFLUOROMETHYL-BENZYL)-AMINO]-5-PHENYL-THIOPHENE-2-CARBOXYLIC ACID |
| Compound 414 | 3-[CYCLOBUTANECARBONYL-(4-TRIFLUOROMETHYL-BENZYL)-AMINO]-5-PHENYL-THIOPHENE-2-CARBOXYLIC ACID |
| Compound 415 | 3-[BUTYRYL-(4-TRIFLUOROMETHYL-BENZYL)-AMINO]-5-PHENYL-THIOPHENE-2-CARBOXYLIC ACID |
| Compound 416 | 3-[(2-CYCLOPENTYL-ACETYL)-(4-TRIFLUOROMETHYL-BENZYL)-AMINO]-5-PHENYL-THIOPHENE-2-CARBOXYLIC ACID |
| Compound 417 | 3-[(4-TERT-BUTYL-BENZYL)-PROPIONYL-AMINO]-5-PHENYL-THIOPHENE-2-CARBOXYLIC ACID |
| Compound 418 | 3-[(4-NITRO-BENZYL)-PROPIONYL-AMINO]-5-PHENYL-THIOPHENE-2-CARBOXYLIC ACID |
| Compound 419 | 3-[(3-METHYL-BUTYRYL)-(4-NITRO-BENZYL)-AMINO]-5-PHENYL-THIOPHENE-2-CARBOXYLIC ACID |
| Compound 420 | 3-[CYCLOPROPANECARBONYL-(4-NITRO-BENZYL)-AMINO]-5-PHENYL-THIOPHENE-2-CARBOXYLIC ACID |
| Compound 421 | 3-[(2-CHLORO-BENZYL)-ISOBUTYRYL-AMINO]-5-PHENYL-THIOPHENE-2-CARBOXYLIC ACID |
| Compound 422 | 3-[(2-CHLORO-BENZYL)-(3-METHYL-BUTYRYL)-AMINO]-5-PHENYL-THIOPHENE-2-CARBOXYLIC ACID |
| Compound 423 | 3-[(2-CHLORO-BENZYL)-CYCLOPROPANECARBONYL-AMINO]-5-PHENYL-THIOPHENE-2-CARBOXYLIC ACID |
| Compound 424 | 3-[(ADAMANTANE-1-CARBONYL)-ISOPROPYL-AMINO]-5-PHENYL-THIOPHENE-2-CARBOXYLIC ACID |
| Compound 425 | 3-[(2-CHLORO-BENZYL)-CYCLOBUTANECARBONYL-AMINO]-5-PHENYL-THIOPHENE-2-CARBOXYLIC ACID |
| Compound 426 | 3-[ACETYL-(2-METHYL-BENZYL)-AMINO]-5-PHENYL-THIOPHENE-2-CARBOXYLIC ACID |

-continued

| | |
|---|---|
| Compound 427 | 3-[(2-METHYL-BENZYL)-PROPIONYL-AMINO]-5-PHENYL-THIOPHENE-2-CARBOXYLIC ACID |
| Compound 428 | 3-[(2-HYDROXY-4-METHYL-BENZOYL)-ISOPROPYL-AMINO]-5-(3-TRIFLUOROMETHYL-PHENYL)-THIOPHENE-2-CARBOXYLIC ACID |
| Compound 429 | 3-[(1-ACETYL-PIPERIDIN-4-YL)-(2,4-DICHLORO-BENZOYL)-AMINO]-5-PHENYL-THIOPHENE-2-CARBOXYLIC ACID |
| Compound 430 | 3-[(2,4-DICHLORO-BENZOYL)-ISOPROPYL-AMINO]-5-[4-(1H-TETRAZOL-5-YL)-PHENYL]-THIOPHENE-2-CARBOXYLIC ACID |
| Compound 431 | 3-[(2-CYANO-4-METHYL-BENZOYL)-ISOPROPYL-AMINO]-5-PHENYL-THIOPHENE-2-CARBOXYLIC ACID |
| Compound 432 | 3-[CYCLOBUTANECARBONYL-(2-METHYL-BENZYL)-AMINO]-5-PHENYL-THIOPHENE-2-CARBOXYLIC ACID |
| Compound 433 | 3-[BUTYRYL-(2-METHYL-BENZYL)-AMINO]-5-PHENYL-THIOPHENE-2-CARBOXYLIC ACID |
| Compound 434 | 3-[ACETYL-(3-METHYL-BENZYL)-AMINO]-5-PHENYL-THIOPHENE-2-CARBOXYLIC ACID |
| Compound 435 | 3-[CYCLOBUTANECARBONYL-(4-METHYL-BENZYL)-AMINO]-5-PHENYL-THIOPHENE-2-CARBOXYLIC ACID |
| Compound 436 | 3-[CYCLOHEXANECARBONYL-(4-TRIFLUOROMETHYL-BENZYL)-AMINO]-5-PHENYL-THIOPHENE-2-CARBOXYLIC ACID |
| Compound 437 | 3-[(4-TERT-BUTYL-BENZYL)-ISOBUTYRYL-AMINO]-5-PHENYL-THIOPHENE-2-CARBOXYLIC ACID |
| Compound 438 | 3-[(4-TERT-BUTYL-BENZYL)-CYCLOPROPANECARBONYL-AMINO]-5-PHENYL-THIOPHENE-2-CARBOXYLIC ACID |
| Compound 439 | 3-[(4-TERT-BUTYL-BENZYL)-CYCLOBUTANECARBONYL-AMINO]-5-PHENYL-THIOPHENE-2-CARBOXYLIC ACID |
| Compound 440 | 3-[(4-TERT-BUTYL-BENZYL)-BUTYRYL-AMINO]-5-PHENYL-THIOPHENE-2-CARBOXYLIC ACID |
| Compound 441 | 3-[(4-TERT-BUTYL-BENZYL)-CYCLOHEXANECARBONYL-AMINO]-5-PHENYL-THIOPHENE-2-CARBOXYLIC ACID |
| Compound 442 | 3-[(4-TERT-BUTYL-BENZYL)-(2-CYCLOPENTYL-ACETYL)-AMINO]-5-PHENYL-THIOPHENE-2-CARBOXYLIC ACID |
| Compound 443 | 3-[(2-CYCLOPENTYL-ACETYL)-(4-NITRO-BENZYL)-AMINO]-5-PHENYL-THIOPHENE-2-CARBOXYLIC ACID |
| Compound 444 | 3-[(2-CHLORO-BENZYL)-CYCLOHEXANECARBONYL-AMINO]-5-PHENYL-THIOPHENE-2-CARBOXYLIC ACID |
| Compound 445 | 3-[(2-CYCLOPENTYL-ACETYL)-(3-METHYL-BENZYL)-AMINO]-5-PHENYL-THIOPHENE-2-CARBOXYLIC ACID |
| Compound 446 | 3-[BUTYRYL-(3-METHYL-BENZYL)-AMINO]-5-PHENYL-THIOPHENE-2-CARBOXYLIC ACID |
| Compound 447 | 3-[BUTYRYL-(2-CHLORO-BENZYL)-AMINO]-5-PHENYL-THIOPHENE-2-CARBOXYLIC ACID |
| Compound 448 | 3-[ISOPROPYL-(4-METHYL-CYCLOHEXANECARBONYL)-AMINO]-5-M-TOLYL-THIOPHENE-2-CARBOXYLIC ACID |
| Compound 449 | 3-[(2,4-DICHLORO-BENZOYL)-ISOPROPYL-AMINO]-5-THIAZOL-2-YL-THIOPHENE-2-CARBOXYLIC ACID |
| Compound 450 | 3-(ACETYL-BENZYL-AMINO)-5-PHENYL-THIOPHENE-2-CARBOXYLIC ACID |
| Compound 451 | 3-(BENZYL-PROPIONYL-AMINO)-5-PHENYL-THIOPHENE-2-CARBOXYLIC ACID |
| Compound 452 | 3-[BENZYL-(2-METHOXY-ACETYL)-AMINO]-5-PHENYL-THIOPHENE-2-CARBOXYLIC ACID |
| Compound 453 | 3-[BENZYL-(3-METHYL-BUTYRYL)-AMINO]-5-PHENYL-THIOPHENE-2-CARBOXYLIC ACID |
| Compound 454 | 3-(BENZYL-CYCLOPROPANECARBONYL-AMINO)-5-PHENYL-THIOPHENE-2-CARBOXYLIC ACID |
| Compound 455 | 3-[ACETYL-(4-CHLORO-BENZYL)-AMINO]-5-PHENYL-THIOPHENE-2-CARBOXYLIC ACID |
| Compound 456 | 3-[(4-CHLORO-BENZYL)-PROPIONYL-AMINO]-5-PHENYL-THIOPHENE-2-CARBOXYLIC ACID |
| Compound 457 | 3-[(4-CHLORO-BENZYL)-ISOBUTYRYL-AMINO]-5-PHENYL-THIOPHENE-2-CARBOXYLIC ACID |
| Compound 458 | 3-[(4-CHLORO-BENZYL)-(3-METHYL-BUTYRYL)-AMINO]-5-PHENYL-THIOPHENE-2-CARBOXYLIC ACID |
| Compound 459 | 3-[(4-CHLORO-BENZYL)-CYCLOPROPANECARBONYL-AMINO]-5-PHENYL-THIOPHENE-2-CARBOXYLIC ACID |
| Compound 460 | 5-(4-ACETYL-PHENYL)-3-[ISOPROPYL-(4-METHYL-CYCLOHEXANECARBONYL)-AMINO]-THIOPHENE-2-CARBOXYLIC ACID |
| Compound 461 | 3-[(4-CHLORO-BENZYL)-CYCLOBUTANECARBONYL-AMINO]-5-PHENYL-THIOPHENE-2-CARBOXYLIC ACID |
| Compound 462 | 3-[BUTYRYL-(4-CHLORO-BENZYL)-AMINO]-5-PHENYL-THIOPHENE-2-CARBOXYLIC ACID |
| Compound 463 | 3-[(4-CHLORO-BENZYL)-(2-CYCLOPENTYL-ACETYL)-AMINO]-5-PHENYL-THIOPHENE-2-CARBOXYLIC ACID |
| Compound 464 | 3-[ACETYL-(4-TRIFLUOROMETHYL-BENZYL)-AMINO]-5-PHENYL-THIOPHENE-2-CARBOXYLIC ACID |
| Compound 465 | 3-[ISOBUTYRYL-(3-METHYL-BENZYL)-AMINO]-5-PHENYL-THIOPHENE-2-CARBOXYLIC ACID |
| Compound 466 | 3-[CYCLOPROPANECARBONYL-(3-METHYL-BENZYL)-AMINO]-5-PHENYL-THIOPHENE-2-CARBOXYLIC ACID |
| Compound 467 | 3-[(4-METHYL-BENZYL)-PROPIONYL-AMINO]-5-PHENYL-THIOPHENE-2-CARBOXYLIC ACID |

-continued

| | |
|---|---|
| Compound 468 | 3-[ISOBUTYRYL-(4-METHYL-BENZYL)-AMINO]-5-PHENYL-THIOPHENE-2-CARBOXYLIC ACID |
| Compound 469 | 3-[CYCLOPROPANECARBONYL-(4-METHYL-BENZYL)-AMINO]-5-PHENYL-THIOPHENE-2-CARBOXYLIC ACID |
| Compound 470 | 3-[(BUTYRYL-(4-METHYL-BENZYL)-AMINO]-5-PHENYL-THIOPHENE-2-CARBOXYLIC ACID |
| Compound 471 | 3-[(3-METHOXY-BENZYL)-PROPIONYL-AMINO]-5-PHENYL-THIOPHENE-2-CARBOXYLIC ACID |
| Compound 472 | 3-[(3-METHOXY-BENZYL)-(3-METHYL-BUTYRYL)-AMINO]-5-PHENYL-THIOPHENE-2-CARBOXYLIC ACID |
| Compound 473 | 3-[CYCLOBUTANECARBONYL-(3-METHOXY-BENZYL)-AMINO]-5-PHENYL-THIOPHENE-2-CARBOXYLIC ACID |
| Compound 474 | 3-[(2-CARBAMOYL-4-METHYL-BENZOYL)-ISOPROPYL-AMINO]-5-PHENYL-THIOPHENE-2-CARBOXYLIC ACID |
| Compound 475 | 3-[BUTYRYL-(3-METHOXY-BENZYL)-AMINO]-5-PHENYL-THIOPHENE-2-CARBOXYLIC ACID |
| Compound 476 | 3-[ACETYL-(3-CHLORO-BENZYL)-AMINO]-5-PHENYL-THIOPHENE-2-CARBOXYLIC ACID |
| Compound 477 | 3-[(3-CHLORO-BENZYL)-PROPIONYL-AMINO]-5-PHENYL-THIOPHENE-2-CARBOXYLIC ACID |
| Compound 478 | 3-[(3-CHLORO-BENZYL)-(2-METHOXY-ACETYL)-AMINO]-5-PHENYL-THIOPHENE-2-CARBOXYLIC ACID |
| Compound 479 | 3-[(3-CHLORO-BENZYL)-(3-METHYL-BUTYRYL)-AMINO]-5-PHENYL-THIOPHENE-2-CARBOXYLIC ACID |
| Compound 480 | 3-[(3-CHLORO-BENZYL)-CYCLOPROPANECARBONYL-AMINO]-5-PHENYL-THIOPHENE-2-CARBOXYLIC ACID |
| Compound 481 | 3-[(3-CHLORO-BENZYL)-CYCLOBUTANECARBONYL-AMINO]-5-PHENYL-THIOPHENE-2-CARBOXYLIC ACID |
| Compound 482 | 3-[BUTYRYL-(3-CHLORO-BENZYL)-AMINO]-5-PHENYL-THIOPHENE-2-CARBOXYLIC ACID |
| Compound 483 | 3-[ACETYL-(2,4-DIFLUORO-BENZYL)-AMINO]-5-PHENYL-THIOPHENE-2-CARBOXYLIC ACID |
| Compound 484 | 3-[(2,4-DIFLUORO-BENZYL)-(2-METHOXY-ACETYL)-AMINO]-5-PHENYL-THIOPHENE-2-CARBOXYLIC ACID |
| Compound 485 | 3-[(2,4-DIFLUORO-BENZYL)-ISOBUTYRYL-AMINO]-5-PHENYL-THIOPHENE-2-CARBOXYLIC ACID |
| Compound 486 | 3-[(2,4-DIFLUORO-BENZYL)-(3-METHYL-BUTYRYL)-AMINO]-5-PHENYL-THIOPHENE-2-CARBOXYLIC ACID |
| Compound 487 | 3-[BENZYL-(2-CYCLOPENTYL-ACETYL)-AMINO]-5-PHENYL-THIOPHENE-2-CARBOXYLIC ACID |
| Compound 488 | 3-[(2,4-DICHLORO-BENZOYL)-ISOPROPYL-AMINO]-5-(1H-INDOL-5-YL)-THIOPHENE-2-CARBOXYLIC ACID |
| Compound 489 | 3-(BENZYL-CYCLOBUTANECARBONYL-AMINO)-5-PHENYL-THIOPHENE-2-CARBOXYLIC ACID |
| Compound 490 | 3-[CYCLOHEXANECARBONYL-(2,4-DIFLUORO-BENZYL)-AMINO]-5-PHENYL-THIOPHENE-2-CARBOXYLIC ACID |
| Compound 491 | 3-{ALLYL-[2-(4-METHOXY-PHENYL)-ACETYL]-AMINO}-5-PHENYL-THIOPHENE-2-CARBOXYLIC ACID |
| Compound 492 | 3-(ETHYL-HEXANOYL-AMINO)-5-PHENYL-THIOPHENE-2-CARBOXYLIC ACID |
| Compound 493 | 3-(BUTYRYL-ETHYL-AMINO)-5-PHENYL-THIOPHENE-2-CARBOXYLIC ACID |
| Compound 494 | 3-[ETHYL-(4-METHYL-PENTANOYL)-AMINO]-5-PHENYL-THIOPHENE-2-CARBOXYLIC ACID |
| Compound 495 | 3-[CYCLOBUTANECARBONYL-(2,4-DIFLUORO-BENZYL)-AMINO]-5-PHENYL-THIOPHENE-2-CARBOXYLIC ACID |
| Compound 496 | 3-[BUTYRYL-(2,4-DIFLUORO-BENZYL)-AMINO]-5-PHENYL-THIOPHENE-2-CARBOXYLIC ACID |
| Compound 497 | 3-(CYCLOPENTANECARBONYL-METHYL-AMINO)-5-PHENYL-THIOPHENE-2-CARBOXYLIC ACID |
| Compound 498 | 3-(CYCLOHEXANECARBONYL-METHYL-AMINO)-5-PHENYL-THIOPHENE-2-CARBOXYLIC ACID |
| Compound 499 | 3-[(2-CARBOXY-5-PHENYL-THIOPHEN-3-YL)-(2,4-DICHLORO-BENZOYL)-AMINO]-PYRROLIDINE-1-CARBOXYLIC ACID TERT-BUTYL ESTER |
| Compound 500 | 3-[(1,4-DIMETHYL-CYCLOHEXANECARBONYL)-ISOPROPYL-AMINO]-5-PHENYL-THIOPHENE-2-CARBOXYLIC ACID |
| Compound 501 | 5-(4-ETHYL-PHENYL)-3-[(2-HYDROXY-4-METHYL-BENZOYL)-ISOPROPYL-AMINO]-THIOPHENE-2-CARBOXYLIC ACID |
| Compound 502 | 3-[(2-HYDROXY-4-METHYL-BENZOYL)-ISOPROPYL-AMINO]-5-M-TOLYL-THIOPHENE-2-CARBOXYLIC ACID |
| Compound 503 | 3-[(2,4-DICHLORO-BENZOYL)-PYRROLIDIN-3-YL-AMINO]-5-PHENYL-THIOPHENE-2-CARBOXYLIC ACID |
| Compound 504 | 4-{5-CARBOXY-4-[(2,4-DICHLORO-BENZOYL)-ISOPROPYL-AMINO]-THIOPHEN-2-YL}-3,6-DIHYDRO-2H-PYRIDINE-1-CARBOXYLIC ACID BENZYL ESTER |
| Compound 505 | 3-{[2-(HYDROXYIMINO-METHYL)-4-METHYL-BENZOYL]-ISOPROPYL-AMINO}-5-PHENYL-THIOPHENE-2-CARBOXYLIC ACID |
| Compound 506 | 3-[(1-CARBAMIMIDOYL-PIPERIDIN-4-YL)-(2,4-DICHLORO-BENZOYL)-AMINO]-5-PHENYL-THIOPHENE-2-CARBOXYLIC ACID |
| Compound 507 | 4-[(2-CARBOXY-5-PHENYL-THIOPHEN-3-YL)-(2,4-DICHLORO-BENZOYL)-AMINO]-AZEPANE-1-CARBOXYLIC ACID TERT-BUTYL ESTER |
| Compound 508 | 4-{[(2-CARBOXY-5-PHENYL-THIOPHEN-3-YL)-(2,4-DICHLORO-BENZOYL)-AMINO]-METHYL}-PIPERIDINE-1-CARBOXYLIC ACID BENZYL ESTER |

-continued

| | |
|---|---|
| Compound 509 | 3-[AZEPAN-4-YL-(2,4-DICHLORO-BENZOYL)-AMINO]-5-PHENYL-THIOPHENE-2-CARBOXYLIC ACID |
| Compound 510 | 3-[(4-METHYL-CYCLOHEXANECARBONYL)-PIPERIDIN-4-YL-AMINO]-5-PHENYL-THIOPHENE-2-CARBOXYLIC ACID LITHIUM SALT |
| Compound 511 | 3-[(2-CARBOXY-5-PHENYL-THIOPHEN-3-YL)-(2,4-DICHLORO-BENZOYL)-AMINO]-PIPERIDINE-1-CARBOXYLIC ACID TERT-BUTYL ESTER |
| Compound 512 | 3-[(4-BENZYLOXYCARBONYLAMINO-CYCLOHEXYL)-(2,4-DICHLORO-BENZOYL)-AMINO]-5-PHENYL-THIOPHENE-2-CARBOXYLIC ACID |
| Compound 513 | 3-[ISOPROPYL-(4-METHYL-2-OXO-CYCLOHEXANECARBONYL)-AMINO]-5-PHENYL-THIOPHENE-2-CARBOXYLIC ACID |
| Compound 514 | 3-[(2,4-DICHLORO-BENZOYL)-PIPERIDIN-3-YL-AMINO]-5-PHENYL-THIOPHENE-2-CARBOXYLIC ACID; COMPOUND WITH GENERIC INORGANIC NEUTRAL COMPONENT |
| Compound 515 | 3-[(4-BENZYLOXYCARBONYLAMINO-CYCLOHEXYL)-(2,4-DICHLORO-BENZOYL)-AMINO]-5-PHENYL-THIOPHENE-2-CARBOXYLIC ACID |
| Compound 516 | 3-[(2-BENZYLOXY-1-METHYL-ETHYL)-(2,4-DICHLORO-BENZOYL)-AMINO]-5-PHENYL-THIOPHENE-2-CARBOXYLIC ACID |
| Compound 517 | 3-[(2,2-DIMETHYL-[1,3]DIOXAN-5-YL)-(4-METHYL-CYCLOHEXANECARBONYL)-AMINO]-5-PHENYL-THIOPHENE-2-CARBOXYLIC ACID |
| Compound 518 | 3-[(2,4-DICHLORO-BENZOYL)-(2-HYDROXY-1-HYDROXYMETHYL-ETHYL)-AMINO]-5-PHENYL-THIOPHENE-2-CARBOXYLIC ACID |
| Compound 519 | 3-[(2,4-DICHLORO-BENZOYL)-PIPERIDIN-4-YLMETHYL-AMINO]-5-PHENYL-THIOPHENE-2-CARBOXYLIC ACID |
| Compound 520 | 3-[(2-CHLORO-BENZOYL)-PIPERIDIN-4-YLMETHYL-AMINO]-5-PHENYL-THIOPHENE-2-CARBOXYLIC ACID |
| Compound 521 | 3-[(4,6-DICHLORO-1H-INDOLE-2-CARBONYL)-ISOPROPYL-AMINO]-5-PHENYL-THIOPHENE-2-CARBOXYLIC ACID |
| Compound 522 | 3-[(2,4-DICHLORO-BENZOYL)-(2-HYDROXY-1-METHYL-ETHYL)-AMINO]-5-PHENYL-THIOPHENE-2-CARBOXYLIC ACID |
| Compound 523 | 4-{1-[(2-CARBOXY-5-PHENYL-THIOPHEN-3-YL)-(2,4-DICHLORO-BENZOYL)-AMINO]-ETHYL}-PIPERIDINE-1-CARBOXYLIC ACID BENZYL ESTER |
| Compound 524 | 4-{5-CARBOXY-4-[ISOPROPYL-(4-METHYL-CYCLOHEXANECARBONYL)-AMINO]-THIOPHEN-2-YL}-3,6-DIHYDRO-2H-PYRIDINE-1-CARBOXYLIC ACID BENZYL ESTER |
| Compound 525 | 3-[(4-METHYL-CYCLOHEXANECARBONYL)-PYRIDIN-4-YL-AMINO]-5-PHENYL-THIOPHENE-2-CARBOXYLIC ACID |
| Compound 526 | 3-[(2,4-DICHLORO-BENZOYL)-ISOPROPYL-AMINO]-5-PIPERIDIN-4-YL-THIOPHENE-2-CARBOXYLIC ACID; COMPOUND WITH TRIFLUORO-ACETIC ACID |
| Compound 527 | 3-[ISOPROPYL-(4-PROPYL-CYCLOHEXANECARBONYL)-AMINO]-5-PHENYL-THIOPHENE-2-CARBOXYLIC ACID |
| Compound 528 | 4-[(2-CARBOXY-5-PHENYL-THIOPHEN-3-YL)-(2,4-DICHLORO-BENZOYL)-AMINO]-CYCLOHEXYL-AMMONIUM; TRIFLUORO-ACETATE |
| Compound 529 | 3-[(2,4-DICHLORO-BENZOYL)-(1-PIPERIDIN-4-YL-ETHYL)-AMINO]-5-PHENYL-THIOPHENE-2-CARBOXYLIC ACID; COMPOUND WITH TRIFLUORO-ACETIC ACID |
| Compound 530 | 3-[(CYCLOHEX-3-ENECARBONYL)-ISOPROPYL-AMINO]-5-PHENYL-THIOPHENE-2-CARBOXYLIC ACID |
| Compound 531 | 3-[(4-ETHYL-CYCLOHEXANECARBONYL)-ISOPROPYL-AMINO]-5-PHENYL-THIOPHENE-2-CARBOXYLIC ACID |
| Compound 532 | 3-[(4-CHLORO-CYCLOHEXANECARBONYL)-ISOPROPYL-AMINO]-5-PHENYL-THIOPHENE-2-CARBOXYLIC ACID |
| Compound 533 | 4[(2-CARBOXY-5-PHENYL-THIOPHEN-3-YL)-(2,4-DICHLORO-BENZOYL)-AMINO]-3-METHYL-PIPERIDINE-1-CARBOXYLIC ACID BENZYL ESTER |
| Compound 534 | 3-[(2,4-DICHLORO-BENZOYL)-(2-METHOXY-CYCLOHEXYL)-AMINO]-5-PHENYL-THIOPHENE-2-CARBOXYLIC ACID |
| Compound 535 | 3-[(2,4-DICHLORO-BENZOYL)-(2,2-DIMETHYL-[1,3]DIOXAN-5-YL)-AMINO]-5-PHENYL-THIOPHENE-2-CARBOXYLIC ACID |
| Compound 536 | 3-[ISOPROPYL-(4-METHYL-CYCLOHEXANECARBONYL)-AMINO]-5-(1-METHYL-PIPERIDIN-4-YL)-THIOPHENE-2-CARBOXYLIC ACID |
| Compound 537 | 3-[(2,4-DICHLORO-BENZOYL)-(3-METHYL-PIPERIDIN-4-YL)-AMINO]-5-PHENYL-THIOPHENE-2-CARBOXYLIC ACID; COMPOUND WITH TRIFLUORO-ACETIC ACID |
| Compound 538 | 3-[(2,4-DICHLORO-BENZOYL)-(2-HYDROXY-CYCLOHEXYL)-AMINO]-5-PHENYL-THIOPHENE-2-CARBOXYLIC ACID |
| Compound 539 | 4-{[(2-CARBOXY-5-PHENYL-THIOPHEN-3-YL)-(4-METHYLCYCLOHEXANE CARBONYL)-AMINO]-METHYL}-PIPERIDINE-1-CARBOXYLIC ACID BENZYL ESTER |
| Compound 540 | 3-[((1R,2S,4R)-2-HYDROXY-4-METHYL-CYCLOHEXANECARBONYL)-ISOPROPYL-AMINO]-5-PHENYL-THIOPHENE-2-CARBOXYLIC ACID |
| Compound 541 | 3-{ISOPROPYL[8 1(4-METHOXY-2,3,6-TRIMETHYL-BENZENESULFONYL)-5-METHYL-1,2,3,6-TETRAHYDRO-PYRIDINE-2-CARBONYL]-AMINO}-5-PHENYL-THIOPHENE-2-CARBOXYLIC ACID |
| Compound 542 | 3-[(2,4-DICHLORO-BENZOYL)-ISOPROPYL-AMINO)-4-FLUORO-5-PHENYL-THIOPHENE-2-CARBOXYLIC ACID |
| Compound 543 | 3-[(2,4-DICHLORO-BENZOYL)-(1-METHYL-PIPERIDIN-4-YL)-AMINO]-5-PHENYL-THIOPHENE-2-CARBOXYLIC ACID |
| Compound 544 | 4-{[(2-CARBOXY-5-PHENYL-THIOPHEN-3-YL)-(4-METHYLCYCLOHEXANE CARBONYL)-AMINO]-METHYL}-PIPERIDINIUM; TRIFLUORO-ACETATE |
| Compound 545 | 3-[(2-TERT-BUTOXYCARBONYLAMINO-1-METHYL-ETHYL)-(2,4-DICHLORO-BENZOYL)-AMINO]-5-PHENYL-THIOPHENE-2-CARBOXYLIC ACID |

-continued

| | |
|---|---|
| Compound 546 | 2-[(2-CARBOXY-5-PHENYL-THIOPHEN-3-YL)-(2,4-DICHLORO-BENZOYL)-AMINO]-PROPYL-AMINE TRIFLUOROACETIC ACID SALT |
| Compound 547 | 3-[(3-CARBOXY-CYCLOPENTYL)-(2,4-DICHLORO-BENZOYL)-AMINO]-5-PHENYL-THIOPHENE-2-CARBOXYLIC ACID |
| Compound 548 | 3-[(3-CARBOXY-CYCLOPENTYL)-(2,4-DICHLORO-BENZOYL)-AMINO]-5-PHENYL-THIOPHENE-2-CARBOXYLIC ACID |
| Compound 549 | 2-[(2-CARBOXY-5-PHENYL-THIOPHEN-3-YL)-(2,4-DICHLORO-BENZOYL)-AMINO]-CYCLOHEXYL-AMMONIUM CHLORIDE |
| Compound 550 | 3-(BENZOYL-METHYL-AMINO)-5-PHENYL-THIOPHENE-2-CARBOXYLIC ACID |
| Compound 551 | {[5-PHENYL-3(TOLUENE-4-SULFONYLAMINO)-THIOPHENE-2-CARBONYL]-AMINO}-ACETIC ACID |
| Compound 552 | 5-BROMO-3(TOLUENE-2-SULFONYLAMINO)-THIOPHENE-2-CARBOXYLIC ACID |
| Compound 553 | 3-[CYCLOHEXYL(2,4-DICHLORO-BENZOYL)-AMINO]-5-PHENYL-THIOPHENE-2-CARBOXYLIC ACID |
| Compound 554 | 3-[[1,3]DIOXAN-5-YL(4-METHYL-CYCLOHEXANECARBONYL)-AMINO]-5-PHENYL-THIOPHENE-2-CARBOXYLIC ACID |
| Compound 555 | 3-[[2-(TERT-BUTYL-DIMETHYL-SILANYLOXY)-1-METHYL-2-PHENYL-ETHYL]-(2,4-DICHLORO-BENZOYL)-AMINO]-5-PHENYL-THIOPHENE-2-CARBOXYLIC ACID |
| Compound 556 | 3-[[2-(TERT-BUTYL-DIMETHYL-SILANYLOXY)-1-METHYL-2-PHENYL-ETHYL]-(2,4-DICHLORO-BENZOYL)-AMINO]-5-PHENYL-THIOPHENE-2-CARBOXYLIC ACID |
| Compound 557 | 3-[(2,4-DICHLORO-BENZOYL)-(2-DIETHYLAMINO-THIAZOL-5-YLMETHYL)-AMINO]-5-PHENYL-THIOPHENE-2-CARBOXYLIC ACID |
| Compound 558 | (5-{[(2-CARBOXY-5-PHENYL-THIOPHEN-3-YL)-(2,4-DICHLORO-BENZOYL)-AMINO]-METHYL}-THIAZOL-2-YL)-DIETHYL-AMMONIUM; CHLORIDE |
| Compound 559 | 5-(4-FLUORO-PHENYL)-3-[ISOPROPYL-(4-METHYL-CYCLOHEXANECARBONYL)-AMINO]-THIOPHENE-2-CARBOXYLIC ACID |
| Compound 560 | 3-[((1S,2R,4S)-2-HYDROXY-4-METHYL-CYCLOHEXANECARBONYL)-ISOPROPYL-AMINO]-5-PHENYL-THIOPHENE-2-CARBOXYLIC ACID |
| Compound 561 | 3-[(2,4-DICHLORO-BENZOYL)-(2-METHOXY-1-METHYL-ETHYL)-AMINO]-5-PHENYL-THIOPHENE-2-CARBOXYLIC ACID |
| Compound 562 | 3-[(4S)-ISOPROPYL-(4-METHYL-CYCLOHEX-1-ENECARBONYL)-AMINO]-5-PHENYL-THIOPHENE-2-CARBOXYLIC ACID |
| Compound 566 | 3-METHYL-(4-METHYLBENZOYL)-AMINO) 5-PHENYL THIOPHENE-2-CARBOXYLIC ACID (2-HYDROXY-ETHYL)AMIDE |
| Compound 567 | 5-PHENYL-3-(TOLUENE-4-SULFONYLAMINO)-THIOPHENE-2-CARBOXYLIC ACID CYCLOBUTYLAMIDE |
| Compound 568 | 3-(2,4-DIMETHYL-BENZENESULFONYLAMINO)-5-PHENYL-THIOPHENE-2-CARBOXYLIC ACID AMIDE |
| Compound 569 | 5-BROMO-3-[(2,4-DICHLORO-BENZOYL)-ISOPROPYL-AMINO]-THIOPHENE-2-CARBOXYLIC ACID |
| Compound 570 | 5-(4-CHLORO-PHENYL)-3-[ISOPROPYL-(4-METHYL-CYCLOHEXANE-CARBONYL)-AMINO]-THIOPHENE-2-CARBOXYLIC ACID |
| Compound 571 | 5-(4'-CHLORO-BIPHENYL-4-YL)-3-[ISOPROPYL-(4-METHYL-CYCLOHEXANECARBONYL)-AMINO]-THIOPHENE-2-CARBOXYLIC ACID |
| Compound 572 | 3-[(4-METHYL-CYCLOHEXANECARBONYL)-(TETRAHYDRO-PYRAN-4-YL)-AMINO]-5-PHENYL-THIOPHENE-2-CARBOXYLIC ACID |
| Compound 573 | 3-[(4-METHYL-CYCLOHEXANECARBONYL)-(1-METHYL-PIPERIDIN-4-YL)-AMINO]-5-PHENYL-THIOPHENE-2-CARBOXYLIC ACID |
| Compound 574 | 3-[(4-METHYL-CYCLOHEXANECARBONYL)-PIPERIDIN-4-YL-AMINO]-5-PHENYL-THIOPHENE-2-CARBOXYLIC ACID |
| Compound 575 | 3-[ISOPROPYL-(4-METHYL-CYCLOHEXANECARBONYL)-AMINO]-5-(4-TRIFLUOROMETHYL-PHENYL)-THIOPHENE-2-CARBOXYLIC ACID |
| Compound 576 | 5-(4-CYANO-PHENYL)-3-[ISOPROPYL-(4-METHYL-CYCLOHEXANECARBONYL)-AMINO]-THIOPHENE-2-CARBOXYLIC ACID |
| Compound 577 | 3-[ISOPROPYL-(4-METHYL-CYCLOHEXANECARBONYL)-AMINO]-5-(4-METHOXY-PHENYL)-THIOPHENE-2-CARBOXYLIC ACID |
| Compound 578 | 3-[2-METHOXY-1-METHYL-ETHYL)-(4-METHYL-CYCLOHEXANECARBONYL)-AMINO]-5-PHENYL-THIOPHENE-2-CARBOXYLIC ACID |
| Compound 579 | 3-[CYCLOHEXYL-(4-METHYL-CYCLOHEXANECARBONYL)-AMINO]-5-PHENYL-THIOPHENE-2-CARBOXYLIC ACID |
| Compound 581 | 5-(4-ISOBUTYL-PHENYL)-3-[5-(5-TRIFLUOROMETHYL-ISOXAZOL-3-YL)-THIOPHENE-2-SULFONYLAMINO]-THIOPHENE-2-CARBOXYLIC ACID |
| Compound 582 | 5-(4-ISOBUTYL-PHENYL)-3-(2,3,4-TRIFLUORO-BENZENESULFONYLAMINO)-THIOPHENE-2-CARBOXYLIC ACID |
| Compound 583 | 3-[(2,4-DICHLORO-PHENYL)-ISOPROPYL-CARBAMOYL]-5-PHENYL-THIOPHENE-2-CARBOXYLIC ACID |
| Compound 584 | 3-(METHYL-P-TOLYL-CARBAMOYL)-5-PHENYL-THIOPHENE-2-CARBOXYLIC ACID |
| Compound 585 | 3-[(2,4-DICHLORO-PHENYL)-METHYL-CARBAMOYL]-5-PHENYL-THIOPHENE-2-CARBOXYLIC ACID | or pharmaceutically acceptable salts thereof.

Preferably, the compounds of the present invention are provided in the form of a single enantiomer at least 95%, more preferrably at least 97% and most preferably at least 99% free of the corresponding enantiomer.

More preferably the compound of the present invention are in the form of the (+) enantiomer at least 95% free of the corresponding (−) enantiomer.

More preferably the compound of the present invention are in the form of the (+) enantiomer at least 97% free of the corresponding (−) enantiomer.

More preferably the compound of the present invention are in the form of the (+) enantiomer at least 99% free of the corresponding (−) enantiomer.

In a more preferred embodiment, the compound of the present invention are in the form of the (−) enantiomer at least 95% free of the corresponding (+) enantiomer.

Most preferably the compound of the present invention are in the form of the (−) enantiomer at least 97% free of the corresponding (+) enantiomer.

More preferably the compound of the present invention are in the form of the (−) enantiomer at least 99% free of the corresponding (+) enantiomer.

There is also provided a pharmaceutically acceptable salts of the present invention. By the term pharmaceutically acceptable salts of compounds of general formula (I) or (Ia) are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toleune-p-sulphonic, tartaric, acetic, trifluoroacetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal (e.g. sodium), alkaline earth metal (e.g. magnesium), ammonium and $NR_4+$ (where R is $C_{1-4}$ alkyl) salts.

References hereinafter to a compound according to the invention includes compounds of the general formula (I) or (Ia) and their pharmaceutically acceptable salts.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

As used in this application, the term "alkyl" represents a straight chain, branched chain or cyclic hydrocarbon moiety which may optionally be substituted by one or more of: halogen, nitro, nitroso, SO3R12, PO3RcRd, CONR13R14, C1-6 alkyl, C2-6 alkenyl, C2-6 alkynyl, C6-12 aralkyl, C6-12 aryl, C1-6 alkyloxy, C2-6 alkenyloxy, C2-6 alkynyloxy, C6-12 aryloxy, C(O)C1-6 alkyl, C(O)C2-6 alkenyl, C(O)C2-6 alkynyl, C(O)C6-12 aryl, C(O)C6-12 aralkyl, C3-10 heterocycle, hydroxyl, NR13R14, C(O)OR12, cyano, azido, amidino or guanido;

wherein R12, Rc, Rd, R13 and R14 are each independently chosen from H, C1-12 alkyl, C2-12 alkenyl, C2-12 alkynyl, C6-14 aryl, C3-12 heterocycle, C3-18 heteroaralkyl, C6-18 aralkyl;

or Rc and Rd are taken together with the oxygens to form a 5 to 10 membered heterocycle;

or R13 and R14 are taken together with the nitrogen to form a 3 to 10 membered heterocycle. Useful examples of alkyls include isopropyl, ethyl, fluorohexyl or cyclopropyl. The term alkyl is also meant to include alkyls in which one or more hydrogen atoms is replaced by an oxygen, (e.g. a benzoyl) or an halogen, more preferably, the halogen is fluoro (e.g. CF3- or CF3CH2-).

The terms "alkenyl" and "alkynyl" represent an alkyl containing at least one unsaturated group (e.g. allyl, acetylene, ethylene).

The term "aryl" represents a carbocyclic moiety containing at least one benzenoid-type ring which may optionally be substituted by one or more of halogen, nitro, nitroso, SO3R12, PO3RcRd, CONR13R14, C1-6 alkyl, C2-6 alkenyl, C2-6 alkynyl, C6-12 aralkyl, C6-12 aryl, C1-6 alkyloxy, C2-6 alkenyloxy, C2-6 alkynyloxy, C6-12 aryloxy, C(O)C1-6 alkyl, C(O)C2-6 alkenyl, C(O)C2-6 alkynyl, C(O)C6-12 aryl, C(O)C6-12 aralkyl, C3-10 heterocycle, hydroxyl, NR13R14, C(O)OR12, cyano, azido, amidino or guanido;

wherein R12, Rc, Rd, R13 and R14 are each independently chosen from H, C1-12 alkyl, C2-12 alkenyl, C2-12 alkynyl, C6-14 aryl, C3-12 heterocycle, C3-18 heteroaralkyl, C6-18 aralkyl;

or Rc and Rd are taken together with the oxygens to form a 5 to 10 membered heterocycle;

or R13 and R14 are taken together with the nitrogen to form a 3 to 10 membered heterocycle. Examples of aryl include phenyl and naphthyl.

The term "aralkyl" represents an aryl group attached to the adjacent atom by a C1-6alkyl, C1-6alkenyl, or C1-6alkynyl (e.g., benzyl).

The term "heterocycle," represents a saturated or unsaturated, cyclic moiety wherein said cyclic moeity is interrupted by at least one heteroatom, (e.g. oxygen, sulfur or nitrogen) which may optionally be substituted halogen, nitro, nitroso, SO3R12, PO3RcRd, CONR13R14, C1-6 alkyl, C2-6 alkenyl, C2-6 alkynyl, C6-12 aralkyl, C6-12 aryl, C1-6 alkyloxy, C2-6 alkenyloxy, C2-6 alkynyloxy, C6-12 aryloxy, C(O)C1-6 alkyl, C(O)C2-6 alkenyl, C(O)C2-6 alkynyl, C(O)C6-12 aryl, C(O)C6-12 aralkyl, C3-10 heterocycle, hydroxyl, NR13R14, C(O)OR12, cyano, azido, amidino or guanido;

wherein R12, Rc, Rd, R13 and R14 are each independently chosen from H, C1-12 alkyl, C2-12 alkenyl, C2-12 alkynyl, C6-14 aryl, C3-12 heterocycle, C3-18 heteroaralkyl, C6-18 aralkyl;

or Rc and Rd are taken together with the oxygens to form a 5 to 10 membered heterocycle;

or R13 and R14 are taken together with the nitrogen to form a 3 to 10 membered heterocycle. It is understood that the term heterocyclic ring represents a mono or polycyclic (e.g., bicyclic) ring. Examples of heterocyclic rings include but are not limited to epoxide; furan; benzofuran; isobenzofuran; oxathiolane; dithiolane; dioxolane; pyrrole; pyrrolidine; imidazole; pyridine; pyrimidine; indole; piperidine; morpholine; thiophene and thiomorpholine.

The term "heteroaralkyl" represents an heterocycle group attached to the adjacent atom by a $C_{1-6}$ alkyl, $C_{1-6}$ alkenyl, or $C_{1-6}$ alkynyl.

When there is a sulfur atom present, the sulfur atom can be at different oxidation levels, ie. S, SO, or SO2. All such oxidation levels are within the scope of the present invention.

The term "independently" means that a: substituent can be the same or different definition for each item.

As used in this application, the term "hydride donating agent" means a suitable ionic or covalent inorganic compound of hydrogen with another element (e.g. boron, sodium, lithium or aluminum) allowing the process to occur under the reaction conditions without causing adverse effect on the reagents or product. Useful examples of hydride donating agent include but are not limited to sodium borohydride ($NaBH_4$), sodium cyanoborohydride ($NaCNBH_3$), sodium triacetoxyborohydride ($Na(OAc)_3BH$) and borane-pyridine complexe ($BH_3$-Py). Alternatively, resin or polymer supported hydride donating agent on a may be used.

The term "organic carboxylic acid" include but is not limited to aliphatic acid (e.g. acetic, formic, trifluoroacetic), aromatic acid (e.g. benzoic and salicylic), dicarboxylic acid (e.g.

oxalic and phthalic). It will be apparent to one of ordinary skill that resin supported organic carboxylic acid may also be used.

The term "enol ether" as used herein have the same meaning as commonly understood by one of ordinary skill in the art to which this invention belongs. Enol ethers may be obtained commercially or prepared by well-known methods. Non-limiting examples of preparation include alkylation or silylation of enolates obtained from carbonyl compounds such as aldehydes, ketones, esters.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, preferably in the range of 0.5 to 60 mg/kg/day, most preferably in the range of 1 to 20 mg/kg/day.

The desired dose may conveniently be presented in a single dose or as divided dose administered at appropriate intervals, for example as two, three, four or more doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 µM, preferably about 2 to 50 µM, most preferably about 3 to about 30 µM. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.91 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation. The invention thus further provides a pharmaceutical formulation comprising compounds of formula (I) or (Ia) or a pharmaceutically acceptable derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulation suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste.

Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing an/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations' suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilising agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The compounds of the invention may also be used in combination with other antiviral agents or in combination with any additional agents useful in therapy and may be administered sequentially or simultaneously.

In one aspect of the invention, the compounds of the invention may be employed together with at least one other antiviral agent chosen from protease inhibitors, polymerase inhibitors, and helicase inhibitors.

In another aspect of the invention, the compounds of the invention may be employed together with at least one other antiviral agent chosen from Interferon-α and Ribavirin.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

The individual components of such combinations may be administered either sequentially or simultaneously in separate or combined pharmaceutical formulations.

When the compounds of formula (I) or (Ia) or a pharmaceutically acceptable salts thereof is used in combination with a second therapeutic agent active against the same virus the dose of each compound may be either the same as or differ from that when the compound is used alone. Appropriate doses will be readily appreciated by those skilled in the art.

The following general schemes and examples are provided to illustrate various embodiments of the present invention and shall not be considered as limiting in scope;

EXAMPLE 1

Preparation of 3-(2-Chloro-benzenesulfonylamino)-5-phenyl-thiophene-2-carboxylic acid, Compound #29

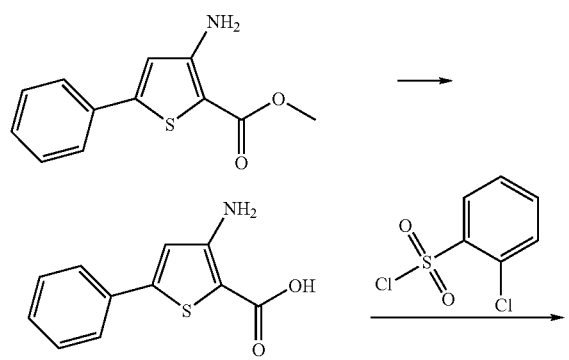

-continued

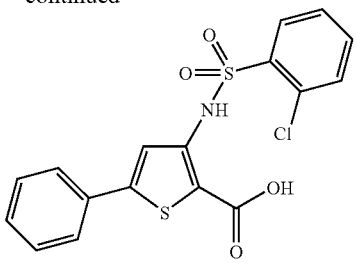

Step I

3-Amino-5-phenyl-thiophene-2-carboxylic acid

To a suspension of 3-Amino-5-phenyl-thiophene-2-carboxylic acid methyl ester (5 g, 21.459 mmol) in a mixture of THF:MeOH:H$_2$O (3:2:1, 75 mL), 1N aqueous solution of LiOH.H$_2$O (64 mL, 64.378 mmol) was added. The reaction mixture was stirred at 85° C. (external temperature) for 4 h. Solvents were removed under reduced pressure and the residue was partitioned between water and ethyl acetate. The water layer was separated and acidified with 1N HCl solution and then ethyl acetate was added to it. The organic phase was separated, dried (Na$_2$SO$_4$) and concentrated to obtain 3-Amino-5-phenyl-thiophene-2-carboxylic acid (4.15 g, 88%) as a yellowish solid. $^1$H NMR (DMSO-D$_6$, 400 MHz): 7.59 (d, 2H), 7.40 (m, 3H), 6.92 (s, 1H).

Step II 3-(2-Chloro-benzenesulfonylamino)-5-phenyl-thiophene-2-carboxylic acid

3-Amino-5-phenyl-thiophene-2-carboxylic acid (100 mg, 0.457 mmol) was taken in a mixture of dioxane and water (1:1, 25 mL) and then added sodium carbonate (242 mg, 2.285 mmol) and 1-chlorobenzenesulfonyl chloride (289 mg, 1.369 mmol). The reaction mixture was stirred at room temperature for 12 h. Half of the solvent was removed under reduced pressure and then diluted with water and ether in a separatory funnel. The ether layer was separated and the aqueous layer was acidified with 10% KHSO$_4$ solution. Ethyl acetate was added to the aqueous phase to dissolve the white precipitate. The ethyl acetate layer was separated, dried (Na$_2$SO$_4$) and concentrated to 5 mL. The white solid was filtered and then washed with cold ethyl acetate to obtain 3-(2-Chloro-benzenesulfonylamino)-5-phenyl-thiophene-2-carboxylic acid (125 mg, 69%). $^1$H NMR (DMSO-D$_6$, 400 MHz): 10.51 (bs, 1H), 8.30 (d, 1H), 7.72-7.60 (m, 4H), 7.57 (m, 1H), 7.44 (m, 4H).

The following compounds were prepared in a similar manner as described in general scheme 1:

Compound #3, Compound #5, Compound #7, Compound #13, Compound #15, Compound #16, Compound #17, Compound #18, Compound #21, Compound #22, Compound #23, Compound #29, Compound #30, Compound #34, Compound #37, Compound #38, Compound #39, Compound #40, Compound #41, Compound #42, Compound #44, Compound #45, Compound #46, Compound #49, Compound #50, Compound #52, Compound #53, Compound #54, Compound #55, Compound #76, Compound #94

EXAMPLE 2

3-(Toluene-2-sulfonylamino)-5-p-tolyl-thiophene-2-carboxylic acid, Compound #62

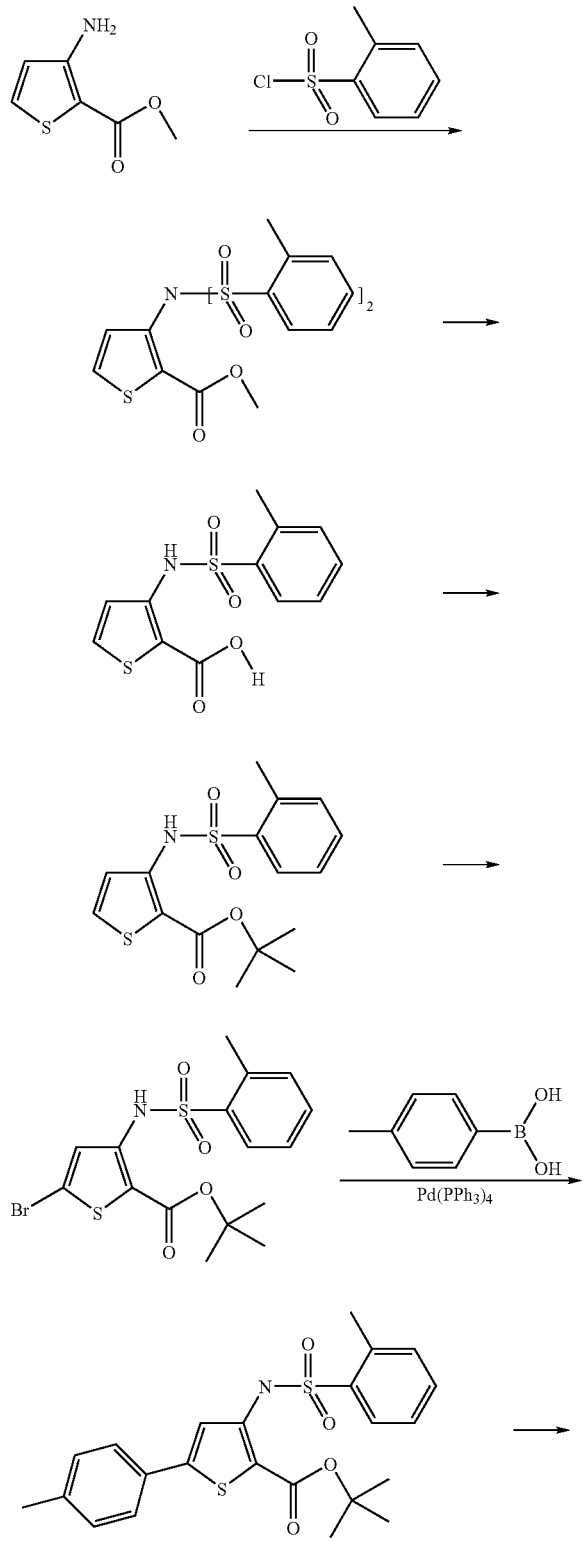

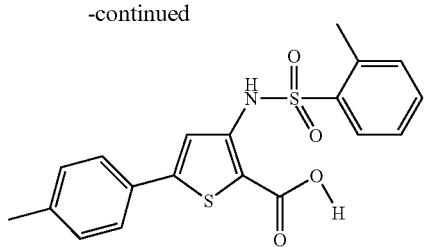

Step I

3-(bis-(Toluene-2-sulfonyl)-amino)-thiophene-2-carboxylic acid methyl ester

To a cold (0° C.) stirred sodium hypochlorite (NaOCl, 10.8% commercial bleach, 124 mL, 180.00 mmol) solution was added o-thiocresol (2.239 g, 2.12 mL, 18.0 mmol). To this vigorous stirred solution was added conc. Sulfuric acid (caution! extremely exothermic, 92 g, 50 mL, 938 mmol) dropwise. The resultant yellow reaction mixture was stirred for 2 h at the same temperature, diluted with water (50 mL) and dichloro-methane 50 mL. The organic solution was separated, aqueous solution was extracted with $CH_2Cl_2$ (2×50 mL). The combined organic extracts were washed with water, brine and dried. Evaporation of the solvent under reduced pressure furnished the 2-methylsulfonyl chloride (3.13 g, 91.5% yield), which was used in the next step without purification. $^1$H NMR (CDCl$_3$, 300 MHz) 8.07 (td, J=7.3, 1.5 Hz, 1H) 7.61 (tt, J=7.5, 1.1 Hz, 1H), 7.44-7.40 (m, 2H), 2.80 (s, 3H).

To a stirred solution of the methyl 3-amino-thiophene-2-carboxylic acid (1.0 g, 6.36 mmol) and DMAP (776 mg, 6.36 mmol) in $CH_2Cl_2$ was sequentially added triethyl amine (1.61 g, 15.9 mmol, 2.5 eq) and o-toluenesulfonyl chloride (3.02 g, 15.9 mmol, 2.5 eq), stirred for 24 h. The reaction mixture was diluted with EtOAc (100 mL), washed with 1.2 N HCl (2×50 mL), 6 N HCl (40 mL), saturated NaHCO$_3$ solution, brine and dried. Evaporation of the solvent under reduced pressure yielded 3-(bis-(Toluene-2-sulfonyl)-amino)-thiophene-2-carboxylic acid methyl ester (2.78 g, 93.3%) as a solid. The crude product was used in the next step without purification. $^1$H NMR (CDCl$_3$, 300 MHz) 8.198 (dd, J=8.0, 1.2 Hz, 2H), 7.52 (d, J=5.3 Hz, 1H), 7.5 (dt, J=7.5 Hz, 1.1 Hz, 2H), 7.36 (t, J=7.5 Hz, 3H), 7.28 (d, J=7.6 Hz, 2H), 7.16 (d, J=5.3 Hz, 1H), 3.44 (s, 3H), 2.43 (s, 3H).

Step II

3-(Toluene-2-sulfonylamino)-thiophene-2-carboxylic acid

To a stirred mixture of 3-(bis-(Toluene-2-sulfonyl)-amino)-thiophene-2-carboxylic acid methyl ester (2.5 g, 5.35 mmol) in 1,4-dioxane/MeOH/water (3:1:1; 62.5 mL) was added aq. 1 N NaOH solution (16.05 mL, 16.05 mmol, 3.0 eq) and heated at 85° C. for 3.5 h and it was then cooled to rt. To the reaction mixture was added 1.2 N HCl (16.0 mL), extracted with CHCl$_3$ (3×30 mL), washed with brine and dried. Evaporation of the solvent gave 3-(Toluene-2-sulfonylamino)-thiophene-2-carboxylic acid (1.5 g, 99%) as a white solid. $^1$H NMR (DMSO-d$_6$, 300 MHz) 7.94 (dd, J=7.9 Hz, 1.3 Hz, 1H), 7.76 (d, J=5.5 Hz, 1H), 7.55 (dt, J=7.5 Hz, 1.3 Hz, 1H), 7.42-7.37 (m, 2H), 7.1 (d, J=5.5 Hz, 1H), 2.57 (s, 3H).

Step III

3-(Toluene-2-sulfonylamino)-thiophene-2-carboxylic acid tert-butyl ester

To a cold (−40° C.) mixture of 3-(Toluene-2-sulfonylamino)-thiophene-2-carboxylic acid (1.5 g, 5.05 mmol) in 1,4-dioxane/CHCl$_3$ (1:2, 12 mL) was bubbled 2-methyl-2-propene gas (15 mL) in a sealed tube. To this was added Conc. H$_2$SO$_4$ (0.070 mL, 1.3 mmol) and slowly warmed up to room temperature. The resultant reaction mixture was heated at 70° C. for 2.5 days in a sealed tube, cooled to −40° C., stopper was removed. The reaction mixture was slowly brought up to room temperature and stirred until the excess gas is released. The mixture was extracted with EtOAc, washed with aq. NaHCO$_3$ solution, brine and dried. Evaporation of the solvent and purification of the residue on silica gel using EtOAc/hexane (1:10) as an eluent furnished 3-(Toluene-2-sulfonylamino)-thiophene-2-carboxylic acid tert-butyl ester (1.31 g 73.5% based on 90% conversion). $^1$H NMR (CDCl$_3$, 300 MHz) 9.89 (s, 1H), 8.01 (d, J=7.9 Hz, 1H), 7.43 (dt, J=7.5 Hz, 1.5 Hz, 1H), 7.3-7.25 (m, 3H), 7.2 (d, J=5.4 Hz, 1H), 2.69 (s, 3H), 1.56 (s, 9H).

Step IV

5-Bromo-3-(toluene-2-sulfonylamino)-thiophene-2-carboxylic acid tert-butyl ester To a cold (−30° C.) stirred solution of diisopropylamine (1.345 g, 1.86 mL, 13.3 mmol, 3.6 eq) in THF (74.0 mL) was added n-BuLi (1.6 M in hexane, 7.63 mL, 12.21 mmol, 3.3 eq) dropwise and stirred for 20 min. To the cold (−78° C.) LDA solution was added a solution of 3-(Toluene-2-sulfonylamino)-thiophene-2-carboxylic acid tert-butyl ester (1.31 g, 3.7 mmol, 1.0 eq) in THF (20 mL) dropwise and the solution was stirred for 2 h at the same temperature. The resultant red colored solution was then quenched with 1,2-dibromotetrafluoroethane (5.77 g, 2.65 mL, 22.2 mmol, 6.0 eq, passed through K$_2$CO$_3$ prior to use) in one portion, stirred for 1 h before being added sat. NH$_4$Cl solution (15.0 mL). The reaction mixture was warmed up to rt, extracted with EtOAc, washed with brine and dried. Evaporation of the solvent and purification of the residue over silica gel column furnished 5-Bromo-3-(toluene-2-sulfonylamino)-thiophene-2-carboxylic acid tert-butyl ester (1.2 g, 75% yield). $^1$H NMR (CDCl$_3$, 300 MHz) 9.72 (s, 1H), 8.0 (dd, J=7.8, 1.3 Hz, 1H), 7.47 (dt, J=7.5, 1.2 Hz, 1H), 7.35-7.30 (m, 2H), 7.24 (s, 1H), 2.68 (s, 3H), 1.53 (s, 9H).

Step V

3-(Toluene-2-sulfonylamino)-5-p-tolyl-thiophene-2-carboxylic acid tert-butyl ester To the mixture of 4-methylbenzeneboronic acid (38.0 mg, 0.279 mmol) and 5-Bromo-3-(toluene-2-sulfonylamino)-thiophene-2-carboxylic acid tert-butyl ester (40 mg, 0.0925 mmol) in 5:1 mixture of toluene/MeOH (2.0 mL) was added a solution of Pd(PPh$_3$)$_4$ (12.0 mg, 0.01 mmol, 10 mol %) in toluene (1.0 mL) followed by aqueous 2M Na$_2$CO$_3$ solution (0.1 mL, 0.2 mmol). The resultant reaction mixture was heated at 70° C. for 16 h, cooled to room temperature, filtered off through MgSO$_4$ and washed with EtOAc. Evaporation of the solvent and purification of the residue over preparative TLC (1 mm, 60 A°) using ethyl acetate/hexane (1:10) as an eluent furnished 3-(Toluene-2-sulfonylamino)-5-p-tolyl-thiophene-2-carboxylic acid tert-butyl ester (36.0 mg, 81% yield). $^1$H NMR (CDCl$_3$, 300 MHz) 9.94 (s, 1H), 8.05 (d, J=8.0 Hz, 1H), 7.44-7.25 (m, 6H), 7.18 (d, J=8.1 Hz, 2H), 2.71 (s, 3H), 2.36 (s, 3H), 1.56 (s, 9H).

Step VI

3-(Toluene-2-sulfonylamino)-5-p-tolyl-thiophene-2-carboxylic acid

To a stirred solution of 3-(Toluene-2-sulfonylamino)-5-p-tolyl-thiophene-2-carboxylic acid tert-butyl ester (36.0 mg, 0.081 mmol) in CH$_2$Cl$_2$ (1.0 mL) was added TFA (0.5 mL), stirred for 1 h at room temperature and diluted with hexane. Evaporation of the solvent under reduced pressure gave essentially the pure product as a solid. The product was purified by triturating with hexane/CH$_2$Cl$_2$ furnished 3-(Toluene-2-sulfonylamino)-5-p-tolyl-thiophene-2-carboxylic acid (28.0 mg, 89% yield). $^1$H NMR (DMSO-d$_6$, 300 MHz) 10.21 (br s, 1H), 8.06 (d, J=7.9 Hz, 1H), 7.56-7.36 (m, 6H), 7.24 (d, J=7.9 Hz, 2H), 2.59 (s, 3H), 2.48 (s, 3H).

The following compounds were prepared in a similar manner as described in general scheme 2:

Compound #6, Compound #8, Compound #11, Compound #14, Compound #24, Compound #56, Compound #57, Compound #181 Compound #59, Compound #60, Compound #62, Compound #63, Compound #64, Compound #65, Compound #66, Compound #67, Compound #68, Compound #69, Compound #70, Compound #71, Compound #552, Compound #79, Compound #80, Compound #81, Compound #83, Compound #84, Compound #85, Compound #86, Compound #87, Compound #88, Compound #89, Compound #90, Compound #91

EXAMPLE 3

3-(4-Choro-benzoylamino)-5-phenyl-thiophene-2-carboxylic acid Compound #72

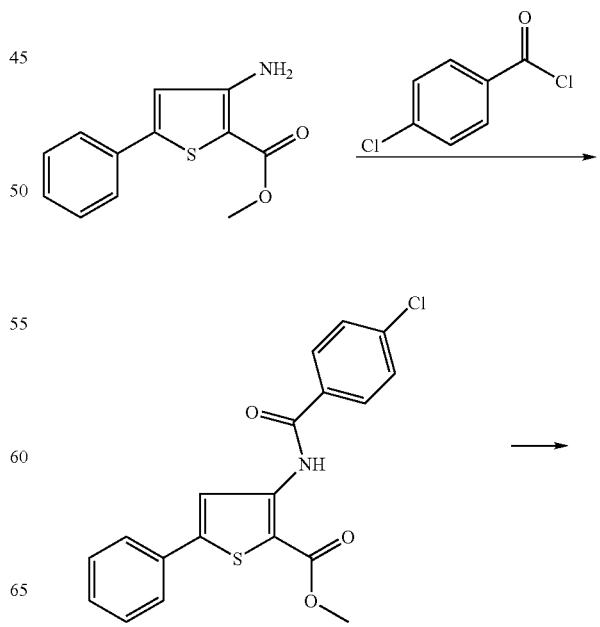

61
-continued

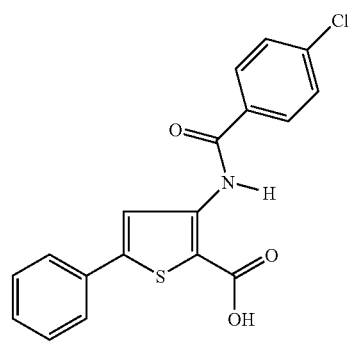

Step I

3-(4-Chloro-benzoylamino)-5-phenyl-thiophene-2-carboxylic acid methyl ester

To mixture of methyl-3-amino-5-phenylthiophene-2-carboxylate (100 mg, 0.428 mmol) in anhydrous pyridine (4.3 ml) was added p-chlorobenzoyl chloride (71 µl, 0.556 mmol). The mixture was stirred for 3 hours at room temperature and concentrated. Purification chromatography (silica gel, hexane to hexane:ethyl acetate; 95:5) gave 145 mg (91% yield) of 3-(4-Chloro-benzoylamino)-5-phenyl-thiophene-2-carboxylic acid methyl ester. $^1$H NMR (CDC$_3$, 400 MHz) 8.54 (s, 1H), 7.99-7.96 (m, 2H), 7.73-7.71 (m, 2H); 7.52-7.50 (m, 2H), 7.46-7.39 (m, 3H), 3.95 (s, 3H).

Step II

3-(4-Chlorobenzoylamino)-5-phenyl-thiophene-2-carboxylic acid

To a mixture of 3-(4-Chloro-benzoylamino)-5-phenyl-thiophene-2-carboxylic acid methyl ester (30 mg, 0.081 mmol) in 1 ml of a 3:2:1 solution made with tetrahydrofuran, methanol and water respectively was added lithium hydroxide monohydrated (20 mg, 0.484 mmol). The mixture was stirred 30 minutes at 60 C, cooled to room temperature, diluted with water and washed with ether (2×). The collected aqueous layer was then acidified with KHSO$_4$ 20% to pH 3 and extracted with ethyl acetate (3×). The combined ethyl acetate layers were washed with brine, dried (Na$_2$SO$_4$) and concentrated. The resulting crude was taken in ethyl acetate and reexctracted with NaOH 0.5 N (2×). The combined aqueous layers were then back-washed with ethyl acetate and acidified to pH3 with KHSO$_4$ 20% and back-extracted with ethyl acetate (2×). The combined organic layers were washed with brine and dried (Na$_2$SO$_4$). $^1$H NMR (DMSO-d$_6$, 400 MHz) 8.35 (s, 1H), 8.02-7.99 (m, 2H), 7.71-7.68 (m, 2H), 7.56-7.53 (m, 2H), 7.43-7.39 (m, 2H), 7.35-7.31 (m, 1H).

The following compounds were prepared in a similar manner as described in example 3:

Compound #74, Compound #77, Compound #92, Compound #96

62
EXAMPLE 4

3-(Benzoyl-methyl-amino)-5-phenyl-thiophene-2-carboxylic acid; Compound #550

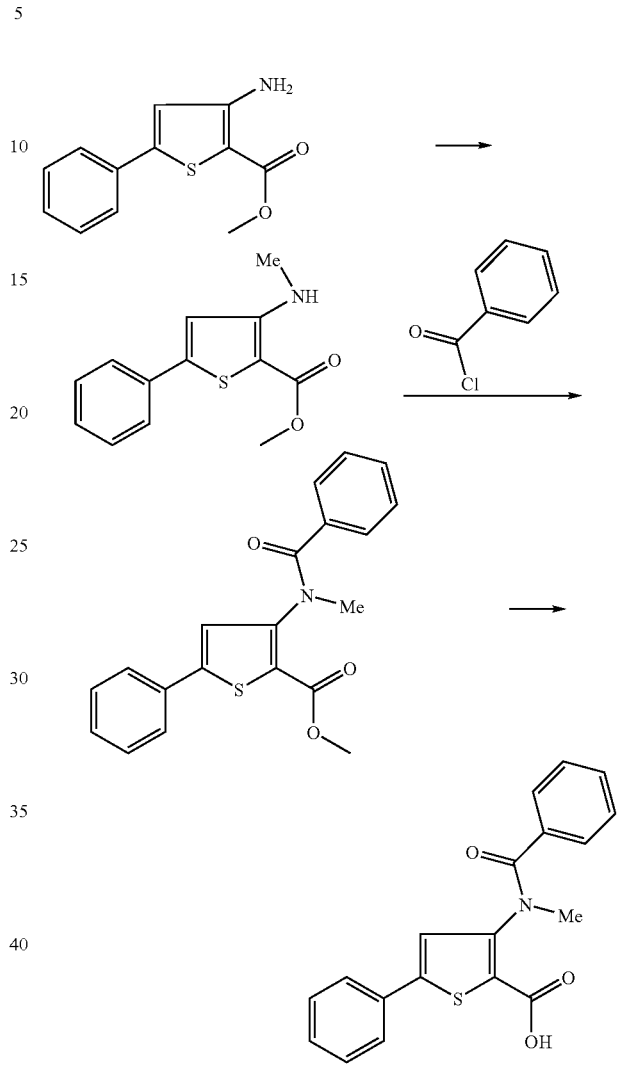

Step I

3-Methylamino-5-phenyl-thiophene-2-carboxylic acid methyl ester

To a mixture of methyl-3-amino-5-phenylthiophene-2-carboxylate (200 mg, 0.855 mmol) in anhydrous N,N-dimethylformamide (4.6 ml) were added 4.2 ml (8.55 mmol) of 2M iodomethane solution in t-buthylmethylether. The mixture was stirred at 60 C for 18 hours, concentrated and purified using biotage technics (silica gel, hexane to hexane:ethyl acetate; 95:5 containing few drops of triethylamine) to give 68 mg (32% yield) of 3-methylamino-5-phenyl-thiophene-2-carboxylic acid methyl ester. $^1$H NMR (CDCl$_3$, 400 MHz) 7.65-7.62 (m, 2H), 7.42-7.36 (m, 3H), 6.86 (broad s, 1H), 3.83 (s, 3H), 3.04 (d, 3H)

Step II

3-(Benzoyl-methyl-amino)-5-phenyl-thiophene-2-carboxylic acid methyl ester

This compound was prepared in a similar manner as for Example 3, Step I; 3-(Benzoyl-methyl-amino)-5-phenylthiophene-2-carboxylic acid methyl ester was obtained ¹H NMR (CDCl₃, 400 MHz) 7.60-7.49 (m, 2H), 7.47-7.35 (m, 5H), 7.28-7.20 (m, 3H), 7.11 (broad s, 1H), 3.83 (s, 3H), 3.44 (s, 3H)

Step III

3-(Benzoyl-methyl-amino)-5-phenyl-thiophene-2-carboxylic acid

This compound was prepared in a similar manner as in Example 3, step II; 3-(Benzoyl-methyl-amino)-5-phenyl-thiophene-2-carboxylic acid was obtained; ¹H NMR (CD₃OD, 400 MHz) 7.64-7.62 (m, 2H), 7.47 (s, 1H), 7.44-7.36 (m, 5H), 7.29-7.20 (m, 3H), 3.42 (s, 3H)

The following compounds were prepared in a similar manner as described in example 4:
Compound #9; Compound #73 Compound #75; Compound #75; Compound #78; Compound #93; Compound #95

EXAMPLE 5

{[5-Phenyl-3-(toluene-4'-sulfonylamino)-thiophene-2-carbonyl]-amino}-acetic acid, Compound #551

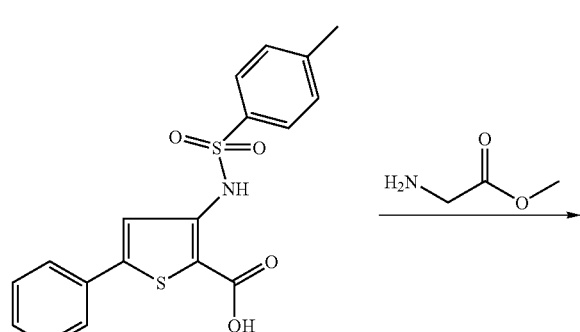

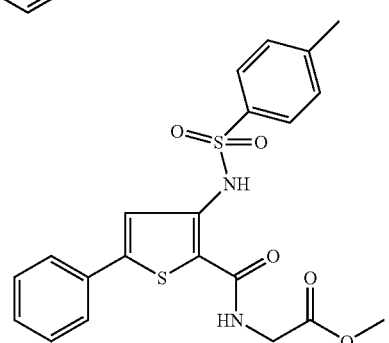

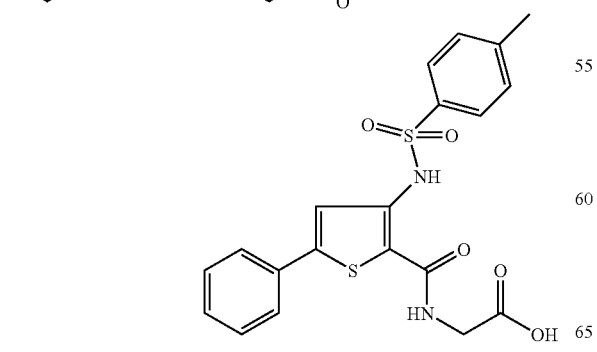

Step I

{[5-Phenyl-3-(toluene-4-sulfonylamino)-thiophene-2-carbonyl]-amino}-acetic acid methyl ester To a mixture of 5-phenyl-3-(toluene-4-sulfonylamino)-thiophene-2-carboxylic acid (prepared according to example 2) (50 mg, 0.134 mmol) in anhydrous dimethylformamide (1.4 ml) were added HATU 152 mg, 0.402 mmol), glycine methyl ester hydrochloride (20 mg, 0.161 mmol) followed by collidine (124 µl, 0.938 mmol). The mixture was stirred at room temperature for 1 hour, concentrated and pre-absorbed on SiO₂. Purification chromatography (hexane to hexane: ethyl acetate; 6:4 to dichloromethane: methanol; 95:5) gave 47 mg of a mixture of {[5-Phenyl-3-(toluene-4-sulfonylamino)-thiophene-2-carbonyl]-amino}-acetic acid methyl ester and collidine. ¹H NMR (CDCl₃, 400 MHz) 7.76-7.73 (m, 2H), 7.61 (s, 1H), 7.57-7.54 (m, 2H), 7.42-7.36 (m, 3H), 7.24-7.22 (m, 2H), 6.19-6.17 (m, 1H), 4.14-4.12 (m, 2H), 3.79 (s, 3H), 2.35 (s, 3H).

Step II

{[5-Phenyl-3-(toluene-4-sulfonylamino)-thiophene-2-carbonyl]-amino}-acetic acid Following the procedure described for example 3 (STEP II), 28 mg (88% yield) of {[5-phenyl-3-(toluene-4-sulfonylamino)-thiophene-2-carbonyl]-amino}-acetic acid were isolated from 33 mg (0.075 mmol) of the {[5-Phenyl-3-(toluene-4-sulfonylamino)-thiophene-2-carbonyl]-amino}-acetic acid methyl ester. ¹H NMR (CD₃OD, 400 MHz): 7.73-7.71 (m, 2H), 7.63-7.61 (m, 2H), 7.54 (s, 1H), 7.45-7.39 (m, 3H), 7.33-7.31 (m, 2H), 4.88 (s, 2H), 2.36 (s, 3H).

EXAMPLE 6

3-(2,4-Dichloro-benzylamino)-5-phenyl-thiophene-2-carboxylic acid

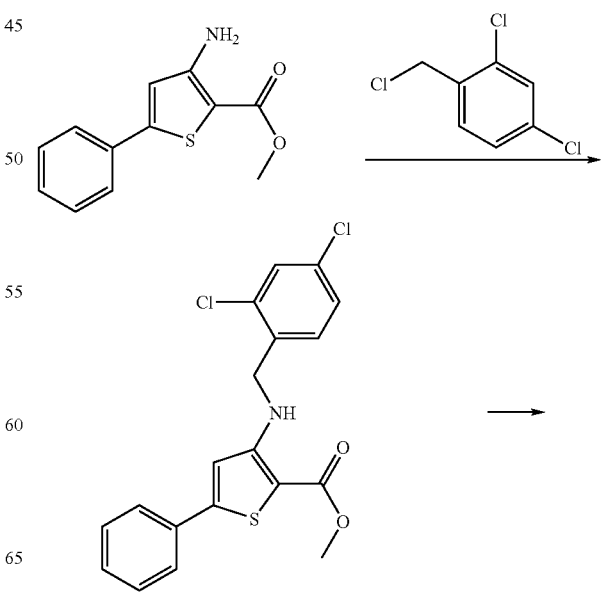

-continued

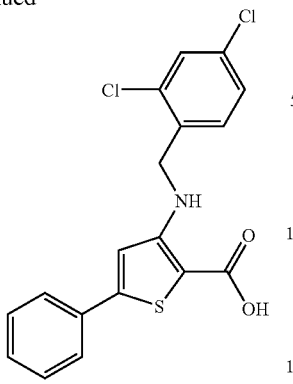

Compound #48

Step I

3-(2,4-Dichloro-benzylamino)-5-phenyl-thiophene-2-carboxylic acid methyl ester Sodium hydride (60% dispersion in oil, 180 mg, 4,72 mmol) was added to an ice-cold solution of 3-Amino-5-phenyl-thiophene-2-carboxylic acid methyl ester (1000 mg, 4,29 mmol) in 25 ml of dimethylformamide in an atmosphere of $N_2$. After 5 min, 2,4-dichloro-1-chloromethyl-benzene (755 mg, 3,86 mmol) was added to the solution and then the reaction mixture was stirred for 30 min at 0° C. and 30 min at room temperature. The mixture was partitioned between ether (20 mL) and water (20 mL) and the organic layer was separated. The aqueous phase was washed twice with ether (2×20 mL) and the combined ether layer was dried ($MgSO_4$) and concentrated. The residue obtained was then purified by precipitation. The crude product was taken in 25 ml of ethyl acetate, a yellow precipitate came out which was filtered to obtain 3-(2,4-Dichloro-benzylamino)-5-phenyl-thiophene-2-carboxylic acid methyl ester, 835 mg (55%). $^1$H-NMR (DMSO, 400 MHz): 7.67 ppm (m, 2H, $H_{aro}$); 7.44-7.35 ppm (m, 6H, $H_{aro}$); 7.26 ppm (s, 1H, $H_{aro}$); 4.63 ppm (d, 2H, N—$CH_2$); 3.75 ppm (s, 3H, O—$CH_3$)

Step II

3-(2,4-Dichloro-benzylamino)-5-phenyl-thiophene-2-carboxylic acid 3-(2,4-Dichloro-benzylamino)-5-phenyl-thiophene-2-carboxylic acid methyl ester (70 mg, 0,18 mmol) was dissolved in a mixture of THF-MeOH—$H_2O$ (3:2:1) (20 mL) and then 1080 ul of LiOH 1N was added to it. After 16 h of stirring at temperature of 100° C., solvents were removed and then partitioned between 10 ml of $H_2O$, 2 ml of $KHSO_4$ 5% and 10 ml of EtOAc. The organic layer was separated and the aqueous phase was washed twice with ethyl acetate (2×10 mL). The combined ethyl acetate layer was dried (MgSO4) and concentrated to obtain 43 mg (63%) of 3-(2,4-Dichloro-benzylamino)-5-phenyl-thiophene-2-carboxylic acid $^1$H-NMR (DMSO, 400 MHz): δ 7.65 ppm (m, 3H, $H_{aro}$); 7.43-7.32 ppm (m, 5H, $H_{aro}$); 7.23 ppm (s, 1H, $H_{aro}$); 4.61 ppm (d, 2H, N—C$H_2$)

EXAMPLE 7

3-{(2,4-Dichloro-benzoyl)-[5-(3-trifluoromethyl-phenyl)-furan-2-ylmethyl]-amino}-5-phenyl-thiophene-2-carboxylic acid, Compound #4

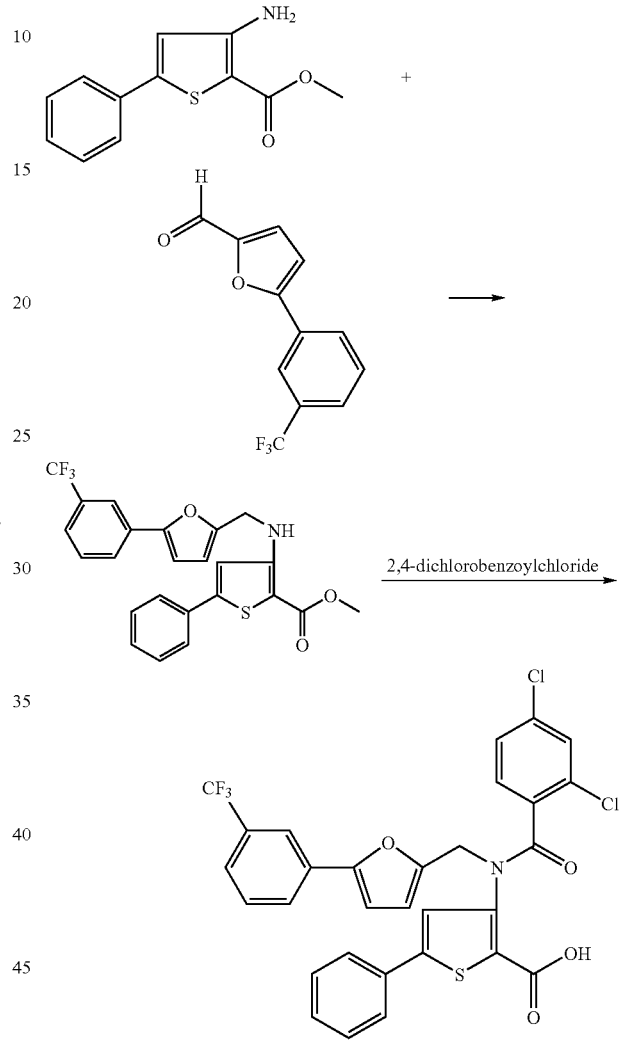

Step I

5-Phenyl-3-{[5-(3-trifluoromethyl-phenyl)-furan-2-ylmethyl]amino}-thiophene-2-carboxylic acid methylester To a stirred solution of 3-Amino-5-phenyl-thiophene-2-carboxylic acid methyl ester (100 mg, 0.416 mmol) in dichloromethane (15 mL) were added 5-(trifluoromethyl-phenyl)-furan-2-carbaldehyde (100 mg, 0.429 mmol) and molecular sieves. The reaction mixture was stirred at room temperature overnight. The solution was filtered over celite and the filtrate was evaporated under reduced pressure. The residue was dissolved in anhydrous methanol (15 mL) and cooled to 0° C. in an ice bath. Sodium borohydride (18 mg, 1.1 eq.) was added. The reaction mixture was stirred at this temperature for 2 h. Saturated ammonium chloride (10 mL) was added and stirring was continued for an additional 15 min. at room temperature. Methanol was removed and the resulted mixture was extracted with dichloromethane (3×30 mL). The organic solution was washed with water, brine and was dried over sodium sulfate. Solvent was evaporated and the crude product was purified on silica gel using hexane: ethylacetate 9:1 as eluent to provide the desired product in 34% yield (65 mg).

$^1$HNMR (CDCl$_3$, 400 MHz): 7.80 (s, 1H), 7.73 (m, 1H), 7.55 (m, 2H), 7.41 (m, 2H), 7.33 (m, 3H), 6.93 (s, 1H), 6.48 (d, 1H), 6.24 (d, 1H), 4.43 (s, 2H), 3.76 (s, 3H).

Step II

3-{(2,4-Dichloro-benzoyl)-[5-(3-trifluoromethyl-phenyl)-furan-2-ylmethyl]-amino}-5-phenyl-thiophene-2-carboxylic acid methyl ester To a stirred solution of 5-Phenyl-3-{[5-(3-trifluoromethyl-phenyl)-furan-2-ylmethyl]-amino}-thiophene-2-carboxylic acid methylester (65 mg 0.142 mmol) in dichloromethane (3 ml) and saturated NaHCO$_3$ solution (3 ml) was added a solution of 2,4-dichloro-benzoyl chloride (36 mg, 1.2 eq.) in dichloromethane (0.9 ml). The reaction mixture was stirred vigorously at room temperature for overnight. The organic phase was collected and the aqueous phase was extracted twice with methylene chloride (2×15 ml). The organic layers were combined, washed with water, brine and dried over anhydrous Na$_2$SO$_4$. Solvent was removed and residue was purified on silica gel using Hexane:EtOAc 9:1 as eluant to give the desired product in 78% yield (70 mg). The proton NMR indicated the presence of rotamers.

$^1$HNMR (CDCl$_3$, 400 MHz): 7.80 (s, 1H), 7.73 (m, 1H), 7.55 (m, 2H), 7.45 (m, 2H), 7.33 (m, 3H), 7.20 (m, 2H), 7.12 (m, 1H), 6.93 (s, 1H), 6.62 (d, 1H), 6.42 (d, 1H), 5.60 (bd, 1H), 4.70 (bd, 1H), 3.76 (s, 3H).

Step III

3-{(2,4-Dichloro-benzoyl)-[5-(3-trifluoromethyl-phenyl)-furan-2-ylmethyl]-amino}-5-phenyl-thiophene-2-carboxylic acid 3-{(2,4-Dichloro-benzoyl)-[5-(3-trifluoromethyl-phenyl)-furan-2-ylmethyl]-amino}-5-phenyl-thiophene-2-carboxylic acid methyl ester (62 mg, 0.098 mmol) was dissolved in THF (5 mL) and water (2 mL). A solution of lithium hydroxide (13 mg, 3 eq. in 2 mL of water) was added dropwise. After first few drop, a pink color appeared and disappeared. Mixture was stirred for 5 hrs and acidified with 1N HCl-solution. The product was extracted into ethyl acetate, washed once with water, dried over magnesium sulfate. Solvent was evaporated and the residue was purified on silica gel (Bond-Elute 2 g). The product was elute with a 20 mL gradient of Hexane:EtOAc 9:1. 4:1, 7:3, 3:2, 1:1, 2:3 and EtOAc to give the desired product in 76% yield (46 mg).

$^1$HNMR (CD$_3$OD, 400 MHz): 7.90 (s, 1H), 7.83 (m, 1H), 7.55 (m, 2H), 7.40-7.20 (m, 8H), 7.10 (s, 1H), 6.82 (d, 1H), 6.42 (d, 1H), 5.60 (bd, 1H), 4.70 (bd, 1H), 3.86 (s, 3H).

EXAMPLE 8

Preparation of 3-[(4-Chloro-2,5-dimethyl-benzenesulfonyl)-(3-iodo-benzyl)-amino]-5-phenyl-thiophene-2-carboxylic acid Compound #1 and 3-[(3-Benzofuran-2-yl-benzyl)-(4-chloro-2,5-dimethyl-benzenesulfonyl)-amino]-5-phenyl-thiophene-2-carboxylic acid Compound #2

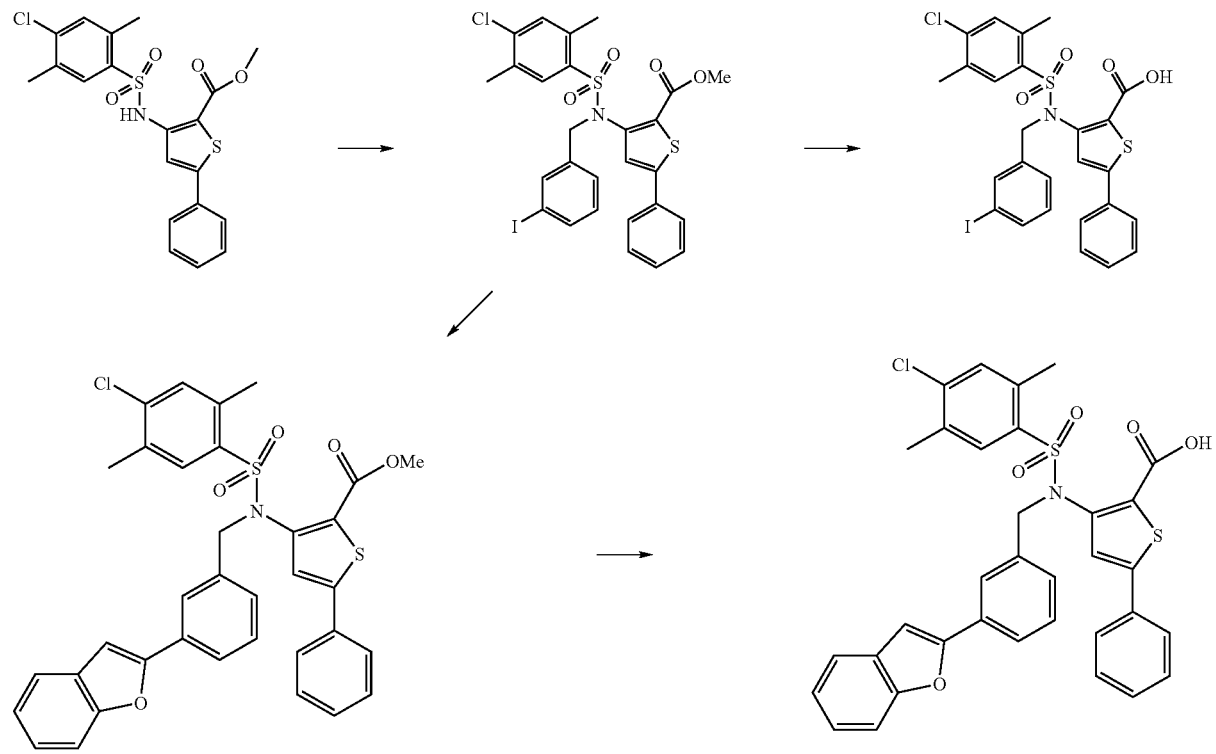

Step I

To a solution of 3-(4-Chloro-2,5-dimethyl-benzenesulfonylamino)-5-phenyl-thiophene-2-carboxylic acid methyl ester (100 mg, 0.229 mmol) in anhydrous DMF (6 mL), 3-iodobenzyl bromide (82 mg, 0.276 mmol) and cesium carbonate (88 mg, 0.276 mmol) were added and the reaction mixture was stirred at room temperature under a $N_2$ atmosphere for 12 h. The reaction mixture was partitioned between water and ether. The ether layer was separated, dried ($Na_2SO_4$), concentrated. The residue was purified by silica gel column chromatography using ethyl acetate and hexane (1:3) as eluent to obtain 3-[(4-Chloro-2,5-dimethyl-benzenesulfonyl)-(3-iodo-benzyl)-amino]-5-phenyl-thiophene-2-carboxylic acid methyl ester (130 mg, 87%) as a syrup.

Step II

3-[(4-Chloro-2,5-dimethyl-benzenesulfonyl)-(3-iodo-benzyl)-amino]-5-phenyl-thiophene-2-carboxylic acid methyl ester (25 mg, 0.038 mmol) was taken in a mixture of THF:MeOH:$H_2O$ (3:2:1, 3 mL) and then added 1N aqueous solution of LiOH.$H_2O$ (0.24 mL, 0.228 mmol). The reaction mixture was stirred at room temperature for 12 h. Solvents were removed and the residue was partitioned between water and ethyl acetate. The aqueous layer was acidified using 10% $KHSO_4$ solution. The organic layer was separated, dried ($Na_2SO_4$) and concentrated. The residue was purified by silica gel column chromatography using dichloromethane and methanol (9:1) to obtain 3-[(4-Chloro-2,5-dimethyl-benzene-sulfonyl)-(3-iodo-benzyl)-amino]-5-phenyl-thiophene-2-carboxylic acid (22 mg, 88%) as a white solid. $^1$H NMR (CDCl$_3$, 400 MHz): 7.69 (m, 3H), 7.57 (m, 3H), 7.42 (m, 3H), 7.33 (d, 1H), 7.16 (s, 1H), 6.04 (dd, 1H), 4.90 (bs, 2H), 2.36 (s, 6H).

Compound #5 was prepared in a similar manner;
3-[(3-Benzofuran-2-yl-benzyl)-(4-chloro-2,5-dimethyl-benzenesulfonyl)-amino]-5-phenyl-thiophene-2-carboxylic acid Compound #2

Step I

To a degassed solution of 3-[(4-Chloro-2,5-dimethyl-benzenesulfonyl)-(3-iodo-benzyl)-amino]-5-phenyl-thiophene-2-carboxylic acid methyl ester (110 mg, 0.169 mmol) and benzofuran-2-boronic acid (55 mg, 0.185 mmol) in a mixture of DME (8 mL) and 2M aqueous $Na_2CO_3$ (4 mL), Pd(PPh$_3$)$_4$ (9 mg) was added and the reaction mixture was stirred at reflux conditions for 2 h under a $N_2$ atmosphere. The reaction mixture was diluted with ethyl acetate and water. The organic layer was separated, dried ($Na_2SO_4$) and concentrated. 3-[(3-Benzofuran-2-yl-benzyl)-(4-chloro-2,5-dimethyl-benzenesulfonyl)-amino]-5-phenyl-thiophene-2-carboxylic acid methyl ester (107 mg, 100%) was isolated as a thick syrup and used for the next reaction without any further purification.

Step II

3-[(3-Benzofuran-2-yl-benzyl)-(4-chloro-2,5-dimethyl-benzenesulfonyl)-amino]-5-phenyl-thiophene-2-carboxylic acid methyl ester (20 mg, 0.031 mmol) was taken in a mixture of THF:MeOH:$H_2O$ (3:2:1, 3 mL) and then added 1N aqueous solution of LiOH.$H_2O$ (0.20 mL, 0.186 mmol). The reaction mixture was stirred at room temperature for 12 h. Solvents were removed and the residue was partitioned between water and ethyl acetate. The aqueous layer was acidified using 10% $KHSO_4$ solution. The organic layer was separated, dried ($Na_2SO_4$) and concentrated. The residue was purified by silica gel column chromatography using dichloromethane and methanol (−9:1) to obtain 3-[(3-Benzofuran-2-yl-benzyl)-(4-chloro-2,5-dimethyl-benzene-sulfonyl)-amino]-5-phenyl-thiophene-2-carboxylic acid (14 mg, 70%) as a white solid. $^1$H NMR (DMSO, 400 MHz): δ7.93 (s, 1H), 7.84 (s, 1H), 7.74 (bd, 1H), 7.65-7.22 (m, 14H), 4.95 (s, 2H), 2.33, 2.23, (2s, 6H).

EXAMPLE 9

3-[(4-Chloro-benzoyl)-isopropyl-amino]-5-phenyl-thiophene-2-carboxylic acid Compound #210

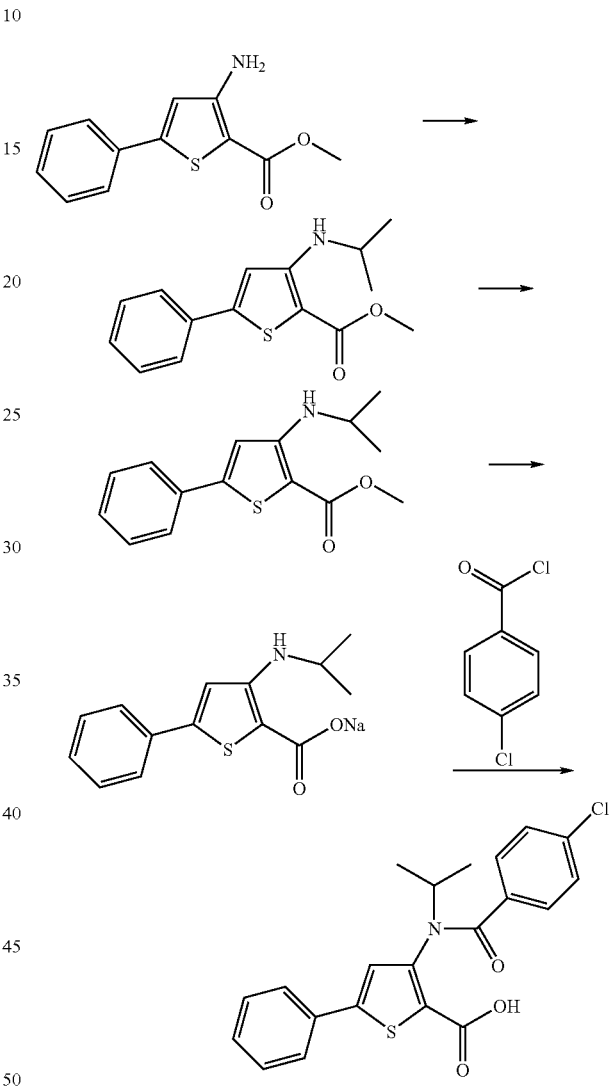

Step I

Method A

A DMF (15 mL) solution of 3-Amino-5-phenyl-thiophene-2-carboxylic acid methyl ester (500 mg, 21.5 mmol) was cooled to 0° C. and then isopropyl iodide (2.57 mL) and NaH (60%, 775 mg, 32.3 mmol) were added under an atmosphere of $N_2$. The ice bath was removed and the reaction mixture was stirred at room temperature for 1 h. The mixture was partitioned between ether and water, the ether layer was separated, dried ($Na_2SO_4$) and concentrated. The residue was purified by silica gel column chromatography using ethyl acetate and hexane (5:95) as eluent to obtain 3-isopropylamino-5-phenyl-thiophene-2-carboxylic acid methyl ester (189 mg, 32%) as a solid. $^1$H NMR (CDCl$_3$, 400 MHz): 7.62 (d, 2H), 7.40 (m, 3H), 6.91 (s, 1H), 3.84 (s, 3H), 1.35 (d, 6H).

Method B

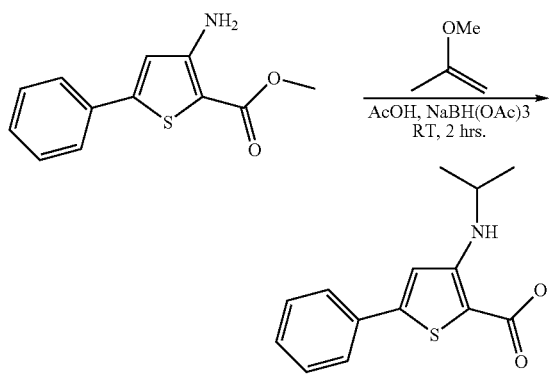

To a stirred solution of 3-Amino-5-phenyl-thiophene-2-carboxylic acid methyl ester (1.82 g, 7.8 mmol) in 1,2-dichloroethane (40 mL) was added sequentially 2-methoxypropene (3.0 mL, 31.2 mmol), AcOH (1.8 mL, 31.2 mmol) and NaBH(OAc)$_3$ (3.31 g, 15.6 mmol) and stirred for 2 hrs. It was then diluted with EtOAc and H$_2$O. The aqueous solution was adjusted to pH=7 by adding NaHCO$_3$. The aqueous phase was extracted with EtOAc, the combined extract was washed with brine and dried on MgSO4 and filtered. Purification on bond elute with hexane to 5% EtOAc-hexane furnished 3-Amino-5-phenyl-thiophene-2-carboxylic acid methyl ester (2.07 g, 96% yield).

The intermediate compounds 3-Cyclohexylamino-5-phenyl-thiophene-2-carboxylic acid methyl ester, 3-(1-Methyl-piperidin-4-ylamino)-5-phenyl-thiophene-2-carboxylic acid methyl ester and 3-(1-Methyl-piperidin-4-ylamino)-5-phenyl-thiophene-2-carboxylic acid methyl ester were prepared in a similar manner as described and used as intermediates in the synthesis of compound #543, compound #553 and compound #573

Step II

To a suspension of 3-isopropylamino-5-phenyl-thiophene-2-carboxylic acid methyl ester (1.2 g, 4.364 mmol) in a mixture of H$_2$O (22 mL) and dioxane (35 mL), 1N aqueous solution of NaOH (13 mL, 13.00 mmol) was added. The reaction mixture was stirred at 100° C. for 3 h. The reaction mixture was used for the next reaction without any further purification.

To this reaction mixture of 3-Amino-5-phenyl-thiophene-2-carboxylic acid sodium salt (23 mL, 1.41 mmol), 4-chlorobenzoyl chloride (0.269 mL, 2.11 mmol) was added at 0° C. The pH of the solution was maintained at 9 by adding 1N NaOH solution and then stirred at room temperature for 5 h. The reaction mixture was diluted with ethyl acetate and water. The water layer was acidified by adding 1N HCl solution. The organic layer was separated, dried (Na$_2$SO$_4$) and concentrated. The crude product was purified by recrystallization from ethyl acetate to obtain the pure 3-[(4-Chloro-benzoyl)-isopropyl-amino]-5-phenyl-thiophene-2-carboxylic acid (45 mg) as a white solid. $^1$H NMR (DMSO-D$_6$, 400 MHz): 7.58 (d, 2H), 7.38-7.26 (m, 6H), 7.13 (d, 1H), 4.77 (m, 1H), 1.25 (d, 3H), 1.02 (d, 3H). ESI$^-$ (M-H): 398.

Similarly, the following compounds were made: Compound #218 Compound #219$^-$, Compound #226, Compound #234, Compound #243, Compound #246, Compound #250, Compound #262, Compound #324, Compound 326, Compound #331.

EXAMPLE 10

3-[(2,4-Dichloro-benzoyl)-isopropyl-amino]-5-phenyl-thiophene-2-carboxylic acid Compound #149

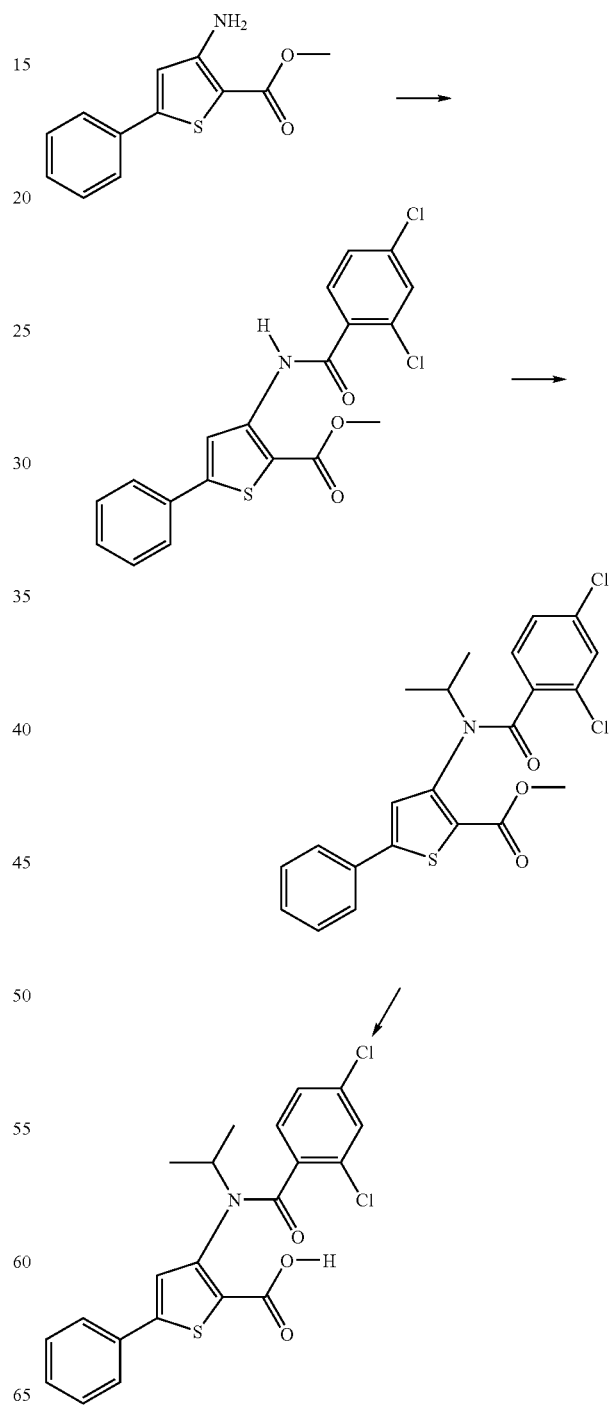

Step I

3-(2,4-Dichloro-benzoylamino)-5-phenyl-thiophene-2-carboxylic acid methyl ester To a ice-cold solution of 3-Amino-5-phenyl-thiophene-2-carboxylic acid methyl ester 1 (5 g, 21.5 mmol) and triethylamine (4.56 g, 45.0 mmol) in dichloromethane (100 ml) was added 2,4-dichlorobenzoyl chloride (3.90 g, 19.4 mmol). The reaction mixture was stirred for 30 min a 0° C. and 16 h at room temperature. Then, the reaction mixture was partitioned between 25 ml of $H_2O$, 50 ml sat. $NaHCO_3$ and 50 ml of $CH_2Cl_2$. The organic layer was separated and the aqueous phase was washed twice with $CH_2Cl_2$ (2×50 mL). The combined dichloromethane layer was dried ($MgSO_4$), concentrated and the residue was purified by recrystallization in $CH_2Cl_2$ to obtain 5.832 g (74%) as a white solid of 3-(2,4-Dichloro-benzoylamino)-5-phenyl-thiophene-2-carboxylic acid methyl ester. NMR $^1H$ ($CDCl_3$, 400 MHz): 8.30 ppm (s, 1H, $H_{aro}$); 7.74-7.66 ppm (m, 3H, $H_{aro}$); 7.51 ppm (d, 1H, $H_{aro}$); 7.46-7.34 ppm (m, 4H, $H_{aro}$); 3.91 ppm (s, 3H).

Step II

3-[(2,4-Dichloro-benzoyl)-isopropyl-amino]-5-phenyl-thiophene-2-carboxylic acid methyl ester Sodium Hydride (60% dispersion in oil, 190 mg, 5,2 mmol) was added to an ice-cold solution of 3-(2,4-Dichloro-benzoylamino)-5-phenyl-thiophene-2-carboxylic acid methyl ester (2) (1.5 g, 3.69 mmol) in 350 ml of N,N-dimethylformamide in an atmosphere of $N_2$. After 5 min, 2-Iodopropane (941 mg, 5.54 mmol) was added to the solution and then the reaction mixture was stirred for 30 min at 0° C. and 64 h at room temperature. The mixture was partitioned between ether (200 mL) and water (350 mL) and the organic layer was separated. The aqueous phase was washed twice with ether (2×70 mL) and the combined ether layer was dried ($MgSO_4$), concentrated and the residue was purified by flash chromatography (10% EtOAc/Hexane) to obtain 908 mg (55%) of 3-[(2,4-Dichloro-benzoyl)-isopropyl-amino]-5-phenyl-thiophene-2-carboxylic acid methyl ester. NMR $^1H$ ($CDCl_3$, 400 MHz): Rotamere 95/05: 7.54 ppm (dd, 2H, $H_{aro}$); 7.49-7.35 ppm (m, 3H, $H_{aro}$); 7.29-7.25 ppm (m, 2H, $H_{aro}$); 7.15 ppm (d, 1H, $H_{aro}$); 7.05 ppm (d, 1H, $H_{aro}$) 5.09 ppm (hex, 1H, N—CH(CH_3), major rotamere); 3.99 ppm (hex, N—CH(CH_3), minor rotamere); 3.89 ppm (s, 3H); 1.40 ppm (d, 3H, N—CH(CH_3), major rotamere); 1.28 ppm (d, N—CH(CH_3), minor rotamere); 1.09 ppm (d, 3H, N—CH(CH_3), major rotamere); 1.01 ppm (d, N—CH(CH_3), minor rotamere).

Step III

3-[(2,4-Dichloro-benzoyl)-isopropyl-amino]-5-phenyl-thiophene-2-carboxylic acid 3-[(2,4-Dichloro-benzoyl)-isopropyl-amino]-5-phenyl-thiophene-2-carboxylic acid methyl ester (3) (345 mg, 0.77 mmol) was dissolved in a mixture of THF-MeOH—$H_2O$ (3:2:1) (30 mL) and then 4.6 ml of LiOH 1N was added to it. After 120 min of stirring at room temperature; solvant was removed and then partitioned between 25 ml of $H_2O$, 4 ml of $KHSO_4$ 5% and 25 ml of EtOAc. The organic, layer was separated and the aqueous phase was washed twice with ethyl acetate (2×10 mL). The combined ethyl acetate layer was dried ($MgSO_4$), concentrated and the residue was purified by preparative chromatography (10% MeOH/$CH_2Cl_2$) to obtain 175 mg (53%) as a white solid of 3-[(2,4-Dichloro-benzoyl)-isopropyl-amino]-5-phenyl-thiophene-2-carboxylic acid. NMR $^1H$ (DMSO, 400 MHz): Rotamer 95/05: 7.82 ppm (m, $H_{aro}$, minor rotamer); 7.69 ppm (d, 2H, $H_{aro}$); 7.61 ppm (d, 1H, $H_{aro}$); 7.51-7.37 ppm (m, 4H, $H_{aro}$); 7.35-7.28 ppm (m, 2H, $H_{aro}$), 4.89 ppm (hex, 1H, N—CH(CH_3), major rotamer); 3.84 ppm (hex, N—CH(CH_3), minor rotamer); 1.36 ppm (d, 3H, N—CH(CH_3), major rotamer); 1.25 ppm (d, N—CH(CH_3), minor rotamer); 1.03 ppm (d, 3H, N—CH(CH_3), major rotamer); 0.93 ppm (d, N—CH(CH_3), minor rotamere).

The following compounds were prepared in a similar manner: Compound #201, Compound #204, Compound #233, Compound #244, Compound #261, Compound #264, Compound #299.

EXAMPLE 11

3-[(2,4-Dichloro-benzoyl)-phenyl-amino]-5-phenyl-thiophene-2-carboxylic acid. Compound #208

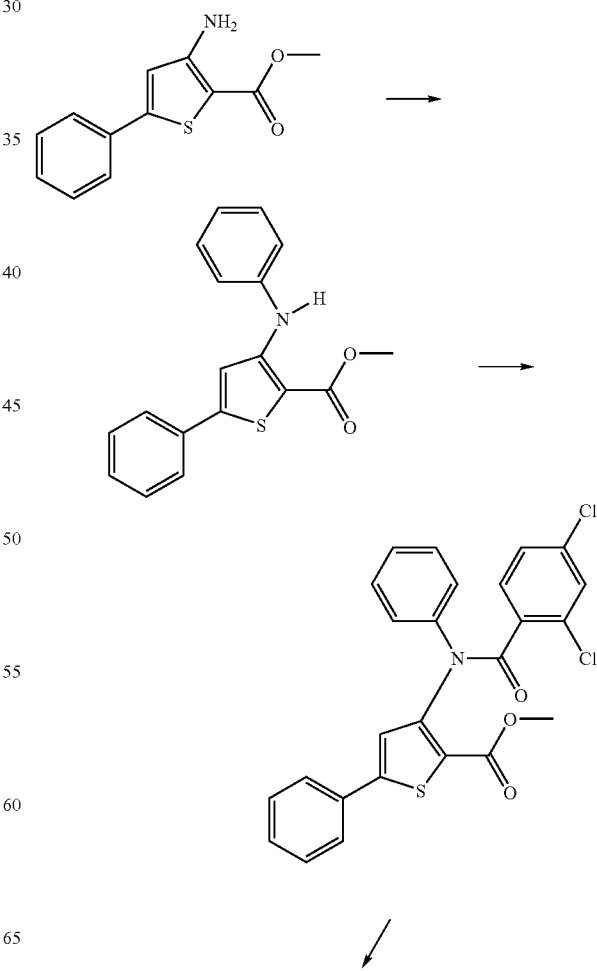

-continued

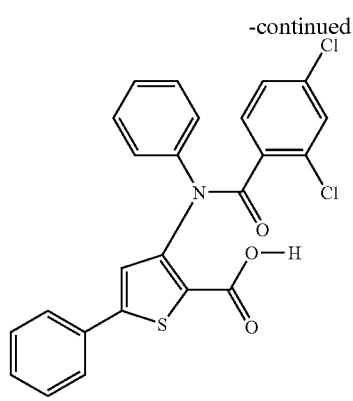

Step I

5-Phenyl-3-phenylamino-thiophene-2-carboxylic acid methyl ester

To a solution of 3-Amino-5-phenyl-thiophene-2-carboxylic acid methyl ester (1 g, 4.29 mmol) in dichloromethane (50 ml) was added phenyl boronic acid (1.05 g, 8.6 mmol), pyridine (680 mg, 8.6 mmol) and copper(II) acetate (1.18 g, 6.5 mmol). The reaction mixture was stirred for 16 h at room temperature. Then, the reaction mixture was filtered through celite, concentrated and the residue was purified by flash chromatography (9:1 Hexane/EtOAc) to obtain 435 mg (33%) of 5-Phenyl-3-phenylamino-thiophene-2-carboxylic acid methyl ester. NMR $^1$H (CDCl$_3$, 400 MHz): 7.38 ppm (dd, 2H, H$_{aro}$); 7.35-7.26 ppm (m, 5H, H$_{aro}$); 7.19 ppm (s, 1H, H$_{aro}$); 7.15 ppm (dd, 2H, H$_{aro}$); 7.02 ppm (ddt, 1H, H$_{aro}$); 3.82 ppm (s, 3H).

Step II

3-[(2,4-Dichloro-benzoyl)-phenyl-amino]-5-phenyl-thiophene-2-carboxylic acid methyl ester Sodium Hydride (60% dispersion in oil, 80 mg, 1,5 mmol) was added to an ice-cold solution 5-Phenyl-3-phenylamino-thiophene-2-carboxylic acid methyl ester (2) (230 mg, 0,74 mmol) in 20 ml of N,N-dimethylformamide in an atmosphere of N$_2$. After 5 min, 2,4-Dichloro-benzoyl chloride (310 mg, 1.48 mmol) was added to the solution and then the reaction mixture was stirred for 30 min at 0° C. and 16 h at room temperature. The mixture was partitioned between ether (20 mL) and water (20 mL) and the organic layer was separated. The aqueous phase was washed twice with ether (2×10 mL) and the combined ether layer was dried (MgSO$_4$), concentrated and the residue was purified by preparative chromatography (30% EtOAc/Hexane) to obtain 58 mg (16%) of 3-[(2,4-Dichloro-benzoyl)-phenyl-amino]-5-phenyl-thiophene-2-carboxylic acid methyl ester. NMR $^1$H (CDCl$_3$, 400 MHz): 7.65-7.10 ppm (m, 14H, H$_{aro}$); 3.77 ppm (s, 3H).

Step III

3-[(2,4-Dichloro-benzoyl)-phenyl-amino]-5-phenyl-thiophene-2-carboxylic acid

3-[(2,4-Dichloro-benzoyl)-phenyl-amino]-5-phenyl-thiophene-2-carboxylic acid methyl ester (55 mg, 0.11 mmol) was dissolved in a mixture of THF-MeOH—H$_2$O (3:2:1) (15 mL) and then 0.66 ml of LiOH 1N was added to it. After 60 min of stirring at room-temperature, solvents were removed and then partitioned between 15 ml of H$_2$O, 4 ml of KHSO$_4$ 5% and 15 ml of EtOAc. The organic layer was separated and the aqueous phase was washed twice with ethyl acetate (2×10 mL). The combined ethyl acetate layer was dried (MgSO$_4$), concentrated and the residue was purified by preparative chromatography (10% MeOH/CH$_2$Cl$_2$) to obtain 32 mg (60%) of 3-[(2,4-Dichloro-benzoyl)-phenyl-amino]-5-phenyl-thiophene-2-carboxylic acid. NMR $^1$H (DMSO, 400 MHz): Rotamer: 7.75 ppm (d, 1H, H$_{aro}$); 7.68 ppm (2H, H$_{aro}$); 7.53 ppm (d, H$_{aro}$, minor rotamer); 7.51-7.23 ppm (m, 11H, H$_{aro}$, minor rotamer); 7.17 ppm (H$_{aro}$, minor rotamer).

Compound #525 was prepared in a similar manner.

EXAMPLE 12

3-[tert-Butyl-(2,4-dichloro-benzoyl)-amino]-5-phenyl-thiophene-2-carboxylic acid Compound #327

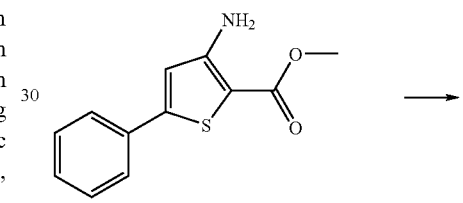

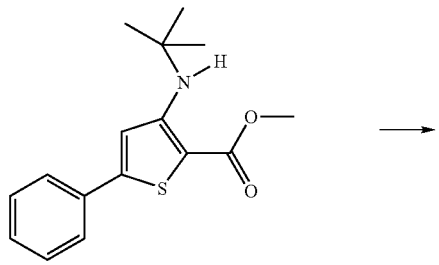

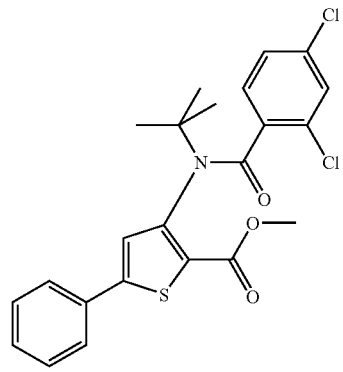

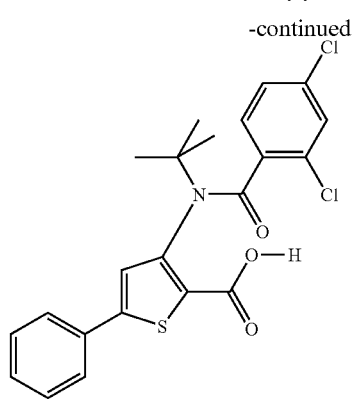

Step I

3-tert-Butylamino-5-phenyl-thiophene-2-carboxylic acid methyl ester

Concentrated sulfuric acid (10 drop) was added to a solution of 3-Amino-5-phenyl-thiophene-2-carboxylic acid methyl ester (500 mg, 2,15 mmol) in 20 ml of dioxane/chloroforme (2:3) in a sealed tube. After cooling the solution at −78° C., put 20 ml of isobutene gaz. The sealed tube was closed and then the reaction mixture was stirred for 6 days at 60° C. The solvant was removed and then partitioned between 15 ml of sat. $Na_2CO_3$ solution and 15 ml of EtOAc. The organic layer was separated, the aqueous phase was washed twice with ethyl acetate and the combined ethyl acetate layer was dried ($MgSO_4$), concentrated and the residue was purified by flash chromatography (5% EtOAc/Hexane) to obtain 385 mg (62%) of 3-tert-Butylamino-5-phenyl-thiophene-2-carboxylic acid methyl ester. NMR $^1H$ ($CDCl_3$, 400 MHz): 7.65 ppm (d, 2H, $H_{aro}$); 7.44-7.38 ppm (m, 3H, $H_{aro}$); 7.07 ppm (s, 1H, $H_{aro}$); 3.86 ppm (s, 3H); 1.48 ppm (s, 9H).

Step II

3-[tert-Butyl-(2,4-dichloro-benzoyl)-amino]-5-phenyl-thiophene-2-carboxylic acid methyl ester To a solution of 3-tert-Butylamino-5-phenyl-thiophene-2-carboxylic acid methyl ester (100 mg, 0.35 mmol) in dichloroethane (10 ml) in an atmosphere of $N_2$ was added 2,4-dichloro-benzoyl chloride (79 mg, 0.38 mmol). The reaction mixture was stirred for 16 h at reflux. Then, the solvents were removed and the residue was purified by flash chromatography (9:1 Hexane/EtOAc) to obtain 112 mg (69%) of 3-[tert-Butyl-(2,4-dichloro-benzoyl)-amino]-5-phenyl-thiophene-2-carboxylic acid methyl ester. NMR $^1H$ ($CDCl_3$, 400 MHz): 7.50 ppm (m, 2H, $H_{aro}$) 7.44-7.34 ppm (m, 3H, $H_{aro}$); 7.27 ppm (s, 1H, $H_{aro}$); 7.18 ppm (dl, 1H, $H_{aro}$); 7.14 ppm (d, 1H, $H_{aro}$); 7.00 ppm (dd, 1H, $H_{aro}$); 3.93 ppm (s, 3H); 1.56 ppm (s, 9H).

Step III

3-[tert-Butyl-(2,4-dichloro-benzoyl)-amino]-5-phenyl-thiophene-2-carboxylic acid 3-[tert-Butyl-(2,4-dichloro-benzoyl)-amino]-5-phenyl-thiophene-2-carboxylic acid methyl ester (112 mg, 0.24 mmol) was dissolved in a mixture of THF-MeOH—$H_2O$ (3:2:1) (15 mL) and then 1.5 ml of LiOH 1N was added to it. After 3 h of stirring at room temperature, solvent was removed and then partitioned between 15 ml of $H_2O$, 4 ml of $KHSO_4$ 5% and 15 ml of EtOAc. The organic layer was separated and the aqueous phase was washed twice with ethyl acetate (2×10 mL). The combined ethyl acetate layer was dried ($MgSO_4$), concentrated and the residue was purified by preparative chromatography (10% MeOH/$CH_2Cl_2$) to obtain 32 mg (29%) of 3-[tert-Butyl-(2,4-dichloro-benzoyl)-amino]-5-phenyl-thiophene-2-carboxylic acid. NMR $^1H$ (DMSO, 400 MHz): 7.62 ppm (d, 2H, $H_{aro}$); 7.44-7.34 ppm (m, 4H, $H_{aro}$); 7.32-7.12 ppm (m, 3H, $H_{aro}$); 2.48 ppm (s, 9H).

EXAMPLE 13

3-[Cyclopropyl-(2,4-dichloro-benzoyl)-amino]-5-phenyl-thiophene-2-carboxylic acid. Compound #333

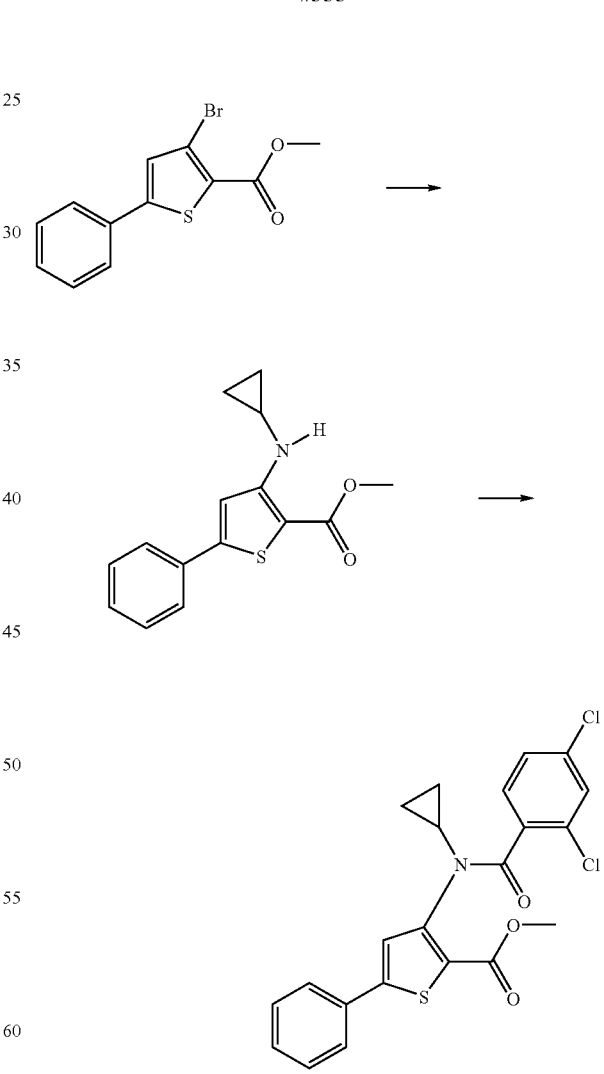

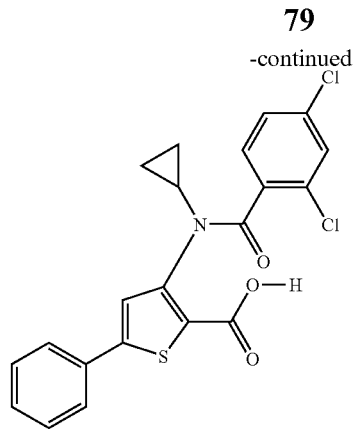

Step I

3-Cyclopropylamino-5-phenyl-thiophene-2-carboxylic acid methyl ester

To a solution of 3-Bromo-5-phenyl-thiophene-2-carboxylic acid methyl ester (250 mg, 0.89 mmol) in toluene (25 ml) was added cyclopropylamine (57 mg, 1.0 mmol), cesium carbonate (382 mg, 1.2 mmol), BINAP (50 mg, 0.08 mmol) and tris (dibenzyli-denacetone)dipaladium (0) (38 mg, 0.04 mmol). The reaction mixture was stirred for 16 h at 110° C. in a sealed tube. The mixture was partitioned between toluene (20 mL) and water (20 mL) and the organic layer was separated. The aqueous phase was washed twice with toluene (2×10 mL) and the combined toluene layer was dried ($MgSO_4$), concentrated and the residue was purified by preparative chromatography (10% EtOAc/Hexane) to obtain 52 mg (22%) of 3-Cyclopropylamino-5-phenyl-thiophene-2-carboxylic acid methyl ester. NMR $^1$H ($CDCl_3$, 400 MHz): 7.67-7.62 ppm (m, 2H, $H_{aro}$); 7.43-7.32 ppm (m, 3H, $H_{aro}$); 7.16 ppm (s, 1H, $H_{aro}$); 3.82 ppm (S, 3H); 2.65 ppm (m, 1H); 0.62 ppm (m, 2H); 0.35 ppm (m, 2H).

Step II

3-[Cyclopropyl-(2,4-dichloro-benzoyl)-amino]-5-phenyl-thiophene-2-carboxylic acid methyl ester To a solution of 3-Cyclopropylamino-5-phenyl-thiophene-2-carboxylic acid methyl ester (52 mg, 0.19 mmol) in dichloroethane (10 ml) in an atmosphere of $N_2$ was added 2,4-dichlorobenzoyl chloride (45 mg, 0.21 mmol). The reaction mixture was stirred for 16 h at reflux. Then, the solvent was removed and the residue was purified by flash chromatography (8:2 Hexane/EtOAc) to obtain 85 mg (99%) of 3-[Cyclopropyl-(2,4-dichloro-benzoyl)-amino]-5-phenyl-thiophene-2-carboxylic acid methyl ester. NMR $^1$H ($CDCl_3$, 400 MHz): 7.64 ppm (d, 2H, $H_{aro}$); 7.47 ppm (m, 2H, $H_{aro}$); 7.44-7.33 ppm (m, 3H, $H_{aro}$); 7.21-7.12 ppm (m, 2H, $H_{aro}$); 3.89 ppm (s, 3H); 3.33 ppm (m, minor rotamer); 3.13 ppm (m, 1H, major rotamer) 1.01-0.49 ppm (m, 4H).

Step III

3-[Cyclopropyl-(2,4-dichloro-benzoyl)-amino]-5-phenyl-thiophene-2-carboxylic acid 3-[Cyclopropyl-(2,4-dichloro-benzoyl)-amino]-5-phenyl-thiophene-2-carboxylic acid methyl ester (85 mg, 0.19 mmol) was dissolved in a mixture of $THF-MeOH-H_2O$ (3:2:1) (10 mL) and then 1.2 ml of LiOH 1N was added to it. After 60 min of stirring at room temperature, solvent was removed and then partitioned between 15 ml of $H_2O$, 4 ml of $KHSO_4$ 5% and 15 ml of EtOAc. The organic layer was separated and the aqueous phase was washed twice with ethyl acetate (2×10 mL). The combined ethyl acetate layer was dried ($MgSO_4$), concentrated and the residue was purified by preparative chromatography (10% $MeOH/CH_2Cl_2$) to obtain 22 mg (27%) of 3-[Cyclopropyl-(2,4-dichloro-benzoyl)-amino]-5-phenyl-thiophene-2-carboxylic acid. NMR $^1$H (DMSO, 400 MHz): rotamer: 7.75 ppm (m, 2H, $H_{aro}$); 7.68 ppm (m, $H_{aro}$, minor rotamer); 7.62-7.55 ppm (m, 2H, $H_{aro}$); 7.52 ppm (m, $H_{aro}$, minor rotamer); 7.48-7.27 ppm (m, 5H, $H_{aro}$); 3.14 ppm (m, minor rotamer); 3.04 ppm (m, 1H, major rotamer); 0.87-0.42 ppm (m, 4H). The following compounds were prepared in a similar manner: Compound #403, Compound #404

EXAMPLE 14

3-[(2,4-dichloro-benzoyl)-piperidin-4-ylmethylamino]-5-phenyl-thiophene-2-carboxylic acid Compound #519

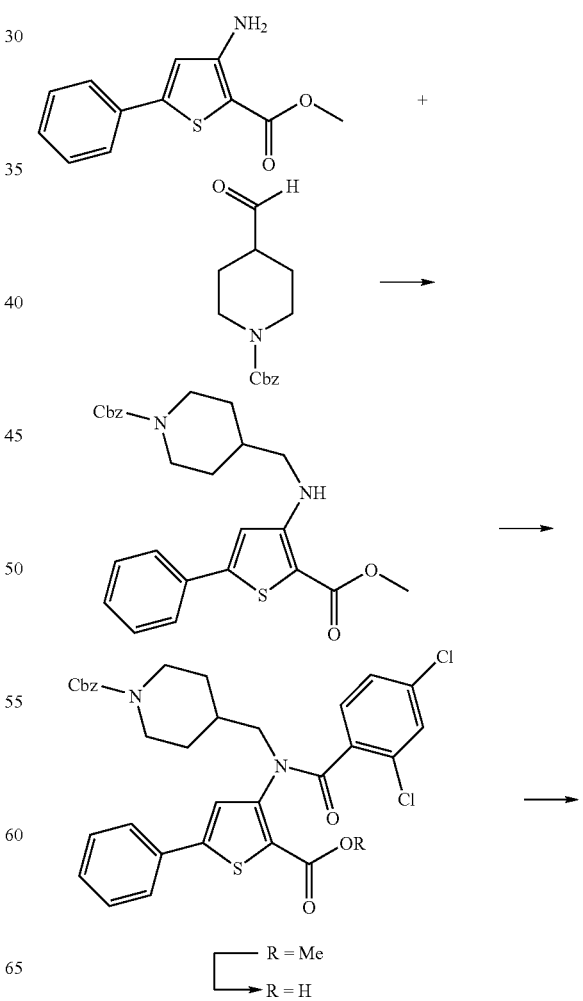

-continued

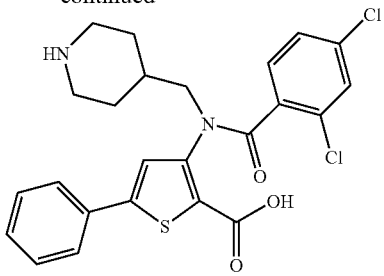

Step I

A suspension of 3-amino-5-phenyl-thiophene-2-carboxylic acid methyl ester (0.70 g, 3 mmol) and 4-formyl N-Cbz-piperidine (0.74 g, 3 mmol) in THF (1.2 mL) was treated with dibutyltin dichloride (46 mg, 0.15 mol) followed by phenylsilane (0.41 mL, 3.3 mmol). The mixture was stirred for 2 days at room temperature. The solvent was then evaporated and the residue was purified by silica gel column chromatography using $CH_2Cl_2$:hexanes:EtOAc as eluent to provide 4-[(2-Methoxycarbonyl-5-phenyl-thiophen-3-ylamino)-methyl]-piperidine-1-carboxylic acid-benzyl ester (0.6906 g, 50% yield).

Step II

4-[(2-Methoxycarbonyl-5-phenyl-thiophen-3-ylamino)-methyl]-piperidine-1-carboxylic acid benzyl ester (133 mg, 0.28 mmol) was dissolved in 1,2-dichloroethane (2.8 mL) and was treated with 2,4-dichlorobenzoyl chloride (60 μL, 0.43 mmol). The solution was heated at reflux for 1 day. The solvent was then evaporated and the residue purified by silica gel column chromatography using hexanes:EtOAc as eluent to provide 4-{[(2,4-Dichloro-benzoyl)-(2-methoxycarbonyl-5-phenyl-thiophen-3-yl)-amino]-methyl}-piperidine-1-carboxylic acid benzyl ester (0.156 g, 85% yield).

Step III

4-{[(2,4-Dichloro-benzoyl)-(2-methoxycarbonyl-5-phenyl-thiophen-3-yl)-amino]-methyl}-piperidine-1-carboxylic acid benzyl ester (150 mg, 0.24 mmol) was dissolved in a mixture of $THF:MeOH:H_2O$ (3:2:1, 2.4 mL) and treated with $LiOH.H_2O$ (29.6 mg, 0.7 mmol). The solution was heated at 55° C. for 2 h. The solvents were removed and the residue was acidified using HCl. The product was extracted with EtOAc and the organic layers were washed with brine and dried. The residue was purified by silica gel column chromatography using EtOAc:MeOH:AcOH as eluent to provide 4-{[(2-Carboxy-5-phenyl-thiophen-3-yl)-(2,4-dichloro-benzoyl)-amino]-methyl}-piperidine-1-carboxylic acid benzyl ester (124 mg, 85% yield).

Step IV

4-{[(2-Carboxy-5-phenyl-thiophen-3-yl)-(2,4-dichloro-benzoyl)-amino]-methyl}-piperidine-1-carboxylic acid benzyl ester (124 mg, 0.2 mmol) was dissolved in MeOH (2 mL) and treated with 10% Pd/C (200 mg) under $H_2$ balloon. The reaction was stirred at room temperature for 18 h and the mixture was filtered on celite. The solution was evaporated to a residue that was purified by reverse-phase HPLC to provide 3-[(2,4-Dichloro-benzoyl)-piperidin-4-ylmethyl-amino]-5-phenyl-thiophene-2-carboxylic acid (17.3 mg, 18% yield). $^1$H NMR ($CD_3OD$, 300 MHz): 7.55 (d, 1 H), 7.50 (m, 2 H), 7.27-7.39 (m, 4 H), 7.25 (s, 1 H), 7.18 (dd, 1 H), 4.12 (m, 1 H), 3.75 (m, 1 H), 3.43 (m, 2H), 2.96 (q, 2 H), 2.65 (d, 2 H), 2.05 (m, 1 H), 1.62 (m, 2 H).

The following compounds were prepared in a similar manner: Compound #503, Compound #509, Compound #519, Compound #529, Compound #537, Compound #538, Compound #516, Compound #522, Compound #535.

EXAMPLE 15

3-[Isopropyl-(3-methyl-cyclopent-3-enecarbonyl)-amino]-5 phenyl-thiophene-2-carboxylic acid Compound #405

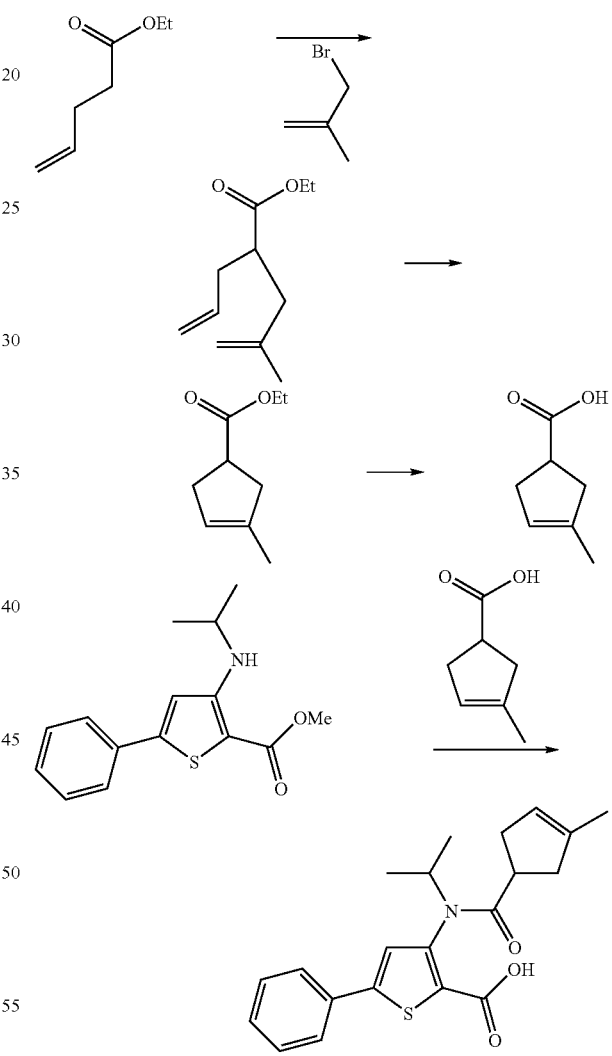

Step I:

To a cold (−78° C.) stirred solution of LDA (generated from DIPA (1.42 mL, 10.14 mmol), BuLi (5.85 mL, 9.36 mmol) in THF at −78° C. for 20 min) in THF (31 mL) was added a solution of Pent-4-enoic acid ethyl ester (1.0 g, 7.8 mmol, 1.2 eq.) in THF (9.0 mL). After stirred for 1 h, neat 3-Bromo-2-methyl-propene (2.03 g, 15.0 mmol, 1.51 mL) was added and slowly warmed up to room temperature for overnight. The reaction mixture was then quenched with saturated NH₄Cl solution, extracted with ether, washed with brine and dried. Evaporation of the solution furnished the 2-Allyl-4-methyl-pent-4-enoic acid ethyl ester (1.45 g, 100%) as an oil which was used in the next step without purification. ¹H NMR (400 MHz, CDCl₃), 5.78-5.71 (m, 1H), 5.05 (d, J=18.6 Hz, 1H), 5.02 (d, J=9.4 Hz, 1H), 4.76 (brs, 1H), 4.70 (s, 1H), 4.11 (dq, J=7.2, 1.0 Hz, 2H), 2.66-2.13 (m, 5H), 1.72 (s, 3H), 1.23 (dt, J=7.2, 1.3 Hz, 3H).

Step II:

To a refluxing stirred solution of the 2-Allyl-4-methyl-pent-4-enoic acid ethyl ester (364 mg, 2.0 mmol) in CH₂Cl₂ (100 mL, 0.02 M solution) was added drop wise a solution of the tricyclohexylphosphine (1,3-Bis(2,4,6-trimethylphenyl)-4,5-dihydroimidazol-2-ylidene)(benzylidine)ruthenium(IV) dichloride (85 mg, 0.1 mmol) in CH₂Cl₂ (3.0 mL). After 50 min, the reaction mixture was cooled to room temperature, concentrated and purified on silica gel bond elute using EtOAc/hexane (1:20) as an eluent furnished the 3-Methyl-cyclopent-3-enecarboxylic acid ethyl ester (286 mg, 93% yield) as an oil. ¹H NMR (CDCl₃, 400 MHz), 5.25 (brs, 1H), 4.17 (q, J=7.1 Hz, 2H), 3.2-3.1 (m, 1H), 2.65-2.46 (m, 4H), 1.74 (s, 3H), 1.28 (t, J=7.1 Hz, 3H).

Step III:

A solution of the 3-Methyl-cyclopent-3-enecarboxylic acid ethyl ester (255 mg, 1.65 mmol) in MeOH (4.0 mL) and 10% aq. NaOH (3.3 mL, 8.25 mmol) was heated at 50° C. for 16 h, reaction mixture was cooled to room temperature, solvent was evaporated, diluted with water. The aqueous solution was washed with ether, and acidified with aq. 1 N HCl, extracted with ether. The ethereal solution was washed with brine and dried. Evaporation of the solvent furnished the 3-Methyl-cyclopent-3-enecarboxylic acid (200 mg, 97% yield). 1H NMR (CDCl₃, 400 MHz), 5.27 (brs, 1H), 3.26-3.17 (m, 1H), 2.7-2.55 (m, 4H), 1.74 (s; 3H).

Step IV:

The coupling of the 3-Isopropylamino-5-phenyl-thiophene-2-carboxylic acid methyl ester (82 mg, 0.3 mmol) and the 3-Methyl-cyclopent-3-enecarboxylic acid (45 mg, 0.357 mmol) using PPh₃ (95.4 mg, 0.363 mmol) and NCS (48.5 mg, 0.363 mmol) furnished the 3-[Isopropyl-(3-methyl-cyclopent-3-enecarbonyl)-amino]-5-phenyl-thiophene-2-carboxylic acid methyl ester (70 mg, 61% yield) ¹H NMR (CDCl₃, 400 MHz 1:1 mixture of, rotamers), 7.68-7.64 (m, 4H), 7.5-7.4 (m, 6H), 7.1 (s, 1H), 7.09 (s, 1H), 5.2 (s, 1H), 5.1 (s, 1H), 5.06-4.98 (m, 2H), 3.88 (s, 3H), 3.87 (s, 3H), 3.08-3.0 (m, 2H), 2.85-2.76 (m, 2H), 2.5-2.42 (m, 2H), 2.3-2.1 (m, 4H), 1.69 (s, 3H), 1.64 (s, 3H), 1.24 (d, J=6.7 Hz, 3H), 1.23 (d, J=6.7 Hz, 3H), 1.01 (d, J=6.9 Hz, 3H), 1.007 (d, J=6.8 Hz, 3H).

Saponification of 3-[Isopropyl-(3-methyl-cyclopent-3-enecarbonyl)-amino]-5-phenyl-thiophene-2-carboxylic acid methyl ester (50 mg, 0.13 mmol) using LiOH.H₂O (22 mg) as previously described furnished the 3-[Isopropyl-(3-methyl-cyclopent-3-enecarbonyl)-amino]-5-phenyl-thiophene-2-carboxylic acid (30 mg, 62.5% yield) as a solid. ¹H NMR (CD₃OD, 400 MHz 1:1 mixture of rotamers) 7.73-7.70 (m, 4H), 7.47-7.35 (m, 6H), 7.29 (s, 1H), 7.27 (s, 1H), 5.16 (s, 1H), 5.08 (s, 1H), 4.9-4.8 (m, 2H), 3.15-3.05 (m, 2H), 2.76-2.65 (m, 2H), 2.42-2.12 (m, 6H), 1.65 (s, 3H), 1.61 (s, 3H), 1.25 (d, J=6.6 Hz, 3H), 1.24 (d, J=6.6 Hz, 3H), 1.03 (d, J=6.9 Hz, 6H).

EXAMPLE 16

5-tert-Butyl-3-(2,4-dimethyl-benzenesulfonylamino)-thiophene-2-carboxylic acid Compound #315

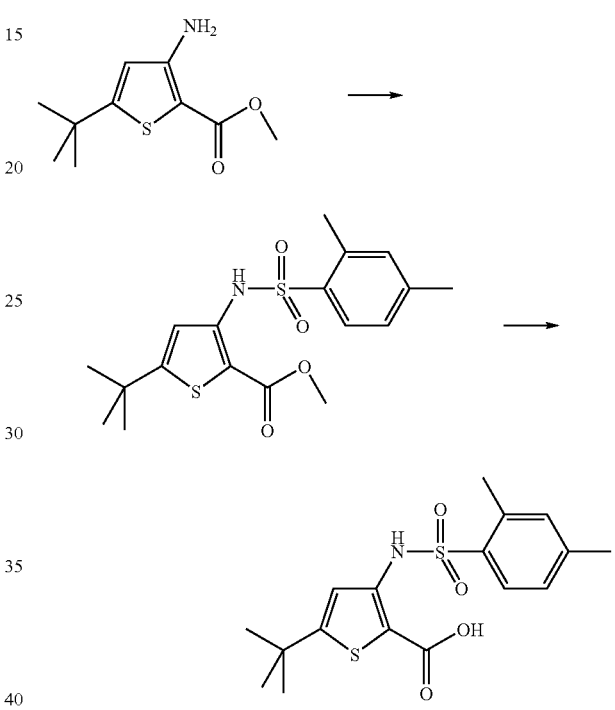

Step I

A mixture of 3-Amino-5-tert-butyl-thiophene-2-carboxylic acid methyl ester (106.5 mg, 0.5 mmol) and 2,4-dimethylsulfonyl chloride (156 mg, 0.75 mmol) in pyridine (1.5 mL) was heated at 72° C. for 16 h. The reaction mixture was diluted with EtOAc, washed with aq. 1N HCl, brine and dried. Evaporation of the solvent and purification of the residue on silica gel bond elute using EtOAc (1:20 to 1:10) as an eluent furnished the 5-tert-Butyl-3-(2,4-dimethyl-benzenesulfonylamino)-thiophene-2-carboxylic acid methyl ester (188 mg, 99% yield). ¹H NMR (CDCl₃, 400 MHz) 9.73 (s, 1H), 7.89 (d, J=8.6 Hz, 1H), 7.04-7.08 (m, 2H), 7.03 (s, 1H), 3.82 (s, 3H), 2.62 (s, 3H), 2.33 (s, 3H), 1.28 (s, 9H).

Step II

Hydrolysis of the 5-tert-Butyl-3-(2,4-dimethyl-benzenesulfonylamino)-thiophene-2-carboxylic acid methyl ester (55 mg, 0.14 mmol) using LiOH.H₂O (22 mg) as previously described provided the 5-tert-Butyl-3-(2,4-dimethyl-benzenesulfonylamino)-thiophene-2-carboxylic acid (36 mg, 70% yield) as a solid. ¹H NMR (CD₃OD, 400 MHz) 7.85 (d, J=8.6 Hz, 1H), 7.14-7.10 (m, 2H), 7.0 (s, 1H), 2.56 (s, 3H), 2.31 (s, 3H), 1.27 (s, 9H).

EXAMPLE 17

5-Benzo[b]thiophen-2-yl-3-(toluene-2-sulfonylamino)-thiophene-2-carboxylic acid Compound #230

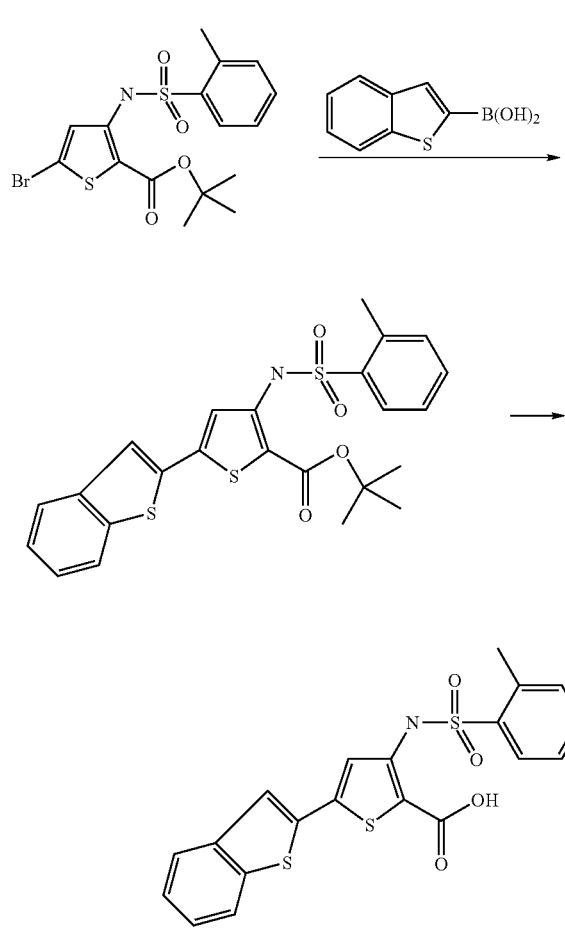

Step I

Suzuki coupling of 5-Bromo-3-(toluene-2-sulfonylamino)-thiophene-2-carboxylic acid tert-butyl ester (43 mg, 0.1 mmol) and bezothiophene-2-boronic acid (53.4 mg, 0.3 mmol) was carried out using Pd(PPh$_3$)$_4$ and Na$_2$CO$_3$ (as described in example 2) resulted in 5-Benzo[b]thiophen-2-yl-3-(toluene-2-sulfonylamino)-thiophene-2-carboxylic acid tert-butyl ester (27 mg, 55% yield). $^1$H NMR (CDCl$_3$, 400 MHz) 9.92 (s, 1H), 8.07 (d, J=7.8 Hz, 1H), 7.79-7.71 (m, 2H), 7.45-7.24 (m, 7H), 2.7 (s, 3H), 1.56 (s, 9H).

Step II

5-Benzo[b]thiophen-2-yl-3-(toluene-2-sulfonylamino)-thiophene-2-carboxylic acid tert-butyl ester was hydrolyzed to the acid using TFA as described for example 2 providing 5-Benzo[b]thiophen-2-yl-3-(toluene-2-sulfonylamino)-thiophene-2-carboxylic acid (24 mg, 99% yield). $^1$H NMR (DMSO-D$_6$, 400 MHz) 10.19 (s, 1H), 8.0 (d, J=7.7 Hz, 1H), 7.79-7.74 (m, 1H), 7.86 (s, 1H), 7.84-7.81 (m, 1H), 7.54 (t, J=7.7 Hz, 1H), 7.53-7.36 (m, 4H), 7.32 (s, 1H), 2.58 (s, 3H).

EXAMPLE 18

5-(1H-Pyrazol-3-yl)-3-(toluene-2-sulfonylamino)-thiophene-2-carboxylic acid Compound #170

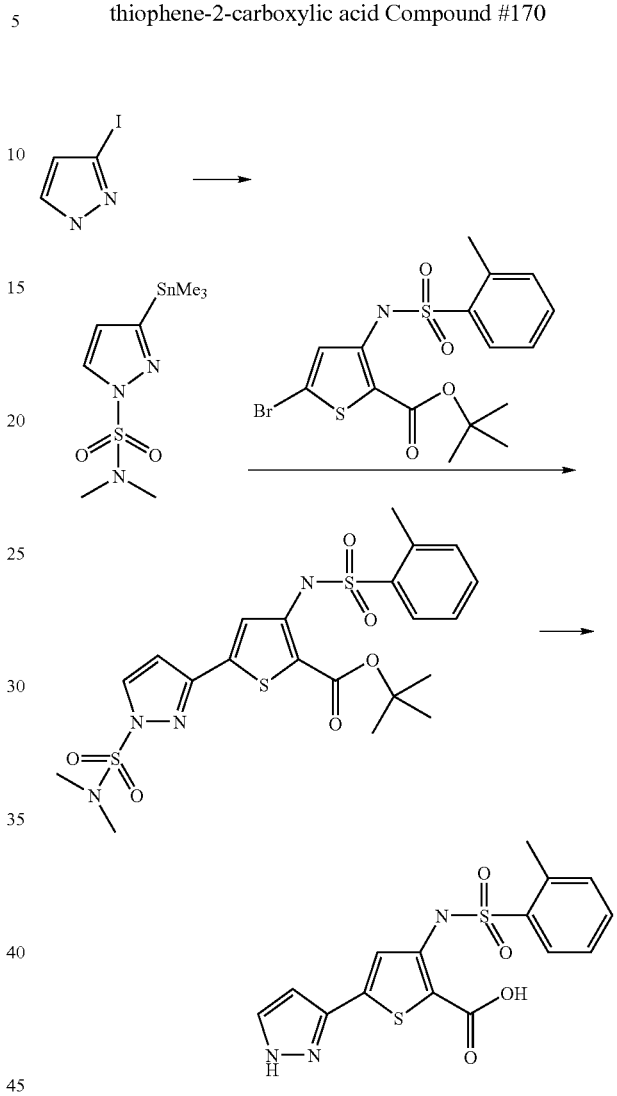

Step I

To a stirred solution of 5-Bromo-3-(toluene-2-sulfonylamino)-thiophene-2-carboxylic acid tert-butyl ester (43 mg, 0.1 mmol) in toluene (3.0 mL) was sequentially added a solution of Pd(PPh3)4 (12 mg, 0.01 mmol) in toluene (1.0 mL) and 3-Trimethylstannanyl-pyrazole-1-sulfonic acid dimethylamide (prepared according to *J. Med. Chem* (1998), 41, p-2019) (75 mg, 0.2 mmol, 2.0 eq), and heated the resulting overnight at 80° C. It was then cooled to room temperature, the solvent was evaporated and the crude was purified on preparative TLC using EtOAc/hexane (1:5). 5-(1-Dimethylsulfamoyl-1H-pyrazol-3-yl)-3-(toluene-2-sulfonylamino)-thiophene-2-carboxylic acid tert-butyl ester (35 mg, 66.5% yield) was isolated. $^1$H NMR (CDCl$_3$, 400 MHz) 9.93 (s, 1H), 8.11 (d, J=0.7 Hz, 1H), 8.02 (dd, J=6.7, 1.32 Hz, 1H), 7.84 (d, J=0.7 Hz, 1H), 7.45 (dt, J=7.5, 1.3 Hz, 1H), 7.31 (t, J=8.2 Hz, 2H), 7.26 (d, J=1.0 Hz, 1H), 2.98 (s, 6H), 2.7 (s, 3H), 1.55 (s, 9H).

Step II

A reaction mixture of 5-(1-Dimethylsulfamoyl-1H-pyrazol-3-yl)-3-(toluene-2-sulfonylamino)-thiophene-2-carboxylic acid tert-butyl ester (10 mg, 0.019 mmol) and 4N HCl (0.3 mL) solution in dioxane in MeOH (0.3 mL) was stirred at room temperature 26 h. Reaction mixture was then diluted with water and extracted with EtOAc, concentrated and purified on preparative TLC using MeOH/CH$_2$Cl$_2$/AcOH (5:95:1) furnished the 5-(1H-Pyrazol-3-yl)-3-(toluene-2-sulfonylamino)-thiophene-2-carboxylic acid (4.5 mg, 65.2% yield). $^1$H NMR (CD$_3$OD, 400 MHz) 7.99 (d, J=7.9 Hz, 1H), 7.81 (s, 1H), 7.43 (t, J=7.5, 1.3 Hz, 1H), 7.42-7.26 (m, 2H), 7.19 (s, 1H), 2.69 (s, 3H).

EXAMPLE 19

3-Isopropyl-[(4-methyl-cyclohexanecarbonyl)-amino]-5-m-tolyl-thiophene-2-carboxylic acid Compound #448

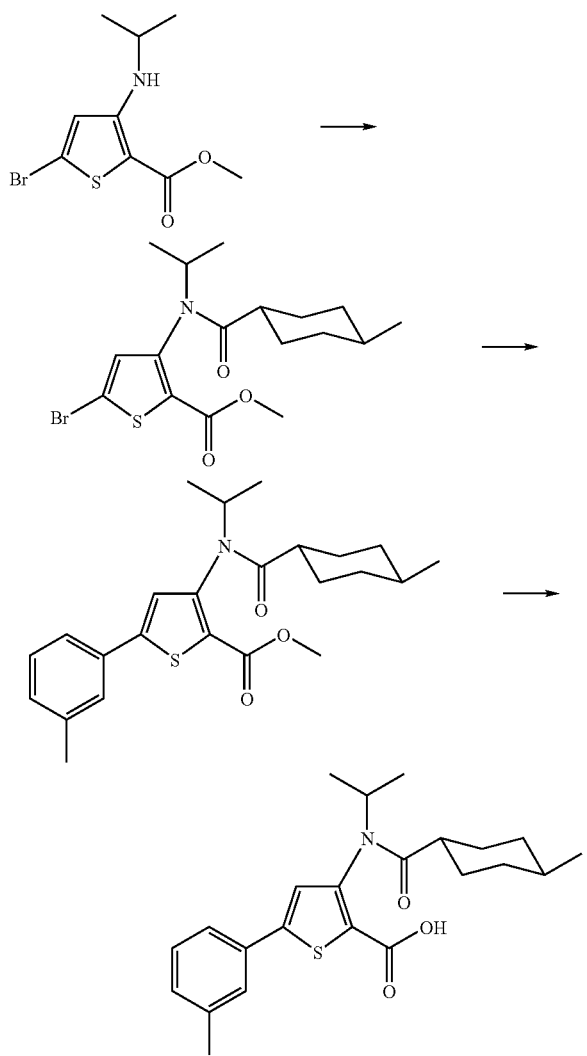

Step I

Trans-4-methyl-cyclohexanecarbonyl chloride was prepared by heating to reflux trans-4-methyl-cyclohexanecarboxylic acid (5 g, 0.035 mmol) in thionylchloride (5.0 ml) for 2 h followed by purification of the corresponding acyl chloride under reduced pressure in a Kugel-Rhorr apparatus collecting the fraction distilling at 95° C. yielding 5.1 g of the desired material which was used in the next step without further purification. This acyl chloride (1.5 ml, aprox. 10 mmol) was dissolved along with 5-Bromo-3-isopropylamino-thiophene-2-carboxylic acid methyl ester (2 g, 7.12 mmol) in anhydrous dichloroethane (2 mL) and heated at 80° C. (closed vial) for 12 h. The solvents were evaporated, the resulting crude material was dissolved in methanol and left 30 min. at room temperature, concentrated and purified via flash chromatography on silica gel using a 5% EtOAc 95% hexanes mixture of eluents, in this manner 600 mg (21%) of 5-Bromo-3-[isopropyl-(4-methyl-cyclohexanecarbonyl)-amino]-thiophene-2-carboxylic acid methyl ester the was isolated. $^1$H NMR(CDCl$_3$, 300 MHz): 6.78 (s, 1H), 4.93 (m, 1H), 3.69 (s, 3H), 2.00-1.20 (m, 8H), 1.14 (d, 3H), 0.93 (d, 3H), 0.81 (d, 3H), 0.72-0.70 (m, 2H).

Step II

To a degassed solution of 5-Bromo-3-[isopropyl-(4-methyl-cyclohexanecarbonyl)-amino]-thiophene-2-carboxylic acid methyl ester (100 mg, 0.249 mmol) and 3-methyl boronic acid (38 mg, 0.279 mmol) in a mixture of DME (6 mL) and 2M aqueous Na$_2$CO$_3$ (3 mL), Pd(PPh$_3$)$_4$ (12 mg) was added and the reaction mixture was stirred at reflux conditions for 12 h under a N$_2$ atmosphere. The reaction mixture was diluted with ethyl acetate and water. The organic layer was separated, dried (Na$_2$SO$_4$), concentrated. The residue was purified by column chromatography using ethyl acetate and hexane (1:3) as eluent. 35 mg (34%) of 3-Isopropyl-[(4-methyl-cyclohexanecarbonyl)-amino]-5-m-tolyl-thiophene-2-carboxylic acid methyl ester was isolated. $^1$H NMR (CDCl$_3$, 400 MHz): 7.45 (bs, 2H), 7.36 (t, 1H), 7.23 (m, 1H), 7.01 (s, 1H), 4.99 (m, 1H), 3.83 (s, 3H), 2.41 (s, 3H), 2.01-0.61 (m, 20H).

Step III

3-Isopropyl-[(4-methyl-cyclohexanecarbonyl)-amino]-5-m-tolyl-thiophene-2-carboxylic acid methyl ester (30 mg, 0.073 mmol) was taken in a mixture of THF:MeOH:H$_2$O (3:2:1, 3 mL) and then added 1N aqueous solution of LiOH.H$_2$O (0.44 mL, 0.438 mmol). The reaction mixture was stirred at room temperature for 12 h. Solvents were removed and the residue was partitioned between water and ethyl acetate. The aqueous layer was acidified using 10% KHSO$_4$ solution. The organic layer was separated, dried (Na$_2$SO$_4$)— and concentrated. The residue was purified by preparative TLC using chloroform:methanol:acetic acid (9:1:0.1) to obtain 3-Isopropyl-[(4-methyl-cyclohexanecarbonyl)-amino]-5-m-tolyl-thiophene-2-carboxylic acid (15 mg, 52%) as a white solid. $^1$H NMR (CDCl$_3$, 400 MHz): (s, 2H), 7.38 (t, 1H), 7.24 (m, 1H), 7.08 (s, 1H), 5.01 (s, 1H), 2.42 (s, 3H), 2.10-0.62 (m, 20H). ESI$^-$ (M-H): 398.

EXAMPLE 20

(1R,2S,4R)-3-[Isopropyl-(2-hydroxy-4-methyl-cyclohexanecarbonyl)-amino]-5-phenyl-thiophene-2-carboxylic acid Compound #402

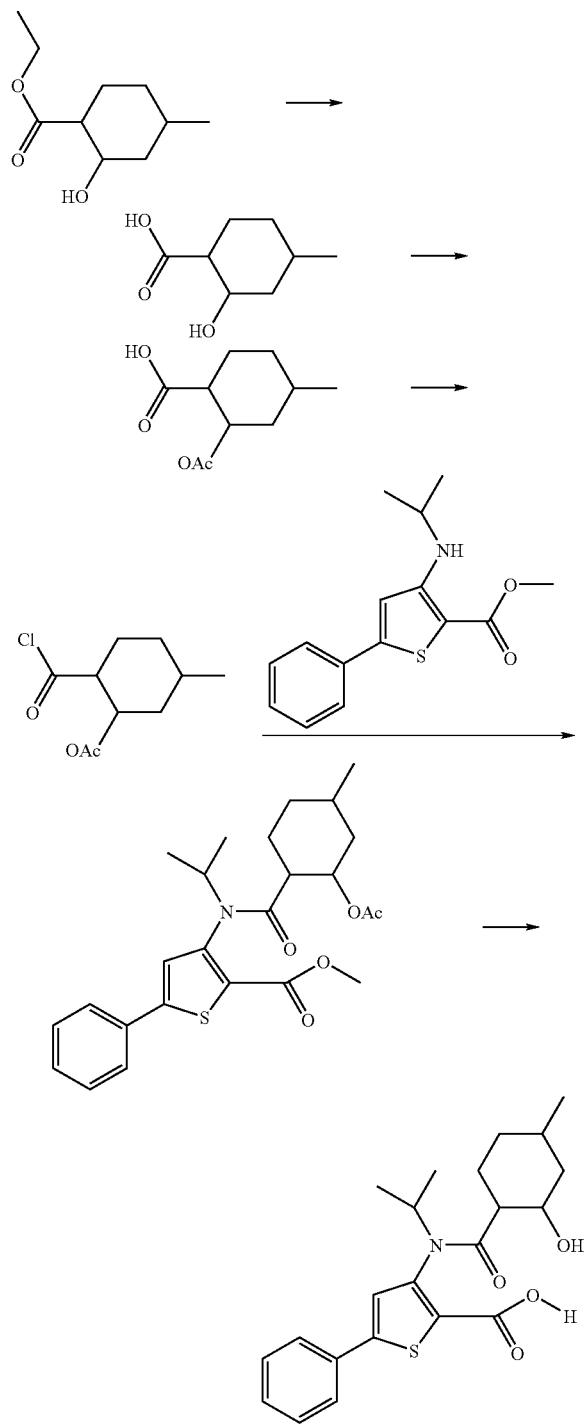

(1R,2S,4R)-2-Hydroxy-4-methyl-cyclohexanecarboxylic acid methyl ester was prepared as described in J. Org. Chem, (1993), 58, pp. 6255-6265. NMR $^1$H (CDCl$_3$, 400 MHz): 4.26 ppm (s, 1H); 4.19-4.13 ppm (m, 2H); 3.16 ppm (s, 1H); 2.35-2.29 ppm (m, 1H); 1.92-1.74 ppm (m, 5H); 1.31-1.24 ppm (m, 3H); 1.08-1.01 ppm (m, 1H); 0.96-0.92 ppm (m, 1H); 0.88 ppm (d, 3H).

Step I

To a solution of (1R,2S,4R)-2-Hydroxy-4-methyl-cyclohexanecarboxylic acid methyl ester (450 mg, 2.42 mmol) in methanol (12 ml) was added a 2.5 M solution of sodium hydroxide (9.7 ml, 24.2 mmol). The reaction mixture was stirred for 4 h at 50° C. Then, the solvents were removed and the residue was partitioned between 20 ml of H$_2$O acidified to pH 4 and 20 ml of EtOAc. The organic layer was separated and the aqueous phase was washed with ethyl acetate (2×20 ml). The combined ethyl acetate layers were dried (Na$_2$SO$_4$) and concentrated to obtain 313 mg (82%) of (1R,2S,4R)-2-Hydroxy-4-methyl-cyclohexanecarboxylic acid. NMR $^1$H (CDCl$_3$, 400 MHz) 4.34 ppm (s, 1H); 2.43-2.39 ppm (m, 1H); 1.96-1.76 ppm (m, 5H); 1.14-1.08 ppm (m, 1H); 1.02-0.93 ppm (m, 1H); 0.90 ppm (d, 3H).

Step II

To a solution of (1R,2S,4R)-2-Hydroxy-4-methyl-cyclohexanecarboxylic acid (162 mg, 1.02 mmol) in dichloromethane (5 ml) was added pyridine (495 ul, 6.12 mmol) followed by acetic anhydride (385 ul, 4.08 mmol). The reaction mixture was stirred for 20 h at room temperature. Then, the solvents were removed and 10 ml of 3N HCl solution was added. This mixture was stirred for 30 minutes and then a saturated solution of NaHCO$_3$ was slowly added until pH=9-10. This solution was then extracted with ethyl acetate (2×5 ml). The aqueous phase was then acidified with a 10% HCl solution and extracted with ethyl acetate (3×5 ml). The following ethyl acetate layers were combined, dried (Na$_2$SO$_4$) and concentrated to obtain 109 mg (53%) of (1R,2S,4R)-2-Acetoxy-4-methyl-cyclohexanecarboxylic acid. NMR $^1$H (CDCl$_3$, 400 MHz): 5.45 ppm (s, 1H); 2.46-2.42 ppm (m, 1H); 2.02 ppm (s, 3H); 2.02-1.96 ppm (m, 1H); 1.91-1.76 ppm (m, 3H); 1.70-1.61 ppm (m, 1H); 1.16-1.08 ppm (m, 1H); 0.99-0.88 ppm (m, 1H); 0.87 ppm (d, 3H).

Step III

To a solution of (1R,2S,4R)-2-Acetoxy-4-methyl-cyclohexanecarboxylic acid (109 mg, 0.54 mmol) in dichloromethane (2.7 ml) was added oxalyl chloride (545 µl, 1.09 mmol) followed by 1 drop of dimethylformamide. The reaction mixture was stirred for 4 h at room temperature. The solvents were then removed to obtain 119 mg (99%) of (1R,2S,4R)-2-Acetoxy-4-methyl-cyclohexanecarboxylic acid chloride.

Step IV

To a solution of 3-Isopropylamino-5-phenyl-thiophene-2-carboxylic acid methyl ester (136 mg, 0.50 mmol) in 1,2-dichloroethane (1.0 ml) was added (1R,2S,4R)-2-Acetoxy-4-methyl-cyclohexanecarboxylic acid chloride (119 mg, 0.54 mmol) dissolved in 1,2-dichloroethane (0.6 ml) followed by PPh$_3$ (136 mg, 0.52 mmol). The resulting solution was stirred for 20 h at 90° C. and then cooled to room temperature. It was then diluted with ethyl acetate (10 ml) and a solution of saturated NaHCO$_3$ (10 ml). The aqueous phase was separated and washed with ethyl acetate (2×10 ml) and the combined organic layers were dried (Na$_2$SO$_4$), filtered and concentrated. The residue was purified by flash chromatography (0% to 25% EtOAc/Hexane) to obtain 110 mg (45%) of (1R,2S,4R)-3-[Isopropyl-(2-Acetoxy-4-methyl-cyclohexanecarbonyl)-amino]-5-phenyl-thiophene-2-carboxylic acid methyl ester. NMR $^1$H (CDCl$_3$, 400 MHz): 1.5:1.0 mixture of rotamers 7.73-7.70 ppm (m, 2H, H$_{aro}$); 7.69-7.63 ppm (m, 1H, H$_{aro}$); 7.51-7.41 ppm (m, 4H, H$_{aro}$); 7.13 ppm (s, 0.6H, H$_{aro}$, major rotamer); 5.79 ppm (s, 0.4H, minor rotamer); 5.21 ppm (s, 0.6H, major rotamer); 4.95-4.88 ppm (m, 1H); 3.88 ppm (s, 1.8H, major rotamer); 3.87 ppm (s, 1.2H, minor rotamer); 2.40-2.36 ppm (m, 0.6H, major rotamer); 2.11 ppm (s, 3H); 1.78-0.77 ppm (m, 16H).

Step V (1R,2S,4R)-3-[Isopropyl-(2-Acetoxy-4-methyl-cyclohexanecarbonyl)-amino]-5-phenyl-thiophene-2-carboxylic acid methyl ester (36 mg, 0.17 mmol) was dissolved in a mixture of dioxane:$H_2O$ (4:1) (700 µl) and then 470 µl of LiOH 1N was added to it. After 3 h at 50° C. the reaction mixture was cooled to room temperature and the solvents were removed. The residue was then partitioned between 10 ml of $H_2O$ acidified to pH 4 and 10 ml of EtOAc. The organic layer was separated and the aqueous phase was washed with ethyl acetate (2×10 ml). The combined ethyl acetate layers were dried ($Na_2SO_4$), concentrated and the residue was purified by preparative chromatography to obtain 9 mg (29%) of (1R,2S,4R)-3-[Isopropyl-(2-hydroxy-4-methyl-cyclohexanecarbonyl)-amino]-5-phenyl-thiophene-2-carboxylic acid. NMR $^1$H ($CDCl_3$, 400 MHz): 3:2 mixture of rotamers. 7.76-7.73 ppm (m, 2H, $H_{aro}$); 7.50-7.38 ppm (m, 3H, $H_{aro}$); 7.36 ppm (s, 1H, $H_{aro}$); 4.93-4.87 ppm (m, 1H); 4.25 ppm (s, 0.70H, major rotamer); 3.97 ppm (s, 0.3H, minor rotamer); 2.35-2.28 ppm (m, 1H); 1.99-1.53 ppm (m, 5H); 1.28 ppm (d, 0.6H, minor rotamer); 1.25 ppm (d, 1,4H, major rotamer); 1.06-1.03 ppm (m, 3H), 0.96-0.72 ppm (m, 1H); 0.79 ppm (d, 3H); 0.67-0.56 ppm (m, 1H).

EXAMPLE 21

3-[(2,4-Dichloro-benzoyl)-piperidin-4-yl-amino]-5-phenyl-thiophene-2-carboxylic acid hydrochloride salt Compound #368

1-piperidine carboxylate (673 mg, 3.2 mmol), followed by dibutyltin dichloride (19 mg, 0.064 mmol, 0.02 eq.). After 5 min the reaction was treated with phenyl silane (435 µL, 380 mg, 3.52 mmol, 1.1 eq). The mixture was left to stir for 74 h when a clear solution resulted. The reaction was stripped off solvent to leave a thick bright yellow gum (1.59 g). The crude material was purified by column chromatography using ($CH_2Cl_2$:Hexane:EtOAc)=15:5:1 as eluent to provide 4-(2-Methoxycarbonyl-5-phenyl-thiophen-3-ylamino)-piperidine-1-carboxylic acid tert-butyl ester as a yellow foam (713 mg, 54%). $^1$H NMR ($CDCl_3$, 400 MHz) 7.63-7.60 (m, 2H), 7.74-7.36 (m, 3H), 6.90-6.84 (bs, 1H), 6.84 (s, 1H), 3.97-4.01 (m, 2H), 3.80 (s, 3H), 3.48 (bs, 1H), 3.06-2.99 (m, 2H), 2.03-1.99 (m, 2H), 1.51-1.48 (m, 2H), 1.47 (bs, 9H)

Step II 4-(2-Methoxycarbonyl-5-phenyl-thiophen-3-ylamino)-piperidine-1-carboxylic acid tert-butyl ester (200 mg, 0.48 mmol) was treated with 2,4 dichlorobenzoylchloride (202 µL, 302 mg, 1.44 mmol, 3 eq) under previously described conditions (e.g. Example 14) to provide, after column chromatography using ($CH_2Cl_2$:Hexane:EtOAc=15:5:1) as eluent, 4-[(2,4-Dichloro-benzoyl)-(2-methoxycarbonyl-5-phenyl-thiophen-3-yl)-amino]-piperidine-1-carboxylic acid tert-butyl ester as a pale yellow foam (165 mg, 58%), $^1$H NMR ($CDCl_3$, 400 MHz) 7.54-7.51 (m, 2H), 7.45-7.39 (m, 3H), 7.27-7.25 (m, 2H), 7.17 (d, J=1.96 Hz, 1H), 7.06 (dd, J=1.92 Hz, J=8.34 Hz, 1H), 4.86-4.92 (m, 1H), 4.11-4.21 (m, 2H), 3.89 (s, 3H), 2.82-2.89 (m, 2H), 2.17-2.20 (m, 1H), 1.89-1.92 (m, 1H), 1.49-1.61 (m, 1H), 1.40 (bs, 9H), 1.19-1.25 (m, 1H)

Step III

A suspension of 4-[(2,4-Dichloro-benzoyl)-(2-methoxycarbonyl-5-phenyl-thiophen-3-yl)-amino]-piperidine-1-car-

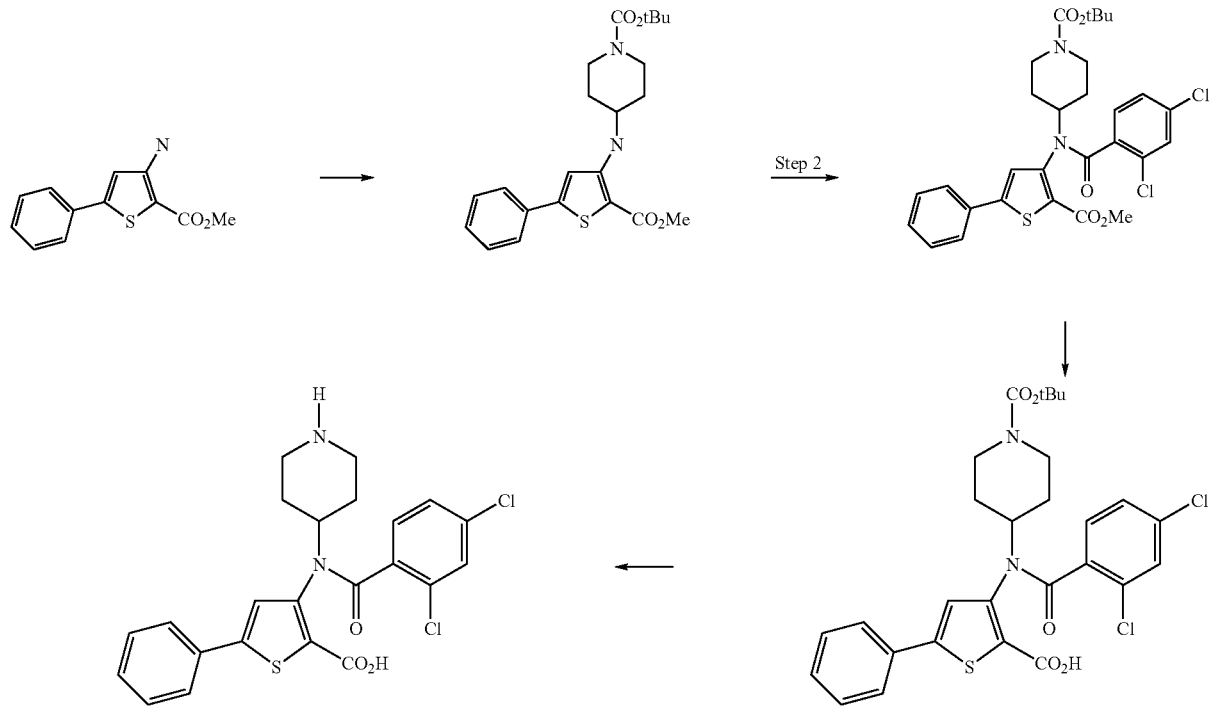

Step I

A suspension of 3-amino-5-phenyl-thiophene-2-carboxylic acid methyl ester (745 mg, 3.2 mmol) in dry THF (1.3 ml), at 21° C., under nitrogen, was treated with tert-butyl 4-oxoboxylic acid tert-butyl ester (160 mg, 0.27 mmol) above in dioxane: water (4:1, 3 ml) was treated with lithium hydroxide (2M aqueous solution, 41 µL, 341 mg, 0.814 mmol, 3 eq) and the reaction allowed to stir overnight for 18 h. The reaction was stripped-off solvent and the residue partitioned between EtOAc:water (4:1). The aqueous phase was separated and extracted several times, with EtOAc, following acidification to pH 5.5 with 0.1N HCl. The combined organic extract was evaporated to a solid. The solid was taken into EtOAc and the above acid wash repeated to give, after drying and evaporation, 4-[(2-Carboxy-5-phenyl-thiophen-3-yl)-(2,4-dichloro-benzoyl)-amino]-piperidine-1-carboxylic acid tert-butyl ester as a colourless solid (128 mg, 91%), $^1$H NMR (Acetone, 400 MHz) 7.75-7.70 (m, 1H), 7.64 (s, 1H), 7.52-7.40 (m, 3H), 7.52 (d, J=1.98 Hz, 1H), 7.21 (dd, J=1.96 Hz, J=8.19 Hz, 1H), 4.80-4.71 (m, 1H), 4.26-4.01 (m, 2H), 2.71-2.30 (bs, 3H), 2.25-2.17 (m, 1H), 1.82-1.69 (m, 1H), 1.40 (bs, 9H), 1.33-1.24 (m, 1H).

Step 1V

A solution of 4-[(2-Carboxy-5-phenyl-thiophen-3-yl)-(2,4-dichloro-benzoyl)-amino]-piperidine-1-carboxylic acid tert-butyl ester (240 mg, 0.42 mmol) in dioxane (4 ml) at 21° C. under nitrogen was treated with anhydrous 4M HCl (3 ml, 12.6 mmol, 30 eq). After 4 h the reaction was stripped off solvent and the residue triturated with ether to give 3-[(2,4-Dichloro-benzoyl)-piperidin-4-yl-amino]-5-phenyl-thiophene-2-carboxylic acid as a pale yellow powder (214 mg, 100%) $^1$H NMR (Acetone, 400 MHz) 7.76-7.73 (m, 2H), 7.64 (s, 1H), 7.45-7.38 (m, 3H), 7.30 (bs, 1H), 7.28-7.24 (m, 1H), 4.93-4.84 (m, 1H), 3.56-3.49 (m, 2H), 3.25-3.14 (m, 2H), 3.05-2.55 (bs, 1H), 2.50-2.37 (m, 2H), 2.13-1.83 (m, 1H).

Similarly prepared were Compound #366, Compound #553, Compound #543

EXAMPLE 22

3-(Benzyl-cyclopropanecarbonyl-amino)-5-phenyl-thiophene-2-carboxylic acid. Compound #454

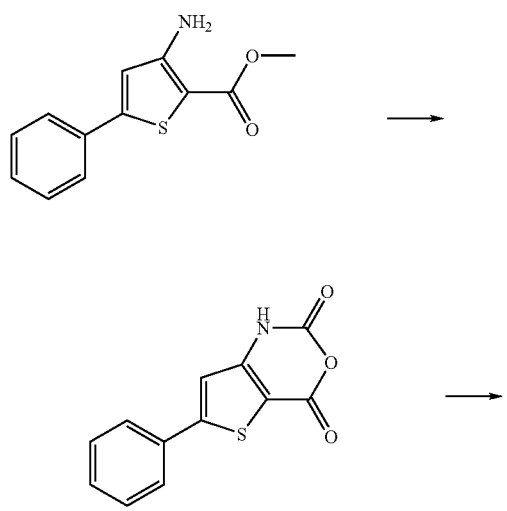

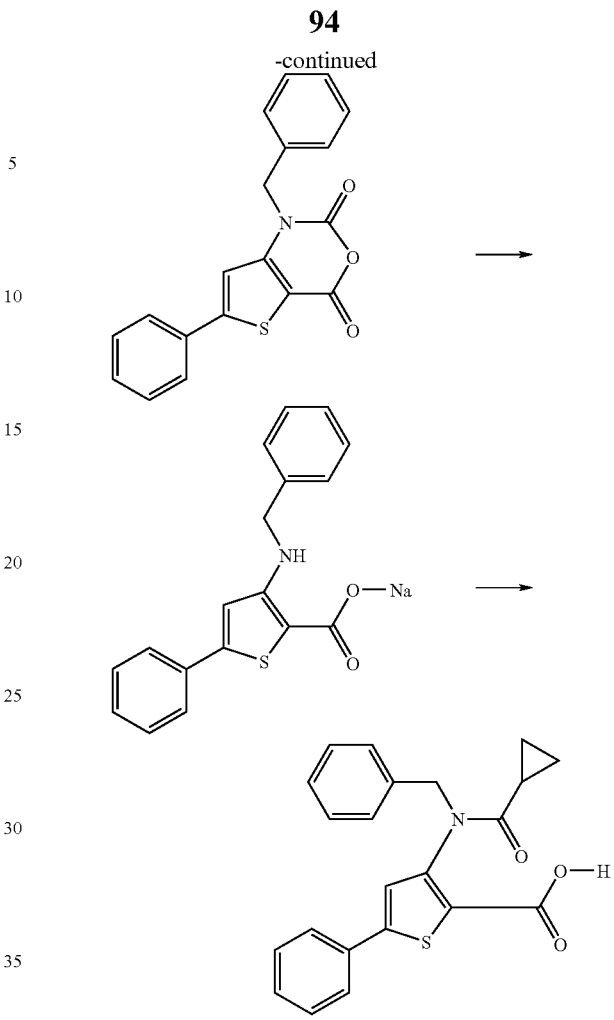

Step I

A solvent mixture of THF/MeOH/H$_2$O (3:2:1) was added to 3.04 g of methyl(3-amino-5-phenyl)thiophene-2-carboxylate (13 mmol) and 1.64 g of lithium hydroxide monohydrate (39 mmol). The mixture was refluxed for 8 hours and concentrated in vacuo. The crude material was taken in 100 ml of water, washed with ethyl acetate (2×100 ml) and transferred into a multineck flask. A 20% phosgene solution in toluene (11 ml, 39 mmol) was added dropwise at 0° C. A precipitate was then collected by filtration and sequentially washed by trituration with a saturated solution of bicarbonate, water, acetone and diethyl ether. 2.52 g (79%) of 6-phenyl-1H-thieno[3,2-d][1,3]oxazine-2,4-dione were isolated as a white solid. NMR $^1$H (DMSO D$_6$, 400 MHz): 7.79-7.76 ppm (m, 2H, H$_{aro}$); 7.52-7.47 ppm (m, 3H, H$_{aro}$); 7.25 ppm (s, 1H, H$_{azole}$); 0.4 ppm (s, 1H, NH).

Step II

A solution of 6-phenyl-1H-thieno[3,2-d][1,3]oxazine-2,4-dione (1 g, 4.1 mmol) and anhydrous sodium carbonate (477 mg, 4.5 mmol) diluted in 15 ml of anhydrous dimethylacetamide was stirred for one hour under nitrogen before adding benzyl bromide (785 mg, 4.5 mmol). The mixture was stirred overnight at room temperature. 912 mg (66.3%) of 1-benzyl-6-phenyl-1H-thieno[3,2-d][1,3]oxazine-2,4-dione were obtained as a pale yellow solid after filtration and washing the precipitate with acetone and pentane. NMR $^1$H (DMSO D$_6$, 400 MHz) 7.8-7.76 ppm (m, 3H, H$_{aro}$); 7.51-7.45 ppm (m, 3H, H$_{aro}$); 7.43-7.41 ppm (m, 2H, H$_{aro}$); 7.35-7.3 ppm (m, 2H, H$_{aro}$); 7.28-7.24 ppm (m, 1H, H$_{aro}$); 5.22 ppm (s, 1H, NCH$_2$).

Step III

To a solution of 1-benzyl-6-phenyl-1H-thieno[3,2-d][1,3]oxazine-2,4-dione (880 mg, 2.62 mmol) were successively added 32 ml of dioxane and 7.87 ml of NaOH 1N aqueous solution. The mixture was vigourously stirred for 2 h and then the solvents were concentrated in vacuo. Dichloromethane was added to the crude material and sodium 3-benzylamino-5-phenyl-thiophene-2-carboxylate (1.07 g, 100%) precipitated as a pale yellow solid. NMR $^1$H (DMSO D$_6$, 400 MHz): 7.76 ppm (t, 1H, J=6.4 Hz, NH); 7.53-7.51 ppm (m, 2H, H$_{aro}$); 7.33-7.26 ppm (m, 6H, H$_{aro}$); 7.23-7.16 ppm (m, 2H, H$_{aro}$); 7.07 ppm (s, 1H, H$_{azole}$); 4.36 ppm (d, 2H, J=6.4 Hz, NHCH$_2$).

Step IV

To a solution of sodium 3-benzylamino-5-phenyl-thiophene-2-carboxylate (41.1 mg, 0.1 mmol) was added 32 mg (0.3 mmol) of cyclopropanecarbonyl chloride, 1.5 ml of dioxane and 0.5 ml of water. The mixture was stirred overnight at room temperature and concentrated in vacuo. A 4N hydrogen chloride solution in dioxane (1 ml) was added and the mixture was stirred for one hour at room temperature. The mixture was again concentrated and the crude material was purified by reverse phase HPLC giving access to 11.9 mg (31.5%) of 3-(benzyl-cyclopropanecarbonyl-amino)-5-phenyl-thiophene-2-carboxylic acid as a pale yellow solid. NMR $^1$H (DMSO D$_6$, 400 MHz): 7.56-7.54 ppm (m, 2H, H$_{aro}$); 7.39-7.13 ppm (m, 10H, H$_{aro}$, H$_{azole}$ and COOH); 5.27 ppm (d, 1H, J=15.2 Hz); 4.48 ppm (d, 1H, J=15.2 Hz); 1.49 ppm (m, 1H); 0.77 ppm (m, 2H); 0.61 ppm (m, 2H).

The following compounds were prepared in a similar manner: Compound #172, Compound #173, Compound #175, Compound #186, Compound #187, Compound #188, Compound #241, Compound #247, Compound #251, Compound #252, Compound #253, Compound #254, Compound #255, Compound #256, Compound #257, Compound #276, Compound #277, Compound #278, Compound #279, Compound #280, Compound #281, Compound #330, Compound #334, Compound #335, Compound #336, Compound #339, Compound #340, Compound #341, Compound #342, Compound #343, Compound #344, Compound #345, Compound #347, Compound #349, Compound #350, Compound #351, Compound #352, Compound #353, Compound #354, Compound #384, Compound #385, Compound #386, Compound #388, Compound #389, Compound #390, Compound #391, Compound #392, Compound #393, Compound #394, Compound #397, Compound #398, Compound #399, Compound #400, Compound #401.

EXAMPLE 23

3-[(2,4-Dichloro-phenyl)-isopropyl-carbamoyl]-5-phenyl-thiophene-2-carboxylic acid

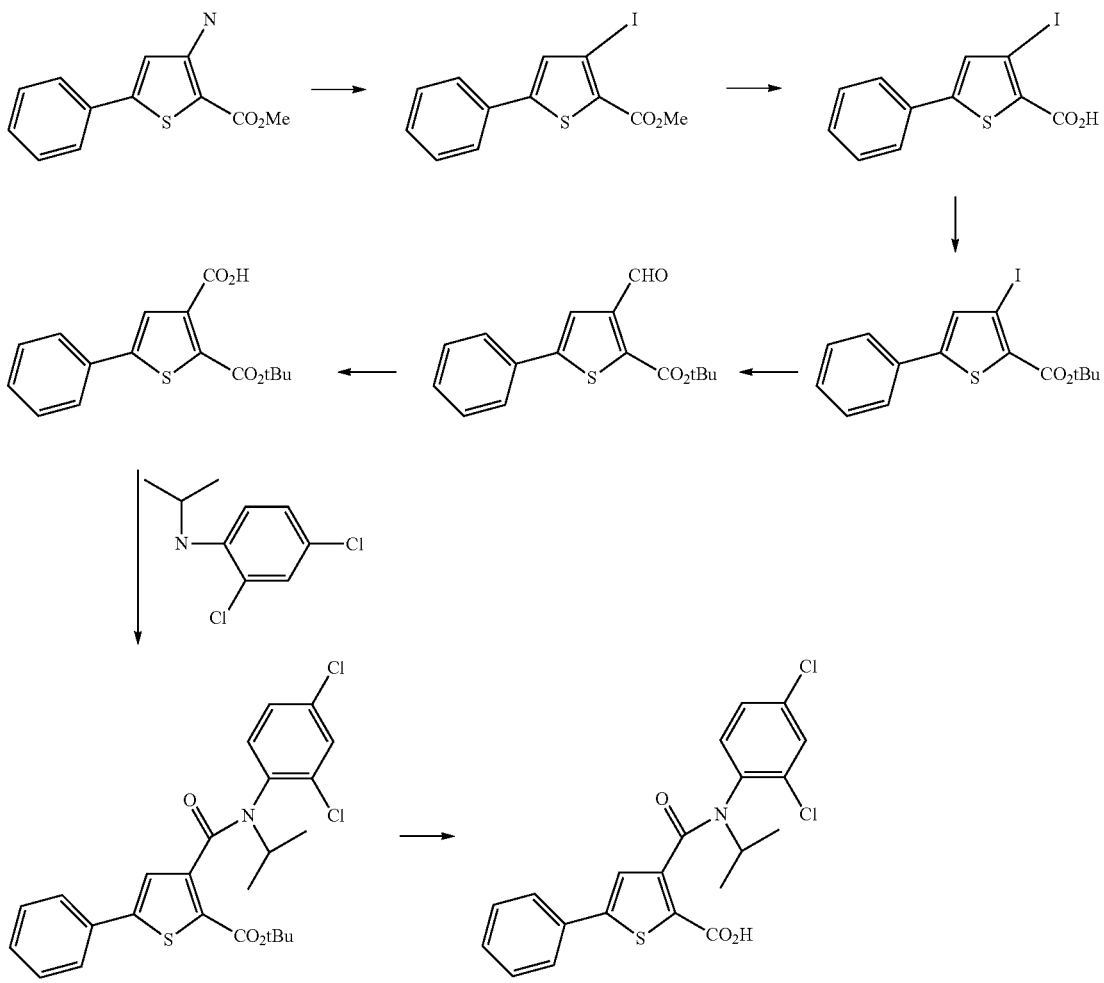

Step I

3-Iodo-5-phenyl-thiophene-2-carboxylic acid methyl ester

A suspension of 3-Amino-5-phenyl-thiophene-2-carboxylic acid methyl ester (10 g, 43 mmol) in anhydrous benzene (200 ml), at 21° C., under $N_2$, was treated with t-butyl nitrite (21.8 g, 86 mmol) and the dark mixture cooled to 0° C. and treated dropwise, over 15 min, with iodine (21.8 ml, 184 mmol). After 30 min at 0° C., the solution was allowed to warm-up to ambient temperature and stirred for 2 h. The reaction mixture was then poured into water (300 ml) and stirred vigorously for 15 min. The organic phase was separated and washed several times with 20% sodium thiosulfate (4×100 ml). The resulting emulsion was filtered through celite. The celite pad was washed with EtOAc and the combined filtrate and washings were washed with more sodium thiosulfate (100 ml) to give an orange solution which was washed with brine and dried. Evaporation of the solvent afforded an oil (7.4 g). The crude oil was purified by biotage flash chromatography using Hexane/$CH_2Cl_2$/EtbAc (20/2/1) as eluent to give 4.42 g (29%) of 3-Iodo-5-phenyl-thiophene-2-carboxylic acid methyl ester as a pale yellow oil. NMR $^1$H ($CDCl_3$, 400 MHz): 7.62-7.57 (m, 2H); 7.58 (s, 1H); 7.50-7.36 (m, 3H); 3.91 (s, 3H).

Step II

3-Iodo-5-phenyl-thiophene-2-carboxylic acid

A solution of 3-Iodo-5-phenyl-thiophene-2-carboxylic acid methyl ester (4.4 g, 12.78 mmol) in dioxane/water 4/1 (50 ml), at 21° C., under $N_2$, was treated with lithium hydroxyde (2N, 19.3 ml, 38 mmol) and the solution left to stir for 21.5 h. The reaction mixture was evaporated to dryness and the residue partitioned between EtOAc (75 ml) and water (25 ml) and acidified with 2N HCl to pH 5.5. The aqueous phase was separated and extracted with EtOAc (3×50 ml). The combined organic extract were washed with brine, dried and evaporated to give 4.12 g (97%) of 3-Iodo-5-phenyl-thiophene-2-carboxylic acid as a pale yellow solid. NMR $^1$H ($CD_3OD$, 400 MHz): 7.69-7.67 (m, 2H); 7.55 (s, 1H); 7.46-7.39 (m, 3H).

Step III

3-Iodo-5-phenyl-thiophene-2-carboxylic acid tert-butyl ester

A suspension of magnesium sulfate (4.61 g, 38.32 mmol) in dichloromethane (37 ml) at 21° C., under $N_2$, was treated with conc $H_2SO_4$ (510 µl, 9.58 mmol). After 15 min solid 3-Iodo-5-phenyl-thiophene-2-carboxylic acid (3.7 g, 9.58 mmol) was added followed by t-butanol (4.55 ml, 47.9 mmol) and the flask was stoppered and left over-night for 19.5 h. The reaction mixture was treated with saturated bicarbonate aqueous solution, and filtered. The solid was washed with $CH_2Cl_2$ and the filtrate dried and concentrated to an oil. The crude material was purified by flash chromatography using Hexane/$CH_2Cl_2$ (3:1) as eluent to give 1.63 g (44%) of 3-Iodo-5-phenyl-thiophene-2-carboxylic acid tert-butyl ester as a colorless solid. NMR $^1$H ($CDCl_3$, 400 MHz) 7.61-7.59 (m, 2H); 7.43-7.35 (m, 3H), 7.25 (s, 1H), 1.60 (bs, 9H).

Step IV

3-Formyl-5-phenyl-thiophene-2-carboxylic acid tert-butyl ester

A solution of 3-Iodo-5-phenyl-thiophene-2-carboxylic acid tert-butyl ester (1.41 g, 3.65 mmol) in dry THF (37 ml) at −78° C., under nitrogen, was treated dropwise, over 5 min with n-butyl lithium (4.8 ml, 7.66 mmol). The reaction gradually darkened to a red-brown color. After 15 min at −78° C. dimethylformamide (1.7 ml, 21.9 mmol) was added dropwise over 7 min. The dark solution was allowed to stirr for 2 h then quenched with saturated $NH_4Cl$ solution (10 ml) and allowed to reach 21° C. The aqueous phase was separated and extracted with EtOAc (3×50 ml). The combined organic extracts were evaporated and the residue taken into EtOAc and washed with water, brine, dried and concentrated to give 1.14 g of a brown oil. The crude material was purified by flash chromatography using Hexane/CH2Cl2 (1/1) as eluent to provide 303 mg (28%) of 3-Formyl-5-phenyl-thiophene-2-carboxylic acid tert-butyl ester as a colorless solid. NMR $^1$H: ($CDCl_3$, 400 MHz) 10.62 (s, 1H); 7.78 (s, 1H); 7.64-7.62 (m, 2H); 7.48-7.38 (m, 3H); 1.62 (bs, 9H).

Step V

5-Phenyl-thiophene-2,3-dicarboxylic acid 2-tert-butyl ester

A solution of 3-Formyl-5-phenyl-thiophene-2-carboxylic acid tert-butyl ester (300 mg, 1.04 mmol) in dry THF (20 ml), at 0° C., under nitrogen, was treated with methyl sulfide (10% w/w in THF, 3.8 ml, 5.2 mmol) followed by sodium dihydrogenphosphate (30% aqueous solution, 9.56 ml, 2.05 mmol). After 0.5 h, the solution was treated with sodium chlorite (30% w/w aqueous solution, 1.9 ml, 2.08 mmol) added over 1 min via a syringe. The pale yellow solution was stirred for 1.5 h at 0° C., then diluted with water (20 ml) and extracted with EtOAc (4×40 ml). The aqueous phase was separated, extracted with more EtOAc (40 ml) and the combined extracts were washed with brine dried and concentrated to give 316 mg (100%) of 5-Phenyl-thiophene-2,3-dicarboxylic acid 2-tert-butyl ester as a pale brown solid. NMR $^1$H ($CD_3CO$; 400 MHz): 7.87 (s, 1H); 7.83-7.81 (m, 2H); 7.17-7.53 (m, 3H); 1.65 (bs, 9H).

Step VI

3-[(2,4-Dichloro-phenyl)-isopropyl-carbamoyl]-5-phenyl-thiophene-2-carboxylic acid tert-butyl ester A solution of 5-Phenyl-thiophene-2,3-dicarboxylic acid 2-tert-butyl ester (40 mg, 0.13 mmol) in $CH_2Cl_2$ (1.3 ml), under nitrogen, at 0° C., was treated with diisopropylethylamine (27 L, 0.16 mmol) followed by dimethylformamide (10 L, 0.13 mmol) and oxalyl chloride (170 L, 0.34 mmol). Slight effervescence was observed. The reaction was kept at 0° C. for 30 min before being treated with (2,4-Dichloro-phenyl)-isopropyl-amine (described previously) (79 mg, 0.39 mmol). The reaction was allowed to reach 21° C. and then placed in a bath at 90° C. for 15 h. Solvent was removed to leave a pale brown gum (144 mg). The crude material was purified on bond-elute using Hexane/$CH_2Cl_2$/EtOAc (12.5/2/1) as eluent to give 39 mg, (62%) of 3-[(2,4-Dichloro-phenyl)-isopropyl-carbamoyl]-5-phenyl-thiophene-2-carboxylic acid tert-butyl ester as a pale brown solid. NMR $^1$H ($CDCl_3$; 400 MHz) 7.50-7.48 (m, 2H); 7.38-7.25 (m, 6H); 7.10-7.03 (m, 1H); 5.05 (quint, J=6.88 Hz, 1H); 1.57 (bs, 9H); 1.40 (d, J=6.88 Hz, 3H); 1.12 (d, J=6.88 Hz, 3H)

Step VII

3-[(2,4-Dichloro-phenyl)-isopropyl-carbamoyl]-5-phenyl-thiophene-2-carboxylic acid A solution of 3-[(2,4-Dichloro-phenyl)-isopropyl-carbamoyl]-5-phenyl-thiophene-2-carboxylic acid tert-butyl ester (37 mg, 0.08 mmol) in CH$_2$Cl$_2$ (0.2 ml) at room temperature, under nitrogen was treated with trifluoroacetic acid (0.8 ml). After 1 h the reaction was concentrated the residue was taken into EtOAc and washed sequentially with 2N HCl (2×15 ml), water, brine dried and evaporated to a foam (33 mg). The foam was redissolved in EtOAc and above acidic wash was repeated to yield 27 mg (84%) of 3-[(2,4-Dichloro-phenyl)-isopropyl-carbamoyl]-5-phenyl-thiophene-2-carboxylic acid compound as pale brown foam. NMR $^1$H: (CD$_3$OD; 400 MHz) 7.57-7.55 (m, 2H); 7.49-7.36 (m, 6H), 7.30-7.27 (m, 1H); 4.89 (quint, J=6.73 Hz, 1H); 1.42 (d, J=6.73 Hz, 3H); 1.12 (d, J=6.73 Hz, 3H).

EXAMPLE 24

The following compound was obtained from Discovery Technology:
3-(4-Chloro-2,5-dimethyl-benzenesulfonylamino)-5-phenyl-thiophene-2-carboxylic acid amide Compound #580

EXAMPLE 25

The following compounds were obtained from Maybridge:
5-(4-Chloro-phenyl)-3-(toluene-4-sulfonylamino)-thiophene-2-carboxylic acid amide, Compound #563
5-(4-Fluoro-phenyl)-3-(toluene-4-sulfonylamino)-thiophene-2-carboxylic acid amide, Compound #564, GK 01137
5-(4-Methoxy-phenyl)-3-(toluene-4-sulfonylamino)-thiophene-2-carboxylic acid amide, Compound #565, GK 01175

EXAMPLE 26

Evaluation of Compounds in the HCV RNA-Dependent RNA Polymerase Assay

The following references are all incorporated by reference:
1. Behrens, S., Tomei, L., De Francesco, R. (1996) *EMBO* 15, 12-22
2. Harlow, E, and Lane, D. (1988) *Antibodies: A Laboratory Manual*. Cold Spring Harbord Laboratory. Cold Spring Harbord. NY.
3. Lohmann, V., Körner, F., Herian, U., and Bartenschlager, R. (1997) *J. Virol.* 71, 8416-8428
4. Tomei, L., Failla, C., Santolini, E., De Francesco, R., and La Monica, N. (1993) *J Virol* 67, 4017-4026

Compounds were evaluated using an in vitro polymerase assay containing purified recombinant HCV RNA-dependent RNA polymerase (NS5B protein). HCV NS5B was expressed in insect cells using a recombinant baculovirus as vector. The experimental procedures used for the cloning, expression and purification of the HCV NS5B protein are described below. Follows, are details of the RNA-dependent RNA polymerase assays used to test the compounds.
Expression of the HCV NS5B Protein in Insect Cells:

The cDNA encoding the entire NS5B protein of HCV-Bk strain, genotype 1b, was amplified by PCR using the primers NS5Nhe5' (5'-<u>GCTAGCGCTAGC</u>TCAATGTCCTACA-CATGG-3') and XhoNS53' (5'-<u>CTCGAGCTCGAG</u>CGTC-CATCGGTTGGGGAG-3') and the plasmid pCD 3.8-9.4 as template (Tomei et al, 1993). NS5Nhe5' and XhoNS53' contain two NheI and XhoI sites (underlined sequences), respectively, at their 5' end. The amplified DNA fragment was cloned in the bacterial expression plasmid pET-21b (Novagen) between the restriction sites NheI and XhoI, to generate the plasmid pET/NS5B. This plasmid was later used as template to PCR-amplify the NS5B coding region, using the primers NS5B-H9 (5'-ATACATATGGCTAGCATGT-CAATGTCCTACACATGG-3') and NS5B-R4 (5'-<u>GGATC-CGGATC</u>CCGTTCATCGGTTGGGGAG-3'). NS5B-H9 spans a region of 15 nucleotides in the plasmid pET-21b followed by the translation initiation codon (ATG) and 8 nucleotides corresponding to the 5' end of the NS5B coding region (nt. 7590-7607 in the HCV sequence with the accession number M58335). NS5B-R4 contains two BamHI sites (underlined) followed by 18 nucleotides corresponding to the region around the stop codon in the HCV genome (nt. 9365-9347). The amplified sequence, of 1.8 kb, was digested with NheI and BamHI and ligated to a predigested pBlueBacII plasmid (Invitrogen). The resulting recombinant plasmid was designated pBac/NS5B. Sf9 cells were co-transfected with 3 µg of pBac/NS5B, together with 1 µg of linearized baculovirus DNA (Invitrogen), as described in the manufacturer's protocol. Following two rounds of plaque purification, an NS5B-recombinant baculovirus, BacNS5B, was isolated. The presence of the recombinant NS5B protein was determined by western blot analysis (Harlow and Lane, 1988) of BacNS5B-infected Sf9 cells, using a rabbit polyclonal antiserum (anti-NS5B) raised against a His-tagged version of the NS5B protein expressed in *E. coli*. Infections of Sf9 cells with this plaque purified virus were performed in one-liter spinner flasks at a cell density of 1.2×10$^6$ cells/ml and a multiplicity of infection of 5.
Preparation of a Soluble Recombinant NS5B Protein Sf9 cells were infected as described above. Sixty hours post-infection, cells were harvested then washed twice with phosphate buffer saline (PBS). Total proteins were solubilized as described in Lohmann et al. (1997) with some modifications. In brief, proteins were extracted in three steps, S1, S2, S3, using lysis buffers (LB) I, LB II and LB III (Lohmann et al, 1997). The composition of LBII was modified to contain 0.1% triton X-100 and 150 mM NaCl to reduce the amount of solubilized NS5B protein at this step. In addition, sonication of cell extracts was avoided throughout the protocol to preserve the integrity of the protein structure.
Purification of Recombinant NS5B Using Fast Protein Liquid Chromatography (FPLC):

Soluble NS5B protein in the S3 fraction was diluted to lower the NaCl concentration to 300 mM, then it incubated batchwise with DEAE sepharose beads (Amersham-Pharmacia) for 2 hrs at 4° C., as described by Behrens et al. (1996). Unbound material was cleared by centrifugation for 15 min at 4° C., at 25 000 rpm using a SW41 rotor (Beckman). The supernatant was further diluted to lower the NaCl concentration to 200 mM and subsequently loaded, with a flow rate of 1 ml/min, on a 5 ml HiTrap® heparin column (Amersham-Pharmacia) connected to an FPLC system (Amersham-Pharmacia). Bound proteins were eluted in 1 ml fractions, using a continuous NaCl gradient of 0.2 to 1 M, over a 25 ml volume. NS5B-containing fractions were identified by sodium dodecyl sulfate polyacrylamide gel electrophoresis (SDS-PAGE), followed by western blotting using the anti-NSSB antiserum at a dilution of 1:2000. Positive fractions were pooled and the elution buffer was exchanged against a 50 mM NaPO$_4$ pH 7.0, 20% glycerol, 0.5% triton X-100 and 10 mM DTT, using a PD-10 column (Amersham-Pharmacia). The sample was then loaded onto a 1 ml HiTrap® SP column (Amersham-Pharmacia), with a flow rate of 0.1 ml/min. Bound proteins were eluted using a continuous 0 to 1 M NaCl gradient over a 15 ml volume. Eluted fractions were analyzed by SDS-PAGE and western blotting. Alternatively, proteins were visualized, following SDS-PAGE, by silver staining using the Silver Stain Plus kit (BioRad) as described by the manufacturer. Positive fractions were tested for RdRp activity (see below) and the most active ones were pooled, and stored as a 40% glycerol solution at −70° C.

In Vitro HCV RdRp Flashplate Scintillation Proximity Assay (STREP-FLASH ASSAY) Used to Evaluate Analogues:

This assay consists on measuring the incorporation of [$^3$H] radiolabelled UTP in a polyrA/biotinylated-oligo dT template-primer, captured on the surface of streptavidin-coated scintillant-embeded microtiter Flashplates™ (NEN Life Science Products inc, MA, USA, SMP 103A). In brief, a 400 ng/μl polyrA solution (Amersham Pharmacia Biotech) was mixed volume-to-volume with 5' biotin-oligo dT$_{15}$ at 20 pmol/μl. The template and primers were denatured at 95 C for 5 minutes then incubated at 37 C for 10 minutes. Annealed template-primers were subsequently diluted in a Tris-HCl containing buffer and allowed to bind to streptavidin-coated flashplates overnight. Unbound material was discarded, compounds were added in a 10 μl solution followed by a 10 μl of a solution containing 50 mM MgCl$_2$, 100 mM Tris-HCl pH 7.5, 250 mM NaCl and 5 mM DTT. The enzymatic reaction was initiated upon addition of a 30 μl solution containing the enzyme and substrate to obtain the following concentrations: 25 μM UTP, 1 μCi [$^3$H] UTP and 100 nM recombinant HCV NS5B. RdRp reactions were allowed to proceed for 2 hrs at room temperature after which wells were washed three times with a 250 μL of 0.15 M NaCl solution, air dried at 37 C, and counted using a liquid scintillation counter (Wallac Microbeta Trilex, Perkin-Elmer, Mass., USA). Results are shown in Table 1.

In Vitro HCV RdRp Filtration Assay Used to Evaluate Analogues

RdRp assays were conducted using the homopolymeric template/primer polyA/oligo dT. All RdRp reactions were performed in a total volume of 50 μl, and in a basic buffer consisting of 20 mM Tris-HCl pH 7.5, 1 mM DTT, 50 mM NaCl, 5 mM MgCl$_2$, 0.5 μCi [±$^{32}$P]-UTP (3000 Ci/mmol), 15 μM cold UTP and 20 U RNasin (Promega). Standard HCV RdRp reactions contained 200 ng of purified NS5B protein. PolyA RNAs (Amersham-Pharmacia) was resuspended at 400 ng/μl. The primer oligodT$_{15}$ (Canadian life technologies) was diluted to a concentration of 20 pmol/μl (7.6 ng/ml). Templates and primers were mixed volume to volume, denatured at 95° C. for 5 min and annealed at 37° C. for 10 min. Following a two hour incubation at 22° C., reactions were stopped by the addition of 100 μg of sonicated salmon sperm DNA (Life Technologies) and 1 ml of 10% trichloroacetic acid-0.5% tetrasodium pyrophosphate (TCA-PPi). Nucleic acids were precipitated at 4° C. for 30 min after which samples were filtered on GF/C glass microfiber filters (Millipore). Membranes were subsequently washed with 25 ml of a 1% TCA-0.1% PPi solution, then air dried. Incorporated radioactivity was quantified using a liquid scintillation counter (1450-Microbeta, Wallac). Results are shown in Table 1.

EXAMPLE 27

Evaluation of Analogues for Measurement of ATPase Activity of HCV NS3 Helicase

Malachite Green Assay:

The measurement of ATPase activity was performed by measuring the amount of free inorganic phosphate released during the conversion of ATP to ADP by the HCV NS3 ATPase activity. The assay is as follows: In a 96-well microtiter-plate, compounds were dissolved at various concentrations in a final volume of 25 μL of ATPase buffer containing 400 μM ATP. The enzymatic reaction was initiated by the addition of 25 μl of ATPase buffer containing 6 nM of HCV NS3 enzyme without ATP to the wells followed by an incubation of 30 min. at 37 C. Essentially, the final concentration of the ATPase buffer components are as follows: 44 mM MOPS pH 7.0, 8.8 mM NaCl, 2.2 mM MgCl$_2$, 125 μg/ml poly A, 1% DMSO, 200 μM ATP, and 3 nM HCV NS3 enzyme. The reaction was stopped by the addition of 100 μl of Biomol Green™ reagent (BIOMOL® Research Laboratories Inc., Plymouth Meeting, Pa.). In order to allow the development of the green color, the plate was incubated for 15 min. at room temperature. Then the plate was read on a micro-plate reader at 620 nm. The 50% inhibitory concentration (IC$_{50}$) for anti-ATPase activity was defined as the concentration of compound that resulted in a 50% reduction of the signal compared to the signal observed in control sample without compound. The signal recorded was also corrected from the background signal obtained with control samples with compound only. The IC$_{50}$ was determined from dose-response curves using six to eight concentrations per compound. Curves were fitted to data points using a non-linear regression analysis, and IC$_{50}$s were interpolated from the resulting curves using GraphPad Prism software, version 2.0 (GraphPad Software Inc, San Diego, Calif.).

HPLC Assay:

The measurement of HCV NS3 ATPase activity was performed by measuring the amount of ADP produced during the conversion of ATP to ADP by the HCV NS3 enzyme using paired-ion HPLC on a reverse phase column. The assay is as follows: The same protocol as mentioned above was used except that the final concentration of HCV NS3 enzyme was reduced to 1 nM in a 50 μl reaction mixture and that the ATPase reaction was stopped by the addition of 12.5 μl of 0.5 M EDTA. A modular liquid chromatography system (TSP Spectrasystem®, ThermoQuest Corporation, San Diego, USA) using a ChromQuest™ software (ThermoQuest Corporation, San Diego, USA) controlled the autosampling of 25 μl from each reaction. The mobile phase was an isocratic solution of 0.15 M triethylamine, 6% methanol, and phosphoric acid to pH 5.5. ADP and ATP peaks were resolved using the Aqua 5μ, C18, 125 Å, (150×4.6 mm) reverse phase column. The extent of ATP conversion to ADP was evaluated by measuring the area under the ADP peak produced which was detected at 259 nm. The amount of ADP was corrected for the presence of ADP contaminant in the original ATP solution. The 50% inhibitory concentration (IC$_{50}$) for anti-ATPase activity was defined as the concentration of compound that resulted in a 50% reduction of the ADP peak area compared to the ADP peak area observed in control sample without compound. The IC$_{50}$ was determined from dose-response curves using six to eight concentrations per compound. Curves were fitted to data points using a non-linear regression analysis, and IC$_{50}$s were interpolated from the resulting curves using GraphPad Prism software, version 2.0 (GraphPad Software Inc, San Diego, Calif.).

EXAMPLE 27

List of Compounds and Related Polymerase Activity*

| MOLSTRUCTURE | COMPOUND NAME | IC50 |
|---|---|---|
| 1 | 3-[(4-CHLORO-2,5-DIMETHYL-BENZENESULFONYL)-(3-IODO-BENZYL)-AMINO]-5-PHENYL-THIOPHENE-2-CARBOXYLIC ACID | ++ |
| 2 | 3-[(3-BENZOFURAN-2-YL-BENZYL)-(4-CHLORO-2,5-DIMETHYL-BENZENESULFONYL)-AMINO]-5-PHENYL-THIOPHENE-2-CARBOXYLIC ACID | ++ |
| 3 | 3-(4-CHLORO-2,5-DIMETHYL-BENZENESULFONYLAMINO)-5-PHENYL-THIOPHENE-2-CARBOXYLIC ACID | ++ |
| 4 | 3-{(2,4-DICHLORO-BENZOYL)-[5-(3-TRIFLUOROMETHYL-PHENYL)-FURAN-2-YLMETHYL]-AMINO}-5-PHENYL-THIOPHENE-2-CARBOXYLIC ACID | +++ |

| MOLSTRUCTURE | COMPOUND NAME | IC50 |
|---|---|---|
| 5 | 3-[(4-CHLORO-2,5-DIMETHYL-BENZENESULFONYL)-METHYL-AMINO]-5-PHENYL-THIOPHENE-2-CARBOXYLIC ACID | ++ |
| 6 | 5-(4-FLUORO-PHENYL)-3-(TOLUENE-4-SULFONYLAMINO)-THIOPHENE-2-CARBOXYLIC ACID | +++ |
| 7 | 3-(2,4-DICHLORO-BENZENESULFONYLAMINO)-5-PHENYL-THIOPHENE-2-CARBOXYLIC ACID | +++ |
| 8 | 3-(4-CHLORO-2,5-DIMETHYL-BENZENESULFONYLAMINO)-5-(4-FLUORO-PHENYL)-THIOPHENE-2-CARBOXYLIC ACID | +++ |

| MOLSTRUCTURE | COMPOUND NAME | IC50 |
|---|---|---|
| 9 | 3-[(2,4-DICHLORO-BENZOYL)-METHYL-AMINO]-5-PHENYL-THIOPHENE-2-CARBOXYLIC ACID | +++ |
| 10 | 5-#TERT!-BUTYL-3-(4-CHLORO-BENZENESULFONYLAMINO)-THIOPHENE-2-CARBOXYLIC ACID | +++ |
| 11 | 4-(TOLUENE-4-SULFONYLAMINO)-[2,3']BITHIOPHENYL-5-CARBOXYLIC ACID | ++ |
| 12 | 3-[(5-BENZOFURAN-2-YL-THIOPHEN-2-YLMETHYL)-(2,4-DICHLORO-BENZOYL)-AMINO]-5-PHENYL-THIOPHENE-2-CARBOXYLIC ACID | ++ |
| 13 | 5-PHENYL-3-(TOLUENE-4-SULFONYLAMINO)-THIOPHENE-2-CARBOXYLIC ACID | +++ |

| MOLSTRUCTURE | COMPOUND NAME | IC50 |
|---|---|---|
| 14 | 3-(4-CHLORO-2,5-DIMETHYL-BENZENESULFONYLAMINO)-5-(4-CHLORO-PHENYL)-THIOPHENE-2-CARBOXYLIC ACID | +++ |
| 15 | 5-PHENYL-3-(TOLUENE-2-SULFONYLAMINO)-THIOPHENE-2-CARBOXYLIC ACID | + |
| 16 | 5-PHENYL-3-(TOLUENE-3-SULFONYLAMINO)-THIOPHENE-2-CARBOXYLIC ACID | ++ |
| 17 | 3-BENZENESULFONYLAMINO-5-PHENYL-THIOPHENE-2-CARBOXYLIC ACID | ++ |
| 18 | 3-(4-CHLORO-BENZENESULFONYLAMINO)-5-PHENYL-THIOPHENE-2-CARBOXYLIC ACID | +++ |

-continued

| | MOLSTRUCTURE | COMPOUND NAME | IC50 |
|---|---|---|---|
| 19 | | 3-(4-CHLORO-2,5-DIMETHYL-BENZENESULFONYLAMINO)-5-(4-ISOBUTYL-PHENYL)-THIOPHENE-2-CARBOXYLIC ACID | ++ |
| 20 | | 5-TERT-BUTYL-3-(4-CHLORO-2,5-DIMETHYL-BENZENESULFONYLAMINO)-THIOPHENE-2-CARBOXYLIC ACID | ++ |
| 21 | | 3-(2,5-DIMETHYL-BENZENESULFONYLAMINO)-5-PHENYL-THIOPHENE-2-CARBOXYLIC ACID | ++ |
| 22 | | 3-(4-METHOXY-2,3,6-TRIMETHYL-BENZENESULFONYLAMINO)-5-PHENYL-THIOPHENE-2-CARBOXYLIC ACID | +++ |
| 23 | | 5-PHENYL-3-(THIOPHENE-2-SULFONYLAMINO)-THIOPHENE-2-CARBOXYLIC ACID | +++ |

| | MOLSTRUCTURE | COMPOUND NAME | IC50 |
|---|---|---|---|
| 24 | | 4-(4-CHLORO-2,5-DIMETHYL-BENZENESULFONYLAMINO)-[2,3']BITHIOPHENYL-5-CARBOXYLIC ACID | +++ |
| 25 | | 5-(3,5-BIS-TRIFLUOROMETHYL-PHENYL)-3-(4-CHLORO-2,5-DIMETHYL-BENZENESULFONYLAMINO)-THIOPHENE-2-CARBOXYLIC ACID | + |
| 26 | | 8-CHLORO-3-(4-CHLORO-2,5-DIMETHYL-BENZENESULFONYLAMINO)-4#H!-1,5-DITHIA-CYCLOPENTA[#A!]NAPHTHALENE-2-CARBOXYLIC ACID | ++ |
| 27 | | 3-(2,4-DIFLUORO-BENZENESULFONYLAMINO)-5-PHENYL-THIOPHENE-2-CARBOXYLIC ACID | +++ |
| 28 | | 3-[3-(2,6-DICHLORO-PYRIDIN-4-YL)-UREIDO]-5-PHENYL-THIOPHENE-2-CARBOXYLIC ACID | +++ |

| MOLSTRUCTURE | COMPOUND NAME | IC50 |
|---|---|---|
| 29 | 3-(2-CHLORO-BENZENESULFONYLAMINO)-5-PHENYL-THIOPHENE-2-CARBOXYLIC ACID | ++ |
| 30 | 3-(2-FLUORO-BENZENESULFONYLAMINO)-5-PHENYL-THIOPHENE-2-CARBOXYLIC ACID | ++ |
| 31 | 5-PHENYL-3-(2-TRIFLUOROMETHOXY-BENZENESULFONYLAMINO)-THIOPHENE-2-CARBOXYLIC ACID | + |
| 32 | 3-(4-#TERT!-BUTYL-BENZENESULFONYLAMINO)-5-PHENYL-THIOPHENE-2-CARBOXYLIC ACID | ++ |
| 33 | 3-(4-CHLORO-PHENOXYCARBONYLAMINO)-5-PHENYL-THIOPHENE-2-CARBOXYLIC ACID | ++ |
| 34 | 3-(3,4-DICHLORO-BENZENESULFONYLAMINO)-5-PHENYL-THIOPHENE-2-CARBOXYLIC ACID | ++ |

| MOLSTRUCTURE | COMPOUND NAME | IC50 |
|---|---|---|
| 35 | 5-PHENYL-3-(2-TRIFLUOROMETHYL-BENZENESULFONYLAMINO)-THIOPHENE-2-CARBOXYLIC ACID | + |
| 36 | 3-(5-BROMO-6-CHLORO-PYRIDINE-3-SULFONYLAMINO)-5-PHENYL-THIOPHENE-2-CARBOXYLIC ACID | + |
| 37 | 3-(5-CHLORO-THIOPHENE-2-SULFONYLAMINO)-5-PHENYL-THIOPHENE-2-CARBOXYLIC ACID | +++ |
| 38 | 3-(5-CHLORO-3-METHYL-BENZO[#B!]THIOPHENE-2-SULFONYLAMINO)-5-PHENYL-THIOPHENE-2-CARBOXYLIC ACID | +++ |

| MOLSTRUCTURE | COMPOUND NAME | IC50 |
|---|---|---|
| 39 | 3-(4-BROMO-BENZENESULFONYLAMINO)-5-PHENYL-THIOPHENE-2-CARBOXYLIC ACID | +++ |
| 40 | 3-(3-CHLORO-BENZENESULFONYLAMINO)-5-PHENYL-THIOPHENE-2-CARBOXYLIC ACID | +++ |
| 41 | 3-(5-CHLORO-1,3-DIMETHYL-1#H!-PYRAZOLE-4-SULFONYLAMINO)-5-PHENYL-THIOPHENE-2-CARBOXYLIC ACID | ++ |
| 42 | 3-(3-BROMO-BENZENESULFONYLAMINO)-5-PHENYL-THIOPHENE-2-CARBOXYLIC ACID | ++ |
| 43 | 3-(4-ISOPROPYL-BENZENESULFONYLAMINO)-5-PHENYL-THIOPHENE-2-CARBOXYLIC ACID | ++ |

| MOLSTRUCTURE | COMPOUND NAME | IC50 |
|---|---|---|
| 44 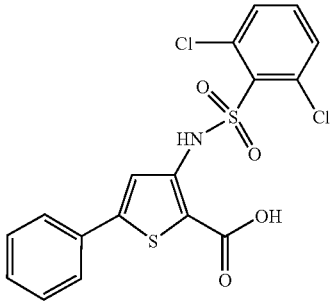 | 3-(2,6-DICHLORO-BENZENESULFONYLAMINO)-5-PHENYL-THIOPHENE-2-CARBOXYLIC ACID | +++ |
| 45 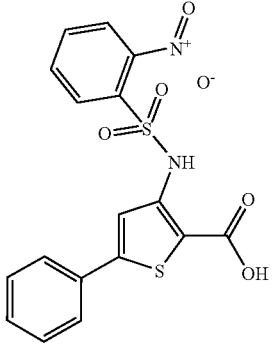 | 3-(2-NITRO-BENZENESULFONYLAMINO)-5-PHENYL-THIOPHENE-2-CARBOXYLIC ACID | +++ |
| 46 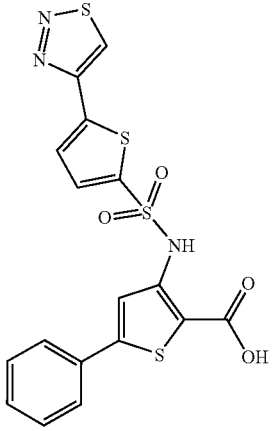 | 5-PHENYL-3-(5-[1,2,3]THIADIAZOL-4-YL-THIOPHENE-2-SULFONYLAMINO)-THIOPHENE-2-CARBOXYLIC ACID | ++ |
| 47 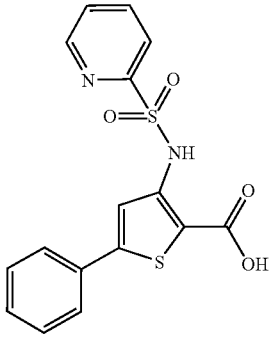 | 5-PHENYL-3-(PYRIDINE-2-SULFONYLAMINO)-THIOPHENE-2-CARBOXYLIC ACID | + |

-continued

| MOLSTRUCTURE | COMPOUND NAME | IC50 |
|---|---|---|
| 48 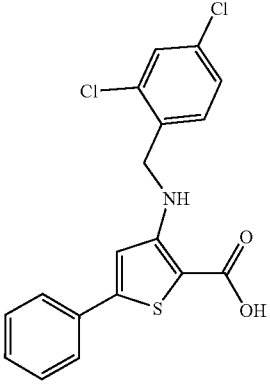 | 3-(2,4-DICHLORO-BENZYLAMINO)-5-PHENYL-THIOPHENE-2-CARBOXYLIC ACID | +++ |
| 49 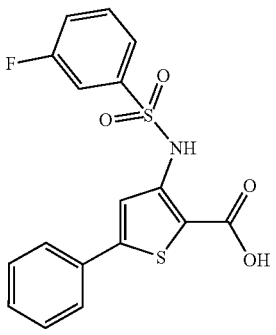 | 3-(3-FLUORO-BENZENESULFONYLAMINO)-5-PHENYL-THIOPHENE-2-CARBOXYLIC ACID | +++ |
| 50 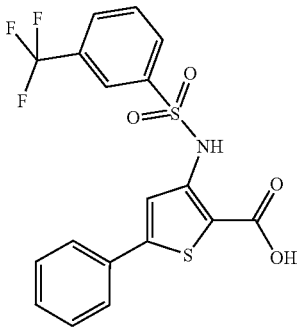 | 5-PHENYL-3-(3-TRIFLUOROMETHYL-BENZENESULFONYLAMINO)-THIOPHENE-2-CARBOXYLIC ACID | ++ |
| 51 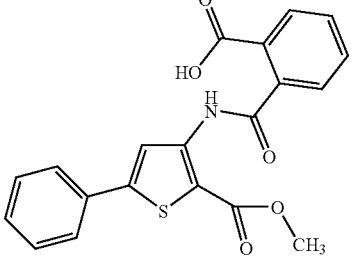 | 3-(2-CARBOXY-BENZOYLAMINO)-5-PHENYL-THIOPHENE-2-CARBOXYLIC ACID METHYL ESTER | ++ |
| 52 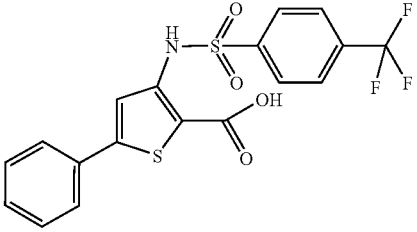 | 5-PHENYL-3-(4-TRIFLUOROMETHYL-BENZENESULFONYLAMINO)-THIOPHENE-2-CARBOXYLIC ACID | +++ |

-continued

| MOLSTRUCTURE | COMPOUND NAME | IC50 |
|---|---|---|
| 53 | 3-(2,5-DIFLUORO-BENZENESULFONYLAMINO)-5-PHENYL-THIOPHENE-2-CARBOXYLIC ACID | +++ |
| 54 | 3-(2-CYANO-BENZENESULFONYLAMINO)-5-PHENYL-THIOPHENE-2-CARBOXYLIC ACID | +++ |
| 55 | 3-(2,5-DICHLORO-THIOPHENE-3-SULFONYLAMINO)-5-PHENYL-THIOPHENE-2-CARBOXYLIC ACID | ++ |
| 56 | 4-(TOLUENE-2-SULFONYLAMINO)-[2,2']BITHIOPHENYL-5-CARBOXYLIC ACID | +++ |
| 57 | 5'-CHLORO-4-(TOLUENE-2-SULFONYLAMINO)-[2,2']BITHIOPHENYL-5-CARBOXYLIC ACID | +++ |

| | MOLSTRUCTURE | COMPOUND NAME | IC50 |
|---|---|---|---|
| 58 | | 5-(2,4-DICHLORO-PHENYL)-3-(TOLUENE-2-SULFONYLAMINO)-THIOPHENE-2-CARBOXYLIC ACID | ++ |
| 59 | | 5-(4-NITRO-PHENYL)-3-(TOLUENE-2-SULFONYLAMINO)-THIOPHENE-2-CARBOXYLIC ACID | +++ |
| 60 | | 3-(TOLUENE-2-SULFONYLAMINO)-5-(4-TRIFLUOROMETHOXY-PHENYL)-THIOPHENE-2-CARBOXYLIC ACID | +++ |
| 61 | | 5-QUINOLIN-8-YL-3-(TOLUENE-2-SULFONYLAMINO)-THIOPHENE-2-CARBOXYLIC ACID | + |
| 62 | | 5-PHENYL-3-(TOLUENE-2-SULFONYLAMINO)-THIOPHENE-2-CARBOXYLIC ACID | +++ |

| MOLSTRUCTURE | COMPOUND NAME | IC50 |
|---|---|---|
| 63 | 5-(3-NITRO-PHENYL)-3-(TOLUENE-2-SULFONYLAMINO)-THIOPHENE-2-CARBOXYLIC ACID | +++ |
| 64 | 3-(TOLUENE-2-SULFONYLAMINO)-5-M-TOLYL-THIOPHENE-2-CARBOXYLIC ACID | +++ |
| 65 | 5-(3-CHLORO-PHENYL)-3-(TOLUENE-2-SULFONYLAMINO)-THIOPHENE-2-CARBOXYLIC ACID | +++ |
| 66 | 5-(4-FLUORO-PHENYL)-3-(TOLUENE-2-SULFONYLAMINO)-THIOPHENE-2-CARBOXYLIC ACID | +++ |
| 67 | 5-(3-FLUORO-PHENYL)-3-(TOLUENE-2-SULFONYLAMINO)-THIOPHENE-2-CARBOXYLIC ACID | +++ |

| MOLSTRUCTURE | COMPOUND NAME | IC50 |
|---|---|---|
| 68 | 5-(4-CHLORO-PHENYL)-3-(TOLUENE-2-SULFONYLAMINO)-THIOPHENE-2-CARBOXYLIC ACID | +++ |
| 69 | 5-(3,5-DIFLUORO-PHENYL)-3-(TOLUENE-2-SULFONYLAMINO)-THIOPHENE-2-CARBOXYLIC ACID | +++ |
| 70 | 5-(3,4-DIFLUORO-PHENYL)-3-(TOLUENE-2-SULFONYLAMINO)-THIOPHENE-2-CARBOXYLIC ACID | +++ |
| 71 | 3-(TOLUENE-2-SULFONYLAMINO)-5-VINYL-THIOPHENE-2-CARBOXYLIC ACID | ++ |
| 72 | 3-(4-CHLORO-BENZOYLAMINO)-5-PHENYL-THIOPHENE-2-CARBOXYLIC ACID | ++ |

| MOLSTRUCTURE | COMPOUND NAME | IC50 |
|---|---|---|
| 73 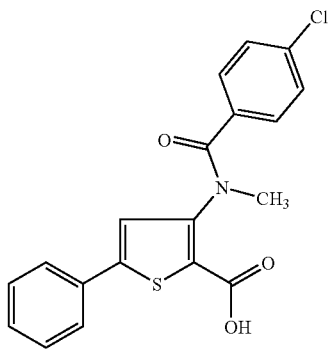 | 3-[(4-CHLORO-BENZOYL)-METHYL-AMINO]-5-PHENYL-THIOPHENE-2-CARBOXYLIC ACID | +++ |
| 74 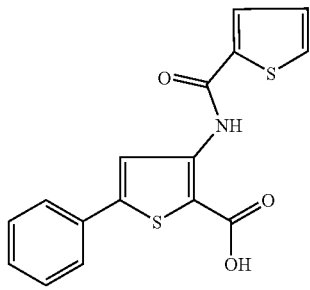 | 5-PHENYL-3-[(THIOPHENE-2-CARBONYL)-AMINO]-THIOPHENE-2-CARBOXYLIC ACID | ++ |
| 75 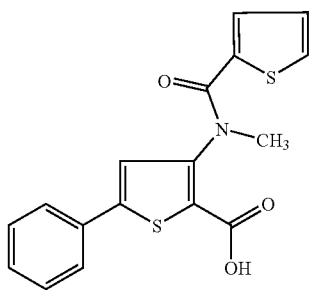 | 3-[METHYL-(THIOPHENE-2-CARBONYL)-AMINO]-5-PHENYL-THIOPHENE-2-CARBOXYLIC ACID | ++ |
| 76 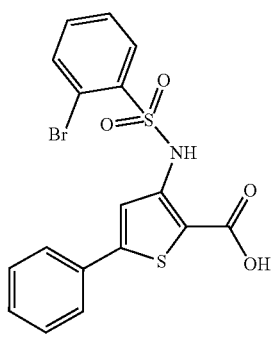 | 3-(2-BROMO-BENZENESULFONYLAMINO)-5-PHENYL-THIOPHENE-2-CARBOXYLIC ACID | +++ |

-continued

| | MOLSTRUCTURE | COMPOUND NAME | IC50 |
|---|---|---|---|
| 77 | | 3-(2,4-DIFLUORO-BENZOYLAMINO)-5-PHENYL-THIOPHENE-2-CARBOXYLIC ACID | + |
| 78 | | 3-[(2,4-DIFLUORO-BENZOYL)-METHYL-AMINO]-5-PHENYL-THIOPHENE-2-CARBOXYLIC ACID | ++ |
| 79 | | 3-(TOLUENE-2-SULFONYLAMINO)-5-TRIMETHYLSILANYLETHYNYL-THIOPHENE-2-CARBOXYLIC ACID | +++ |
| 80 | | 5-ETHYNYL-3-(TOLUENE-2-SULFONYLAMINO)-THIOPHENE-2-CARBOXYLIC ACID | ++ |
| 81 | | 3-(TOLUENE-2-SULFONYLAMINO)-5-(3-TRIFLUOROMETHOXY-PHENYL)-THIOPHENE-2-CARBOXYLIC ACID | ++ |

| MOLSTRUCTURE | COMPOUND NAME | IC50 |
|---|---|---|
| 82 | 5-BENZOYL-3-(TOLUENE-2-SULFONYLAMINO)-THIOPHENE-2-CARBOXYLIC ACID | ++ |
| 83 | 5-(4-CYANO-PHENYL)-3-(TOLUENE-2-SULFONYLAMINO)-THIOPHENE-2-CARBOXYLIC ACID | +++ |
| 84 | 5-(3-CHLORO-4-FLUORO-PHENYL)-3-(TOLUENE-2-SULFONYLAMINO)-THIOPHENE-2-CARBOXYLIC ACID | +++ |
| 85 | 5-(3,4-DICHLORO-PHENYL)-3-(TOLUENE-2-SULFONYLAMINO)-THIOPHENE-2-CARBOXYLIC ACID | ++ |
| 86 | 5-PYRIDIN-4-YL-3-(TOLUENE-2-SULFONYLAMINO)-THIOPHENE-2-CARBOXYLIC ACID | +++ |
| 87 | 5-PYRIDIN-3-YL-3-(TOLUENE-2-SULFONYLAMINO)-THIOPHENE-2-CARBOXYLIC ACID | +++ |

| MOLSTRUCTURE | COMPOUND NAME | IC50 |
|---|---|---|
| 88 | 3-(TOLUENE-2-SULFONYLAMINO)-5-(4-TRIFLUOROMETHYL-PHENYL)-THIOPHENE-2-CARBOXYLIC ACID | +++ |
| 89 | 5-(4-METHANESULFONYL-PHENYL)-3-(TOLUENE-2-SULFONYLAMINO)-THIOPHENE-2-CARBOXYLIC ACID | +++ |
| 90 | 5-(3-ACETYLAMINO-PHENYL)-3-(TOLUENE-2-SULFONYLAMINO)-THIOPHENE-2-CARBOXYLIC ACID | ++ |
| 91 | 5-(3-CHLORO-4-FLUORO-PHENYL)-3-(TOLUENE-2-SULFONYLAMINO)-THIOPHENE-2-CARBOXYLIC ACID | ++ |
| 92 | 3-(4-METHYL-BENZOYLAMINO)-5-PHENYL-THIOPHENE-2-CARBOXYLIC ACID | ++ |

| MOLSTRUCTURE | COMPOUND NAME | IC50 |
|---|---|---|
| 93 | 3-[METHYL-(4-METHYL-BENZOYL)-AMINO]-5-PHENYL-THIOPHENE-2-CARBOXYLIC ACID | +++ |
| 94 | 3-(3,5-DIMETHYL-ISOXAZOLE-4-SULFONYLAMINO)-5-PHENYL-THIOPHENE-2-CARBOXYLIC ACID | ++ |
| 95 | 3-[(2-CHLORO-BENZOYL)-METHYL-AMINO]-5-PHENYL-THIOPHENE-2-CARBOXYLIC ACID | ++ |
| 96 | 3-(2-METHYL-BENZOYLAMINO)-5-PHENYL-THIOPHENE-2-CARBOXYLIC ACID | ++ |

| MOLSTRUCTURE | COMPOUND NAME | IC50 |
|---|---|---|
| 97 | 3-[METHYL-(2-METHYL-BENZOYL)-AMINO]-5-PHENYL-THIOPHENE-2-CARBOXYLIC ACID | + |
| 98 | 5-PHENYL-3-(5-TRIFLUOROMETHYL-PYRIDINE-2-SULFONYLAMINO)-THIOPHENE-2-CARBOXYLIC ACID | ++ |
| 99 | 5-PHENYLETHYNYL-3-(TOLUENE-2-SULFONYLAMINO)-THIOPHENE-2-CARBOXYLIC ACID | +++ |
| 100 | 3-(2,5-DIMETHYL-BENZENESULFONYLAMINO)-5-(4-NITRO-PHENYL)-THIOPHENE-2-CARBOXYLIC ACID | +++ |

| MOLSTRUCTURE | COMPOUND NAME | IC50 |
|---|---|---|
| 101 | 5-(2-FLUORO-PHENYL)-3-(TOLUENE-2-SULFONYLAMINO)-THIOPHENE-2-CARBOXYLIC ACID | +++ |
| 102 | 5-(2-CYANO-PHENYL)-3-(TOLUENE-2-SULFONYLAMINO)-THIOPHENE-2-CARBOXYLIC ACID | ++ |
| 103 | 5-(2-ETHOXYCARBONYL-PHENYL)-3-(TOLUENE-2-SULFONYLAMINO)-THIOPHENE-2-CARBOXYLIC ACID | ++ |
| 104 | 5-(2-METHOXY-PHENYL)-3-(TOLUENE-2-SULFONYLAMINO)-THIOPHENE-2-CARBOXYLIC ACID | ++ |
| 105 | 3'-METHYL-4-(TOLUENE-2-SULFONYLAMINO)-[2,2']-BITHIOPHENYL-5-CARBOXYLIC ACID | ++ |

| MOLSTRUCTURE | COMPOUND NAME | IC50 |
|---|---|---|
| 106 | 3-(TOLUENE-2-SULFONYLAMINO)-5-(2-TRIFLUOROMETHYL-PHENYL)-THIOPHENE-2-CARBOXYLIC ACID | ++ |
| 107 | 3-(2,5-DIMETHYL-BENZENESULFONYLAMINO)-5-(4-FLUORO-PHENYL)-THIOPHENE-2-CARBOXYLIC ACID | +++ |
| 108 | 5-STYRYL-3-(TOLUENE-2-SULFONYLAMINO)-THIOPHENE-2-CARBOXYLIC ACID | +++ |
| 109 | 3-(2,4-DIFLUORO-BENZENESULFONYLAMINO)-5-(4-NITRO-PHENYL)-THIOPHENE-2-CARBOXYLIC ACID | +++ |
| 110 | 3-(2,4-DIFLUORO-BENZENESULFONYLAMINO)-5-(4-FLUORO-PHENYL)-THIOPHENE-2-CARBOXYLIC ACID | +++ |

-continued

| | MOLSTRUCTURE | COMPOUND NAME | IC50 |
|---|---|---|---|
| 111 | 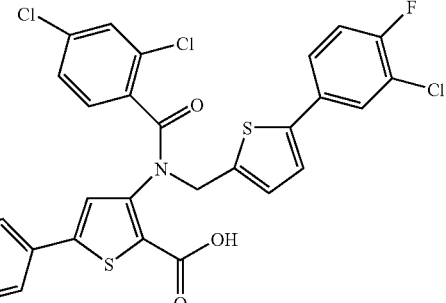 | 3-[[5-(3-CHLORO-4-FLUORO-PHENYL)-THIOPHEN-2-YLMETHYL]-(2,4-DICHLORO-BENZOYL)-AMINO]-5-PHENYL-THIOPHENE-2-CARBOXYLIC ACID | +++ |
| 112 | 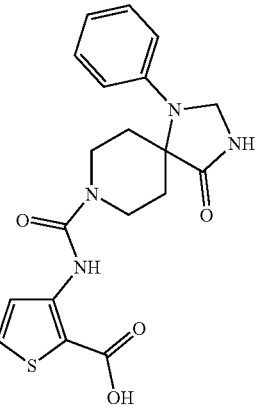 | 3-[(4-OXO-1-PHENYL-1,3,8-TRIAZA-SPIRO[4.5]DECANE-8-CARBONYL)-AMINO]-5-PHENYL-THIOPHENE-2-CARBOXYLIC ACID | +++ |
| 113 | 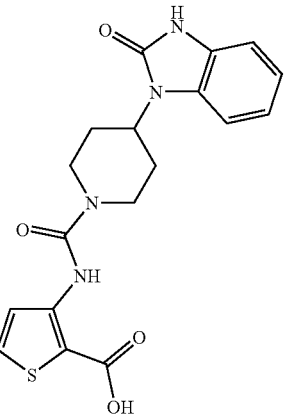 | 3-{[4-(2-OXO-2,3-DIHYDRO-BENZOIMIDAZOL-1-YL)-PIPERIDINE-1-CARBONYL]-AMINO}-5-PHENYL-THIOPHENE-2-CARBOXYLIC ACID | + |
| 114 | 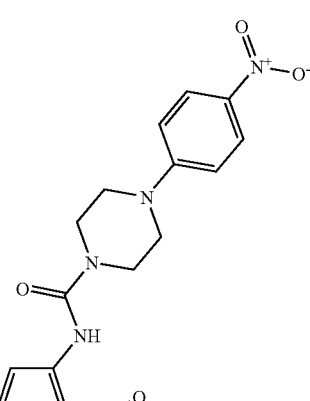 | 3-{[4-(4-NITRO-PHENYL)-PIPERAZINE-1-CARBONYL]-AMINO}-5-PHENYL-THIOPHENE-2-CARBOXYLIC ACID | +++ |

| MOLSTRUCTURE | COMPOUND NAME | IC50 |
|---|---|---|
| 115 | 5-(2-CARBOXY-PHENYL)-3-(TOLUENE-2-SULFONYLAMINO)-THIOPHENE-2-CARBOXYLIC ACID | ++ |
| 116 | 5-(4-CHLORO-PHENYL)-3-(PYRIDINE-2-SULFONYLAMINO)-THIOPHENE-2-CARBOXYLIC ACID | ++ |
| 117 | 5-(3-CYANO-PHENYL)-3-(TOLUENE-2-SULFONYLAMINO)-THIOPHENE-2-CARBOXYLIC ACID | +++ |
| 118 | 3-(2,5-DIMETHYL-BENZENESULFONYLAMINO)-5-P-TOLYL-THIOPHENE-2-CARBOXYLIC ACID | +++ |
| 119 | 3-(2,4-DIFLUORO-BENZENESULFONYLAMINO)-5-P-TOLYL-THIOPHENE-2-CARBOXYLIC ACID | +++ |

| MOLSTRUCTURE | COMPOUND NAME | IC50 |
|---|---|---|
| 120 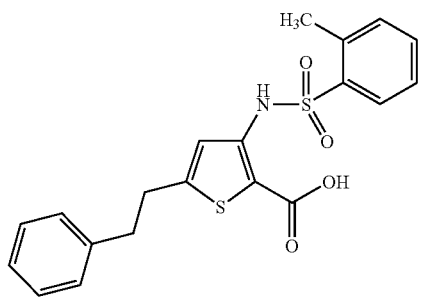 | 5-PHENETHYL-3-(TOLUENE-2-SULFONYLAMINO)-THIOPHENE-2-CARBOXYLIC ACID | ++ |
| 121 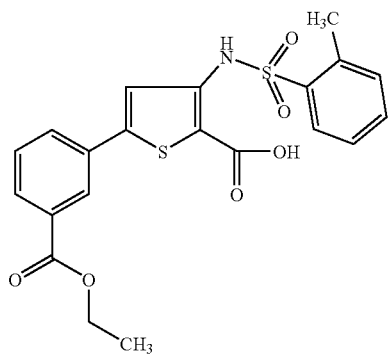 | 5-(3-ETHOXYCARBONYL-PHENYL)-3-(TOLUENE-2-SULFONYLAMINO)-THIOPHENE-2-CARBOXYLIC ACID | ++ |
| 122 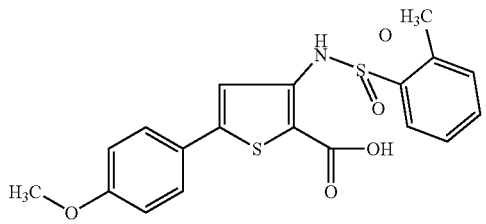 | 5-(4-METHOXY-PHENYL)-3-(TOLUENE-2-SULFONYLAMINO)-THIOPHENE-2-CARBOXYLIC ACID | +++ |
| 123 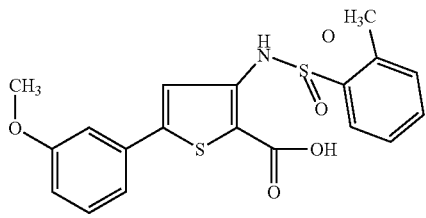 | 5-(3-METHOXY-PHENYL)-3-(TOLUENE-2-SULFONYLAMINO)-THIOPHENE-2-CARBOXYLIC ACID | +++ |
| 124 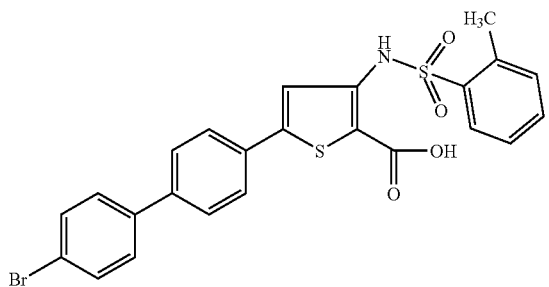 | 5-(4'-BROMO-BIPHENYL-4-YL)-3-(TOLUENE-2-SULFONYLAMINO)-THIOPHENE-2-CARBOXYLIC ACID | +++ |

| MOLSTRUCTURE | COMPOUND NAME | IC50 |
|---|---|---|
| 125 | 5-(4-HYDROXYMETHYL-PHENYL)-3-(TOLUENE-2-SULFONYLAMINO)-THIOPHENE-2-CARBOXYLIC ACID | +++ |
| 126 | 5-FURAN-3-YL-3-(TOLUENE-2-SULFONYLAMINO)-THIOPHENE-2-CARBOXYLIC ACID | +++ |
| 127 | 5-BENZOFURAN-2-YL-3-(TOLUENE-2-SULFONYLAMINO)-THIOPHENE-2-CARBOXYLIC ACID | +++ |
| 128 | 5-PYRIDIN-2-YL-3-(TOLUENE-2-SULFONYLAMINO)-THIOPHENE-2-CARBOXYLIC ACID | +++ |
| 129 | 5-(4-NITRO-PHENYL)-3-(PYRIDINE-2-SULFONYLAMINO)-THIOPHENE-2-CARBOXYLIC ACID | ++ |

| MOLSTRUCTURE | COMPOUND NAME | IC50 |
|---|---|---|
| 130 | 3-[(BENZOFURAN-2-CARBONYL)-METHYL-AMINO]-5-PHENYL-THIOPHENE-2-CARBOXYLIC ACID | + |
| 131 | 3-[(2,4-DIMETHYL-BENZOYL)-METHYL-AMINO]-5-PHENYL-THIOPHENE-2-CARBOXYLIC ACID | +++ |
| 132 | 3-[[5-(2-CYANO-PHENYL)-THIOPHEN-2-YLMETHYL]-(2,4-DICHLORO-BENZOYL)-AMINO]-5-PHENYL-THIOPHENE-2-CARBOXYLIC ACID | +++ |
| 133 | 5-(4-FLUORO-PHENYL)-3-(PYRIDINE-2-SULFONYLAMINO)-THIOPHENE-2-CARBOXYLIC ACID | +++ |
| 134 | 5-[2-(4-CHLORO-PHENYL)-VINYL]-3-(TOLUENE-2-SULFONYLAMINO)-THIOPHENE-2-CARBOXYLIC ACID | ++ |

-continued

| | MOLSTRUCTURE | COMPOUND NAME | IC50 |
|---|---|---|---|
| 135 | 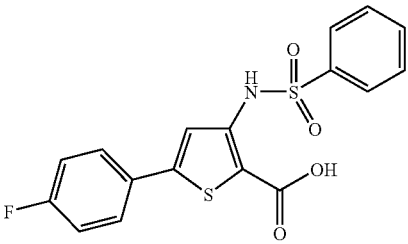 | 3-BENZENESULFONYLAMINO-5-(4-FLUORO-PHENYL)-THIOPHENE-2-CARBOXYLIC ACID | +++ |
| 136 | 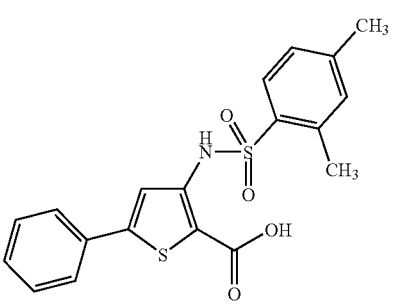 | 3-(2,4-DIMETHYL-BENZENESULFONYLAMINO)-5-PHENYL-THIOPHENE-2-CARBOXYLIC ACID | +++ |
| 137 | 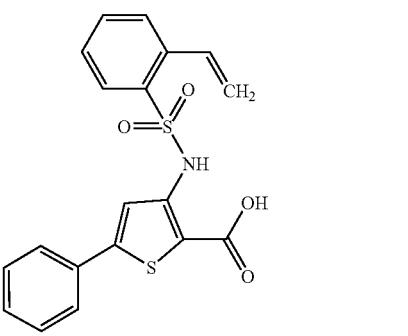 | 5-PHENYL-3-(2-VINYL-BENZENESULFONYLAMINO)-THIOPHENE-2-CARBOXYLIC ACID | ++ |
| 138 | 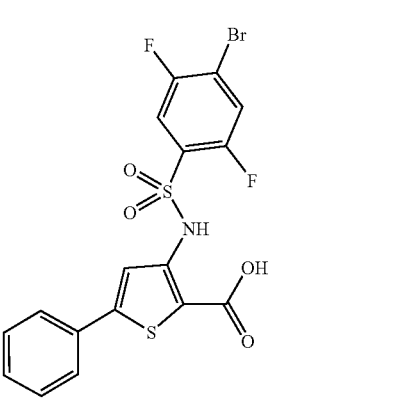 | 3-(4-BROMO-2,5-DIFLUORO-BENZENESULFONYLAMINO)-5-PHENYL-THIOPHENE-2-CARBOXYLIC ACID | +++ |
| 139 | 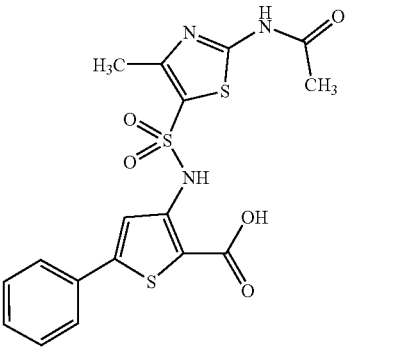 | 3-(2-ACETYLAMINO-4-METHYL-THIAZOLE-5-SULFONYLAMINO)-5-PHENYL-THIOPHENE-2-CARBOXYLIC ACID | ++ |

-continued
| MOLSTRUCTURE | COMPOUND NAME | IC50 |
| --- | --- | --- |
| 140 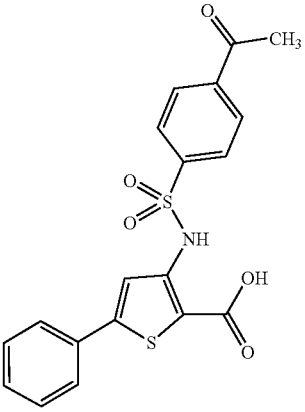 | 3-(4-ACETYL-BENZENESULFONYLAMINO)-5-PHENYL-THIOPHENE-2-CARBOXYLIC ACID | ++ |
| 141 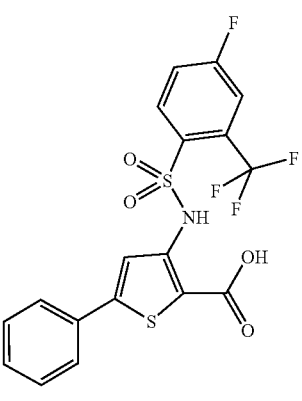 | 3-(4-FLUORO-2-TRIFLUOROMETHYL-BENZENESULFONYLAMINO)-5-PHENYL-THIOPHENE-2-CARBOXYLIC ACID | ++ |
| 142 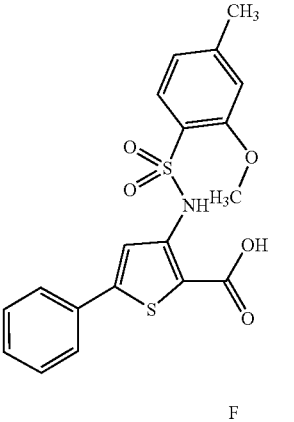 | 3-(2-METHOXY-4-METHYL-BENZENESULFONYLAMINO)-5-PHENYL-THIOPHENE-2-CARBOXYLIC ACID | ++ |
| 143 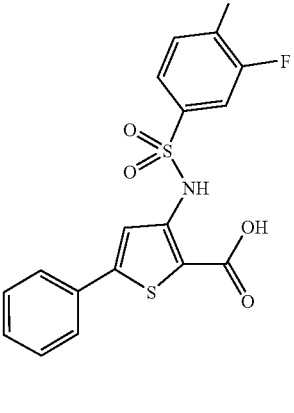 | 3-(3,4-DIFLUORO-BENZENESULFONYLAMINO)-5-PHENYL-THIOPHENE-2-CARBOXYLIC ACID | +++ |

-continued

| MOLSTRUCTURE | COMPOUND NAME | IC50 |
|---|---|---|
| 144 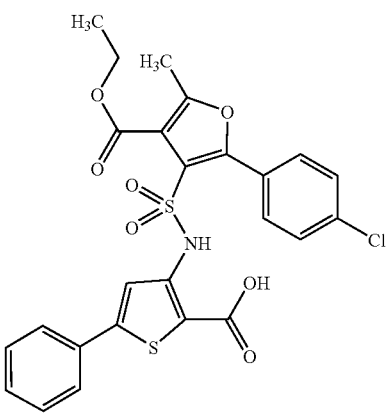 | 4-(2-CARBOXY-5-PHENYL-THIOPHEN-3-YLSULFAMOYL)-5-(4-CHLORO-PHENYL)-2-METHYL-FURAN-3-CARBOXYLIC ACID ETHYL ESTER | ++ |
| 145 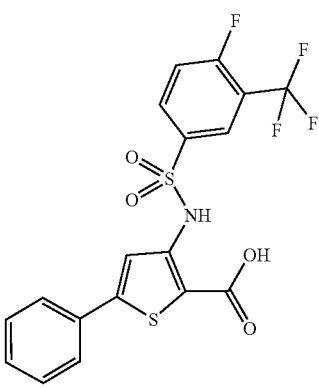 | 3-(4-FLUORO-3-TRIFLUOROMETHYL-BENZENESULFONYLAMINO)-5-PHENYL-THIOPHENE-2-CARBOXYLIC ACID | ++ |
| 146 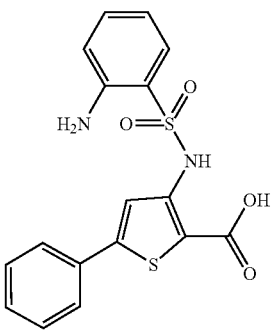 | 3-(2-AMINO-BENZENESULFONYLAMINO)-5-PHENYL-THIOPHENE-2-CARBOXYLIC ACID | +++ |
| 147 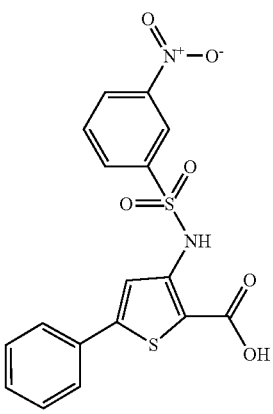 | 3-(3-NITRO-BENZENESULFONYLAMINO)-5-PHENYL-THIOPHENE-2-CARBOXYLIC ACID | +++ |

| MOLSTRUCTURE | COMPOUND NAME | IC50 |
|---|---|---|
| 148 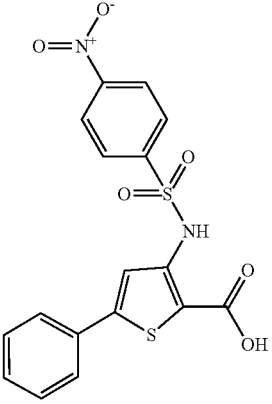 | 3-(4-NITRO-BENZENESULFONYLAMINO)-5-PHENYL-THIOPHENE-2-CARBOXYLIC ACID | ++ |
| 149 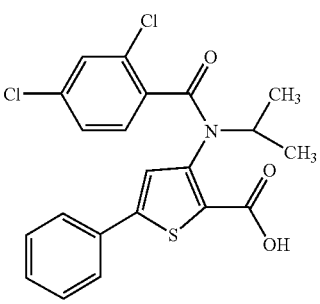 | 3-[(2,4-DICHLORO-BENZOYL)-ISOPROPYL-AMINO]-5-PHENYL-THIOPHENE-2-CARBOXYLIC ACID | +++ |
| 150 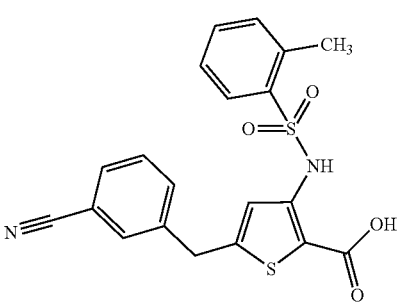 | 5-(3-CYANO-BENZYL)-3-(TOLUENE-2-SULFONYLAMINO)-THIOPHENE-2-CARBOXYLIC ACID | + |
| 151 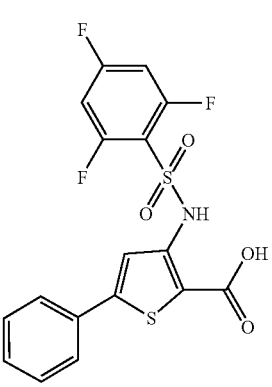 | 5-PHENYL-3-(2,4,6-TRIFLUORO-BENZENESULFONYLAMINO)-THIOPHENE-2-CARBOXYLIC ACID | +++ |

| MOLSTRUCTURE | COMPOUND NAME | IC50 |
|---|---|---|
| 152 | 3-(4-METHOXY-2-NITRO-BENZENESULFONYLAMINO)-5-PHENYL-THIOPHENE-2-CARBOXYLIC ACID | ++ |
| 153 | 5-PHENYL-3-(2,3,4-TRICHLORO-BENZENESULFONYLAMINO)-THIOPHENE-2-CARBOXYLIC ACID | +++ |
| 154 | 5-(2-CARBOXY-5-PHENYL-THIOPHEN-3-YLSULFAMOYL)-2-METHYL-FURAN-3-CARBOXYLIC ACID METHYL ESTER | +++ |
| 155 | 4-(2-CARBOXY-5-PHENYL-THIOPHEN-3-YLSULFAMOYL)-2-METHYL-1,5-DIPHENYL-1H-PYRROLE-3-CARBOXYLIC ACID ETHYL ESTER | +++ |

| MOLSTRUCTURE | COMPOUND NAME | IC50 |
|---|---|---|
| 156 | 5-PHENYL-3-{[4-(3-TRIFLUOROMETHYL-PHENYL)-PIPERAZINE-1-CARBONYL]-AMIN}-THIOPHENE-2-CARBOXYLIC ACID | ++ |
| 157 | 3-{[4-(4-FLUORO-PHENYL)-PIPERAZINE-1-CARBONYL]-AMINO}-5-PHENYL-THIOPHENE-2-CARBOXYLIC ACID | + |
| 158 | 3-{[4-(2,6-DIMETHYL-PHENYL)-PIPERAZINE-1-CARBONYL]-AMINO}-5-PHENYL-THIOPHENE-2-CARBOXYLIC ACID | + |
| 159 | 3-{[4-(2-CHLORO-PHENYL)-PIPERAZINE-1-CARBONYL]-AMINO}-5-PHENYL-THIOPHENE-2-CARBOXYLIC ACID | ++ |

| MOLSTRUCTURE | COMPOUND NAME | IC50 |
|---|---|---|
| 160 | 3-{[4-(3-CHLORO-PHENYL)-PIPERAZINE-1-CARBONYL]-AMINO}-5-PHENYL-THIOPHENE-2-CARBOXYLIC ACID | ++ |
| 161 | 4,4'-BIS-(TOLUENE-2-SULFONYLAMINO)-[2,2']BITHIOPHENYL-5,5'-DICARBOXYLIC ACID | +++ |
| 162 | 3-[ALLYL-(4-METHYL-BENZOYL)-AMINO]-5-PHENYL-THIOPHENE-2-CARBOXYLIC ACID | +++ |
| 163 | 5-(1-DIMETHYLSULFAMOYL-1#H!-PYRAZOL-4-YL)-3-(TOLUENE-2-SULFONYLAMINO)-THIOPHENE-2-CARBOXYLIC ACID | ++ |

-continued

| | MOLSTRUCTURE | COMPOUND NAME | IC50 |
|---|---|---|---|
| 164 | | 5-(3-AMINO-PHENYL)-3-(TOLUENE-2-SULFONYLAMINO)-THIOPHENE-2-CARBOXYLIC ACID | ++ |
| 165 | | 5-(4-AMINO-PHENYL)-3-(TOLUENE-2-SULFONYLAMINO)-THIOPHENE-2-CARBOXYLIC ACID | ++ |
| 166 | | 5-(4-ACETYL-PHENYL)-3-(TOLUENE-2-SULFONYLAMINO)-THIOPHENE-2-CARBOXYLIC ACID | +++ |
| 167 | | 4-(2-CARBOXY-5-PHENYL-THIOPHEN-3-YLSULFAMOYL)-2,5-DIMETHYL-1H-PYRROLE-3-CARBOXYLIC ACID ETHYL ESTER | ++ |
| 168 | | 4-(2-CARBOXY-5-PHENYL-THIOPHEN-3-YLSULFAMOYL)-5-(4-CHLORO-PHENYL)-3-METHYL-1-PHENYL-1H-PYRROLE-2-CARBOXYLIC ACID ETHYL ESTER | ++ |

| MOLSTRUCTURE | COMPOUND NAME | IC50 |
|---|---|---|
| 169 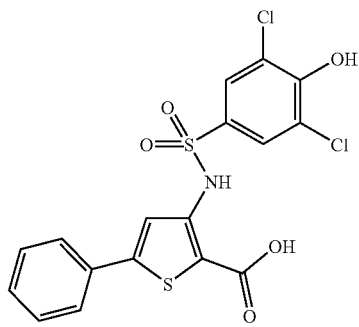 | 3-(3,5-DICHLORO-4-HYDROXY-BENZENESULFONYLAMINO)-5-PHENYL-THIOPHENE-2-CARBOXYLIC ACID | ++ |
| 170 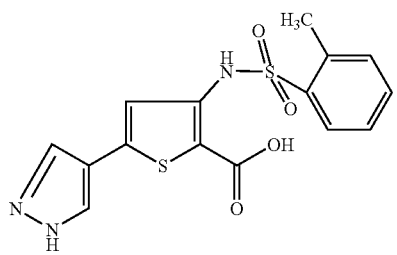 | 5-(1#H!-PYRAZOL-4-YL)-3-(TOLUENE-2-SULFONYLAMINO)-THIOPHENE-2-CARBOXYLIC ACID | +++ |
| 171 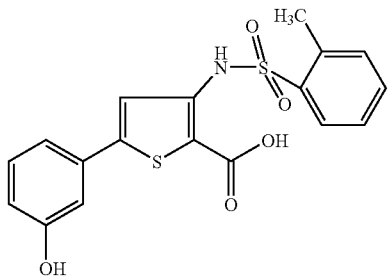 | 5-(3-HYDROXY-PHENYL)-3-(TOLUENE-2-SULFONYLAMINO)-THIOPHENE-2-CARBOXYLIC ACID | +++ |
| 172 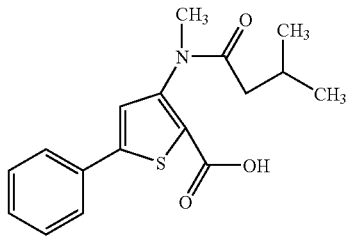 | 3-[METHYL-(3-METHYL-BUTYRYL)-AMINO]-5-PHENYL-THIOPHENE-2-CARBOXYLIC ACID | +++ |
| 173 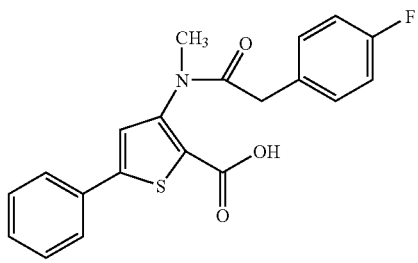 | 3-{[2-(4-FLUORO-PHENYL)-ACETYL]-METHYL-AMINO}-5-PHENYL-THIOPHENE-2-CARBOXYLIC ACID | +++ |

| MOLSTRUCTURE | COMPOUND NAME | IC50 |
|---|---|---|
| 174 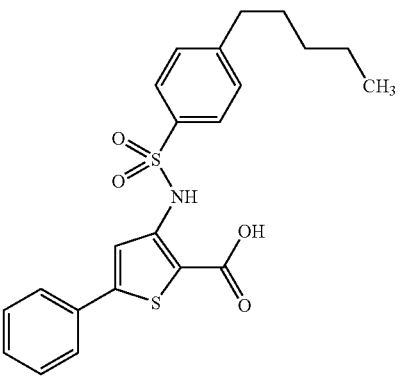 | 3-(4-PENTYL-BENZENESULFONYLAMINO)-5-PHENYL-THIOPHENE-2-CARBOXYLIC ACID | ++ |
| 175 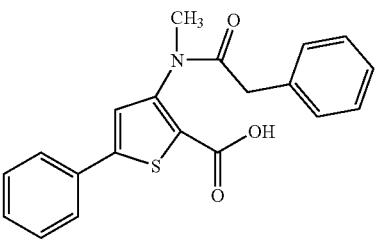 | 3-(METHYL-PHENYLACETYL-AMINO)-5-PHENYL-THIOPHENE-2-CARBOXYLIC ACID | +++ |
| 176 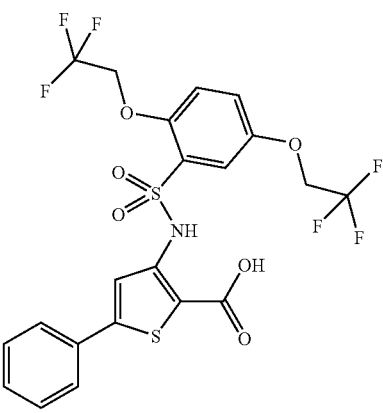 | 3-[2,5-BIS-(2,2,2-TRIFLUORO-ETHOXY)-BENZENESULFONYLAMINO]-5-PHENYL-THIOPHENE-2-CARBOXYLIC ACID | ++ |
| 177 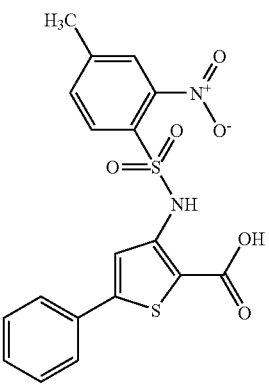 | 3-(4-METHYL-2-NITRO-BENZENESULFONYLAMINO)-5-PHENYL-THIOPHENE-2-CARBOXYLIC ACID | ++ |

| MOLSTRUCTURE | COMPOUND NAME | IC50 |
|---|---|---|
| 178 | 5-THIAZOL-2-YL-3-(TOLUENE-2-SULFONYLAMINO)-THIOPHENE-2-CARBOXYLIC ACID | +++ |
| 179 | 5-PHENYL-3-[3-(3-PHENYL-PROPYL)-UREIDO]-THIOPHENE-2-CARBOXYLIC ACID | ++ |
| 180 | 3-[(3,4-DIHYDRO-1H-ISOQUINOLINE-2-CARBONYL)-AMINO]-5-PHENYL-THIOPHENE-2-CARBOXYLIC ACID | ++ |
| 181 | 3-{[4-(4-METHOXY-PHENYL)-PIPERAZINE-1-CARBONYL]-AMINO}-5-PHENYL-THIOPHENE-2-CARBOXYLIC ACID | ++ |

| MOLSTRUCTURE | COMPOUND NAME | IC50 |
|---|---|---|
| 182 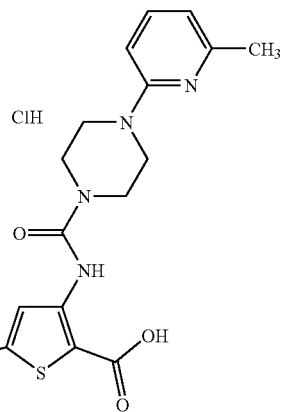 | 3-{[4-(6-METHYL-PYRIDIN-2-YL)-PIPERAZINE-1-CARBONYL]-AMINO}-5-PHENYL-THIOPHENE-2-CARBOXYLIC ACID HYDROCHLORIDE | ++ |
| 183 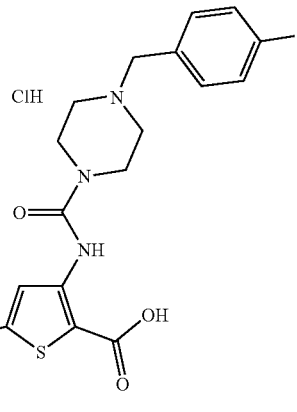 | 3-{[4-(4-CHLORO-BENZYL)-PIPERAZINE-1-CARBONYL]-AMINO}-5-PHENYL-THIOPHENE-2-CARBOXYLIC ACID HYDROCHLORIDE | ++ |
| 184 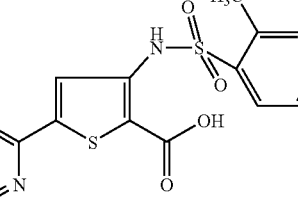 | 5-(5-METHYL-PYRIDIN-2-YL)-3-(TOLUENE-2-SULFONYLAMINO)-THIOPHENE-2-CARBOXYLIC ACID | +++ |
| 185 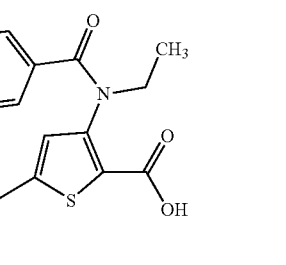 | 3-[ETHYL-(4-METHYL-BENZOYL)-AMINO]-5-PHENYL-THIOPHENE-2-CARBOXYLIC ACID | +++ |
| 186 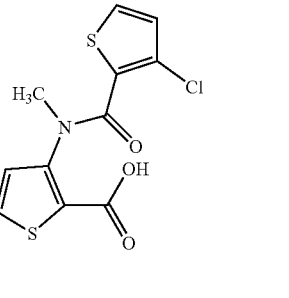 | 3-[(3-CHLORO-THIOPHENE-2-CARBONYL)-METHYL-AMINO]-5-PHENYL-THIOPHENE-2-CARBOXYLIC ACID | ++ |

| MOLSTRUCTURE | COMPOUND NAME | IC50 |
|---|---|---|
| 187 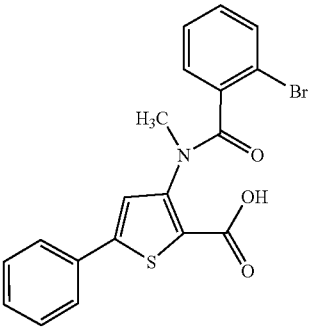 | 3-[(2-BROMO-BENZOYL)-METHYL-AMINO]-5-PHENYL-THIOPHENE-2-CARBOXYLIC ACID | ++ |
| 188 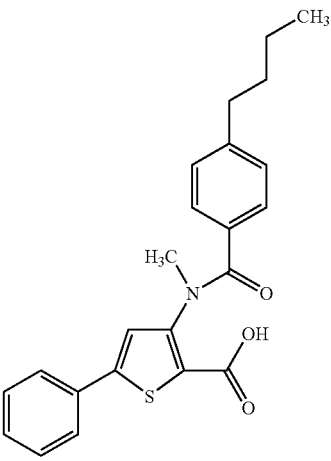 | 3-[(4-BUTYL-BENZOYL)-METHYL-AMINO]-5-PHENYL-THIOPHENE-2-CARBOXYLIC ACID | + |
| 189 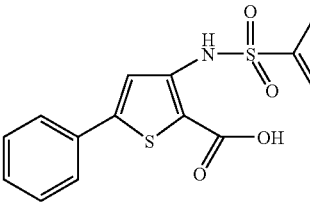 | 3-(2-CHLOROMETHYL-BENZENESULFONYLAMINO)-5-PHENYL-THIOPHENE-2-CARBOXYLIC ACID | ++ |
| 190 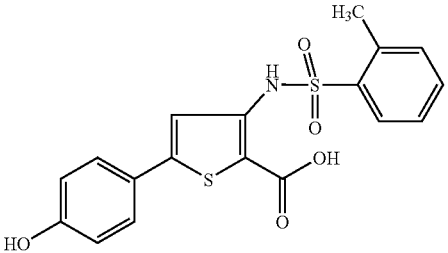 | 5-(4-HYDROXY-PHENYL)-3-(TOLUENE-2-SULFONYLAMINO)-THIOPHENE-2-CARBOXYLIC ACID | +++ |
| 191 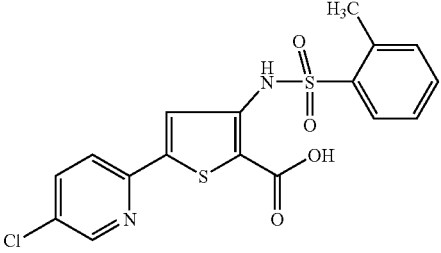 | 5-(5-CHLORO-PYRIDIN-2-YL)-3-(TOLUENE-2-SULFONYLAMINO)-THIOPHENE-2-CARBOXYLIC ACID | +++ |

| MOLSTRUCTURE | COMPOUND NAME | IC50 |
|---|---|---|
| 192 | 5-(4-CHLORO-PHENYL)-3-[METHYL-(4-METHYL-BENZOYL)-AMINO]-THIOPHENE-2-CARBOXYLIC ACID | ++ |
| 193 | 5-(4-CYANO-PHENYL)-3-[METHYL-(4-METHYL-BENZOYL)-AMINO]-THIOPHENE-2-CARBOXYLIC ACID | ++ |
| 194 | 3-[METHYL-(4-METHYL-BENZOYL)-AMINO]-5-(4-NITRO-PHENYL)-THIOPHENE-2-CARBOXYLIC ACID | ++ |
| 195 | 5-(4-HYDROXYMETHYL-PHENYL)-3-[METHYL-(4-METHYL-BENZOYL)-AMINO]-THIOPHENE-2-CARBOXYLIC ACID | ++ |
| 196 | 3-[METHYL-(4-METHYL-BENZOYL)-AMINO]-5-(3-NITRO-PHENYL)-THIOPHENE-2-CARBOXYLIC ACID | +++ |
| 197 | 5-(4-FLUORO-PHENYL)-3-[METHYL-(4-METHYL-BENZOYL)-AMINO]-THIOPHENE-2-CARBOXYLIC ACID | +++ |

-continued

| | MOLSTRUCTURE | COMPOUND NAME | IC50 |
|---|---|---|---|
| 198 | 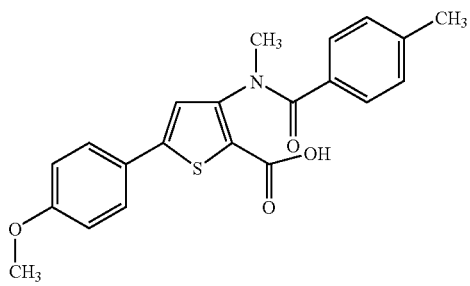 | 5-(4-METHOXY-PHENYL)-3-[METHYL-(4-METHYL-BENZOYL)-AMINO]-THIOPHENE-2-CARBOXYLIC ACID | ++ |
| 199 | 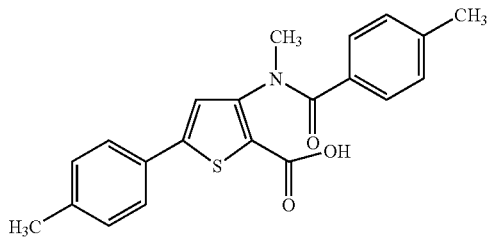 | 3-[METHYL-(4-METHYL-BENZOYL)-AMINO]-5-#P!-TOLYL-THIOPHENE-2-CARBOXYLIC ACID | ++ |
| 200 | 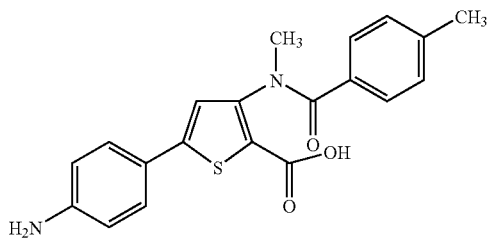 | 5-(4-AMINO-PHENYL)-3-[METHYL-(4-METHYL-BENZOYL)-AMINO]-THIOPHENE-2-CARBOXYLIC ACID | ++ |
| 201 | 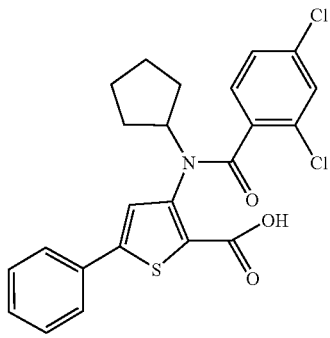 | 3-[CYCLOPENTYL-(2,4-DICHLORO-BENZOYL)-AMINO]-5-PHENYL-THIOPHENE-2-CARBOXYLIC ACID | +++ |
| 202 | 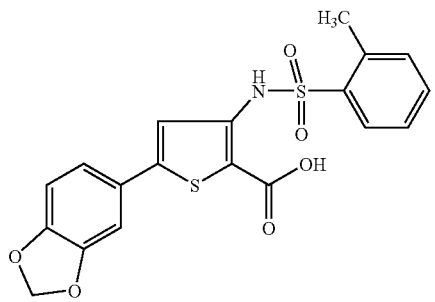 | 5-BENZO[1,3]DIOXOL-5-YL-3-(TOLUENE-2-SULFONYLAMINO)-THIOPHENE-2-CARBOXYLIC ACID | +++ |

| MOLSTRUCTURE | COMPOUND NAME | IC50 |
|---|---|---|
| 203 | 3-[(2-HYDROXY-ETHYL)-(4-METHYL-BENZOYL)-AMINO]-5-PHENYL-THIOPHENE-2-CARBOXYLIC ACID | +++ |
| 204 | 3-[(2,4-DICHLORO-BENZOYL)-ISOBUTYL-AMINO]-5-PHENYL-THIOPHENE-2-CARBOXYLIC ACID | +++ |
| 205 | 3-[(2-METHOXY-4-METHYL-BENZOYL)-METHYL-AMINO]-5-PHENYL-THIOPHENE-2-CARBOXYLIC ACID | ++ |
| 206 | 5-(3-CYANO-PHENYL)-3-[METHYL-(4-METHYL-BENZOYL)-AMINO]-THIOPHENE-2-CARBOXYLIC ACID | +++ |
| 207 | 5-(2-CHLORO-PHENYL)-3-[METHYL-(4-METHYL-BENZOYL)-AMINO]-THIOPHENE-2-CARBOXYLIC ACID | ++ |

| MOLSTRUCTURE | COMPOUND NAME | IC50 |
|---|---|---|
| 208 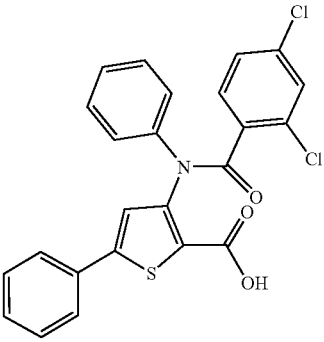 | 3-[(2,4-DICHLORO-BENZOYL)-PHENYL-AMINO]-5-PHENYL-THIOPHENE-2-CARBOXYLIC ACID | +++ |
| 209 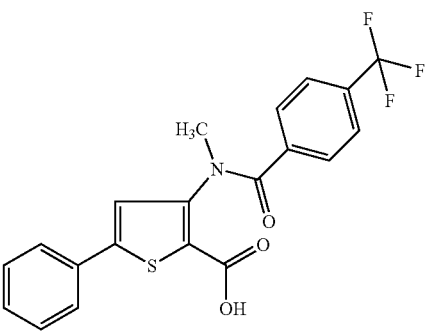 | 3-[4-(TRIFLUOROMETHYL-BENZOYL)METHYLAMINE]-5-PHENYL-THIOPHENE-2-CARBOXYLIC ACID | ++ |
| 210 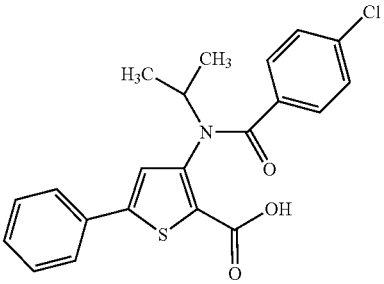 | 3-[(4-CHLORO-BENZOYL)-ISOPROPYL-AMINO]-5-PHENYL-THIOPHENE-2-CARBOXYLIC ACID | +++ |
| 211 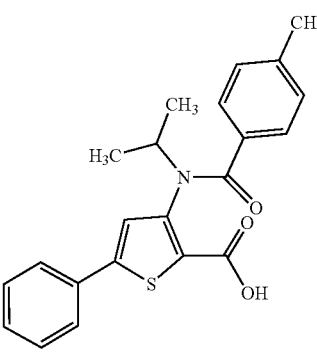 | 3-[ISOPROPYL-(4-METHYL-BENZOYL)-AMINO]-5-PHENYL-THIOPHENE-2-CARBOXYLIC ACID | +++ |
| 212 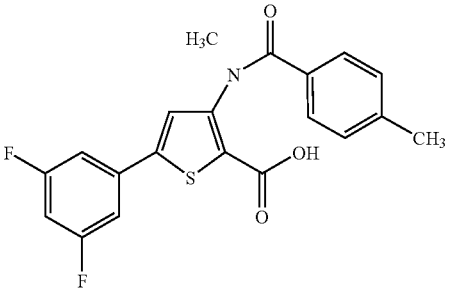 | 5-(3,5-DIFLUORO-PHENYL)-3-[METHYL-(4-METHYL-BENZOYL)-AMINO]-THIOPHENE-2-CARBOXYLIC ACID | +++ |

| MOLSTRUCTURE | COMPOUND NAME | IC50 |
|---|---|---|
| 213 | 5-(3-FLUORO-PHENYL)-3-[METHYL-(4-METHYL-BENZOYL)-AMINO]-THIOPHENE-2-CARBOXYLIC ACID | +++ |
| 214 | 5-(2,4-DIFLUORO-PHENYL)-3-[METHYL-(4-METHYL-BENZOYL)-AMINO]-THIOPHENE-2-CARBOXYLIC ACID | ++ |
| 215 | 5-(4-HYDROXY-PHENYL)-3-[METHYL-(4-METHYL-BENZOYL)-AMINO]-THIOPHENE-2-CARBOXYLIC ACID | +++ |
| 216 | 3-[METHYL-(4-METHYL-BENZOYL)-AMINO]-5-(4-TRIFLUOROMETHOXY-PHENYL)-THIOPHENE-2-CARBOXYLIC ACID | ++ |
| 217 | 5-(2-HYDROXY-PHENYL)-3-(TOLUENE-2-SULFONYLAMINO)-THIOPHENE-2-CARBOXYLIC ACID | ++ |
| 218 | 3-[(2-CHLORO-BENZOYL)-ISOPROPYL-AMINO]-5-PHENYL-THIOPHENE-2-CARBOXYLIC ACID | ++ |

| MOLSTRUCTURE | COMPOUND NAME | IC50 |
|---|---|---|
| 219 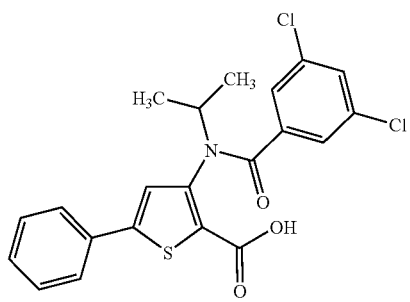 | 3-[(3,5-DICHLORO-BENZOYL)-ISOPROPYL-AMINO]-5-PHENYL-THIOPHENE-2-CARBOXYLIC ACID | ++ |
| 220 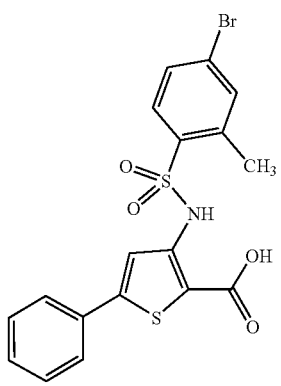 | 3-(4-BROMO-2-METHYL-BENZENESULFONYLAMINO)-5-PHENYL-THIOPHENE-2-CARBOXYLIC ACID | +++ |
| 221 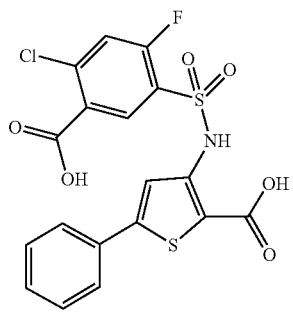 | 3-(5-CARBOXY-4-CHLORO-2-FLUORO-BENZENESULFONYLAMINO)-5-PHENYL-THIOPHENE-2-CARBOXYLIC ACID | + |
| 222 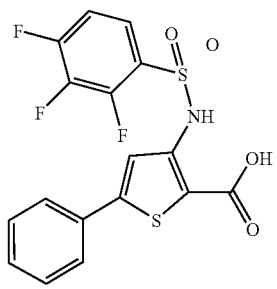 | 5-PHENYL-3-(2,3,4-TRIFLUORO-BENZENESULFONYLAMINO)-THIOPHENE-2-CARBOXYLIC ACID | ++ |

| MOLSTRUCTURE | COMPOUND NAME | IC50 |
|---|---|---|
| 223 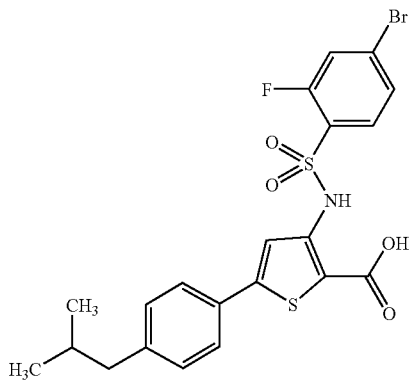 | 3-(4-BROMO-2-FLUORO-BENZENESULFONYLAMINO)-5-(4-ISOBUTYL-PHENYL)-THIOPHENE-2-CARBOXYLIC ACID | ++ |
| 224 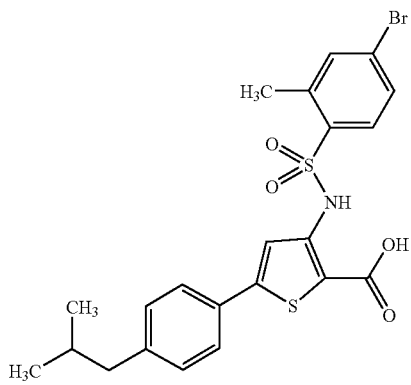 | 3-(4-BROMO-2-METHYL-BENZENESULFONYLAMINO)-5-(4-ISOBUTYL-PHENYL)-THIOPHENE-2-CARBOXYLIC ACID | + |
| 225 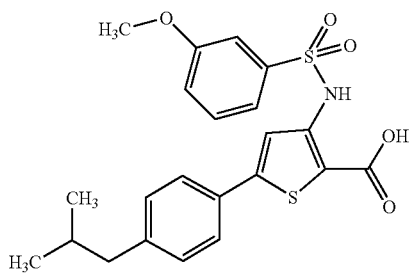 | 5-(4-ISOBUTYL-PHENYL)-3-(3-METHOXY-BENZENESULFONYLAMINO)-THIOPHENE-2-CARBOXYLIC ACID | + |
| 226 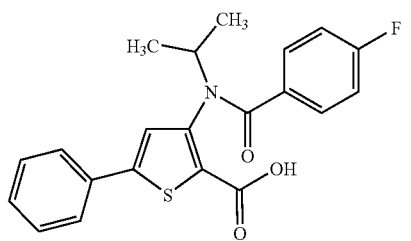 | 3-[(4-FLUORO-BENZOYL)-ISOPROPYL-AMINO]-5-PHENYL-THIOPHENE-2-CARBOXYLIC ACID | ++ |

| MOLSTRUCTURE | COMPOUND NAME | IC50 |
|---|---|---|
| 227 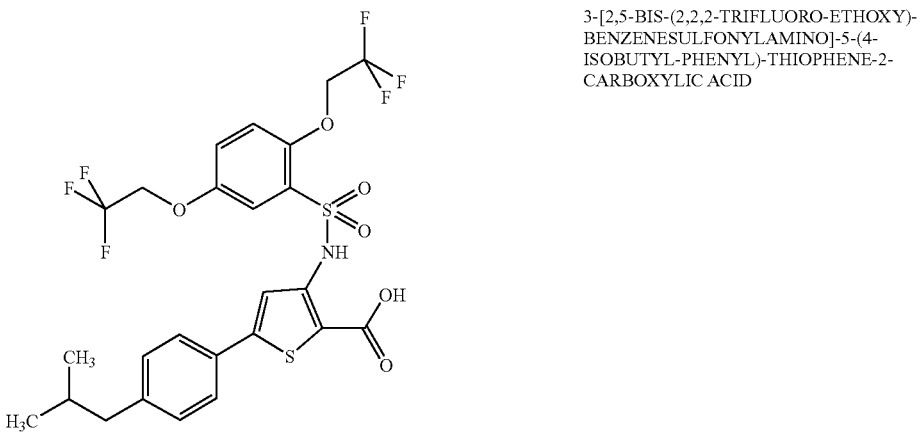 | 3-[2,5-BIS-(2,2,2-TRIFLUORO-ETHOXY)-BENZENESULFONYLAMINO]-5-(4-ISOBUTYL-PHENYL)-THIOPHENE-2-CARBOXYLIC ACID | + |
| 228 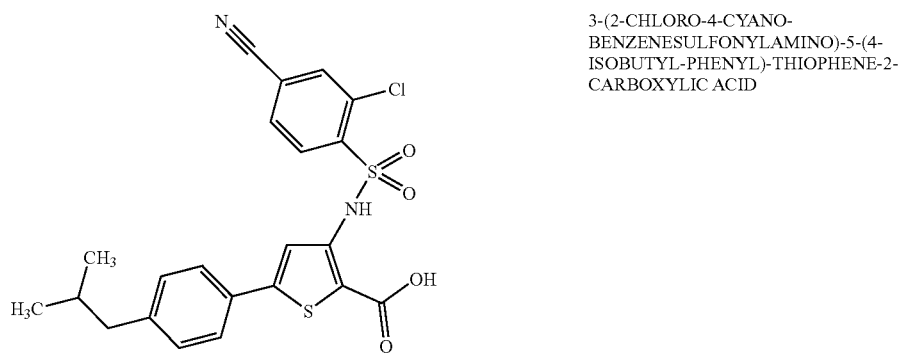 | 3-(2-CHLORO-4-CYANO-BENZENESULFONYLAMINO)-5-(4-ISOBUTYL-PHENYL)-THIOPHENE-2-CARBOXYLIC ACID | + |
| 229 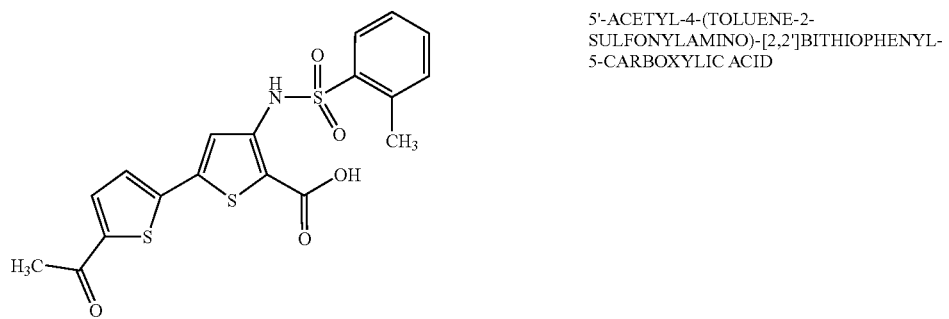 | 5'-ACETYL-4-(TOLUENE-2-SULFONYLAMINO)-[2,2']BITHIOPHENYL-5-CARBOXYLIC ACID | +++ |
| 230 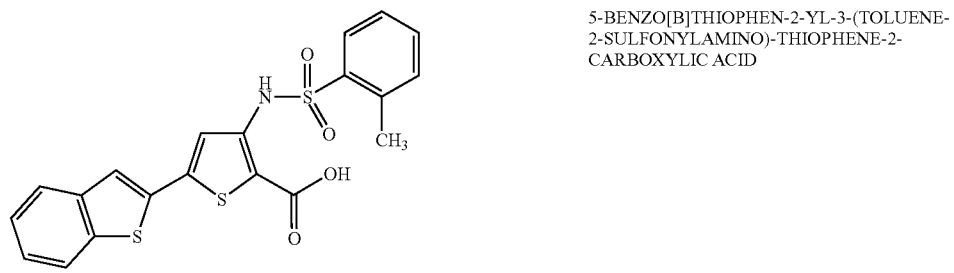 | 5-BENZO[B]THIOPHEN-2-YL-3-(TOLUENE-2-SULFONYLAMINO)-THIOPHENE-2-CARBOXYLIC ACID | +++ |

-continued

| MOLSTRUCTURE | COMPOUND NAME | IC50 |
|---|---|---|
| 231 | 5-(4-BUTYL-PHENYL)-3-(TOLUENE-2-SULFONYLAMINO)-THIOPHENE-2-CARBOXYLIC ACID | +++ |
| 232 | 5-(4-ETHYL-PHENYL)-3-(TOLUENE-2-SULFONYLAMINO)-THIOPHENE-2-CARBOXYLIC ACID | +++ |
| 233 | 3-[BENZYL-(2,4-DICHLORO-BENZOYL)-AMINO]-5-PHENYL-THIOPHENE-2-CARBOXYLIC ACID | +++ |
| 234 | 3-[(4-CHLORO-2-METHYL-BENZOYL)-ISOPROPYL-AMINO]-5-PHENYL-THIOPHENE-2-CARBOXYLIC ACID | +++ |
| 235 | 3-[(2,4-DIMETHYL-BENZENESULFONYL)-METHYL-AMINO]-5-PHENYL-THIOPHENE-2-CARBOXYLIC ACID | +++ |

| MOLSTRUCTURE | COMPOUND NAME | IC50 |
|---|---|---|
| 236 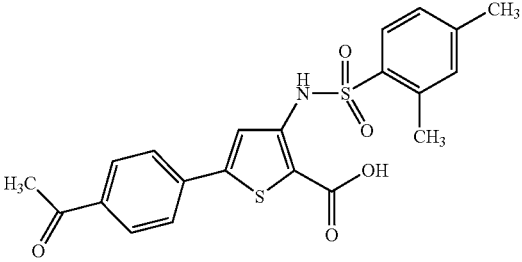 | 5-(4-ACETYL-PHENYL)-3-(2,4-DIMETHYL-BENZENESULFONYLAMINO)-THIOPHENE-2-CARBOXYLIC ACID | +++ |
| 237 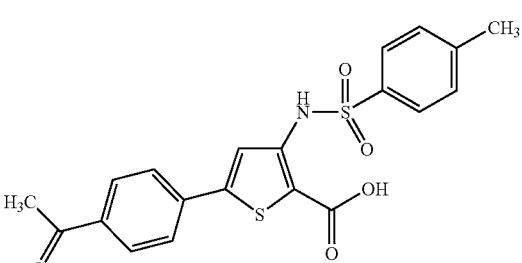 | 5-(4-ACETYL-PHENYL)-3-(TOLUENE-4-SULFONYLAMINO)-THIOPHENE-2-CARBOXYLIC ACID | +++ |
| 238 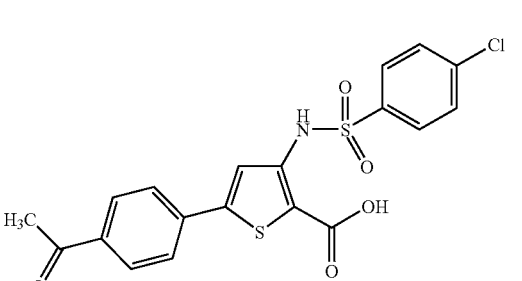 | 5-(4-ACETYL-PHENYL)-3-(4-CHLORO-BENZENESULFONYLAMINO)-THIOPHENE-2-CARBOXYLIC ACID | +++ |
| 239 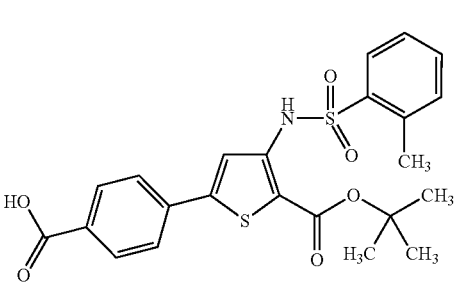 | 5-(4-CARBOXY-PHENYL)-3-(TOLUENE-2-SULFONYLAMINO-THIOPHENE-2-CARBOXYLIC ACID #TERT!-BUTYL ESTER | ++ |
| 240 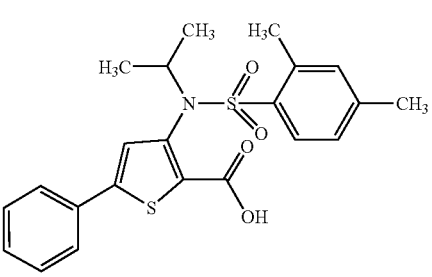 | 3-[(2,4-DIMETHYL-BENZENESULFONYL)-ISOPROPYL-AMINO]-5-PHENYL-THIOPHENE-2-CARBOXYLIC ACID | ++ |

| MOLSTRUCTURE | COMPOUND NAME | IC50 |
|---|---|---|
| 241 | 3-[ACETYL-(4-CHLORO-BENZYL)-AMINO]-5-PHENYL-THIOPHENE-2-CARBOXYLIC ACID | ++ |
| 242 | 3-ETHANESULFONYLAMINO-5-PHENYL-THIOPHENE-2-CARBOXYLIC ACID | ++ |
| 243 | 3-[ISOPROPYL-(4-TRIFLUOROMETHYL-BENZOYL)-AMINO]-5-PHENYL-THIOPHENE-2-CARBOXYLIC ACID | +++ |
| 244 | 3-[(2,4-DICHLORO-BENZOYL)-(3-METHYL-BUT-2-ENYL)-AMINO]-5-PHENYL-THIOPHENE-2-CARBOXYLIC ACID | +++ |
| 245 | 3-[(2,6-DICHLORO-PYRIDINE-3-CARBONYL)-METHYL-AMINO]-5-PHENYL-THIOPHENE-2-CARBOXYLIC ACID | ++ |

| MOLSTRUCTURE | COMPOUND NAME | IC50 |
|---|---|---|
| 246 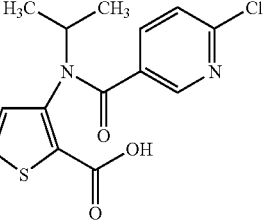 | 3-[(6-CHLORO-PYRIDINE-3-CARBONYL)-ISOPROPYL-AMINO]-5-PHENYL-THIOPHENE-2-CARBOXYLIC ACID | + |
| 247 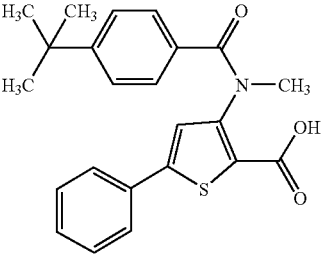 | 3-[(4-TERT-BUTYL-BENZOYL)-METHYL-AMINO]-5-PHENYL-THIOPHENE-2-CARBOXYLIC ACID | ++ |
| 248 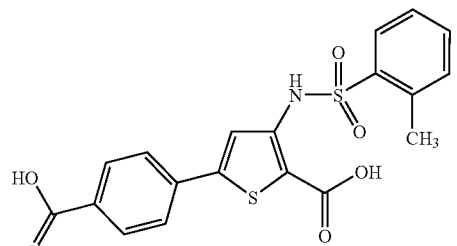 | 5-(4-CARBOXY-PHENYL)-3-(TOLUENE-2-SULFONYLAMINO)-THIOPHENE-2-CARBOXYLIC ACID | +++ |
| 249 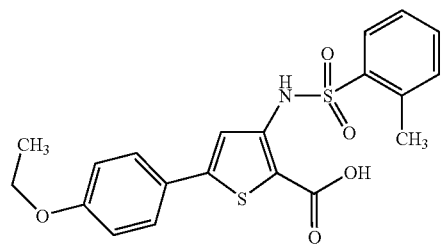 | 5-(4-ETHOXY-PHENYL)-3-(TOLUENE-2-SULFONYLAMINO)-THIOPHENE-2-CARBOXYLIC ACID | +++ |
| 250 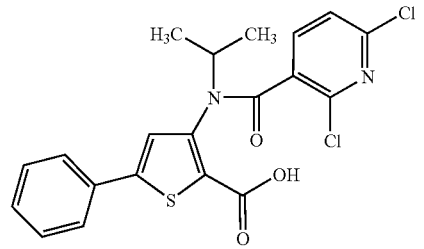 | 3-[(2,6-DICHLORO-PYRIDINE-3-CARBONYL)-ISOPROPYL-AMINO]-5-PHENYL-THIOPHENE-2-CARBOXYLIC ACID | ++ |
| 251 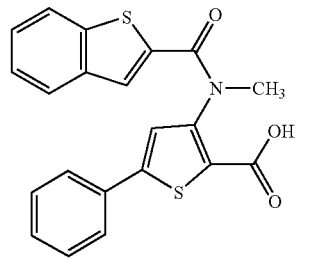 | 3-[(BENZO[B]THIOPHENE-2-CARBONYL)-METHYL-AMINO]-5-PHENYL-THIOPHENE-2-CARBOXYLIC ACID | ++ |

| MOLSTRUCTURE | COMPOUND NAME | IC50 |
|---|---|---|
| 252 | 3-[METHYL-(NAPHTHALENE-2-CARBONYL)-AMINO]-5-PHENYL-THIOPHENE-2-CARBOXYLIC ACID | ++ |
| 253 | 3-[(3,4-DICHLORO-BENZOYL)-METHYL-AMINO]-5-PHENYL-THIOPHENE-2-CARBOXYLIC ACID | ++ |
| 254 | 3-[(3,5-DICHLORO-BENZOYL)-METHYL-AMINO]-5-PHENYL-THIOPHENE-2-CARBOXYLIC ACID | ++ |
| 255 | 3-[(4-BROMO-3-METHYL-BENZOYL)-METHYL-AMINO]-5-PHENYL-THIOPHENE-2-CARBOXYLIC ACID | +++ |
| 256 | 3-[(3-CHLORO-BENZO[B]THIOPHENE-2-CARBONYL)-METHYL-AMINO]-5-PHENYL-THIOPHENE-2-CARBOXYLIC ACID | ++ |

| MOLSTRUCTURE | COMPOUND NAME | IC50 |
|---|---|---|
| 257 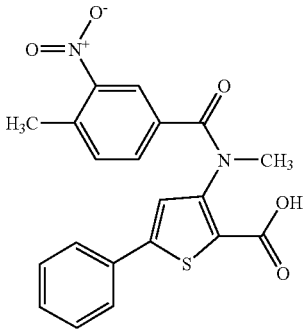 | 3-[METHYL-(4-METHYL-3-NITRO-BENZOYL)-AMINO]-5-PHENYL-THIOPHENE-2-CARBOXYLIC ACID | ++ |
| 258 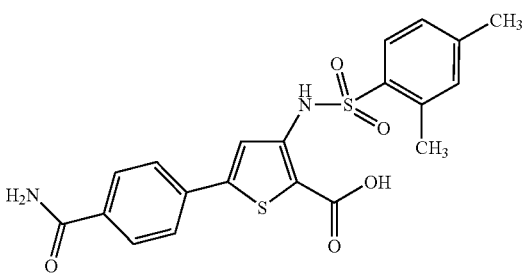 | 5-(4-CARBAMOYL-PHENYL)-3-(2,4-DIMETHYL-BENZENESULFONYLAMINO)-THIOPHENE-2-CARBOXYLIC ACID | ++ |
| 259 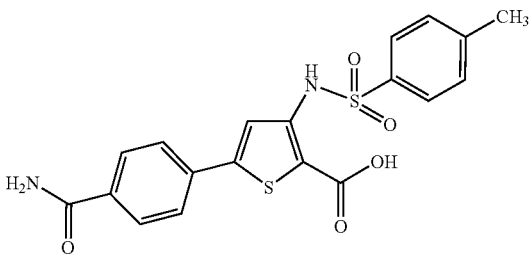 | 5-(4-CARBAMOYL-PHENYL)-3-(TOLUENE-4-SULFONYLAMINO)-THIOPHENE-2-CARBOXYLIC ACID | +++ |
| 260 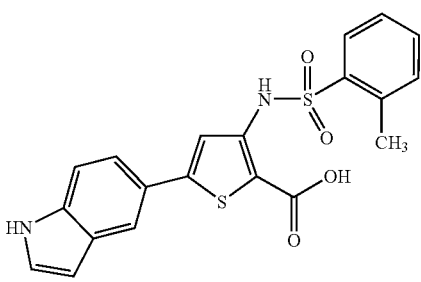 | 5-(1H-INDOL-5-YL)-3-(TOLUENE-2-SULFONYLAMINO)-THIOPHENE-2-CARBOXYLIC ACID | ++ |
| 261 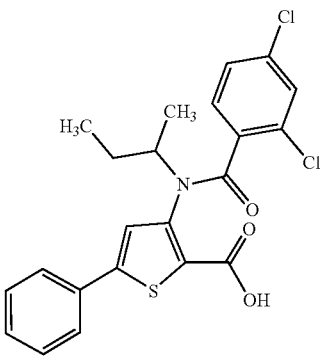 | 3-[#SEC!-BUTYL-(2,4-DICHLORO-BENZOYL)-AMINO]-5-PHENYL-THIOPHENE-2-CARBOXYLIC ACID | +++ |

-continued

| MOLSTRUCTURE | | COMPOUND NAME | IC50 |
|---|---|---|---|
| 262 | | 3-[(2,4-DIMETHYL-BENZOYL)-ISOPROPYL-AMINO]-5-PHENYL-THIOPHENE-2-CARBOXYLIC ACID | +++ |
| 263 | | 5-(4-AZIDO-PHENYL)-3-(TOLUENE-2-SULFONYLAMINO)-THIOPHENE-2-CARBOXYLIC ACID | +++ |
| 264 | | 3-[(2,4-DICHLORO-BENZOYL)-(1-PHENYL-ETHYL)-AMINO]-5-PHENYL-THIOPHENE-2-CARBOXYLIC ACID | +++ |
| 265 | | 5-(4-CARBAMOYL-PHENYL)-3-(4-CHLORO-BENZENESULFONYLAMINO)-THIOPHENE-2-CARBOXYLIC ACID | +++ |
| 266 | | 5-(2-FLUORO-PHENYL)-3-[METHYL-(4-METHYL-BENZOYL)-AMINO]-THIOPHENE-2-CARBOXYLIC ACID | +++ |
| 267 | | 3-[METHYL-(4-METHYL-BENZOYL)-AMINO]-5-#O!-TOLYL-THIOPHENE-2-CARBOXYLIC ACID | +++ |

-continued

| | MOLSTRUCTURE | COMPOUND NAME | IC50 |
|---|---|---|---|
| 268 | 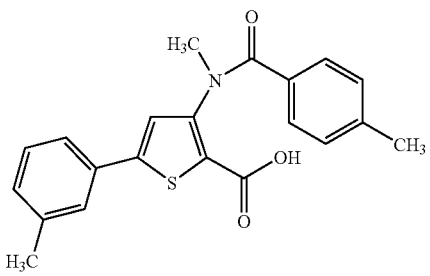 | 3-[METHYL-(4-METHYL-BENZOYL)-AMINO]-5-M-TOLYL-THIOPHENE-2-CARBOXYLIC ACID | +++ |
| 269 | 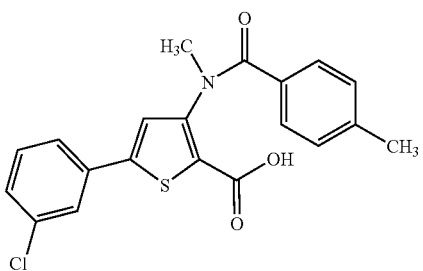 | 5-(3-CHLORO-PHENYL)-3-[METHYL-(4-METHYL-BENZOYL)-AMINO]-THIOPHENE-2-CARBOXYLIC ACID | +++ |
| 270 | 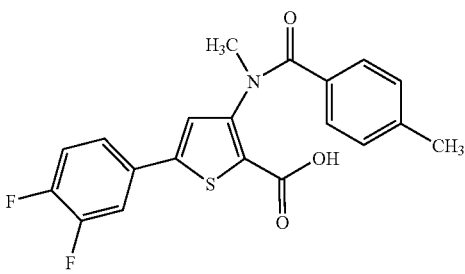 | 5-(3,4-DIFLUORO-PHENYL)-3-[METHYL-(4-METHYL-BENZOYL)-AMINO]-THIOPHENE-2-CARBOXYLIC ACID | +++ |
| 271 | 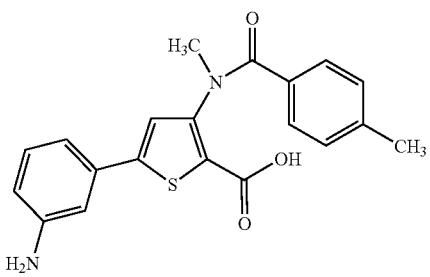 | 5-(3-AMINO-PHENYL)-3-[METHYL-(4-METHYL-BENZOYL)-AMINO]-THIOPHENE-2-CARBOXYLIC ACID | ++ |
| 272 | 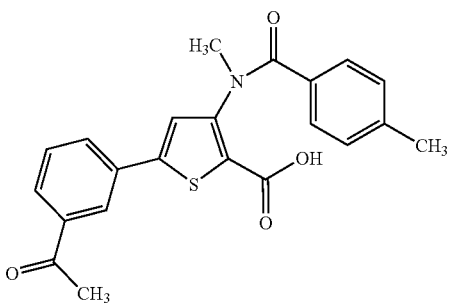 | 5-(3-ACETYL-PHENYL)-3-[METHYL-(4-METHYL-BENZOYL)-AMINO]-THIOPHENE-2-CARBOXYLIC ACID | ++ |

| MOLSTRUCTURE | COMPOUND NAME | IC50 |
|---|---|---|
| 273 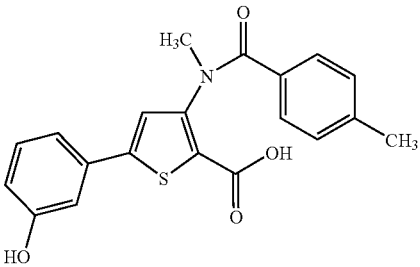 | 5-(3-HYDROXY-PHENYL)-3-[METHYL-(4-METHYL-BENZOYL)-AMINO]-THIOPHENE-2-CARBOXYLIC ACID | +++ |
| 274 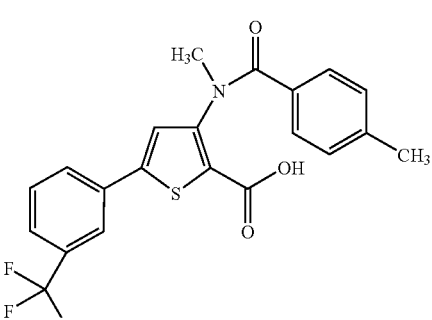 | 3-[METHYL-(4-METHYL-BENZOYL)-AMINO]-5-(3-TRIFLUOROMETHYL-PHENYL)-THIOPHENE-2-CARBOXYLIC ACID | +++ |
| 275 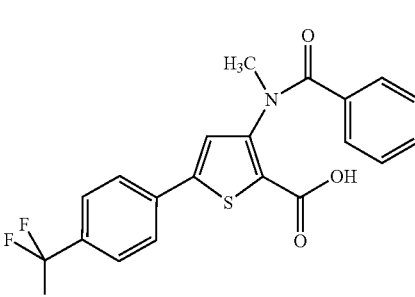 | 3-[METHYL-(4-METHYL-BENZOYL)-AMINO]-5-(4-TRIFLUOROMETHYL-PHENYL)-THIOPHENE-2-CARBOXYLIC ACID | +++ |
| 276 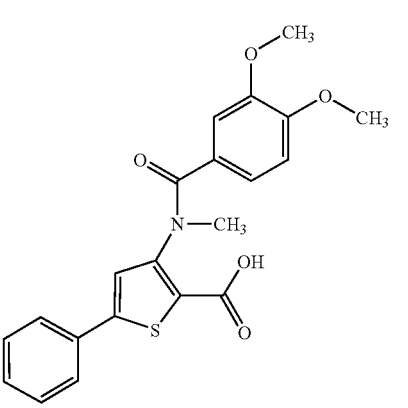 | 3-[(3,4-DIMETHOXY-BENZOYL)-METHYL-AMINO]-5-PHENYL-THIOPHENE-2-CARBOXYLIC ACID | + |
| 277 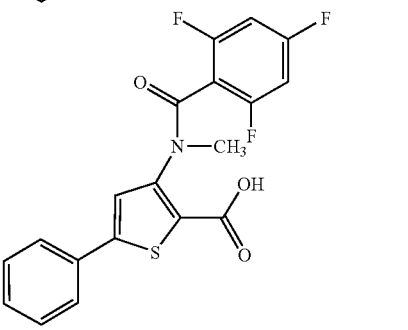 | 3-[METHYL-(2,4,6-TRIFLUORO-BENZOYL)-AMINO]-5-PHENYL-THIOPHENE-2-CARBOXYLIC ACID | ++ |

| MOLSTRUCTURE | COMPOUND NAME | IC50 |
|---|---|---|
| 278 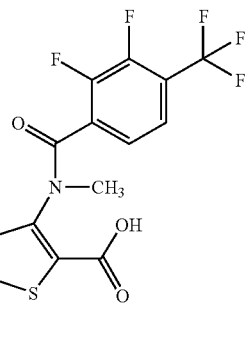 | 3-[(2,3-DIFLUORO-4-TRIFLUOROMETHYL-BENZOYL)-METHYL-AMINO]-5-PHENYL-THIOPHENE-2-CARBOXYLIC ACID | ++ |
| 279 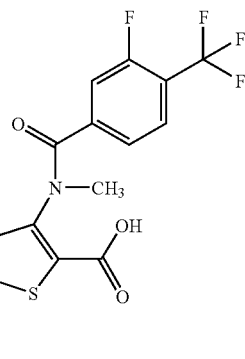 | 3-[(3-FLUORO-4-TRIFLUOROMETHYL-BENZOYL)-METHYL-AMINO]-5-PHENYL-THIOPHENE-2-CARBOXYLIC ACID | ++ |
| 280 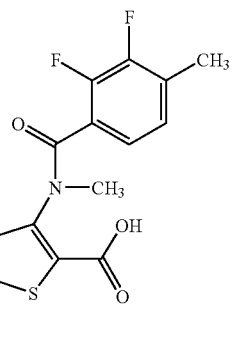 | 3-[(2,3-DIFLUORO-4-METHYL-BENZOYL)-METHYL-AMINO]-5-PHENYL-THIOPHENE-2-CARBOXYLIC ACID | +++ |
| 281 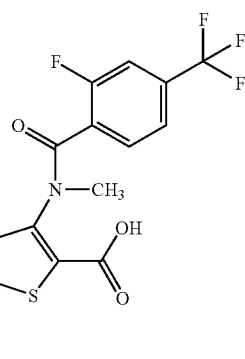 | 3-[(2-FLUORO-4-TRIFLUOROMETHYL-BENZOYL)-METHYL-AMINO]-5-PHENYL-THIOPHENE-2-CARBOXYLIC ACID | ++ |

| MOLSTRUCTURE | COMPOUND NAME | IC50 |
|---|---|---|
| 282 | 5-(4-CARBAMOYL-PHENYL)-3-(TOLUENE-2-SULFONYLAMINO)-THIOPHENE-2-CARBOXYLIC ACID | ++ |
| 283 | 5-(4-FLUORO-PHENYL)-3-[ISOPROPYL-(4-METHYL-BENZOYL)-AMINO]-THIOPHENE-2-CARBOXYLIC ACID | +++ |
| 284 | 3-[(2-BROMO-4-CHLORO-BENZOYL)-METHYL-AMINO]-5-PHENYL-THIOPHENE-2-CARBOXYLIC ACID | +++ |
| 285 | 3-(2,6-DIMETHYL-BENZENESULFONYLAMINO)-5-PHENYL-THIOPHENE-2-CARBOXYLIC ACID | +++ |
| 286 | 3-[METHYL-(4-METHYL-CYCLOHEXANECARBONYL)-AMINO]-5-PHENYL-THIOPHENE-2-CARBOXYLIC ACID | +++ |

-continued

| MOLSTRUCTURE | COMPOUND NAME | IC50 |
| --- | --- | --- |
| 287 | 3-[(2,4-DICHLORO-BENZOYL)-ISOPROPYL-AMINO]-5-PHENYL-THIOPHENE-2-CARBOXYLIC ACID METHYL ESTER | ++ |
| 288 | 5-(4-CYANO-PHENYL)-3-(2,4-DIMETHYL-BENZENESULFONYLAMINO)-THIOPHENE-2-CARBOXYLIC ACID | +++ |
| 289 | 3-(4-CHLORO-BENZENESULFONYLAMINO)-5-(4-CYANO-PHENYL)-THIOPHENE-2-CARBOXYLIC ACID | +++ |
| 290 | 5-(4-CYANO-PHENYL)-3-(TOLUENE-4-SULFONYLAMINO)-THIOPHENE-2-CARBOXYLIC ACID | ++ |
| 291 | 5'-ACETYL-4-(2,4-DIMETHYL-BENZENESULFONYLAMINO)-[2,2']BITHIOPHENYL-5-CARBOXYLIC ACID | +++ |

| MOLSTRUCTURE | COMPOUND NAME | IC50 |
|---|---|---|
| 292 | 5'-ACETYL-4-(2,6-DIMETHYL-BENZENESULFONYLAMINO)-[2,2']BITHIOPHENYL-5-CARBOXYLIC ACID | +++ |
| 293 | 3-[METHYL-(4-METHYL-THIOPHENE-2-CARBONYL)-AMINO]-5-PHENYL-THIOPHENE-2-CARBOXYLIC ACID | ++ |
| 294 | 5-(3-CHLORO-PHENYL)-3-[(2,4-DICHLORO-BENZOYL)-ISOPROPYL-AMINO]-THIOPHENE-2-CARBOXYLIC ACID | +++ |
| 295 | 5'-CYANO-4-(TOLUENE-2-SULFONYLAMINO)-[2,2']BITHIOPHENYL-5-CARBOXYLIC ACID | +++ |
| 296 | 3-[METHYL-(4-METHYL-BENZOYL)-AMINO]-5-PYRIDIN-2-YL-THIOPHENE-2-CARBOXYLIC ACID | ++ |

| MOLSTRUCTURE | COMPOUND NAME | IC50 |
|---|---|---|
| 297 | 3-[(2,4-DICHLORO-THIOBENZOYL)-ISOPROPYL-AMINO]-5-PHENYL-THIOPHENE-2-CARBOXYLIC ACID | +++ |
| 298 | 5-PHENYL-3-(2,4,6-TRIMETHYL-BENZENESULFONYLAMINO)-THIOPHENE-2-CARBOXYLIC ACID | +++ |
| 299 | 3-[(1-CARBOXY-ETHYL)-(2,4-DICHLORO-BENZOYL)-AMINO]-5-PHENYL-THIOPHENE-2-CARBOXYLIC ACID | +++ |
| 300 | 3-[(4-METHYL-BENZOYL)-(3-METHYL-BUT-2-ENYL)-AMINO]-5-PHENYL-THIOPHENE-2-CARBOXYLIC ACID | ++ |
| 301 | 3-[(2-HYDROXY-4-METHYL-BENZOYL)-ISOPROPYL-AMINO]-5-PHENYL-THIOPHENE-2-CARBOXYLIC ACID | ++ |

| MOLSTRUCTURE | COMPOUND NAME | IC50 |
|---|---|---|
| 302 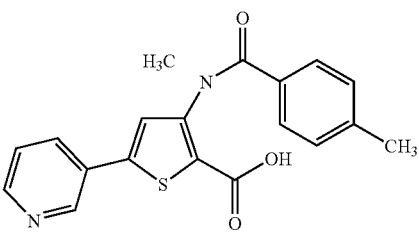 | 3-[METHYL-(4-METHYL-BENZOYL)-AMINO]-5-PYRIDIN-3-YL-THIOPHENE-2-CARBOXYLIC ACID | ++ |
| 303 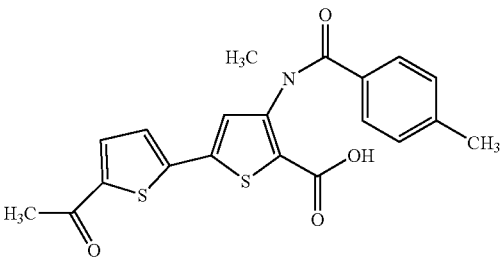 | 5'-ACETYL-4-[METHYL-(4-METHYL-BENZOYL)-AMINO]-[2,2']-BITHIOPHENYL-5-CARBOXYLIC ACID | +++ |
| 304 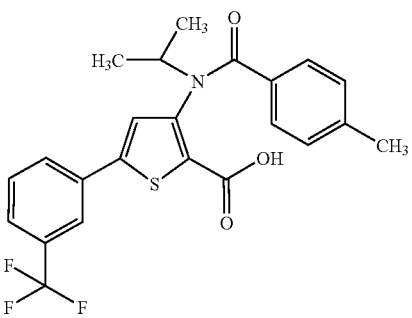 | 3-[ISOPROPYL-(4-METHYL-BENZOYL)-AMINO]-5-(3-TRIFLUOROMETHYL-PHENYL)-THIOPHENE-2-CARBOXYLIC ACID | +++ |
| 305 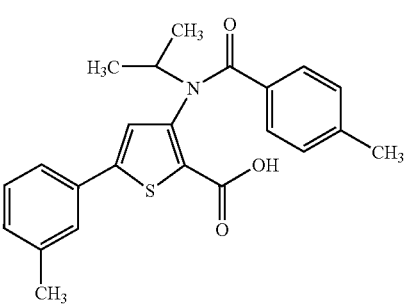 | 3-[ISOPROPYL-(4-METHYL-BENZOYL)-AMINO]-5-M-TOLYL-THIOPHENE-2-CARBOXYLIC ACID | +++ |
| 306 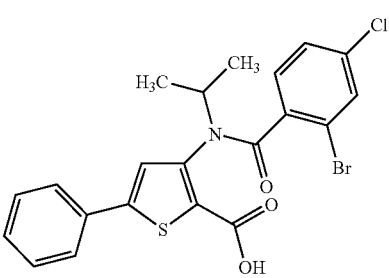 | 3-[(2-BROMO-4-CHLORO-BENZOYL)-ISOPROPYL-AMINO]-5-PHENYL-THIOPHENE-2-CARBOXYLIC ACID | +++ |

| | MOLSTRUCTURE | COMPOUND NAME | IC50 |
|---|---|---|---|
| 307 | | 3-[(4-CHLORO-2-FLUORO-BENZOYL)-ISOPROPYL-AMINO]-5-PHENYL-THIOPHENE-2-CARBOXYLIC ACID | +++ |
| 308 | | 3-(2,4-DIMETHYL-BENZENESULFONYLAMINO)-4-METHYL-5-PHENYL-THIOPHENE-2-CARBOXYLIC ACID | ++ |
| 309 | | 3-[(2-BROMO-4-METHYL-BENZOYL)-ISOPROPYL-AMINO]-5-PHENYL-THIOPHENE-2-CARBOXYLIC ACID | +++ |
| 310 | | 3-[(4-CHLORO-2-IODO-BENZOYL)-ISOPROPYL-AMINO]-5-PHENYL-THIOPHENE-2-CARBOXYLIC ACID | +++ |
| 311 | | 3-[(4-CYANO-BENZOYL)-ISOPROPYL-AMINO]-5-PHENYL-THIOPHENE-2-CARBOXYLIC ACID | ++ |
| 312 | | 3-[ALLYL-(4-METHYL-BENZOYL)-AMINO]-5-[4-(2-CARBOXY-VINYL)-PHENYL]-THIOPHENE-2-CARBOXYLIC ACID | +++ |

| MOLSTRUCTURE | COMPOUND NAME | IC50 |
|---|---|---|
| 313 | 3-[(4-CHLORO-2-HYDROXY-BENZOYL)-ISOPROPYL-AMINO]-5-PHENYL-THIOPHENE-2-CARBOXYLIC ACID | +++ |
| 314 | 3-[(2,4-DICHLORO-BENZOYL)-ISOPROPYL-AMINO]-4-METHYL-5-PHENYL-THIOPHENE-2-CARBOXYLIC ACID | ++ |
| 315 | 5-#TERT!-BUTYL-3-(2,4-DIMETHYL-BENZENESULFONYLAMINO)-THIOPHENE-2-CARBOXYLIC ACID | ++ |
| 316 | 3-[ISOPROPYL-(4-METHYL-CYCLOHEXANECARBONYL)-AMINO]-5-PHENYL-THIOPHENE-2-CARBOXYLIC ACID | + |
| 317 | 3-[ISOPROPYL-(4-METHYL-CYCLOHEXANECARBONYL)-AMINO]-5-PHENYL-THIOPHENE-2-CARBOXYLIC ACID | +++ |

| MOLSTRUCTURE | COMPOUND NAME | IC50 |
|---|---|---|
| 318 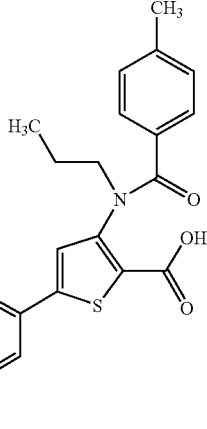 | 5-[4-(2-CARBOXY-ETHYL)-PHENYL]-3-[(4-METHYL-BENZOYL)-PROPYL-AMINO]-THIOPHENE-2-CARBOXYLIC ACID | ++ |
| 319 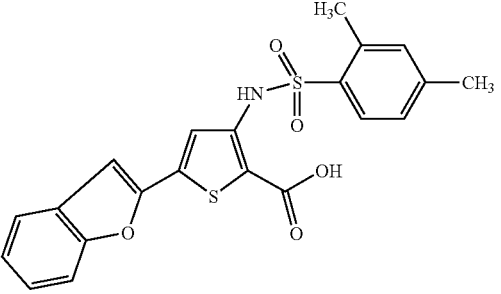 | 5-BENZOFURAN-2-YL-3-(2,4-DIMETHYL-BENZENESULFONYLAMINO)-THIOPHENE-2-CARBOXYLIC ACID | +++ |
| 320 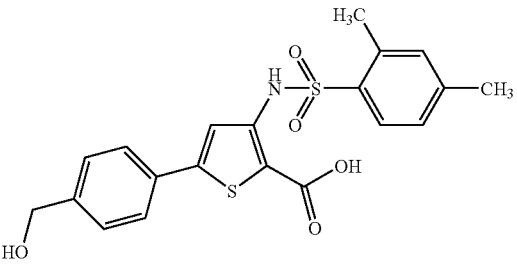 | 3-(2,4-DIMETHYL-BENZENESULFONYLAMINO)-5-(4-HYDROXYMETHYL-PHENYL)-THIOPHENE-2-CARBOXYLIC ACID | +++ |
| 321 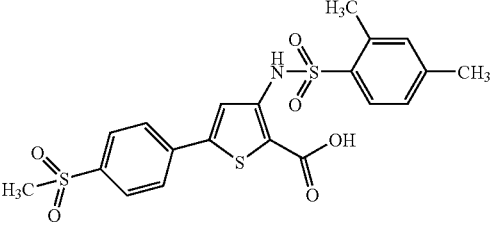 | 3-(2,4-DIMETHYL-BENZENESULFONYLAMINO)-5-(4-METHANESULFONYL-PHENYL)-THIOPHENE-2-CARBOXYLIC ACID | +++ |
| 322 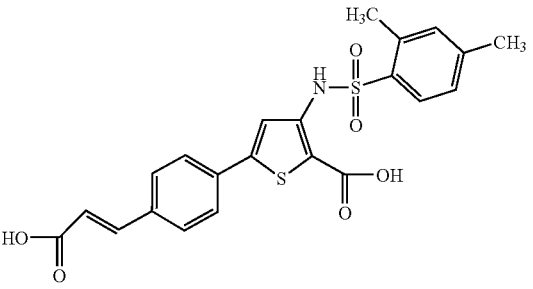 | 5-[4-(2-CARBOXY-VINYL)-PHENYL]-3-(2,4-DIMETHYL-BENZENESULFONYLAMINO)-THIOPHENE-2-CARBOXYLIC ACID | +++ |

| MOLSTRUCTURE | | COMPOUND NAME | IC50 |
|---|---|---|---|
| 323 | 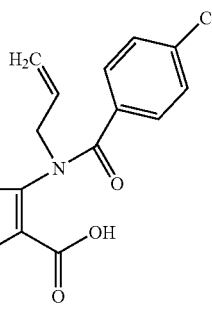 | 3-[ALLYL-(4-METHYL-BENZOYL)-AMINO]-5-[3-(2-CARBOXY-VINYL)-PHENYL]-THIOPHENE-2-CARBOXYLIC ACID | ++ |
| 324 | 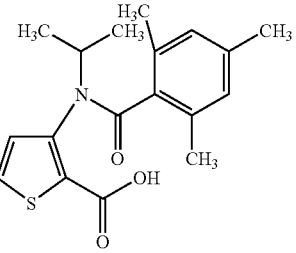 | 3-[ISOPROPYL-(2,4,6-TRIMETHYL-BENZOYL)-AMINO]-5-PHENYL-THIOPHENE-2-CARBOXYLIC ACID | ++ |
| 325 | 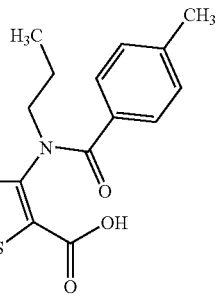 | 5-[3-(2-CARBOXY-ETHYL)-PHENYL]-3-[(4-METHYL-BENZOYL)-PROPYL-AMINO]-THIOPHENE-2-CARBOXYLIC ACID | ++ |
| 326 | 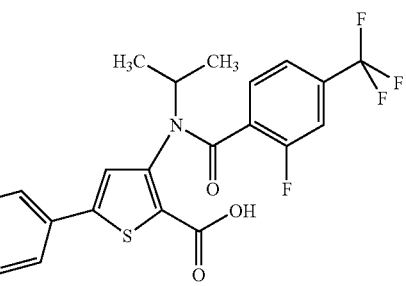 | 3-[(2-FLUORO-4-TRIFLUOROMETHYL-BENZOYL)-ISOPROPYL-AMINO]-5-PHENYL-THIOPHENE-2-CARBOXYLIC ACID | +++ |
| 327 | 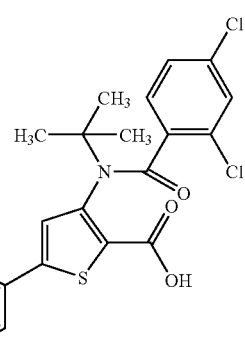 | 3-[#TERT!-BUTYL-(2,4-DICHLORO-BENZOYL)-AMINO]-5-PHENYL-THIOPHENE-2-CARBOXYLIC ACID | +++ |

| MOLSTRUCTURE | COMPOUND NAME | IC50 |
|---|---|---|
| 328 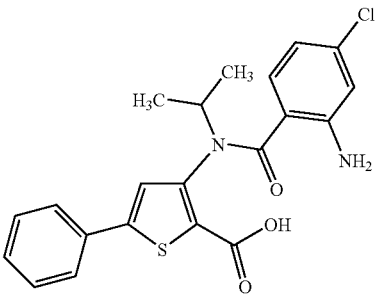 | 3-[(2-AMINO-4-CHLORO-BENZOYL)-ISOPROPYL-AMINO]-5-PHENYL-THIOPHENE-2-CARBOXYLIC ACID | +++ |
| 329 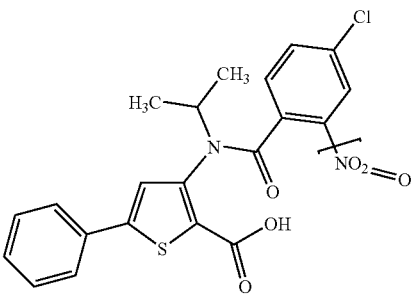 | 3-[(4-CHLORO-2-NITRO-BENZOYL)-ISOPROPYL-AMINO]-5-PHENYL-THIOPHENE-2-CARBOXYLIC ACID | +++ |
| 330 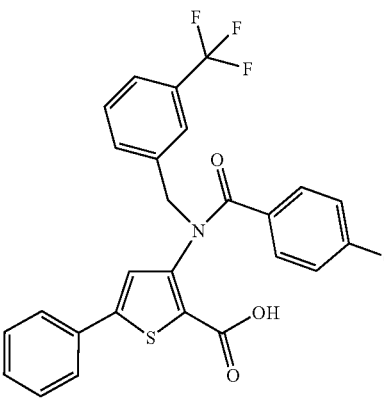 | 3-[(4-METHYL-BENZOYL)-(3-TRIFLUOROMETHYL-BENZYL)-AMINO]-5-PHENYL-THIOPHENE-2-CARBOXYLIC ACID | +++ |
| 331 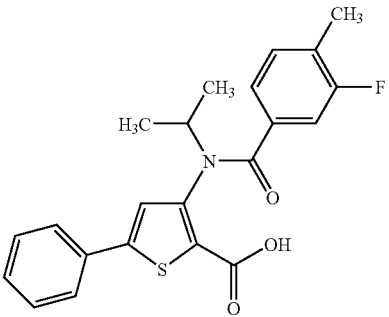 | 3-[(3-FLUORO-4-METHYL-BENZOYL)-ISOPROPYL-AMINO]-5-PHENYL-THIOPHENE-2-CARBOXYLIC ACID | +++ |
| 332 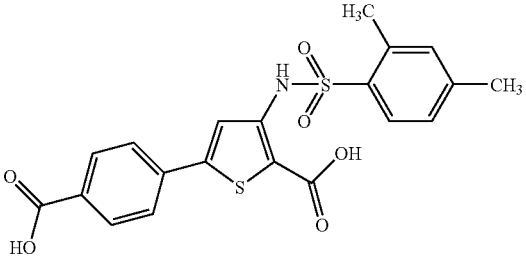 | 5-(4-CARBOXY-PHENYL)-3-(2,4-DIMETHYL-BENZENESULFONYLAMINO)-THIOPHENE-2-CARBOXYLIC ACID | +++ |

| MOLSTRUCTURE | COMPOUND NAME | IC50 |
|---|---|---|
| 333 | 3-[CYCLOPROPYL-(2,4-DICHLORO-BENZOYL)-AMINO]-5-PHENYL-THIOPHENE-2-CARBOXYLIC ACID | +++ |
| 334 | 3-[(3-TERT-BUTYL-BENZYL)-(4-METHYL-BENZOYL)-AMINO]-5-PHENYL-THIOPHENE-2-CARBOXYLIC ACID | +++ |
| 335 | 3-[(3-CHLORO-BENZYL)-(4-METHYL-BENZOYL)-AMINO]-5-PHENYL-THIOPHENE-2-CARBOXYLIC ACID | +++ |
| 336 | 3-[(2,4-DIFLUORO-BENZYL)-(4-METHYL-BENZOYL)-AMINO]-5-PHENYL-THIOPHENE-2-CARBOXYLIC ACID | +++ |

-continued
| MOLSTRUCTURE | COMPOUND NAME | IC50 |
|---|---|---|
| 337 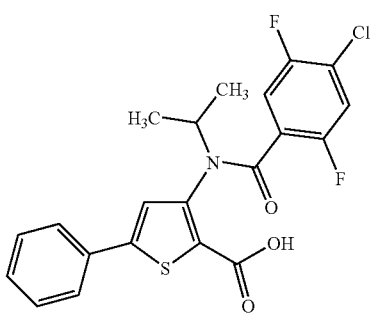 | 3-[(4-CHLORO-2,5-DIFLUORO-BENZOYL)-ISOPROPYL-AMINO]-5-PHENYL-THIOPHENE-2-CARBOXYLIC ACID | ++ |
| 338 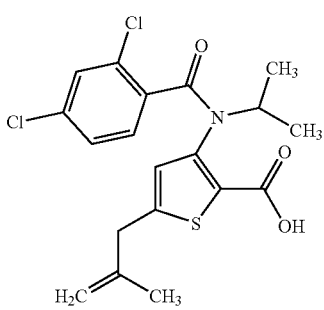 | 3-[(2,4-DICHLORO-BENZOYL)-ISOPROPYL-AMINO]-5-(2-METHYL-ALLYL)-THIOPHENE-2-CARBOXYLIC ACID | +++ |
| 339 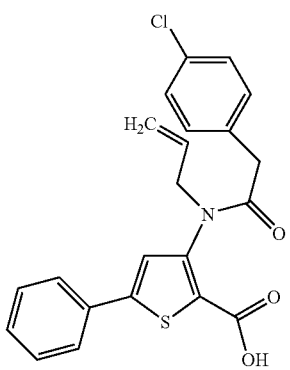 | 3-{ALLYL-[2-(4-CHLORO-PHENYL)-ACETYL]-AMINO}-5-PHENYL-THIOPHENE-2-CARBOXYLIC ACID | ++ |
| 340 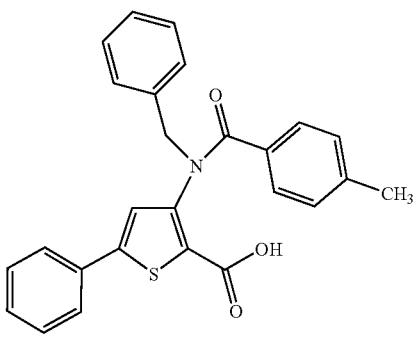 | 3-[BENZYL-(4-METHYL-BENZOYL)-AMINO]-5-PHENYL-THIOPHENE-2-CARBOXYLIC ACID | +++ |

| MOLSTRUCTURE | COMPOUND NAME | IC50 |
|---|---|---|
| 341 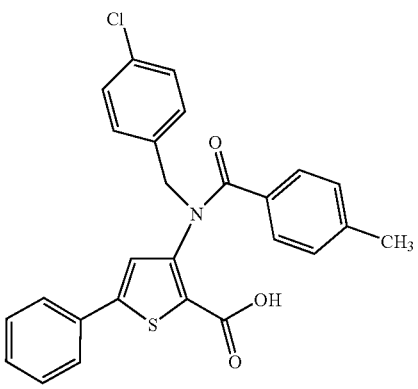 | 3-[(4-CHLORO-BENZYL)-(4-METHYL-BENZOYL)-AMINO]-5-PHENYL-THIOPHENE-2-CARBOXYLIC ACID | +++ |
| 342 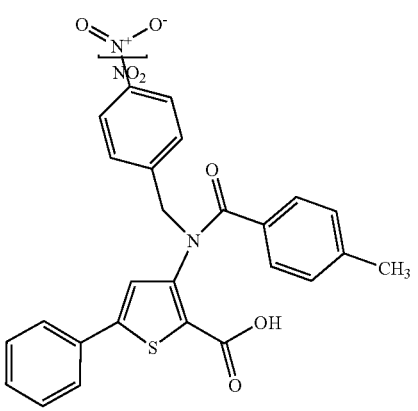 | 3-[(4-METHYL-BENZOYL)-(4-NITRO-BENZYL)-AMINO]-5-PHENYL-THIOPHENE-2-CARBOXYLIC ACID | +++ |
| 343 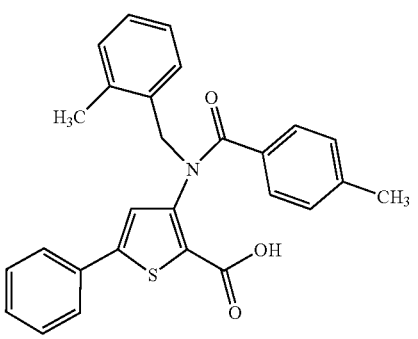 | 3-[(4-METHYL-BENZOYL)-(2-METHYL-BENZYL)-AMINO]-5-PHENYL-THIOPHENE-2-CARBOXYLIC ACID | +++ |
| 344 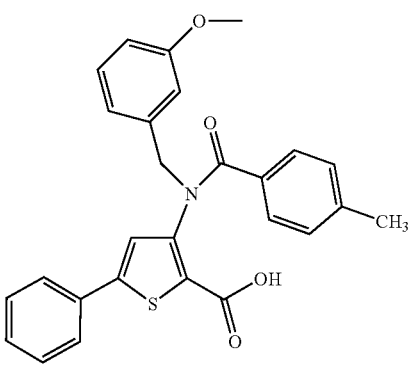 | 3-[(3-METHOXY-BENZYL)-(4-METHYL-BENZOYL)-AMINO]-5-PHENYL-THIOPHENE-2-CARBOXYLIC ACID | +++ |

| MOLSTRUCTURE | COMPOUND NAME | IC50 |
|---|---|---|
| 345 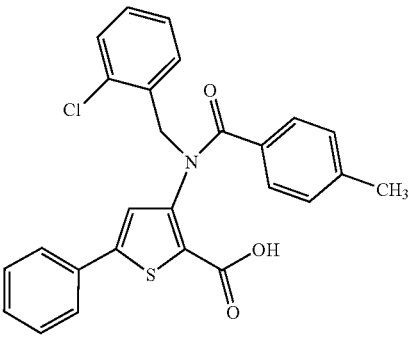 | 3-[(2-CHLORO-BENZYL)-(4-METHYL-BENZOYL)-AMINO]-5-PHENYL-THIOPHENE-2-CARBOXYLIC ACID | +++ |
| 346 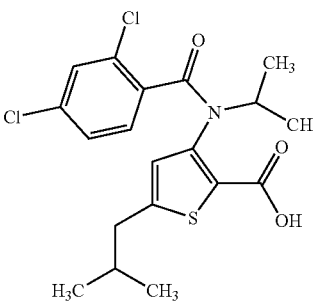 | 3-[(2,4-DICHLORO-BENZOYL)-ISOPROPYL-AMINO]-5-ISOBUTYL-THIOPHENE-2-CARBOXYLIC ACID | +++ |
| 347 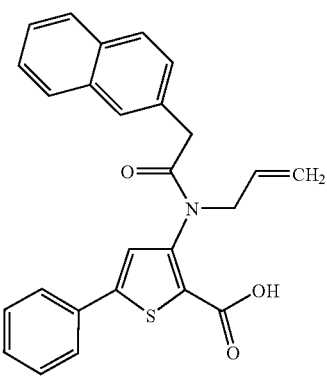 | 3-[ALLYL-(2-NAPHTHALEN-2-YL-ACETYL)-AMINO]-5-PHENYL-THIOPHENE-2-CARBOXYLIC ACID | + |
| 348 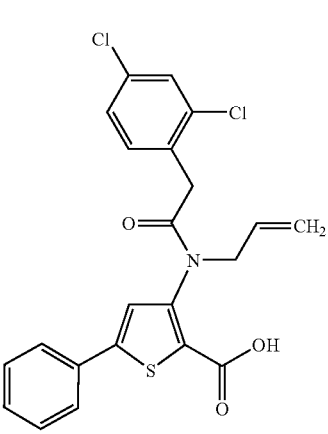 | 3-{ALLYL-[2-(2,4-DICHLORO-PHENYL)-ACETYL]-AMINO}-5-PHENYL-THIOPHENE-2-CARBOXYLIC ACID | ++ |

| MOLSTRUCTURE | COMPOUND NAME | IC50 |
|---|---|---|
| 349 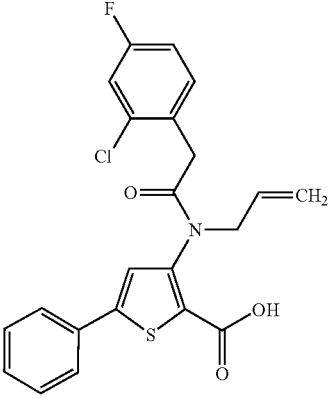 | 3-{ALLYL-[2-(2-CHLORO-4-FLUORO-PHENYL)-ACETYL]-AMINO}-5-PHENYL-THIOPHENE-2-CARBOXYLIC ACID | ++ |
| 350 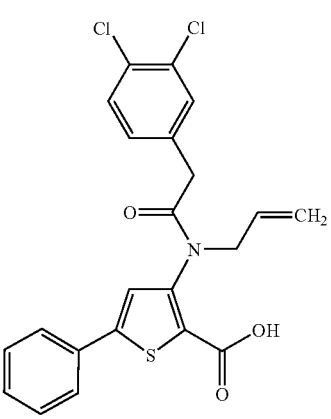 | 3-{ALLYL-[2-(3,4-DICHLORO-PHENYL)-ACETYL]-AMINO}-5-PHENYL-THIOPHENE-2-CARBOXYLIC ACID | ++ |
| 351 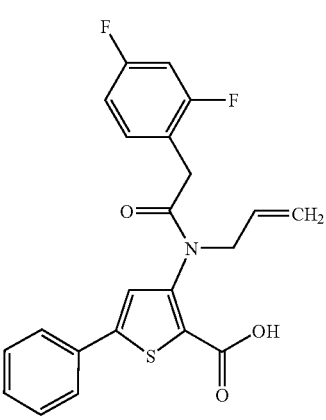 | 3-{ALLYL-[2-(2,4-DIFLUORO-PHENYL)-ACETYL]-AMINO}-5-PHENYL-THIOPHENE-2-CARBOXYLIC ACID | ++ |

-continued
| MOLSTRUCTURE | COMPOUND NAME | IC50 |
|---|---|---|
| 352 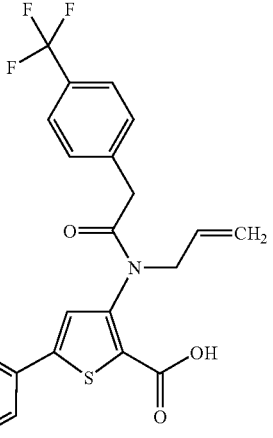 | 3-{ALLYL-[2-(4-TRIFLUOROMETHYL-PHENYL)-ACETYL]-AMINO}-5-PHENYL-THIOPHENE-2-CARBOXYLIC ACID | + |
| 353 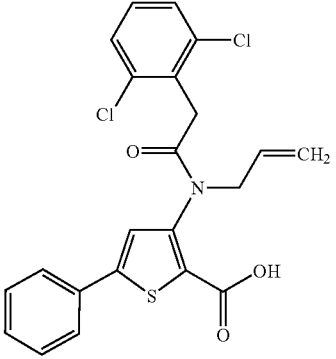 | 3-{ALLYL-[2-(2,6-DICHLORO-PHENYL)-ACETYL]-AMINO}-5-PHENYL-THIOPHENE-2-CARBOXYLIC ACID | ++ |
| 354 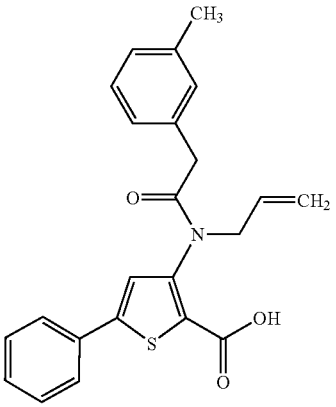 | 3-[ALLYL-(2-M-TOLYL-ACETYL)-AMINO]-5-PHENYL-THIOPHENE-2-CARBOXYLIC ACID | ++ |
| 355 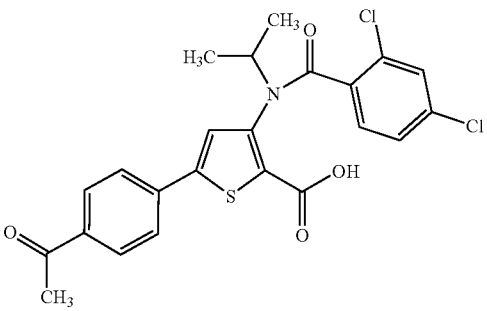 | 5-(4-ACETYL-PHENYL)-3-[(2,4-DICHLORO-BENZOYL)-ISOPROPYL-AMINO]-THIOPHENE-2-CARBOXYLIC ACID | +++ |

-continued

| MOLSTRUCTURE | COMPOUND NAME | IC50 |
|---|---|---|
| 356 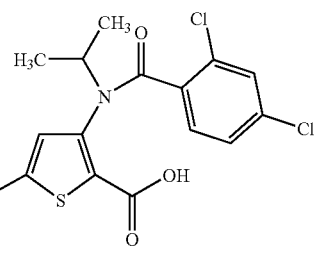 | 3-[(2,4-DICHLORO-BENZOYL)-ISOPROPYL-AMINO]-5-(4-FLUORO-PHENYL)-THIOPHENE-2-CARBOXYLIC ACID | +++ |
| 357 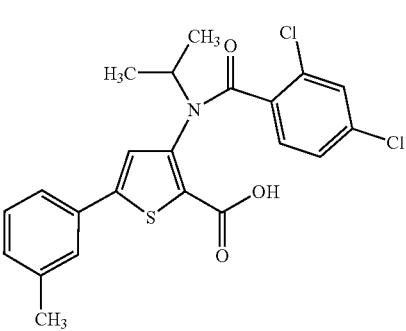 | 3-[(2,4-DICHLORO-BENZOYL)-ISOPROPYL-AMINO]-5-M-TOLYL-THIOPHENE-2-CARBOXYLIC ACID | +++ |
| 358 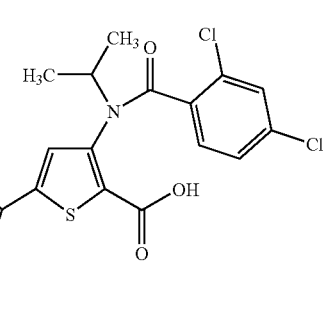 | 5'-ACETYL-4-[(2,4-DICHLORO-BENZOYL)-ISOPROPYL-AMINO]-[2,2']BITHIOPHENYL-5-CARBOXYLIC ACID | +++ |
| 359 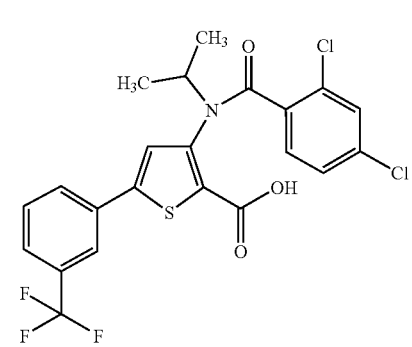 | 3-[(2,4-DICHLORO-BENZOYL)-ISOPROPYL-AMINO]-5-(3-TRIFLUOROMETHYL-PHENYL)-THIOPHENE-2-CARBOXYLIC ACID | +++ |
| 360 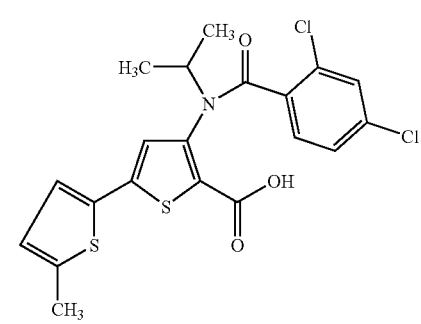 | 4-[(2,4-DICHLORO-BENZOYL)-ISOPROPYL-AMINO]-5'-METHYL-[2,2']BITHIOPHENYL-5-CARBOXYLIC ACID | +++ |

| MOLSTRUCTURE | COMPOUND NAME | IC50 |
|---|---|---|
| 361 | 3-(2,4-DIMETHYL-BENZENESULFONYLAMINO)-5-(4-METHOXY-PHENYL)-THIOPHENE-2-CARBOXYLIC ACID | +++ |
| 362 | 3-(CYCLOHEXANECARBONYL-ISOPROPYL-AMINO)-5-PHENYL-THIOPHENE-2-CARBOXYLIC ACID | ++ |
| 363 | 3-{(2,4-DICHLORO-BENZOYL)-[1-(2,4-DICHLORO-BENZOYL)-PIPERIDIN-4-YL]-AMINO}-5-PHENYL-THIOPHENE-2-CARBOXYLIC ACID | +++ |
| 364 | 4-[(2-CARBOXY-5-PHENYL-THIOPHEN-3-YL)-(4-METHYL-BENZOYL)-AMINO]-PIPERIDINE-1-CARBOXYLIC ACID #TERT!-BUTYL ESTER | +++ |

| MOLSTRUCTURE | COMPOUND NAME | IC50 |
|---|---|---|
| 365 | 4-[(2-CARBOXY-5-PHENYL-THIOPHEN-3-YL)-(2,4-DICHLORO-BENZOYL)-AMINO]-PIPERIDINE-1-CARBOXYLIC ACID #TERT!-BUTYL ESTER | +++ |
| 366 | 3-[(4-METHYL-BENZOYL)-PIPERIDIN-4-YL-AMINO]-5-PHENYL-THIOPHENE-2-CARBOXYLIC ACID | +++ |
| 367 | 5'-ACETYL-4-(2,4-DIMETHYL-BENZENESULFONYLAMINO)-[2,3']BITHIOPHENYL-5-CARBOXYLIC ACID | +++ |
| 368 | 3-[(2,4-DICHLORO-BENZOYL)-PIPERIDIN-4-YL-AMINO]-5-PHENYL-THIOPHENE-2-CARBOXYLIC ACID | +++ |

| MOLSTRUCTURE | COMPOUND NAME | IC50 |
|---|---|---|
| 369 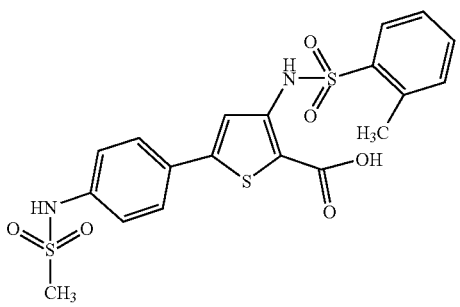 | 5-(4-METHANESULFONYLAMINOPHENYL)-3-(TOLUENE-2-SULFONYLAMINO)-THIOPHENE-2-CARBOXYLIC ACID | ++ |
| 370 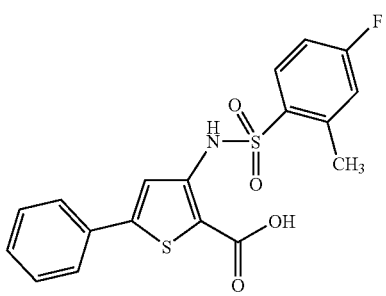 | 3-(4-FLUORO-2-METHYL-BENZENESULFONYLAMINO)-5-PHENYL-THIOPHENE-2-CARBOXYLIC ACID | ++ |
| 371 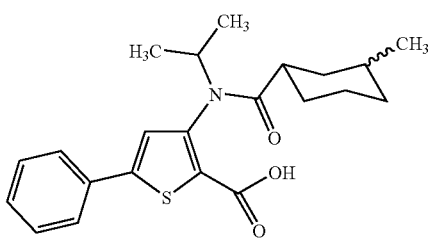 | 3-[(3-METHYL-CYCLOHEXANECARBONYL)-ISOPROPYL-AMINO]-5-PHENYL-THIOPHENE-2-CARBOXYLIC ACID | + |
| 372 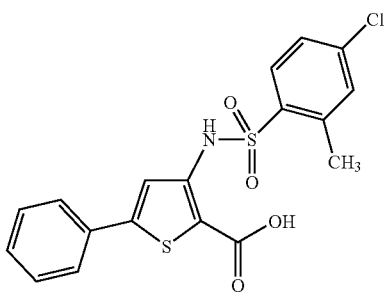 | 3-(4-CHLORO-2-METHYL-BENZENESULFONYLAMINO)-5-PHENYL-THIOPHENE-2-CARBOXYLIC ACID | +++ |
| 373 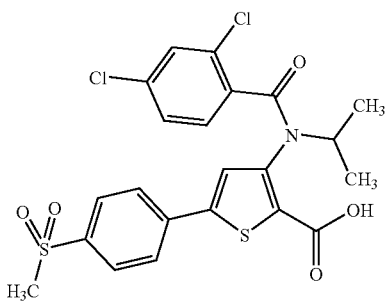 | 3-[(2,4-DICHLORO-BENZOYL)-ISOPROPYL-AMINO]-5-(4-METHANESULFONYL-PHENYL)-THIOPHENE-2-CARBOXYLIC ACID | +++ |

| MOLSTRUCTURE | COMPOUND NAME | IC50 |
|---|---|---|
| 374 | 3-[(2,4-DICHLORO-BENZOYL)-ISOPROPYL-AMINO]-5-(4-METHANESULFINYL-PHENYL)-THIOPHENE-2-CARBOXYLIC ACID | +++ |
| 375 | 5-(4-CARBOXY-PHENYL)-3-[(2,4-DICHLORO-BENZOYL)-ISOPROPYL-AMINO]-THIOPHENE-2-CARBOXYLIC ACID | +++ |
| 376 | 5-BENZOFURAN-2-YL-3-[(2,4-DICHLORO-BENZOYL)-ISOPROPYL-AMINO]-THIOPHENE-2-CARBOXYLIC ACID | +++ |
| 377 | 3-[(2-ACETOXY-4-METHYL-BENZOYL)-ISOPROPYL-AMINO]-5-PHENYL-THIOPHENE-2-CARBOXYLIC ACID | ++ |
| 378 | 3-[ISOPROPYL-(2-METHYL-CYCLOHEXANECARBONYL)-AMINO]-5-PHENYL-THIOPHENE-2-CARBOXYLIC ACID | ++ |

| MOLSTRUCTURE | COMPOUND NAME | IC50 |
|---|---|---|
| 379 | 3-[ISOPROPYL-(2-METHYL-CYCLOHEXANECARBONYL)-AMINO]-5-PHENYL-THIOPHENE-2-CARBOXYLIC ACID | ++ |
| 380 | 3-(CYCLOHEPTANECARBONYL-ISOPROPYL-AMINO)-5-PHENYL-THIOPHENE-2-CARBOXYLIC ACID | +++ |
| 381 | 3-[ISOPROPYL-(4-METHYL-CYCLOHEXANECARBONYL)-AMINO]-5-(3-TRIFLUOROMETHYL-PHENYL)-THIOPHENE-2-CARBOXYLIC ACID | +++ |
| 382 | 3-[(2,4-DICHLORO-BENZOYL)-ISOPROPYL-AMINO]-5-METHYL-THIOPHENE-2-CARBOXYLIC ACID | +++ |
| 383 | 3-[ISOPROPYL-(4-METHYL-CYCLOHEXANECARBONYL)-AMINO]-5-(3-NITRO-PHENYL)-THIOPHENE-2-CARBOXYLIC ACID | +++ |

| MOLSTRUCTURE | COMPOUND NAME | IC50 |
|---|---|---|
| 384 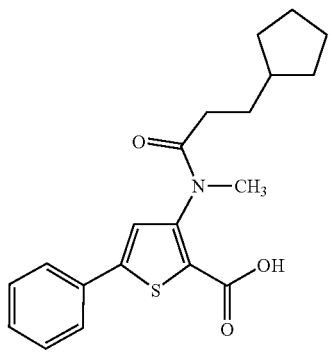 | 3-[(3-CYCLOPENTYL-PROPIONYL)-METHYL-AMINO]-5-PHENYL-THIOPHENE-2-CARBOXYLIC ACID | +++ |
| 385 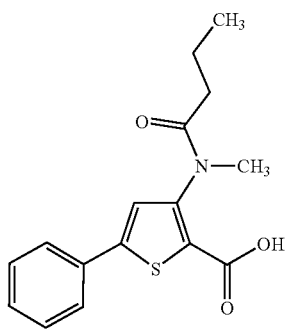 | 3-(BUTYRYL-METHYL-AMINO)-5-PHENYL-THIOPHENE-2-CARBOXYLIC ACID | ++ |
| 386 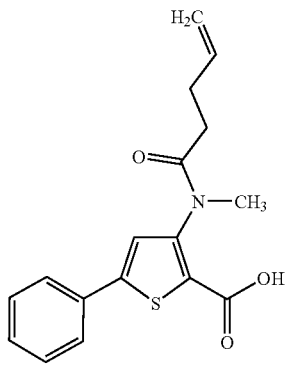 | 3-(METHYL-PENT-4-ENOYL-AMINO)-5-PHENYL-THIOPHENE-2-CARBOXYLIC ACID | ++ |
| 387 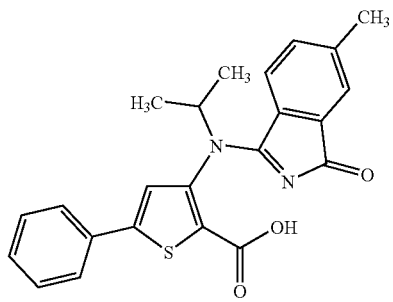 | 3-[ISOPROPYL-(5-METHYL-3-OXO-3H-ISOINDOL-1-YL)-AMINO]-5-PHENYL-THIOPHENE-2-CARBOXYLIC ACID | ++ |

| MOLSTRUCTURE | COMPOUND NAME | IC50 |
|---|---|---|
| 388 | 3-[METHYL-(3-METHYL-BUTYRYL)-AMINO]-5-PHENYL-THIOPHENE-2-CARBOXYLIC ACID | +++ |
| 389 | 3-(METHYL-PENTANOYL-AMINO)-5-PHENYL-THIOPHENE-2-CARBOXYLIC ACID | +++ |
| 390 | 3-[METHYL-(4-METHYL-PENTANOYL)-AMINO]-5-PHENYL-THIOPHENE-2-CARBOXYLIC ACID | ++ |
| 391 | 3-(CYCLOPENTANECARBONYL-ETHYL-AMINO)-5-PHENYL-THIOPHENE-2-CARBOXYLIC ACID | ++ |

| MOLSTRUCTURE | COMPOUND NAME | IC50 |
| --- | --- | --- |
| 392 | 3-[(3-CYCLOPENTYL-PROPIONYL)-ETHYL-AMINO]-5-PHENYL-THIOPHENE-2-CARBOXYLIC ACID | +++ |
| 393 | 3-(CYCLOBUTANECARBONYL-ETHYL-AMINO)-5-PHENYL-THIOPHENE-2-CARBOXYLIC ACID | ++ |
| 394 | 3-(BUT-2-ENOYL-ETHYL-AMINO)-5-PHENYL-THIOPHENE-2-CARBOXYLIC ACID | ++ |
| 395 | 3-[ISOPROPYL-(4-METHYL-2-VINYL-BENZOYL)-AMINO]-5-PHENYL-THIOPHENE-2-CARBOXYLIC ACID | ++ |

| MOLSTRUCTURE | COMPOUND NAME | IC50 |
|---|---|---|
| 396 | 3-[ISOPROPYL-(4-METHYL-CYCLOHEX-1-ENECARBONYL)-AMINO]-5-PHENYL-THIOPHENE-2-CARBOXYLIC ACID | +++ |
| 397 | 3-(ALLYL-HEXANOYL-AMINO)-5-PHENYL-THIOPHENE-2-CARBOXYLIC ACID | ++ |
| 398 | 3-(ALLYL-CYCLOBUTANECARBONYL-AMINO)-5-PHENYL-THIOPHENE-2-CARBOXYLIC ACID | + |
| 399 | 3-(ALLYL-PENTANOYL-AMINO)-5-PHENYL-THIOPHENE-2-CARBOXYLIC ACID | ++ |

-continued
| MOLSTRUCTURE | COMPOUND NAME | IC50 |
|---|---|---|
| 400 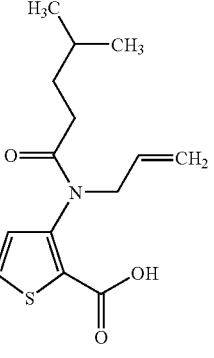 | 3-[ALLYL-(4-METHYL-PENTANOYL)-AMINO]-5-PHENYL-THIOPHENE-2-CARBOXYLIC ACID | ++ |
| 401 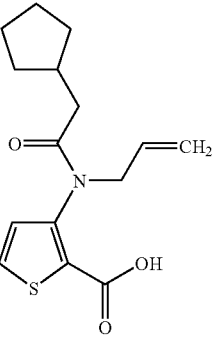 | 3-[ALLYL-(2-CYCLOPENTYL-ACETYL)-AMINO]-5-PHENYL-THIOPHENE-2-CARBOXYLIC ACID | +++ |
| 402 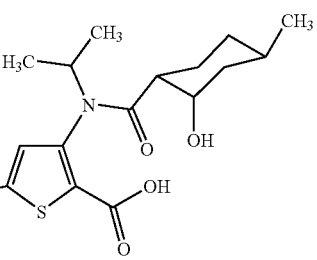 | 3-[(2-HYDROXY-4-METHYL-CYCLOHEXANECARBONYL)-ISOPROPYL-AMINO]-5-PHENYL-THIOPHENE-2-CARBOXYLIC ACID | +++ |
| 403 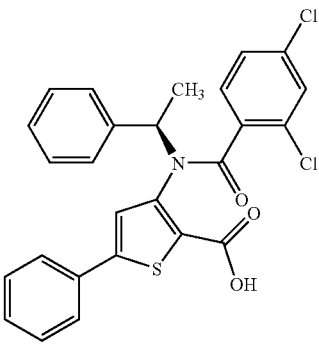 | 3-[(2,4-DICHLORO-BENZOYL)-(1-PHENYL-ETHYL)-AMINO]-5-PHENYL-THIOPHENE-2-CARBOXYLIC ACID | +++ |

-continued

| | MOLSTRUCTURE | COMPOUND NAME | IC50 |
|---|---|---|---|
| 404 | 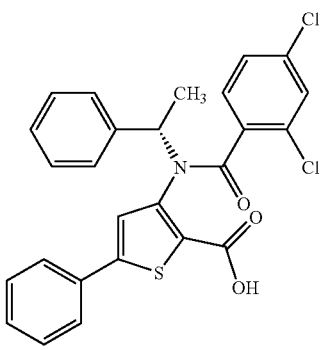 | 3-[(2,4-DICHLORO-BENZOYL)-(1-PHENYL-ETHYL)-AMINO]-5-PHENYL-THIOPHENE-2-CARBOXYLIC ACID | +++ |
| 405 | 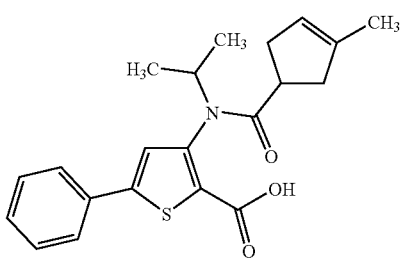 | 3-[ISOPROPYL-(3-METHYL-CYCLOPENT-3-ENECARBONYL)-AMINO]-5-PHENYL-THIOPHENE-2-CARBOXYLIC ACID | +++ |
| 406 | 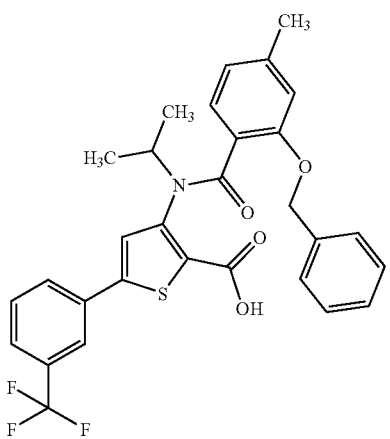 | 3-[(2-BENZYLOXY-4-METHYL-BENZOYL)-ISOPROPYL-AMINO]-5-(3-TRIFLUOROMETHYL-PHENYL)-THIOPHENE-2-CARBOXYLIC ACID | +++ |
| 407 | 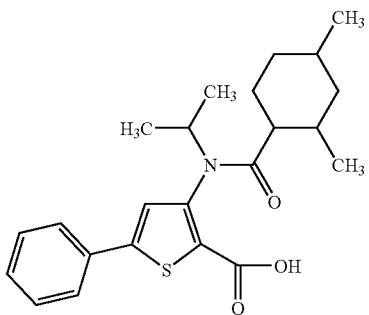 | 3-[(2,4-DIMETHYL-CYCLOHEXANECARBONYL)-ISOPROPYL-AMINO]-5-PHENYL-THIOPHENE-2-CARBOXYLIC ACID | +++ |

-continued

| | MOLSTRUCTURE | COMPOUND NAME | IC50 |
|---|---|---|---|
| 408 | | 3-[ISOPROPYL-(3-METHYL-CYCLOPENTANECARBONYL)-AMINO]-5-PHENYL-THIOPHENE-2-CARBOXYLIC ACID | ++ |
| 409 | | 3-[(2-HYDROXY-4-METHYL-CYCLOHEXANECARBONYL)-ISOPROPYL-AMINO]-5-PHENYL-THIOPHENE-2-CARBOXYLIC ACID | +++ |
| 410 | | 5-PHENYL-3-[PROPIONYL-(4-TRIFLUOROMETHYL-BENZYL)-AMINO]-THIOPHENE-2-CARBOXYLIC ACID | ++ |
| 411 | | 3-[ISOBUTYRYL-(4-TRIFLUOROMETHYL-BENZYL)-AMINO]-5-PHENYL-THIOPHENE-2-CARBOXYLIC ACID | ++ |

| MOLSTRUCTURE | COMPOUND NAME | IC50 |
|---|---|---|
| 412 | 3-[(3-METHYL-BUTYRYL)-(4-TRIFLUOROMETHYL-BENZYL)-AMINO]-5-PHENYL-THIOPHENE-2-CARBOXYLIC ACID | ++ |
| 413 | 3-[CYCLOPROPANECARBONYL-(4-TRIFLUOROMETHYL-BENZYL)-AMINO]-5-PHENYL-THIOPHENE-2-CARBOXYLIC ACID | ++ |
| 414 | 3-[CYCLOBUTANECARBONYL-(4-TRIFLUOROMETHYL-BENZYL)-AMINO]-5-PHENYL-THIOPHENE-2-CARBOXYLIC ACID | ++ |

| MOLSTRUCTURE | COMPOUND NAME | IC50 |
|---|---|---|
| 415 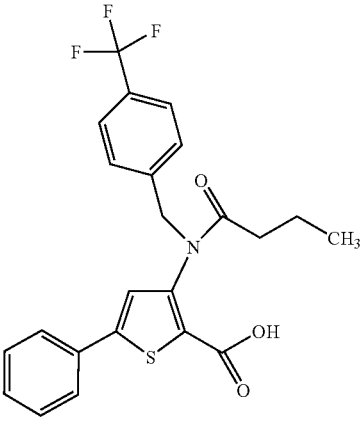 | 3-(BUTYRYL-(4-TRIFLUOROMETHYL-BENZYL)-AMINO]-5-PHENYL-THIOPHENE-2-CARBOXYLIC ACID | ++ |
| 416 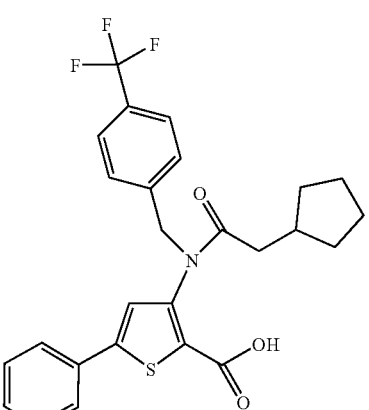 | 3-[(2-CYCLOPENTYL-ACETYL)-(4-TRIFLUOROMETHYL-BENZYL)-AMINO]-5-PHENYL-THIOPHENE-2-CARBOXYLIC ACID | ++ |
| 417 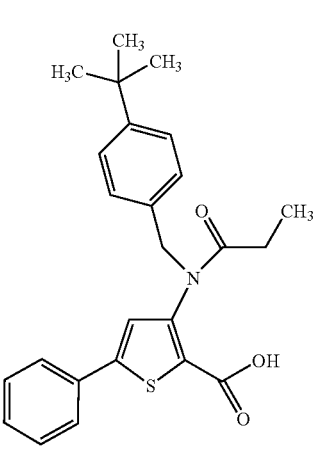 | 3-[(4-TERT-BUTYL-BENZYL)-PROPIONYL-AMINO]-5-PHENYL-THIOPHENE-2-CARBOXYLIC ACID | ++ |

| MOLSTRUCTURE | COMPOUND NAME | IC50 |
|---|---|---|
| 418 | 3-[(4-NITRO-BENZYL)-PROPIONYL-AMINO]-5-PHENYL-THIOPHENE-2-CARBOXYLIC ACID | ++ |
| 419 | 3-[(3-METHYL-BUTYRYL)-(4-NITRO-BENZYL)-AMINO]-5-PHENYL-THIOPHENE-2-CARBOXYLIC ACID | +++ |
| 420 | 3-[CYCLOPROPANECARBONYL-(4-NITRO-BENZYL)-AMINO]-5-PHENYL-THIOPHENE-2-CARBOXYLIC ACID | ++ |
| 421 | 3-[(2-CHLORO-BENZYL)-ISOBUTYRYL-AMINO]-5-PHENYL-THIOPHENE-2-CARBOXYLIC ACID | ++ |

| MOLSTRUCTURE | COMPOUND NAME | IC50 |
|---|---|---|
| 422 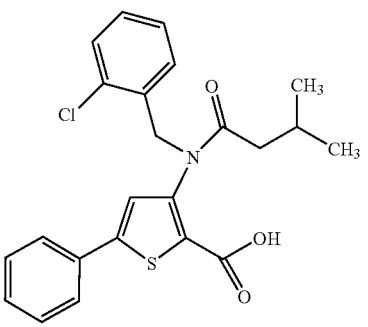 | 3-[(2-CHLORO-BENZYL)-(3-METHYL-BUTYRYL)-AMINO]-5-PHENYL-THIOPHENE-2-CARBOXYLIC ACID | ++ |
| 423 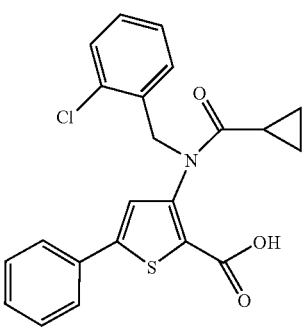 | 3-[(2-CHLORO-BENZYL)-CYCLOPROPANECARBONYL-AMINO]-5-PHENYL-THIOPHENE-2-CARBOXYLIC ACID | + |
| 424 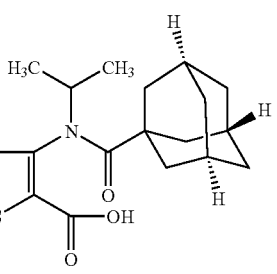 | 3-[(ADAMANTANE-1-CARBONYL)-ISOPROPYL-AMINO]-5-PHENYL-THIOPHENE-2-CARBOXYLIC ACID | + |
| 425 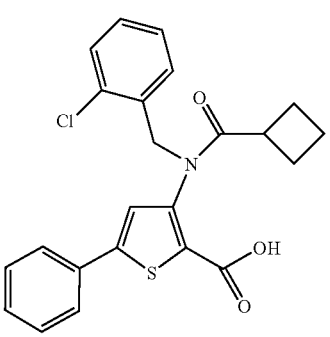 | 3-[(2-CHLORO-BENZYL)-CYCLOBUTANECARBONYL-AMINO]-5-PHENYL-THIOPHENE-2-CARBOXYLIC ACID | ++ |
| 426 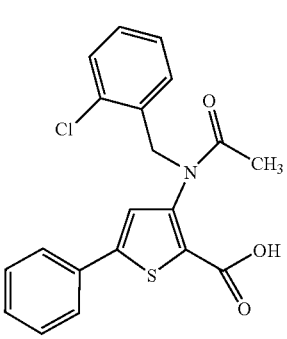 | 3-[ACETYL-(2-METHYL-BENZYL)-AMINO]-5-PHENYL-THIOPHENE-2-CARBOXYLIC ACID | + |

| MOLSTRUCTURE | COMPOUND NAME | IC50 |
|---|---|---|
| 427 | 3-[(2-METHYL-BENZYL)-PROPIONYL-AMINO]-5-PHENYL-THIOPHENE-2-CARBOXYLIC ACID | ++ |
| 428 | 3-[(2-HYDROXY-4-METHYL-BENZOYL)-ISOPROPYL-AMINO]-5-(3-TRIFLUOROMETHYL-PHENYL)-THIOPHENE-2-CARBOXYLIC ACID | ++ |
| 429 | 3-[(1-ACETYL-PIPERIDIN-4-YL)-(2,4-DICHLORO-BENZOYL)-AMINO]-5-PHENYL-THIOPHENE-2-CARBOXYLIC ACID | +++ |
| 430 | 3-[(2,4-DICHLORO-BENZOYL)-ISOPROPYL-AMINO]-5-[4-(1#H!-TETRAZOL-5-YL)-PHENYL]-THIOPHENE-2-CARBOXYLIC ACID | +++ |

| MOLSTRUCTURE | COMPOUND NAME | IC50 |
|---|---|---|
| 431 | 3-[(2-CYANO-4-METHYL-BENZOYL)-ISOPROPYL-AMINO]-5-PHENYL-THIOPHENE-2-CARBOXYLIC ACID | ++ |
| 432 | 3-[CYCLOBUTANECARBONYL-(2-METHYL-BENZYL)-AMINO]-5-PHENYL-THIOPHENE-2-CARBOXYLIC ACID | ++ |
| 433 | 3-[BUTYRYL-(2-METHYL-BENZYL)-AMINO]-5-PHENYL-THIOPHENE-2-CARBOXYLIC ACID | ++ |
| 434 | 3-[ACETYL-(3-METHYL-BENZYL)-AMINO]-5-PHENYL-THIOPHENE-2-CARBOXYLIC ACID | ++ |

| MOLSTRUCTURE | COMPOUND NAME | IC50 |
|---|---|---|
| 435 | 3-[CYCLOBUTANECARBONYL-(4-METHYL-BENZYL)-AMINO]-5-PHENYL-THIOPHENE-2-CARBOXYLIC ACID | +++ |
| 436 | 3-[CYCLOHEXANECARBONYL-(4-TRIFLUOROMETHYL-BENZYL)-AMINO]-5-PHENYL-THIOPHENE-2-CARBOXYLIC ACID | +++ |
| 437 | 3-[(4-TERT-BUTYL-BENZYL)-ISOBUTYRYL-AMINO]-5-PHENYL-THIOPHENE-2-CARBOXYLIC ACID | ++ |
| 438 | 3-[(4-TERT-BUTYL-BENZYL)-CYCLOPROPANECARBONYL-AMINO]-5-PHENYL-THIOPHENE-2-CARBOXYLIC ACID | ++ |

-continued

| | MOLSTRUCTURE | COMPOUND NAME | IC50 |
|---|---|---|---|
| 439 | | 3-[(4-TERT-BUTYL-BENZYL)-CYCLOBUTANECARBONYL-AMINO]-5-PHENYL-THIOPHENE-2-CARBOXYLIC ACID | +++ |
| 440 | | 3-[(4-TERT-BUTYL-BENZYL)-BUTYRYL-AMINO]-5-PHENYL-THIOPHENE-2-CARBOXYLIC ACID | ++ |
| 441 | | 3-[(4-TERT-BUTYL-BENZYL)-CYCLOHEXANECARBONYL-AMINO]-5-PHENYL-THIOPHENE-2-CARBOXYLIC ACID | +++ |

| MOLSTRUCTURE | COMPOUND NAME | IC50 |
|---|---|---|
| 442 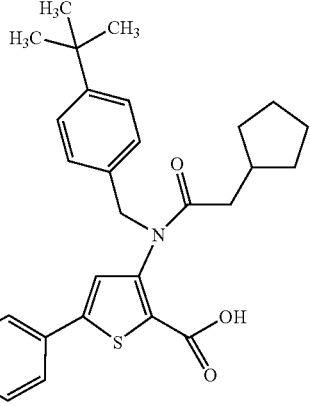 | 3-[(4-TERT-BUTYL-BENZYL)-(2-CYCLOPENTYL-ACETYL)-AMINO]-5-PHENYL-THIOPHENE-2-CARBOXYLIC ACID | +++ |
| 443 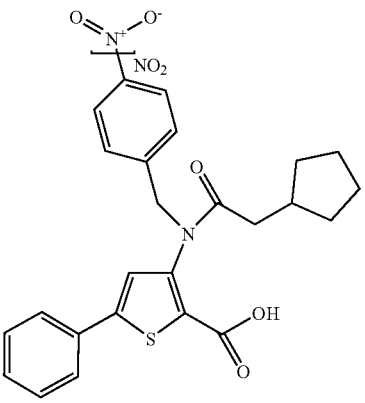 | 3-[(2-CYCLOPENTYL-ACETYL)-(4-NITRO-BENZYL)-AMINO]-5-PHENYL-THIOPHENE-2-CARBOXYLIC ACID | +++ |
| 444 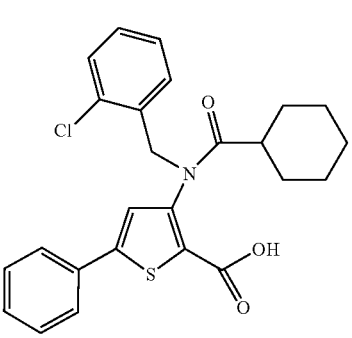 | 3-[(2-CHLORO-BENZYL)-CYCLOHEXANECARBONYL-AMINO]-5-PHENYL-THIOPHENE-2-CARBOXYLIC ACID | +++ |
| 445 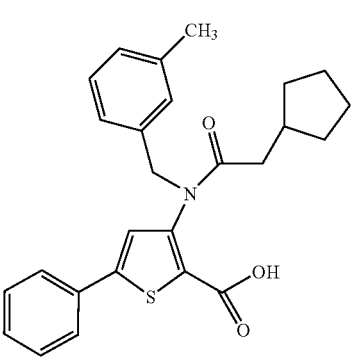 | 3-[(2-CYCLOPENTYL-ACETYL)-(3-METHYL-BENZYL)-AMINO]-5-PHENYL-THIOPHENE-2-CARBOXYLIC ACID | +++ |

| MOLSTRUCTURE | COMPOUND NAME | IC50 |
|---|---|---|
| 446 | 3-[BUTYRYL-(3-METHYL-BENZYL)-AMINO]-5-PHENYL-THIOPHENE-2-CARBOXYLIC ACID | ++ |
| 447 | 3-[BUTYRYL-(2-CHLORO-BENZYL)-AMINO]-5-PHENYL-THIOPHENE-2-CARBOXYLIC ACID | +++ |
| 448 | 3-[ISOPROPYL-(4-METHYL-CYCLOHEXANECARBONYL)-AMINO]-5-#M!-TOLYL-THIOPHENE-2-CARBOXYLIC ACID | +++ |
| 449 | 3-[(2,4-DICHLORO-BENZOYL)-ISOPROPYL-AMINO]-5-THIAZOL-2-YL-THIOPHENE-2-CARBOXYLIC ACID | +++ |
| 450 | 3-(ACETYL-BENZYL-AMINO)-5-PHENYL-THIOPHENE-2-CARBOXYLIC ACID | +++ |

| MOLSTRUCTURE | COMPOUND NAME | IC50 |
|---|---|---|
| 451 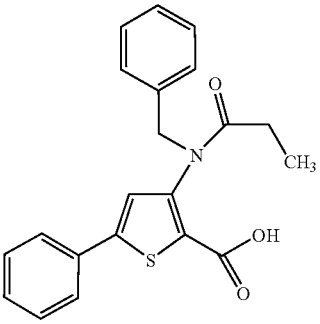 | 3-(BENZYL-PROPIONYL-AMINO)-5-PHENYL-THIOPHENE-2-CARBOXYLIC ACID | +++ |
| 452 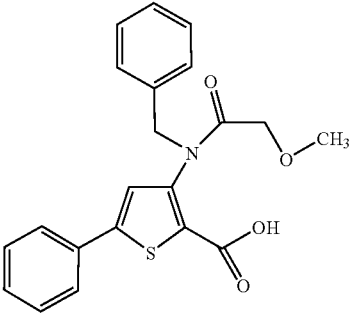 | 3-[BENZYL-(2-METHOXY-ACETYL)-AMINO]-5-PHENYL-THIOPHENE-2-CARBOXYLIC ACID | +++ |
| 453 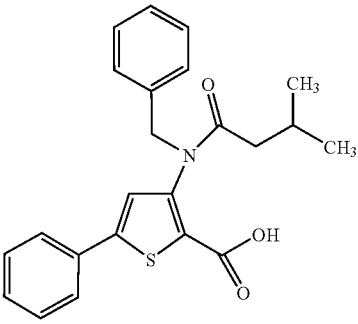 | 3-[BENZYL-(3-METHYL-BUTYRYL)-AMINO]-5-PHENYL-THIOPHENE-2-CARBOXYLIC ACID | +++ |
| 454 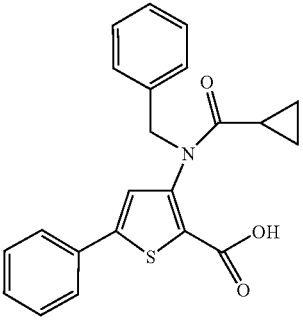 | 3-(BENZYL-CYCLOPROPANECARBONYL-AMINO)-5-PHENYL-THIOPHENE-2-CARBOXYLIC ACID | +++ |

-continued

| | MOLSTRUCTURE | COMPOUND NAME | IC50 |
|---|---|---|---|
| 455 | | 3-[ACETYL-(4-CHLORO-BENZYL)-AMINO]-5-PHENYL-THIOPHENE-2-CARBOXYLIC ACID | ++ |
| 456 | | 3-[(4-CHLORO-BENZYL)-PROPIONYL-AMINO]-5-PHENYL-THIOPHENE-2-CARBOXYLIC ACID | +++ |
| 457 | | 3-[(4-CHLORO-BENZYL)-ISOBUTYRYL-AMINO]-5-PHENYL-THIOPHENE-2-CARBOXYLIC ACID | ++ |
| 458 | | 3-[(4-CHLORO-BENZYL)-(3-METHYL-BUTYRYL)-AMINO]-5-PHENYL-THIOPHENE-2-CARBOXYLIC ACID | ++ |

| MOLSTRUCTURE | COMPOUND NAME | IC50 |
|---|---|---|
| 459 | 3-[(4-CHLORO-BENZYL)-CYCLOPROPANECARBONYL-AMINO]-5-PHENYL-THIOPHENE-2-CARBOXYLIC ACID | ++ |
| 460 | 5-(4-ACETYL-PHENYL)-3-[ISOPROPYL-(4-METHYL-CYCLOHEXANECARBONYL)-AMINO]-THIOPHENE-2-CARBOXYLIC ACID | +++ |
| 461 | 3-[(4-CHLORO-BENZYL)-CYCLOBUTANECARBONYL-AMINO]-5-PHENYL-THIOPHENE-2-CARBOXYLIC ACID | ++ |
| 462 | 3-[BUTYRYL-(4-CHLORO-BENZYL)-AMINO]-5-PHENYL-THIOPHENE-2-CARBOXYLIC ACID | ++ |

-continued

| MOLSTRUCTURE | COMPOUND NAME | IC50 |
|---|---|---|
| 463 | 3-[(4-CHLORO-BENZYL)-(2-CYCLOPENTYL-ACETYL)-AMINO]-5-PHENYL-THIOPHENE-2-CARBOXYLIC ACID | +++ |
| 464 | 3-[ACETYL-(4-TRIFLUOROMETHYL-BENZYL)-AMINO]-5-PHENYL-THIOPHENE-2-CARBOXYLIC ACID | ++ |
| 465 | 3-[ISOBUTYRYL-(3-METHYL-BENZYL)-AMINO]-5-PHENYL-THIOPHENE-2-CARBOXYLIC ACID | ++ |
| 466 | 3-[CYCLOPROPANECARBONYL-(3-METHYL-BENZYL)-AMINO]-5-PHENYL-THIOPHENE-2-CARBOXYLIC ACID | ++ |

| MOLSTRUCTURE | COMPOUND NAME | IC50 |
|---|---|---|
| 467 | 3-[(4-METHYL-BENZYL)-PROPIONYL-AMINO]-5-PHENYL-THIOPHENE-2-CARBOXYLIC ACID | ++ |
| 468 | 3-[ISOBUTYRYL-(4-METHYL-BENZYL)-AMINO]-5-PHENYL-THIOPHENE-2-CARBOXYLIC ACID | ++ |
| 469 | 3-[CYCLOPROPANECARBONYL-(4-METHYL-BENZYL)-AMINO]-5-PHENYL-THIOPHENE-2-CARBOXYLIC ACID | ++ |
| 470 | 3-[BUTYRYL-(4-METHYL-BENZYL)-AMINO]-5-PHENYL-THIOPHENE-2-CARBOXYLIC ACID | ++ |

-continued

| MOLSTRUCTURE | COMPOUND NAME | IC50 |
|---|---|---|
| 471 | 3-[(3-METHOXY-BENZYL)-PROPIONYL-AMINO]-5-PHENYL-THIOPHENE-2-CARBOXYLIC ACID | + |
| 472 | 3-[(3-METHOXY-BENZYL)-(3-METHYL-BUTYRYL)-AMINO]-5-PHENYL-THIOPHENE-2-CARBOXYLIC ACID | +++ |
| 473 | 3-[CYCLOBUTANECARBONYL-(3-METHOXY-BENZYL)-AMINO]-5-PHENYL-THIOPHENE-2-CARBOXYLIC ACID | ++ |
| 474 | 3-[(2-CARBAMOYL-4-METHYL-BENZOYL)-ISOPROPYL-AMINO]-5-PHENYL-THIOPHENE-2-CARBOXYLIC ACID | ++ |
| 475 | 3-[BUTYRYL-(3-METHOXY-BENZYL)-AMINO]-5-PHENYL-THIOPHENE-2-CARBOXYLIC ACID | ++ |

| MOLSTRUCTURE | COMPOUND NAME | IC50 |
|---|---|---|
| 476 | 3-[ACETYL-(3-CHLORO-BENZYL)-AMINO]-5-PHENYL-THIOPHENE-2-CARBOXYLIC ACID | + |
| 477 | 3-[(3-CHLORO-BENZYL)-PROPIONYL-AMINO]-5-PHENYL-THIOPHENE-2-CARBOXYLIC ACID | ++ |
| 478 | 3-[(3-CHLORO-BENZYL)-(2-METHOXY-ACETYL)-AMINO]-5-PHENYL-THIOPHENE-2-CARBOXYLIC ACID | + |
| 479 | 3-[(3-CHLORO-BENZYL)-(3-METHYL-BUTYRYL)-AMINO]-5-PHENYL-THIOPHENE-2-CARBOXYLIC ACID | +++ |

| MOLSTRUCTURE | COMPOUND NAME | IC50 |
|---|---|---|
| 480 | 3-[(3-CHLORO-BENZYL)-CYCLOPROPANECARBONYL-AMINO]-5-PHENYL-THIOPHENE-2-CARBOXYLIC ACID | ++ |
| 481 | 3-[(3-CHLORO-BENZYL)-CYCLOBUTANECARBONYL-AMINO]-5-PHENYL-THIOPHENE-2-CARBOXYLIC ACID | ++ |
| 482 | 3-[BUTYRYL-(3-CHLORO-BENZYL)-AMINO]-5-PHENYL-THIOPHENE-2-CARBOXYLIC ACID | +++ |
| 483 | 3-[ACETYL-(2,4-DIFLUORO-BENZYL)-AMINO]-5-PHENYL-THIOPHENE-2-CARBOXYLIC ACID | ++ |

-continued

| MOLSTRUCTURE | COMPOUND NAME | IC50 |
|---|---|---|
| 484 | 3-[(2,4-DIFLUORO-BENZYL)-(2-METHOXY-ACETYL)-AMINO]-5-PHENYL-THIOPHENE-2-CARBOXYLIC ACID | ++ |
| 485 | 3-[(2,4-DIFLUORO-BENZYL)-ISOBUTYRYL-AMINO]-5-PHENYL-THIOPHENE-2-CARBOXYLIC ACID | ++ |
| 486 | 3-[(2,4-DIFLUORO-BENZYL)-(3-METHYL-BUTYRYL)-AMINO]-5-PHENYL-THIOPHENE-2-CARBOXYLIC ACID | ++ |
| 487 | 3-[BENZYL-(2-CYCLOPENTYL-ACETYL)-AMINO]-5-PHENYL-THIOPHENE-2-CARBOXYLIC ACID | +++ |

| MOLSTRUCTURE | COMPOUND NAME | IC50 |
| --- | --- | --- |
| 488 | 3-[(2,4-DICHLORO-BENZOYL)-ISOPROPYL-AMINO]-5-(1H-INDOL-5-YL)-THIOPHENE-2-CARBOXYLIC ACID | +++ |
| 489 | 3-(BENZYL-CYCLOBUTANECARBONYL-AMINO)-5-PHENYL-THIOPHENE-2-CARBOXYLIC ACID | +++ |
| 490 | 3-[CYCLOHEXANECARBONYL-(2,4-DIFLUORO-BENZYL)-AMINO]-5-PHENYL-THIOPHENE-2-CARBOXYLIC ACID | +++ |
| 491 | 3-{ALLYL-[2-(4-METHOXY-PHENYL)-ACETYL]-AMINO}-5-PHENYL-THIOPHENE-2-CARBOXYLIC ACID | + |

-continued

| MOLSTRUCTURE | COMPOUND NAME | IC50 |
|---|---|---|
| 492 | 3-(ETHYL-HEXANOYL-AMINO)-5-PHENYL-THIOPHENE-2-CARBOXYLIC ACID | +++ |
| 493 | 3-(BUTYRYL-ETHYL-AMINO)-5-PHENYL-THIOPHENE-2-CARBOXYLIC ACID | ++ |
| 494 | 3-[ETHYL-(4-METHYL-PENTANOYL)-AMINO]-5-PHENYL-THIOPHENE-2-CARBOXYLIC ACID | +++ |
| 495 | 3-[CYCLOBUTANECARBONYL-(2,4-DIFLUORO-BENZYL)-AMINO]-5-PHENYL-THIOPHENE-2-CARBOXYLIC ACID | +++ |

-continued

| MOLSTRUCTURE | COMPOUND NAME | IC50 |
|---|---|---|
| 496 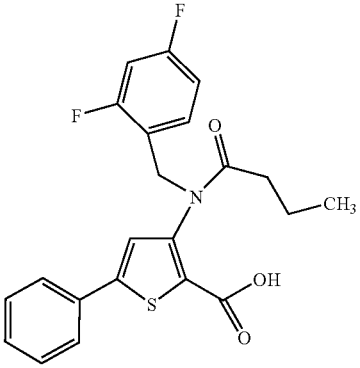 | 3-[BUTYRYL-(2,4-DIFLUORO-BENZYL)-AMINO]-5-PHENYL-THIOPHENE-2-CARBOXYLIC ACID | +++ |
| 497 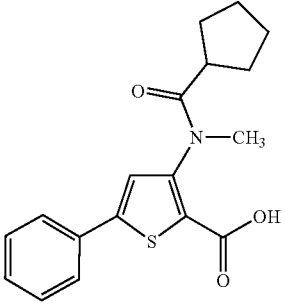 | 3-(CYCLOPENTANECARBONYL-METHYL-AMINO)-5-PHENYL-THIOPHENE-2-CARBOXYLIC ACID | +++ |
| 498 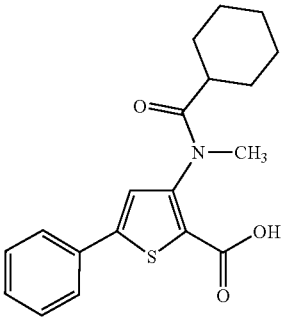 | 3-(CYCLOHEXANECARBONYL-METHYL-AMINO)-5-PHENYL-THIOPHENE-2-CARBOXYLIC ACID | +++ |
| 499 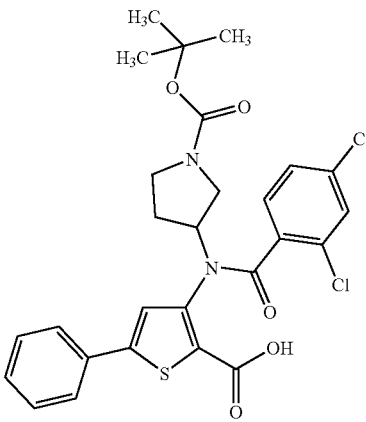 | 3-[(2-CARBOXY-5-PHENYL-THIOPHEN-3-YL)-(2,4-DICHLORO-BENZOYL)-AMINO]-PYRROLIDINE-1-CARBOXYLIC ACID #TERT!-BUTYL ESTER | +++ |

-continued

| MOLSTRUCTURE | COMPOUND NAME | IC50 |
|---|---|---|
| 500 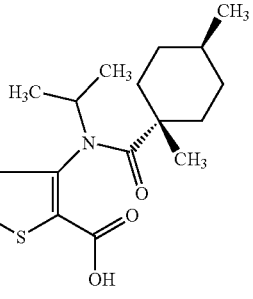 | 3-[(1,4-DIMETHYL-CYCLOHEXANECARBONYL)-ISOPROPYL-AMINO]-5-PHENYL-THIOPHENE-2-CARBOXYLIC ACID | +++ |
| 501 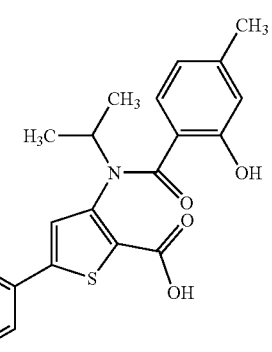 | 5-(4-ETHYL-PHENYL)-3-[(2-HYDROXY-4-METHYL-BENZOYL)-ISOPROPYL-AMINO]-THIOPHENE-2-CARBOXYLIC ACID | +++ |
| 502 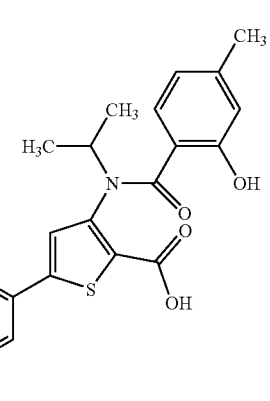 | 3-[(2-HYDROXY-4-METHYL-BENZOYL)-ISOPROPYL-AMINO]-5-#M!-TOLYL-THIOPHENE-2-CARBOXYLIC ACID | +++ |
| 503 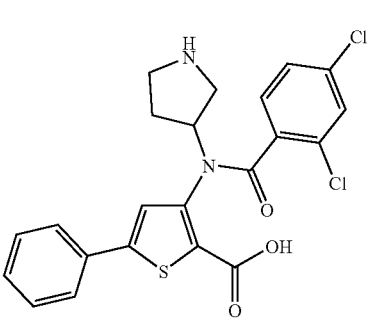 | 3-[(2,4-DICHLORO-BENZOYL)-PYRROLIDIN-3-YL-AMINO]-5-PHENYL-THIOPHENE-2-CARBOXYLIC ACID | ++ |

-continued

| MOLSTRUCTURE | COMPOUND NAME | IC50 |
|---|---|---|
| 504 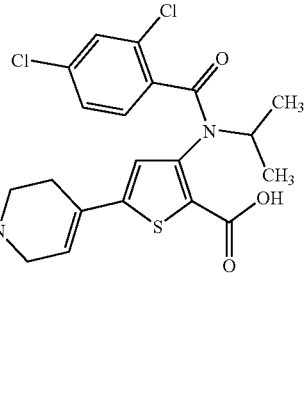 | 4-{5-CARBOXY-4-[(2,4-DICHLORO-BENZOYL)-ISOPROPYL-AMINO]-THIOPHEN-2-YL}-3,6-DIHYDRO-2#H!-PYRIDINE-1-CARBOXYLIC ACID BENZYL ESTER | +++ |
| 505 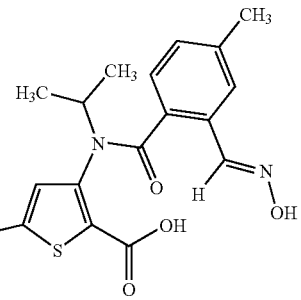 | 3-{[2-(HYDROXYIMINO-METHYL)-4-METHYL-BENZOYL]-ISOPROPYL-AMINO}-5-PHENYL-THIOPHENE-2-CARBOXYLIC ACID | ++ |
| 506 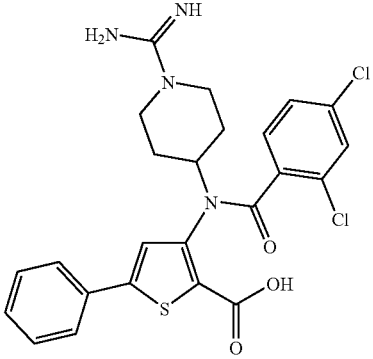 | 3-{[1-CARBAMIMIDOYL-PIPERIDIN-4-YL)-(2,4-DICHLORO-BENZOYL)-AMINO]-5-PHENYL-THIOPHENE-2-CARBOXYLIC ACID +++ | |
| 507 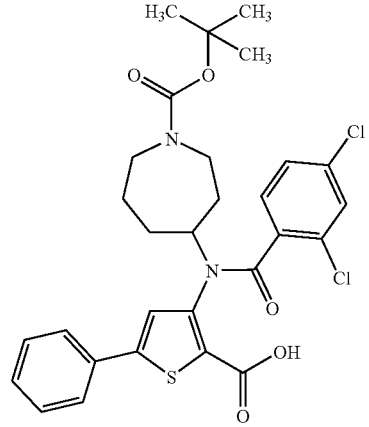 | 4-[(2-CARBOXY-5-PHENYL-THIOPHEN-3-YL)-(2,4-DICHLORO-BENZOYL)-AMINO]-AZEPANE-1-CARBOXYLIC ACID TERT!-BUTYL ESTER | +++ |

| MOLSTRUCTURE | COMPOUND NAME | IC50 |
|---|---|---|
| 508 | 3-{[(2-CARBOXY-5-PHENYL-THIOPHEN-3-YL)-(2,4-DICHLORO-BENZOYL)-AMINO]-METHYL}-PIPERIDINE-1-CARBOXYLIC ACID BENZYL ESTER | +++ |
| 509 | 3-[AZEPAN-4-YL-(2,4-DICHLORO-BENZOYL)-AMINO]-5-PHENYL-THIOPHENE-2-CARBOXYLIC ACID | +++ |
| 510 | 3-[(4-METHYL-CYCLOHEXANECARBONYL)-PIPERIDIN-4-YL-AMINO]-5-PHENYL-THIOPHENE-2-CARBOXYLIC ACID LITHIUM SALT | ++ |
| 511 | 3-[(2-CARBOXY-5-PHENYL-THIOPHEN-3-YL)-(2,4-DICHLORO-BENZOYL)-AMINO]-PIPERIDINE-1-CARBOXYLIC ACID #TERT!-BUTYL ESTER | +++ |

| MOLSTRUCTURE | COMPOUND NAME | IC50 |
|---|---|---|
| 512 | 3-[(4-BENZYLOXYCARBONYLAMINO-CYCLOHEXYL)-(2,4-DICHLORO-BENZOYL)-AMINO]-5-PHENYL-THIOPHENE-2-CARBOXYLIC ACID | +++ |
| 513 | 3-[ISOPROPYL-(4-METHYL-2-OXO-CYCLOHEXANECARBONYL)-AMINO]-5-PHENYL-THIOPHENE-2-CARBOXYLIC ACID | +++ |
| 514 | 3-[(2,4-DICHLORO-BENZOYL)-PIPERIDIN-3-YL-AMINO]-5-PHENYL-THIOPHENE-2-CARBOXYLIC ACID; COMPOUND WITH GENERIC INORGANIC NEUTRAL COMPONENT | +++ |
| 515 | 3-[(4-BENZYLOXYCARBONYLAMINO-CYCLOHEXYL)-(2,4-DICHLORO-BENZOYL)-AMINO]-5-PHENYL-THIOPHENE-2-CARBOXYLIC ACID | +++ |
| 516 | 3-[(2-BENZYLOXY-1-METHYL-ETHYL)-(2,4-DICHLORO-BENZOYL)-AMINO]-5-PHENYL-THIOPHENE-2-CARBOXYLIC ACID | +++ |

| MOLSTRUCTURE | COMPOUND NAME | IC50 |
|---|---|---|
| 517 | 3-[(2,2-DIMETHYL-[1,3]DIOXAN-5-YL)-(4-METHYL-CYCLOHEXANECARBONYL)-AMINO]-5-PHENYL-THIOPHENE-2-CARBOXYLIC ACID | +++ |
| 518 | 3-[(2,4-DICHLORO-BENZOYL)-(2-HYDROXY-1-HYDROXYMETHYL-ETHYL)-AMINO]-5-PHENYL-THIOPHENE-2-CARBOXYLIC ACID | +++ |
| 519 | 3-[(2,4-DICHLORO-BENZOYL)-PIPERIDIN-4-YLMETHYL-AMINO]-5-PHENYL-THIOPHENE-2-CARBOXYLIC ACID | +++ |
| 520 | 3-[(2-CHLORO-BENZOYL)-PIPERIDIN-4-YLMETHYL-AMINO]-5-PHENYL-THIOPHENE-2-CARBOXYLIC ACID | +++ |
| 521 | 3-[(4,6-DICHLORO-1#H!-INDOLE-2-CARBONYL)-ISOPROPYL-AMINO]-5-PHENYL-THIOPHENE-2-CARBOXYLIC ACID | +++ |

| MOLSTRUCTURE | COMPOUND NAME | IC50 |
|---|---|---|
| 522 | 3-[(2,4-DICHLORO-BENZOYL)-(2-HYDROXY-1-METHYL-ETHYL)-AMINO]-5-PHENYL-THIOPHENE-2-CARBOXYLIC ACID | +++ |
| 523 | 4-{1-[(2-CARBOXY-5-PHENYL-THIOPHEN-3-YL)-(2,4-DICHLORO-BENZOYL)-AMINO]-ETHYL}-PIPERIDINE-1-CARBOXYLIC ACID BENZYL ESTER | ++ |
| 524 | 4-{5-CARBOXY-4-[ISOPROPYL-(4-METHYL-CYCLOHEXANECARBONYL)-AMINO]-THIOPHEN-2-YL}-3,6-DIHYDRO-2#H!-PYRIDINE-1-CARBOXYLIC ACID BENZYL ESTER | +++ |
| 525 | 3-[(4-METHYL-CYCLOHEXANECARBONYL)-PYRIDIN-4-YL-AMINO]-5-PHENYL-THIOPHENE-2-CARBOXYLIC ACID | +++ |

-continued

| | MOLSTRUCTURE | COMPOUND NAME | IC50 |
|---|---|---|---|
| 526 | 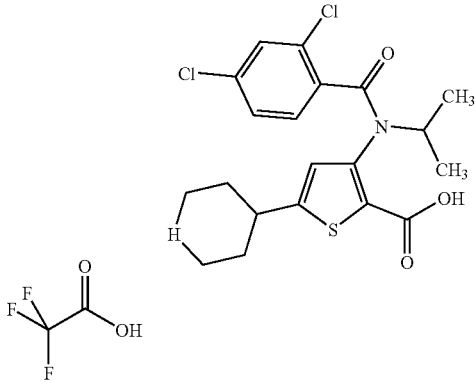 | 3-[(2,4-DICHLORO-BENZOYL)-ISOPROPYL-AMINO]-5-PIPERIDIN-4-YL-THIOPHENE-2-CARBOXYLIC ACID; COMPOUND WITH TRIFLUORO-ACETIC ACID | + |
| 527 | 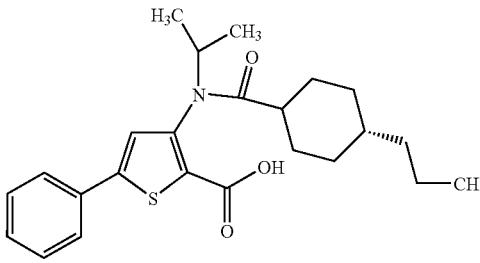 | 3-[ISOPROPYL-(4-PROPYL-CYCLOHEXANECARBONYL)-AMINO]-5-PHENYL-THIOPHENE-2-CARBOXYLIC ACID | +++ |
| 528 | 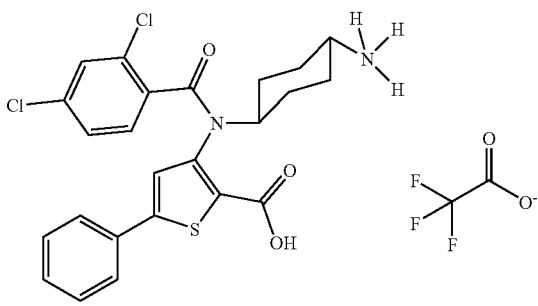 | 4-[(2-CARBOXY-5-PHENYL-THIOPHEN-3-YL)-(2,4-DICHLORO-BENZOYL)-AMINO]-CYCLOHEXYL-AMMONIUM; TRIFLUORO-ACETATE | +++ |
| 529 | 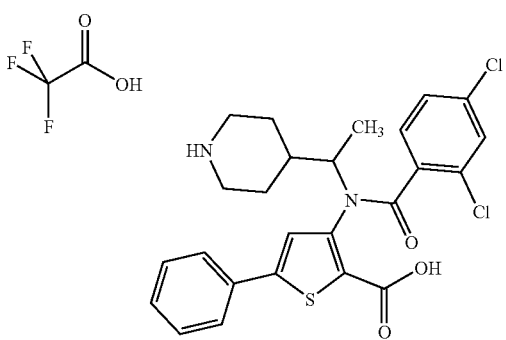 | 3-[(2,4-DICHLORO-BENZOYL)-(1-PIPERIDIN-4-YL-ETHYL)-AMINO]-5-PHENYL-THIOPHENE-2-CARBOXYLIC ACID; COMPOUND WITH TRIFLUORO-ACETIC ACID | +++ |

| MOLSTRUCTURE | COMPOUND NAME | IC50 |
|---|---|---|
| 530 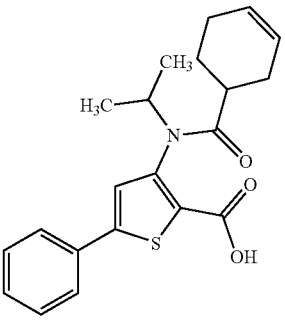 | 3-[(CYCLOHEX-3-ENECARBONYL)-ISOPROPYL-AMINO]-5-PHENYL-THIOPHENE-2-CARBOXYLIC ACID | ++ |
| 531 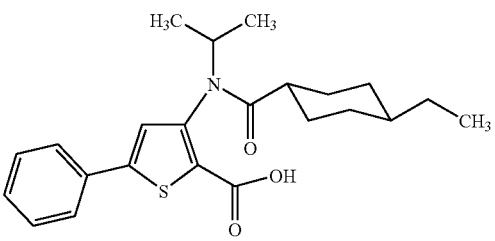 | 3-[(4-ETHYL-CYCLOHEXANECARBONYL)-ISOPROPYL-AMINO]-5-PHENYL-THIOPHENE-2-CARBOXYLIC ACID | +++ |
| 532 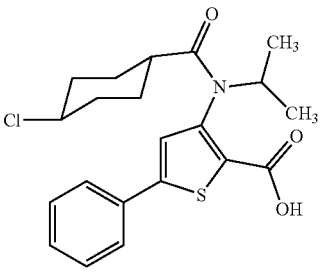 | 3-[(4-CHLORO-CYCLOHEXANECARBONYL)-ISOPROPYL-AMINO]-5-PHENYL-THIOPHENE-2-CARBOXYLIC ACID | +++ |
| 533 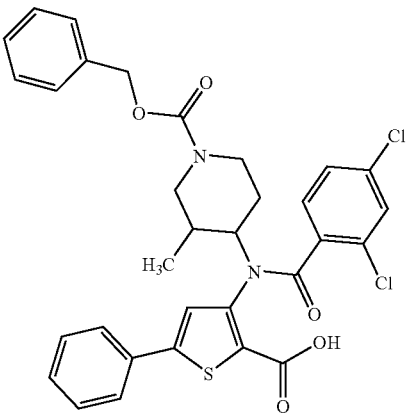 | 4-[(2-CARBOXY-5-PHENYL-THIOPHEN-3-YL)-(2,4-DICHLORO-BENZOYL)-AMINO]-3-METHYL-PIPERIDINE-1-CARBOXYLIC ACID BENZYL ESTER | +++ |
| 534 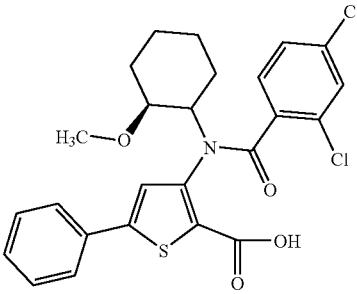 | 3-[(2,4-DICHLORO-BENZOYL)-(2-METHOXY-CYCLOHEXYL)-AMINO]-5-PHENYL-THIOPHENE-2-CARBOXYLIC ACID | +++ |

-continued

| MOLSTRUCTURE | COMPOUND NAME | IC50 |
|---|---|---|
| 535 | 3-[(2,4-DICHLORO-BENZOYL)-(2,2-DIMETHYL-[1,3]DIOXAN-5-YL)-AMINO]-5-PHENYL-THIOPHENE-2-CARBOXYLIC ACID | +++ |
| 536 | 3-[ISOPROPYL-(4-METHYL-CYCLOHEXANECARBONYL)-AMINO]-5-(1-METHYL-PIPERIDIN-4-YL)-THIOPHENE-2-CARBOXYLIC ACID | +++ |
| 537 | 3-[(2,4-DICHLORO-BENZOYL)-(3-METHYL-PIPERIDIN-4-YL)-AMINO]-5-PHENYL-THIOPHENE-2-CARBOXYLIC ACID; COMPOUND WITH TRIFLUORO-ACETIC ACID | +++ |
| 538 | 3-[(2,4-DICHLORO-BENZOYL)-(2-HYDROXY-CYCLOHEXYL)-AMINO]-5-PHENYL-THIOPHENE-2-CARBOXYLIC ACID | +++ |
| 539 | 4-{[(2-CARBOXY-5-PHENYL-THIOPHEN-3-YL)-(4-METHYL-CYCLOHEXANECARBONYL)-AMINO]-METHYL}-PIPERIDINE-1-CARBOXYLIC ACID BENZYL ESTER | +++ |

| MOLSTRUCTURE | COMPOUND NAME | IC50 |
|---|---|---|
| 540 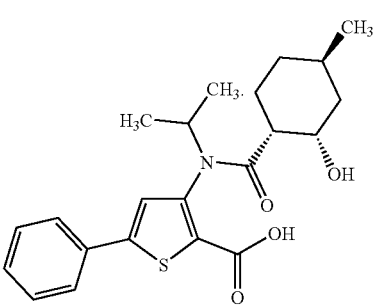 Chiral | 3-[((1R,2S,4R)-2-HYDROXY-4-METHYL-CYCLOHEXANECARBONYL)-ISOPROPYL-AMINO]-5-PHENYL-THIOPHENE-2-CARBOXYLIC ACID | +++ |
| 541 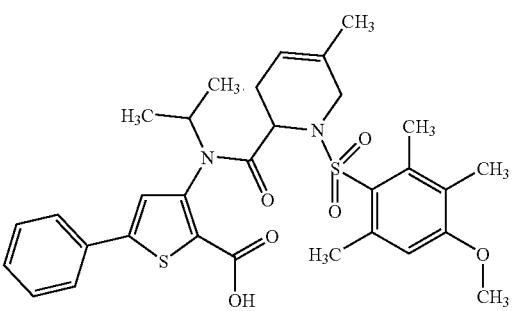 | 3-{ISOPROPYL-[1-(4-METHOXY-2,3,6-TRIMETHYL-BENZENESULFONYL)-5-METHYL-1,2,3,6-TETRAHYDRO-PYRIDINE-2-CARBONYL]-AMINO}-5-PHENYL-THIOPHENE-2-CARBOXYLIC ACID | ++ |
| 542 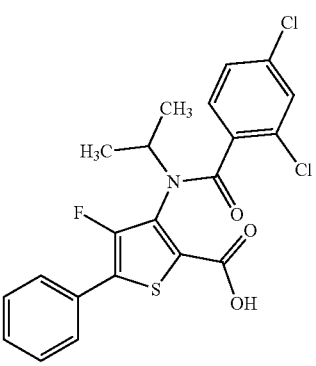 | 3-[(2,4-DICHLORO-BENZOYL)-ISOPROPYL-AMINO]-4-FLUORO-5-PHENYL-THIOPHENE-2-CARBOXYLIC ACID | ++ |
| 543 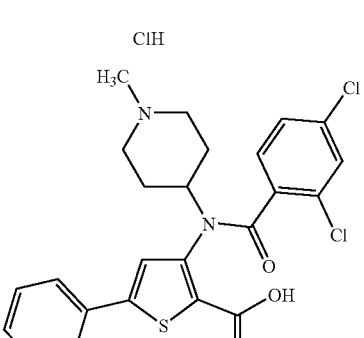 | 3-[(2,4-DICHLORO-BENZOYL)-(1-METHYL-PIPERIDIN-4-YL)-AMINO]-5-PHENYL-THIOPHENE-2-CARBOXYLIC ACID | ++ |

| MOLSTRUCTURE | COMPOUND NAME | IC50 |
| --- | --- | --- |
| 544 | 4-{[(2-CARBOXY-5-PHENYL-THIOPHEN-3-YL)-(4-METHYL-CYCLOHEXANECARBONYL)-AMINO]-METHYL}-PIPERIDINIUM; TRIFLUORO-ACETATE | +++ |
| 545 | 3-[(2-TERT-BUTOXYCARBONYLAMINO-1-METHYL-ETHYL)-(2,4-DICHLORO-BENZOYL)-AMINO]-5-PHENYL-THIOPHENE-2-CARBOXYLIC ACID | +++ |
| 546 | 2-[(2-CARBOXY-5-PHENYL-THIOPHEN-3-YL)-(2,4-DICHLORO-BENZOYL)-AMINO]-PROPYL-AMINE TRIFLUOROACETIC ACID SALT | +++ |
| 547 | 3-[(3-CARBOXY-CYCLOPENTYL)-(2,4-DICHLORO-BENZOYL)-AMINO]-5-PHENYL-THIOPHENE-2-CARBOXYLIC ACID | +++ |

-continued

| MOLSTRUCTURE | COMPOUND NAME | IC50 |
|---|---|---|
| 548 | 3-[(3-CARBOXY-CYCLOPENTYL)-(2,4-DICHLORO-BENZOYL)-AMINO]-5-PHENYL-THIOPHENE-2-CARBOXYLIC ACID | +++ |
| 549 | 2-[(2-CARBOXY-5-PHENYL-THIOPHEN-3-YL)-(2,4-DICHLORO-BENZOYL)-AMINO]-CYCLOHEXYL-AMMONIUM; CHLORIDE | +++ |
| 550 | 3-(BENZOYL-METHYL-AMINO)-5-PHENYL-THIOPHENE-2-CARBOXYLIC ACID | + |
| 551 | {[5-PHENYL-3-(TOLUENE-4-SULFONYLAMINO)-THIOPHENE-2-CARBONYL]-AMINO}-ACETIC ACID | ++ |

-continued

| MOLSTRUCTURE | COMPOUND NAME | IC50 |
|---|---|---|
| 552 | 5-BROMO-3-(TOLUENE-2-SULFONYLAMINO)-THIOPHENE-2-CARBOXYLIC ACID | ++ |
| 553 | 3-[CYCLOHEXYL-(2,4-DICHLORO-BENZOYL)-AMINO]-5-PHENYL-THIOPHENE-2-CARBOXYLIC ACID | +++ |
| 554 | 3-[[1,3]DIOXAN-5-YL-(4-METHYL-CYCLOHEXANECARBONYL)-AMINO]-5-PHENYL-THIOPHENE-2-CARBOXYLIC ACID | +++ |
| 555 Chiral | 3-[[2-(TERT-BUTYL-DIMETHYL-SILANYLOXY)-1-METHYL-2-PHENYL-ETHYL]-(2,4-DICHLORO-BENZOYL)-AMINO]-5-PHENYL-THIOPHENE-2-CARBOXYLIC ACID | ++ |
| 556 Chiral | 3-[[2-(TERT-BUTYL-DIMETHYL-SILANYLOXY)-1-METHYL-2-PHENYL-ETHYL]-(2,4-DICHLORO-BENZOYL)-AMINO]-5-PHENYL-THIOPHENE-2-CARBOXYLIC ACID | ++ |

-continued

| | MOLSTRUCTURE | COMPOUND NAME | IC50 |
|---|---|---|---|
| 557 | | 3-[(2,4-DICHLORO-BENZOYL)-(2-DIETHYLAMINO-THIAZOL-5-YLMETHYL)-AMINO]-5-PHENYL-THIOPHENE-2-CARBOXYLIC ACID | +++ |
| 558 | | (5-{[(2-CARBOXY-5-PHENYL-THIOPHEN-3-YL)-(2,4-DICHLORO-BENZOYL)-AMINO]-METHYL}-THIAZOL-2-YL)-DIETHYL-AMMONIUM; CHLORIDE | +++ |
| 559 | | 5-(4-FLUORO-PHENYL)-3-[ISOPROPYL-(4-METHYL-CYCLOHEXANECARBONYL)-AMINO]-THIOPHENE-2-CARBOXYLIC ACID | +++ |
| 560 | Chiral | 3-[((1S,2R,4S)-2-HYDROXY-4-METHYL-CYCLOHEXANECARBONYL)-ISOPROPYL-AMINO]-5-PHENYL-THIOPHENE-2-CARBOXYLIC ACID | +++ |
| 561 | | 3-[(2,4-DICHLORO-BENZOYL)-(2-METHOXY-1-METHYL-ETHYL)-AMINO]-5-PHENYL-THIOPHENE-2-CARBOXYLIC ACID | +++ |

| MOLSTRUCTURE | COMPOUND NAME | IC50 |
|---|---|---|
| 562 | 3-[(4S)-ISOPROPYL-(4-METHYL-CYCLOHEX-1-ENECARBONYL)-AMINO]-5-PHENYL-THIOPHENE-2-CARBOXYLIC ACID | +++ |
| 563 | 5-(4-CHLORO-PHENYL)-3-(TOLUENE-4-SULFONYLAMINO)-THIOPHENE-2-CARBOXYLIC ACID AMIDE | ++ |
| 564 | 5-(4-FLUORO-PHENYL)-3-(TOLUENE-4-SULFONYLAMINO)-THIOPHENE-2-CARBOXYLIC ACID AMIDE | ++ |
| 565 | 5-(4-METHOXY-PHENYL)-3-(TOLUENE-4-SULFONYLAMINO)-THIOPHENE-2-CARBOXYLIC ACID AMIDE | ++ |
| 566 | 3-METHYL-(4-METHYLBENZOYL)-AMINO)5-PHENYL THIOPHENE-2-CARBOXYLIC ACID (2-HYDROXY-ETHYL)AMIDE | ++ |

-continued

| MOLSTRUCTURE | COMPOUND NAME | IC50 |
|---|---|---|
| 567 | 5-PHENYL-3-(TOLUENE-4-SULFONYLAMINO)-THIOPHENE-2-CARBOXYLIC ACID CYCLOBUTYLAMIDE | ++ |
| 568 | 3-(2,4-DIMETHYL-BENZENESULFONYLAMINO)-5-PHENYL-THIOPHENE-2-CARBOXYLIC ACID AMIDE | ++ |
| 569 | 5-BROMO-3-[(2,4-DICHLORO-BENZOYL)-ISOPROPYL-AMINO]-THIOPHENE-2-CARBOXYLIC ACID | +++ |
| 570 | 5-(4-CHLORO-PHENYL)-3-[ISOPROPYL-(4-METHYL-CYCLOHEXANECARBONYL)-AMINO]-THIOPHENE-2-CARBOXYLIC ACID | +++ |
| 571 | 5-(4'-CHLORO-BIPHENYL-4-YL)-3-[ISOPROPYL-(4-METHYL-CYCLOHEXANECARBONYL)-AMINO]-THIOPHENE-2-CARBOXYLIC ACID | +++ |

-continued

| MOLSTRUCTURE | COMPOUND NAME | IC50 |
|---|---|---|
| 572 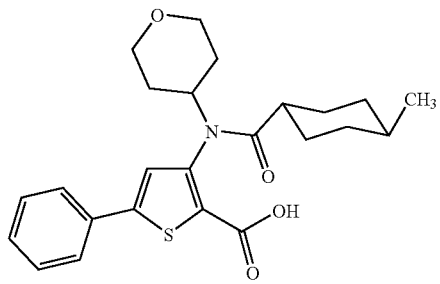 | 3-[(4-METHYL-CYCLOHEXANECARBONYL)-(TETRAHYDRO-PYRAN-4-YL)-AMINO]-5-PHENYL-THIOPHENE-2-CARBOXYLIC ACID | +++ |
| 573 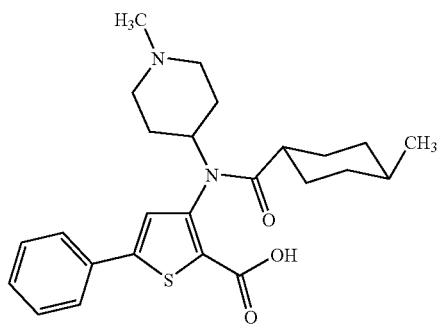 | 3-[(4-METHYL-CYCLOHEXANECARBONYL)-(1-METHYL-PIPERIDIN-4-YL)-AMINO]-5-PHENYL-THIOPHENE-2-CARBOXYLIC ACID | +++ |
| 574 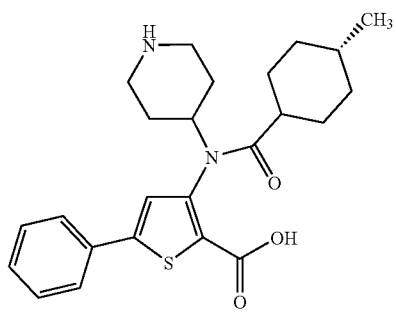 | 3-[(4-METHYL-CYCLOHEXANECARBONYL)-PIPERIDIN-4-YL-AMINO]-5-PHENYL-THIOPHENE-2-CARBOXYLIC ACID | + |
| 575 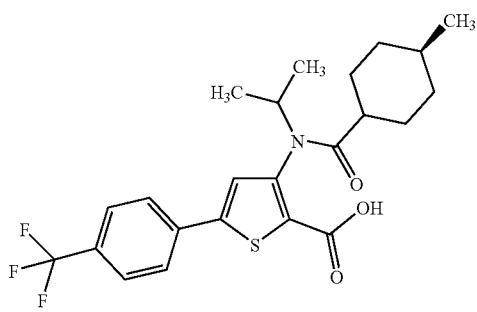 | '3-[ISOPROPYL-(4-METHYL-CYCLOHEXANECARBONYL)-AMINO]-5-(4-TRIFLUOROMETHYL-PHENYL)-THIOPHENE-2-CARBOXYLIC ACID | +++ |
| 576 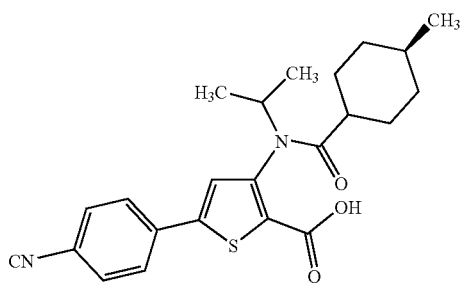 | 5-(4-CYANO-PHENYL)-3-[ISOPROPYL-(4-METHYL-CYCLOHEXANECARBONYL)-AMINO]-THIOPHENE-2-CARBOXYLIC ACID | +++ |

-continued

| MOLSTRUCTURE | COMPOUND NAME | IC50 |
|---|---|---|
| 577 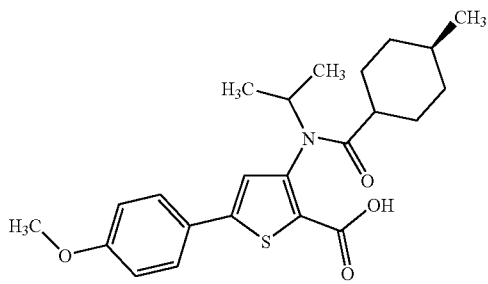 | '3-[ISOPROPYL-(4-METHYL-CYCLOHEXANECARBONYL)-AMINO]-5-(4-METHOXY-PHENYL)-THIOPHENE-2-CARBOXYLIC ACID | +++ |
| 578 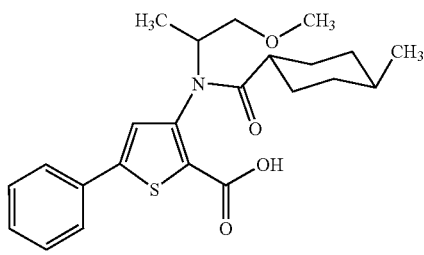 | 3-[(2-METHOXY-1-METHYL-ETHYL)-(4-METHYL-CYCLOHEXANECARBONYL)-AMINO]-5-PHENYL-THIOPHENE-2-CARBOXYLIC ACID | +++ |
| 579 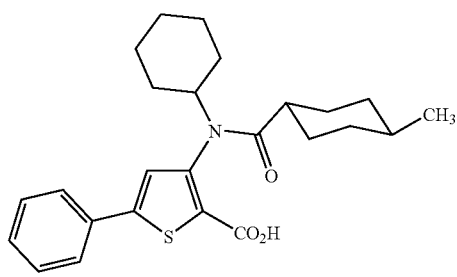 | 3-[CYCLOHEXYL-(4-METHYL-CYCLOHEXANECARBONYL)-AMINO]-5-PHENYL-THIOPHENE-2-CARBOXYLIC ACID | +++ |
| 580 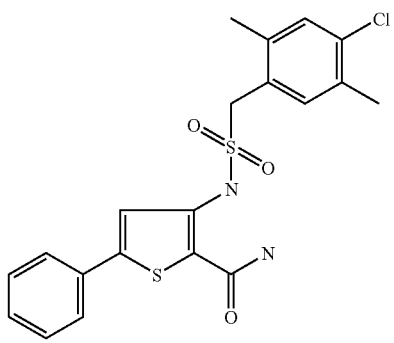 | 3-(4-CHLORO-2,5 DIMETHYL-BENZENESULFONYLAMINO)-5-PHENYL-THIOPHENE-2-CARBOXYLIC ACID AMIDE | +++ |
| 583 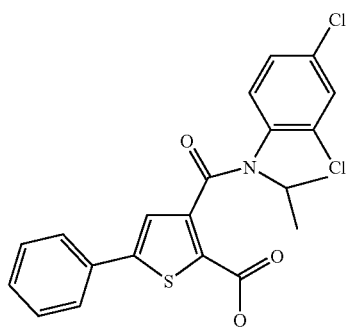 | 3-[(2,4-DICHLORO-PHENYL)-ISOPROPYL-CARBAMOYL]-5-PHENYL-THIOPHENE-2-CARBOXYLIC ACID | +++ |

| MOLSTRUCTURE | COMPOUND NAME | IC50 |
|---|---|---|
| 584 | 3-(METHYL-P-TOLYL-CARBAMOYL)-5-PHENYL-THIOPHENE-2-CARBOXYLIC ACID | ++ |
| 585 | 3-[(2,4-DICHLORO-PHENYL)-METHYL-CARBAMOYL]-5-PHENYL-THIOPHENE-2-CARBOXYLIC ACID | ++ |

*+++ IC$_{50}$ < 5 μM
++ IC$_{50}$ 5 μM-20 μM
+ IC$_{50}$ > 20 μM

EXAMPLE 28

List of Compounds Having Anti-Helicase Activity*

| Compound # | Compound name | Structure | Anti-ATPase (Malachite Green assay) EC$_{50}$ | Anti-ATPase (HPLC method) EC$_{50}$ |
|---|---|---|---|---|
| Compound #14 | 3-(4-Chloro-2,5-dimethyl-benzenesulfonylamino)-5-(4-chloro-phenyl)-thiophene-2-carboxylic acid | 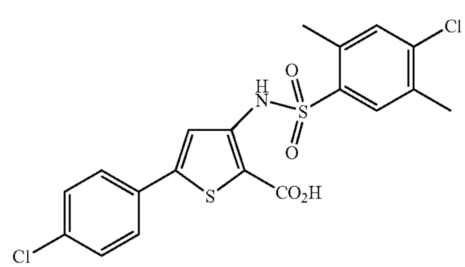 | + | ND |
| Compound #19 | 3-(4-Chloro-2,5-dimethyl-benzenesulfonylamino)-5-(4-isobutyl-phenyl)-thiophene-2-carboxylic acid | 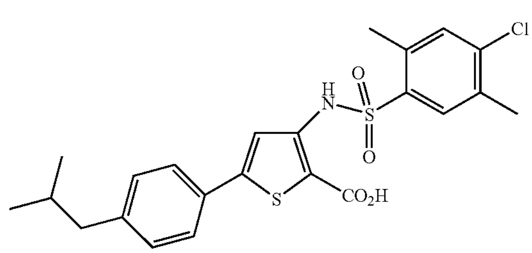 | +++ | ++ |

| Compound # | Compound name | Structure | Anti-ATPase (Malachite Green assay) EC$_{50}$ | Anti-ATPase (HPLC method) EC$_{50}$ |
|---|---|---|---|---|
| Compound #223 | 3-(4-Bromo-2-fluorobenzenesulfonyl-amino)-5-(4-isobutylphenyl)-thiophene-2-carboxylic acid | 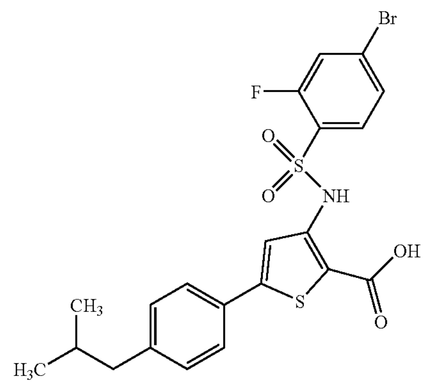 | ND | +++ |
| Compound #224 | 3-(4-Bromo-2-methylbenzenesulfonyl-amino)-5-(4-isobutylphenyl)-thiophene-2-carboxylic acid | 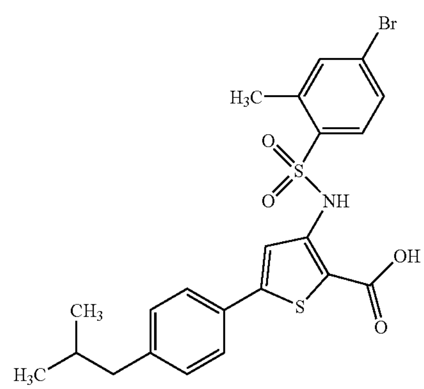 | ND | ++ |
| Compound #225 | 5-(4-Isobutylphenyl 3-(3-methoxy-benzenesulfonyl-amino)-thiophene-2-carboxylic acid | 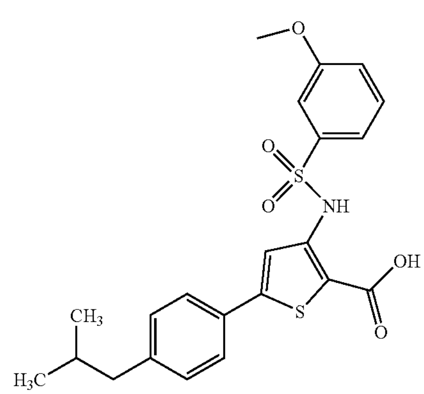 | ND | + |

-continued

| Compound # | Compound name | Structure | Anti-ATPase (Malachite Green assay) EC$_{50}$ | Anti-ATPase (HPLC method) EC$_{50}$ |
| --- | --- | --- | --- | --- |
| Compound #581 | 5-(4-Isobutyl-phenyl)-3-[5-(5-trifluoromethyl-isoxazol-3-yl)-thiophene-2-sulfonylamino]-thiophene-2-carboxylic acid | 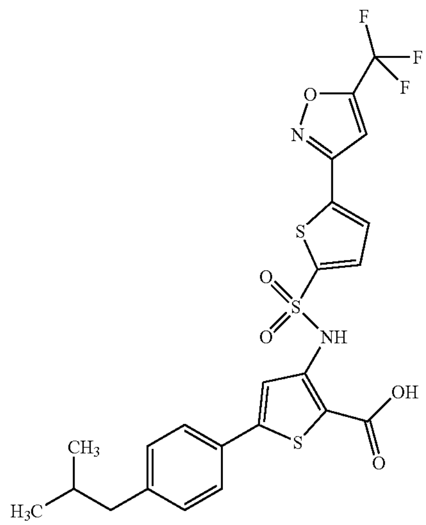 | ND | ++ |
| Compound #227 | 3-[2,5-Bis-(2,2,2-trifluoroethoxy)-benzenesulfonylamino]-5-(4-isobutyl-phenyl)-thiophene-2-carboxylic acid | 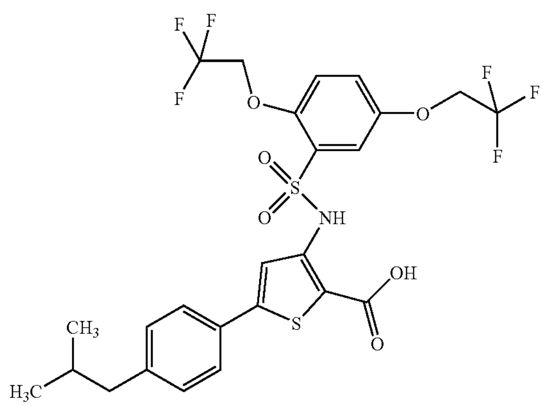 | ND | + |
| Compound #228 | 3-(2-Chloro-4-cyanobenzenesulfonyl-amino)-5-(4-isobutylphenyl)-thiophene-2-carboxylic acid | 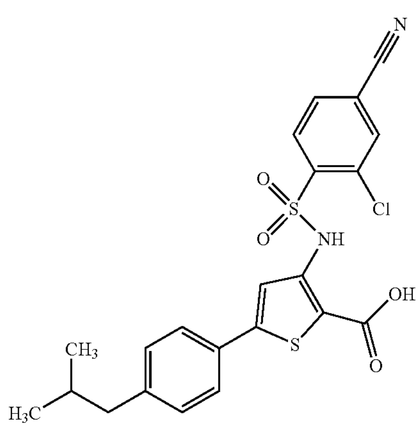 | ND | + |

-continued

| Compound # | Compound name | Structure | Anti-ATPase (Malachite Green assay) EC$_{50}$ | Anti-ATPase (HPLC method) EC$_{50}$ |
|---|---|---|---|---|
| Compound #582 | 5-(4-Isobutyl-phenyl)-3-(2,3,4-trifluoro-benzenesulfonylamino)-thiophene-2-carboxylic acid | 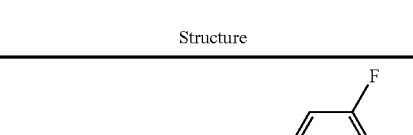 | ND | + |

*+++ IC$_{50}$ < 5 μM
++ IC$_{50}$ 5 μM-20 μM
+ IC$_{50}$ > 20 μM

We claim:

1. A compound having the formula (I):

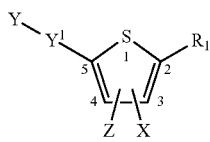

(I)

or a pharmaceutically acceptable salt thereof;
wherein,
X is

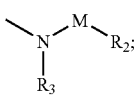

M is

J is

$Y^1$ is a bond;
Y is COOH;
$R_1$ is $C_{2-12}$ alkyl, $C_{2-12}$ alkenyl, $C_2$ alkynyl, $C_{6-14}$ aryl, $C_{3-12}$ heterocycle, $C_{3-18}$ heteroaralkyl or $C_{6-18}$ aralkyl;
$R_2$ is $C_{2-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, or $C_{6-18}$ aralkyl;
$R_3$ is H, $C_{1-12}$ alkyl, $C_{2-12}$ alkenyl, $C_2$ alkynyl, $C_{6-14}$ aryl, $C_{3-12}$ heterocycle, $C_{3-18}$ heteroaralkyl or $C_{6-18}$ aralkyl; and
Z is H, halogen, or $C_{1-6}$ alkyl;
with the proviso that: when X is Benzamide and $R_1$ is phenyl, then $R_3$ is other than hydrogen;
wherein
alkyl in $R_1$, $R_2$, $R_3$, and Z is in each case optionally substituted by one or more of: halogen, nitro, nitroso, SO$_3$R$_{12}$, PO$_3$R$_c$R$_d$, CONR$_{13}$R$_{14}$, C$_{1-6}$ alkyl, C$_{2-6}$ alkenyl, C$_{2-6}$ alkynyl, C$_{6-12}$ aralkyl, C$_{6-12}$ aryl, C$_{1-6}$ alkyloxy, C$_{2-6}$ alkenyloxy, C$_{2-6}$ alkynyloxy, C$_{6-12}$ aryloxy, C(O)C$_{1-6}$ alkyl, C(O)C$_{2-6}$ alkenyl, C(O)C$_{2-6}$ alkynyl, C(O)C$_{6-12}$ aryl, C(O)C$_{6-12}$ aralkyl, C$_{3-10}$ heterocycle, hydroxyl, NR$_{13}$R$_{14}$, C(O)OR$_{12}$, cyano, azido, amidino or guanido;
alkenyl in $R_1$, $R_2$, and $R_3$ is in each case optionally substituted by one or more of: halogen, nitro, nitroso, SO$_3$R$_{12}$, PO$_3$R$_c$R$_d$, CONR$_{13}$R$_{14}$, C$_{1-6}$ alkyl, C$_{2-6}$ alkenyl, C$_{2-6}$ alkynyl, C$_{6-12}$ aralkyl, C$_{6-12}$ aryl, C$_{1-6}$ alkyloxy, C$_{2-6}$ alkenyloxy, C$_{2-6}$ alkynyloxy, C$_{6-12}$ aryloxy, C(O)C$_{1-6}$ alkyl, C(O)C$_{2-6}$ alkenyl, C(O)C$_{2-6}$ alkynyl, C(O)C$_{6-12}$ aryl, C(O)C$_{6-12}$ aralkyl, C$_{3-10}$ heterocycle, hydroxyl, NR$_{13}$R$_{14}$, C(O)OR$_{12}$, cyano, azido, amidino or guanido;
alkynyl in $R_1$, $R_2$, and $R_3$ is in each case optionally substituted by one or more of: halogen, nitro, nitroso, SO$_3$R$_{12}$, PO$_3$R$_c$R$_d$, CONR$_{13}$R$_{14}$, C$_{1-6}$ alkyl, C$_{2-6}$ alkenyl, C$_{2-6}$ alkynyl, C$_{6-12}$ aralkyl, C$_{6-12}$ aryl, C$_{1-6}$ alkyloxy, C$_{2-6}$ alkenyloxy, C$_{2-6}$ alkynyloxy, C$_{6-12}$ aryloxy, C(O)C$_{1-6}$ alkyl, C(O)C$_{2-6}$ alkenyl, C(O)C$_{2-6}$ alkynyl, C(O)C$_{6-12}$ aryl, C(O)C$_{6-12}$ aralkyl, C$_{3-10}$ heterocycle, hydroxyl, NR$_{13}$R$_{14}$, C(O)OR$_{12}$, cyano, azido, amidino or guanido;
aryl in $R_1$, $R_2$, and $R_3$ is in each case optionally substituted by one or more of: halogen, nitro, nitroso, SO$_3$R$_{12}$, PO$_3$R$_c$R$_d$, CONR$_{13}$R$_{14}$, C$_{1-6}$ alkyl, C$_{2-6}$ alkenyl, C$_{2-6}$ alkynyl, C$_{6-12}$ aralkyl, C$_{6-12}$ aryl, C$_{1-6}$ alkyloxy, C$_{2-6}$ alkenyloxy, C$_{2-6}$ alkynyloxy, C$_{6-12}$ aryloxy, C(O)C$_{1-6}$ alkyl, C(O)C$_{2-6}$ alkenyl, C(O)C$_{2-6}$ alkynyl, C(O)C$_{6-12}$ aryl, C(O)C$_{6-12}$ aralkyl, C$_{3-10}$ heterocycle, hydroxyl, NR$_{13}$R$_{14}$, C(O)OR$_{12}$, cyano, azido, amidino or guanido;
aralkyl in $R_1$, $R_2$, and $R_3$ is in each case an aryl group attached to the adjacent atom by a $C_{1-6}$ alkyl, $C_{2-6}$ alkenyl, or $C_{2-6}$ alkynyl, and the aryl group is in each case optionally substituted by one or more of: halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido;

heterocycle in $R_1$, $R_2$, and $R_3$ is in each case optionally substituted by one or more of: halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido;

heteroaralkyl in $R_1$, $R_2$, and $R_3$ in each case an heterocycle group attached to the adjacent atom by a $C_{1-6}$ alkyl, $C_{2-6}$ alkenyl, or $C_{2-6}$ alkynyl, and the heterocycle group is in each case optionally substituted by one or more of: halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido; and $R_{12}$, $R_c$, $R_d$, $R_{13}$ and $R_{14}$, are each independently H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, or $C_{6-18}$ aralkyl, or $R_c$ and $R_d$ are taken together with the oxygens to form a 5 to 10 membered heterocycle, or $R_{13}$ and $R_{14}$ are taken together with the nitrogen to form a 3 to 10 membered heterocycle, in each case above alkyl groups include alkyls in which one or more hydrogen atoms are each replaced by a halogen, and sulfur atoms are in the form of S, SO, or $SO_2$.

2. A compound according to claim 1, wherein said compound is of formula Ia:

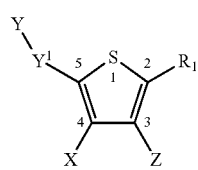

(Ia)

or a pharmaceutically acceptable salt thereof.

3. A compound according to claim 1, wherein X is

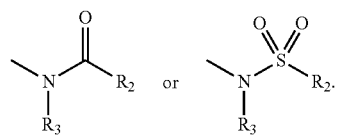

4. A compound according to claim 1, wherein Z is H.

5. A compound according to claim 1, wherein $R_1$ is $C_{2-12}$ alkyl, $C_{6-14}$ aryl, or $C_{3-12}$ heterocycle, which in each case is substituted or unsubstituted.

6. A compound according to claim 1, wherein $R_3$ is H, $C_{1-12}$ alkyl, $C_{6-18}$ aralkyl, $C_{3-12}$ heterocycle, or $C_{3-18}$ heteroaralkyl, which in each case is substituted or unsubstituted.

7. A compound according to claim 6, wherein $R_3$ is $C_{1-12}$ alkyl which is substituted or unsubstituted.

8. A compound according to claim 1, wherein $R_3$ is H, or $R_3$ is methyl, ethyl, isopropyl, cyclopropyl, cyclohexyl, allyl, piperidinyl, piperazinyl, pyrrolidinyl, azetidinyl, aziridinyl, pyridinyl, piperidinylmethyl, dioxanyl, azepanyl or benzyl, which in each case is unsubstituted or substituted by one or more substituents chosen from halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido; and $R_{12}$, $R_c$, $R_d$, $R_{13}$ and $R_{14}$ are each independently H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, or $C_{6-18}$ aralkyl, or $R_c$ and $R_d$, taken together with the oxygens, form a 5 to 10 membered heterocycle, or $R_{13}$ and $R_{14}$, taken together with the nitrogen, form a 3 to 10 membered heterocycle.

9. A compound according to claim 1, wherein $R_3$ is H, or $R_3$ is methyl, isopropyl, piperidinyl, piperidinylmethyl, dioxolanyl or cyclohexyl, which in each case is substituted or unsubstituted by one or more substituents chosen from halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido; and $R_{12}$, $R_c$, $R_d$, $R_{13}$ and $R_{14}$ are each independently H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, or $C_{6-18}$ aralkyl, or $R_c$ and $R_d$, taken together with the oxygens, form a 5 to 10 membered heterocycle, or $R_{13}$ and $R_{14}$, taken together with the nitrogen, form a 3 to 10 membered heterocycle.

10. A compound according to claim 9, wherein $R_3$ is isopropyl which is substituted or unsubstituted.

11. A compound according to claim 9, wherein $R_3$ is cyclohexyl which is substituted or unsubstituted.

12. A compound according to claim 1, wherein $R_2$ is $C_{2-12}$ alkyl, $C_{6-14}$ aryl, or $C_{3-12}$ heterocycle, which in each case is substituted or unsubstituted.

13. A compound according to claim 2, wherein $R_2$ is $C_{2-12}$ alkyl which is substituted or unsubstituted.

14. A compound according to claim 1, wherein $R_2$ is cyclopropyl, cyclobutyl, cyclopentyl, cyclopentenyl cyclohexyl, cycloheptyl, 2-(cyclopentyl)-ethyl, ethyl, vinyl, propyl, propenyl, isopropyl, butyl, butenyl isobutyl, pentyl, neopentyl or t-butyl, which in each case is unsubstituted or substituted by one or more substituents chosen from halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido; and $R_{12}$, $R_c$, $R_d$, $R_{13}$ and $R_{14}$ are each independently H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, or $C_{6-18}$ aralkyl, or $R_c$ and $R_d$, taken together with the oxygens, form a 5 to 10 membered heterocycle, or $R_{13}$ and $R_{14}$, taken together with the nitrogen, form a 3 to 10 membered heterocycle.

15. A compound according to claim 2, wherein X is

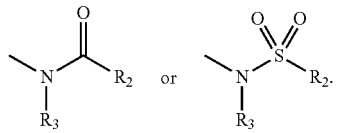

16. A compound according to claim 2, wherein Z is H.

17. A compound according to claim 2, wherein $R_1$ is $C_{2-12}$ alkyl, $C_{6-14}$ aryl, or $C_{3-12}$ heterocycle, which in each case is substituted or unsubstituted.

18. A compound according to claim 2, wherein $R_3$ is H, or $R_3$ is $C_{1-12}$ alkyl, $C_{6-18}$ aralkyl, $C_{3-12}$ heterocycle, or $C_{3-18}$ heteroaralkyl, which in each case is substituted or unsubstituted.

19. A compound according to claim 18, wherein $R_3$ is $C_{1-12}$ alkyl which is substituted or unsubstituted.

20. A compound according to claim 2, wherein $R_3$ is H, or $R^3$ is methyl, ethyl, isopropyl, cyclopropyl, cyclohexyl, allyl, piperidinyl, piperazinyl, pyffolidinyl, azetidinyl, aziridinyl, pyridinyl, piperidinylmethyl, dioxanyl, azepanyl or benzyl, which in each case is unsubstituted or substituted by one or more substituents chosen from halogen, nitro, nitroso, S03R12, PO3RRd, C0NR13R14, C16 alkyl, C26 alkenyl, C26 alkynyl, C6i2 aralkyl, C612 aryl, Ci6 alkyloxy, C26 alkenyloxy, C26 alkynyloxy, C62 aryloxy, C(O)C16 alkyl, C(O)C26 alkenyl, C(O)C26 alkynyl, C(O)C612 aryl, C(O)C612 aralkyl, C3 ioheterocycle, hydroxyl, NR13R14, C(O) OR12, cyano, azido, amidino, and guanido; and R12, R, Rd, R13 and R14 are each independently H, C112 alkyl, C212 alkenyl, C212 alkynyl, C614 aryl, C3i2 heterocycle, C3i8 heteroaralkyl, or C6i8 aralkyl, or R and Rd, taken together with the oxygens, form a 5 to 10 membered heterocycle, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)$ $C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido; and $R_{12}$, $R_c$, $R_d$, $R_{13}$ and $R_{14}$ are each independently H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, or $C_{6-18}$ aralkyl, or $R_c$ and $R_d$, taken together with the oxygens, form a 5 to 10 membered heterocycle, or $R_{13}$ and $R_{14}$, taken together with the nitrogen, form a 3 to 10 membered heterocycle.

21. A compound according to claim 2, wherein $R_3$ is H or $R_3$ is methyl, isopropyl, piperidinyl, piperidinylmethyl, dioxolanyl or cyclohexyl, which in each case is substituted or unsubstituted.

22. A compound according to claim 21, wherein $R_3$ is isopropyl which is substituted or unsubstituted.

23. A compound according to claim 21, wherein $R_3$ is cyclohexyl which is substituted or unsubstituted.

24. A compound according to claim 2, wherein $R_2$ is $C_{2-12}$ alkyl, $C_{6-14}$ aryl, or $C_{3-12}$ heterocycle, which in each case is substituted or unsubstituted.

25. A compound according to claim 24, wherein $R_2$ is $C_{2-12}$ alkyl which is substituted or unsubstituted.

26. A compound according to claim 2, wherein $R_2$ is cyclopropyl, cyclobutyl, cyclopentyl, cyclopentenyl cyclohexyl, cycloheptyl, 2-(cyclopentyl)-ethyl, ethyl, vinyl, propyl, propenyl, isopropyl, butyl, butenyl isobutyl, pentyl, neopentyl or t-butyl, which in each case is unsubstituted or substituted by one or more substituents chosen from halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)$ $C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido; and $R_{12}$, $R_c$, $R_d$, $R_{13}$ and $R_{14}$ are each independently H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, or $C_{6-18}$ aralkyl, or $R_c$ and $R_d$, taken together with the oxygens, form a 5 to 10 membered heterocycle, or $R_{13}$ and $R_{14}$, taken together with the nitrogen, form a 3 to 10 membered heterocycle.

27. A compound according to claim 2, wherein Z is H and X is

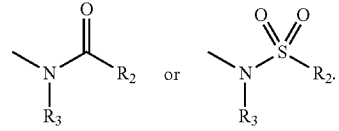

28. A compound according to claim 27, wherein $R_1$ is $C_{2-12}$ alkyl, $C_{6-14}$ aryl, or $C_{3-12}$ heterocycle, which in each case is substituted or unsubstituted;

$R_3$ is H, or $R^3$ is $C_{1-12}$ alkyl, $C_{6-18}$ aralkyl, $C_{3-12}$ heterocycle, or $C_{3-18}$ heteroaralkyl, which in each case is substituted or unsubstituted; and $R_2$ is $C_{2-12}$ alkyl, $C_{6-14}$ aryl, or $C_{3-12}$ heterocycle, which in each case is substituted or unsubstituted.

29. A compound according to claim 27, wherein $R_3$ is $C_{1-12}$ alkyl and $R_2$ is $C_{2-12}$ alkyl, which in each case is substituted or unsubstituted.

30. A compound according to claim 28, wherein $R_3$ is $C_{1-12}$ alkyl and $R_2$ is $C_{2-12}$ alkyl, which in each is substituted or unsubstituted.

31. A compound according to claim 27, wherein $R_3$ is H, or $R^3$ is methyl, ethyl, isopropyl, cyclopropyl, cyclohexyl, allyl, piperidinyl, piperazinyl, pyffolidinyl, azetidinyl, aziridinyl, pyridinyl, piperidinylmethyl, dioxanyl, azepanyl or benzyl, which in each case is unsubstituted or substituted by one or more substituents chosen from halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)$ $C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido;

$R_2$ is cyclopropyl, cyclobutyl, cyclopentyl, cyclopentenyl cyclohexyl, cycloheptyl, 2-(cyclopentyl)-ethyl, ethyl, vinyl, propyl, propenyl, isopropyl, butyl, butenyl isobutyl, pentyl, neopentyl or t-butyl, which in each case is unsubstituted or substituted by one or more substituents chosen from halogen, nitro, nitroso, $SO_3R_{12}$, $PO_3R_cR_d$, $CONR_{13}R_{14}$, $C_{1-6}$ alkyl, $C_{2-6}$ alkenyl, $C_{2-6}$ alkynyl, $C_{6-12}$ aralkyl, $C_{6-12}$ aryl, $C_{1-6}$ alkyloxy, $C_{2-6}$ alkenyloxy, $C_{2-6}$ alkynyloxy, $C_{6-12}$ aryloxy, $C(O)C_{1-6}$ alkyl, $C(O)C_{2-6}$ alkenyl, $C(O)C_{2-6}$ alkynyl, $C(O)C_{6-12}$ aryl, $C(O)C_{6-12}$ aralkyl, $C_{3-10}$ heterocycle, hydroxyl, $NR_{13}R_{14}$, $C(O)OR_{12}$, cyano, azido, amidino or guanido; and $R_{12}$, $R_c$, $R_d$, $R_{13}$ and $R_{14}$ are each independently H, $C_{1-12}$ alkyl, $C_{2-12}$ alkenyl, $C_{2-12}$ alkynyl, $C_{6-14}$ aryl, $C_{3-12}$ heterocycle, $C_{3-18}$ heteroaralkyl, or $C_{6-18}$ aralkyl, or $R_c$ and $R_d$, taken together with the oxygens, form a 5 to 10 membered heterocycle, or $R_{13}$ and $R_{14}$, taken together with the nitrogen, form a 3 to 10 membered heterocycle.

32. A method for treating a Hepatitis C virus (HCV) infection in a host comprising administering to the host a therapeutically effective amount of at least one compound according to claim 1.

33. A method for treating a Hepatitis C virus (HCV) infection in a host comprising administering to the host a therapeutically effective amount of at least one compound according to claim 2.

34. A method for treating a Hepatitis C virus (HCV) infection in a host comprising administering to the host a therapeutically effective amount of at least one compound according to claim 3.

35. A method for treating a Hepatitis C virus (HCV) infection in a host comprising administering to the host a therapeutically effective amount of at least one compound according to claim 4.

36. A method for treating a Hepatitis C virus (HCV) infection in a host comprising administering to the host a therapeutically effective amount of at least one compound according to claim 5.

37. A method for treating a Hepatitis C virus (HCV) infection in a host comprising administering to the host a therapeutically effective amount of at least one compound according to claim 6.

38. A method for treating a Hepatitis C virus (HCV) infection in a host comprising administering to the host a therapeutically effective amount of at least one compound according to claim 7.

39. A method for treating a Hepatitis C virus (HCV) infection in a host comprising administering to the host a therapeutically effective amount of at least one compound according to claim 8.

40. A method for treating a Hepatitis C virus (HCV) infection in a host comprising administering to the host a therapeutically effective amount of at least one compound according to claim 9.

41. A method for treating a Hepatitis C virus (HCV) infection in a host comprising administering to the host a therapeutically effective amount of at least one compound according to claim 10.

42. A method for treating a Hepatitis C virus (HCV) infection in a host comprising administering to the host a therapeutically effective amount of at least one compound according to claim 11.

43. A method for treating a Hepatitis C virus (HCV) infection in a host comprising administering to the host a therapeutically effective amount of at least one compound according to claim 12.

44. A method for treating a Hepatitis C virus (HCV) infection in a host comprising administering to the host a therapeutically effective amount of at least one compound according to claim 13.

45. A method for treating a Hepatitis C virus (HCV) infection in a host comprising administering to the host a therapeutically effective amount of at least one compound according to claim 14.

46. A method for treating a Hepatitis C virus (HCV) infection in a host comprising administering to the host a therapeutically effective amount of at least one compound according to claim 15.

47. A method for treating a Hepatitis C virus (HCV) infection in a host comprising administering to the host a therapeutically effective amount of at least one compound according to claim 16.

48. A method for treating a Hepatitis C virus (HCV) infection in a host comprising administering to the host a therapeutically effective amount of at least one compound according to claim 17.

49. A method for treating a Hepatitis C virus (HCV) infection in a host comprising administering to the host a therapeutically effective amount of at least one compound according to claim 18.

50. A method for treating a Hepatitis C virus (HCV) infection in a host comprising administering to the host a therapeutically effective amount of at least one compound according to claim 19.

51. A method for treating a Hepatitis C virus (HCV) infection in a host comprising administering to the host a therapeutically effective amount of at least one compound according to claim 20.

52. A method for treating a Hepatitis C virus (HCV) infection in a host comprising administering to the host a therapeutically effective amount of at least one compound according to claim 21.

53. A method for treating a Hepatitis C virus (HCV) infection in a host comprising administering to the host a therapeutically effective amount of at least one compound according to claim 22.

54. A method for treating a Hepatitis C virus (HCV) infection in a host comprising administering to the host a therapeutically effective amount of at least one compound according to claim 23.

55. A method for treating a Hepatitis C virus (HCV) infection in a host comprising administering to the host a therapeutically effective amount of at least one compound according to claim 24.

56. A method for treating a Hepatitis C virus (HCV) infection in a host comprising administering to the host a therapeutically effective amount of at least one compound according to claim 25.

57. A method for treating a Hepatitis C virus (HCV) infection in a host comprising administering to the host a therapeutically effective amount of at least one compound according to claim 26.

58. A method for treating a Hepatitis C virus (HCV) infection in a host comprising administering to the host a therapeutically effective amount of at least one compound according to claim 27.

59. A method for treating a Hepatitis C virus (HCV) infection in a host comprising administering to the host a therapeutically effective amount of at least one compound according to claim 28.

60. A method for treating a Hepatitis C virus (HCV) infection in a host comprising administering to the host a therapeutically effective amount of at least one compound according to claim 30.

61. A method for treating a Hepatitis C virus (HCV) infection in a host comprising administering to the host a therapeutically effective amount of at least one compound according to claim 31.

* * * * *